(12) United States Patent
Quattropani et al.

(10) Patent No.: US 7,468,385 B2
(45) Date of Patent: Dec. 23, 2008

(54) TRIAZOLES AS OXYTOCIN ANTAGONISTS

(75) Inventors: Anna Quattropani, Geneva (CH);
Matthias Schwarz, Geneva (CH);
Russell J. Thomas, Siena (IT); Thomas Coulter, Wantage (GB)

(73) Assignee: Laboratoires Serono SA, Coinsins (CH)

( * ) Notice: Subject to any disclaimer, the term of this patent is extended or adjusted under 35 U.S.C. 154(b) by 506 days.

(21) Appl. No.: 10/498,356

(22) PCT Filed: Dec. 19, 2002

(86) PCT No.: PCT/EP02/14594

§ 371 (c)(1),
(2), (4) Date: Mar. 29, 2005

(87) PCT Pub. No.: WO03/053437

PCT Pub. Date: Jul. 3, 2003

(65) Prior Publication Data

US 2005/0187275 A1    Aug. 25, 2005

(30) Foreign Application Priority Data

Dec. 20, 2001 (EP) .................... 01000778

(51) Int. Cl.
*A61K 31/41* (2006.01)
*C07D 249/08* (2006.01)

(52) U.S. Cl. .................... 514/383; 548/262.2

(58) Field of Classification Search ............ 514/383; 548/262.2
See application file for complete search history.

(56) References Cited

U.S. PATENT DOCUMENTS

| 5,336,778 A * | 8/1994 | Ashton et al. ............ 548/250 |
| 5,756,497 A | 5/1998 | Bell et al. |
| 6,346,532 B1 * | 2/2002 | Maruyama et al. ....... 514/252.1 |
| 2005/0187275 A1 | 8/2005 | Quattropani et al. |

FOREIGN PATENT DOCUMENTS

| EP | 048 555 | 3/1982 |
| EP | 409 332 | 1/1991 |
| EP | 469 984 | 2/1992 |
| EP | 505 111 | 9/1992 |
| EP | 526 348 | 2/1993 |
| WO | 96/22775 | 8/1996 |
| WO | 00/46220 | 8/2000 |
| WO | 01/58880 | 8/2001 |

OTHER PUBLICATIONS

Doug W. Hobbs, et al., "Non-peptide oxytocin antagonists: identification and synthesis of a potent camphor aminosuccinimide", Bioorganic & Medicinal Chemistry Letters, vol. 5, No. 2, pp. 119-122 Jan. 19, 1995.
M. Thibonnier, et al., Annu. Rev. Pharmacol. Toxicol., vol. 41, pp. 175-202 2001.
Mariel Birnbaumer, TEM, vol. 11, No. 10, pp. 406-410 2000.
Mario Maggi, et al., Journal of Clinical Endocrinology and Metabolism, vol. 70, No. 4, pp. 1142-1154 1990.
B. F. Mitchell, et al., Society for Gynecologic Investigation, vol. 8, No. 3, pp. 122-133 2001.
Marc Thibonnier, et al., Adv. Exp. Med. Biolog., vol. 449, pp. 251-276 1998.
Steven Thornton, et al., Experimental Physiology, vol. 86, No. 2, pp. 297-302 2001.
Ben E. Evans, et al., J. Med. Chem., vol. 35, pp. 3919-3927 1992.
O.S. Moustafa, Heterocycl. Commun., vol. 6, No. 5, pp. 465-471 2000.
Wallace T. Ashton, et al., Journal of Medicinal Chemistry, vol. 36, No. 5, pp. 591-609 1993.
Paul C. Fritch, et al., Solid-Phase Org. Synth., vol. 1, pp. 105-112 2001.
Dr. Neil Cook, et al., Pharmaceutical Manufacturing International, pp. 49-53 1992.
Gerald Gimpl, et al., Physiological Reviews, vol. 81, No. 2, pp. 629-683 2001.
U.S. Appl. No. 11/449,802, filed Jun. 9, 2006, Schwarz et al.

* cited by examiner

*Primary Examiner*—Joseph K. McKane
*Assistant Examiner*—Susannah Chung
(74) *Attorney, Agent, or Firm*—Oblon, Spivak, McClelland, Maier & Neustadt, P.C.

(57) ABSTRACT

The present invention relates to triazole derivatives of formula (I) notably for use as pharmaceutically active compounds, as well as pharmaceutical formulations containing such triazole derivatives. Said triazoles are useful in the treatment and/or prevention of preterm labor, premature birth, dysmenorrhea, inappropriate secretion of vasopressin, congestive heart failure, arterial hypertension, liver cirrhosis, nephrotic syndrome and ocular hypertension. In particular, the present invention is related to triazole derivatives displaying a substantial modulatory, in particular antagonistic activity, of the oxytocin and/or vasopressin receptor. More preferably, said compounds are useful in the treatment and/or prevention of disease states mediated by oxytocin and/or vasopressin. The present invention is furthermore related to novel triazole derivatives as well as to methods of their preparation.

11 Claims, No Drawings

TRIAZOLES AS OXYTOCIN ANTAGONISTS

FIELD OF THE INVENTION

The present invention is directed to triazole derivatives, in particular for use as medicaments, as well as pharmaceutical formulations containing such triazole derivatives. Said triazole derivatives are useful in the treatment and/or prevention of preterm labor, premature birth, dysmenorrhea, inappropriate, secretion of vasopressin, congestive heart failure, arterial hypertension, liver cirrhosis, nephrotic syndrome and ocular hypertension. Preferably, the triazole derivatives display a modulatory, notably an antagonist activity of the oxytocin and/or vasopressin receptor. More preferably, said compounds are useful in the treatment and/or prevention of disease states mediated by oxytocin and/or vasopressin, including preterm labor, premature birth, inappropriate secretion of vasopressin, congestive heart failure, arterial hypertension, liver cirrhosis, nephrotic syndrome, hypertension and dysmenorrhea.

BACKGROUND OF THE INVENTION

Arginine vasopressin (AVP) and oxytocin (OT) are cyclic nonapeptides whose actions are mediated by activation of specific G protein-coupled receptors currently classified into $V_1$-vascular ($V_1R$), $V_2$-renal ($V_2R$) and $V_3$-pituitary ($V_3R$) AVP receptors, as well as OT receptors (OT-R) (1-2).

Oxytocin (OT) causes the contraction of the uterus of mammals during labor. The corresponding oxytocin receptor belongs to the family of G-protein-coupled receptors and is similar to $V_1$ and $V_2$ vasopressin receptors. OT receptors increase dramatically during the course of pregnancy. The concentration of OT receptors has been shown to correlate with spontaneous uterine activity (3-4). OT-induced contractions of the uterus during labor result in the dilatation of the cervix and eventually in the movement of the foetus through the vaginal canal. In some cases, these contractions occur before the foetus is fully viable, resulting in premature labor. Premature labor and premature birth are undesired as they are major causes of perinatal morbidity. Hence, the management of preterm labor represents a significant problem in the field of obstetrics.

Vasopressin, also called "antidiuretic hormone", is a cyclic nonapeptide hormone that exhibits a series of physiological effects including free water re-absorption, vasoconstriction, cellular proliferation and adrenocorticotrophic hormone (ACTH) secretion. In a healthy organism, vasopressin plays an important role in the homeostasis of fluid osmolality and volume status. However, in several diseases or conditions such as the syndrome of inappropriate secretion of vasopressin, congestive heart failure, arterial hypertension, liver cirrhosis, nephrotic syndrome, dysmenorrhea and ocular hypertension, vasopressin is assumed to play an important role (1, 5).

In recent years, strong evidence has accumulated indicating that the hormone oxytocin plays a major role in initiating labor in mammals, in particular in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterus could be blocked. An oxytocin modulator, e.g. blocker or antagonist would likely be efficacious for treating preterm labor.

A further condition related to oxytocin is dysmenorrhea, which is characterised by pain or discomfort associated with menses. The pain is believed to result from uterine contractions and ischemia, probably mediated by the effect of prostaglandins produced in the secretory endometrium By blocking both the indirect and direct effects of oxytocin on the uterus, an oxytocin antagonist would be a likely candidate for treating dysmenorrhea.

Some agents counteracting the action of oxytocin are currently used in clinical studies (6). Such tocolytic agents (i.e. uterine-relaxin agents) include beta-2-adrenergic agonists, magnesium sulfate and ethanol. The leading beta-2-adrenergic agonist is Ritodrine, which causes a number of cardiovascular and metabolic side effects, including tachycardia, increased renin secretion, hyperglycemia and reactive hypoglycemia in the infant. Further beta-2-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

Atosiban, a peptide OT antagonist, suffers the problem of most peptides: low oral bioavailability resulting from intestinal degradation. Such compounds must be administered parenterally.

The development of non-peptide ligands for peptide hormone receptors is expected to overcome this problem. Small molecule selective oxytocin antagonists have been reported by Merck. In addition to cyclic hexapeptides, Merck suggested indanylpiperidines and tolyl-piperazines as orally deliverable OT antagonists (7). In WO 96/22775 and U.S. Pat. No. 5,756,497, Merck reported benzoxazinylpiperidines or benzoxazinones as OT receptor antagonists.

Specific sulfonamides have been reported to antagonize ocytocin at the ocytocin receptor. Elf Sanofi's EP-A-0469984 and EP-A-0526348 report N-sulfonyl indolines acting as antagonists of the vasopressin and the oxytocin receptors.

SUMMARY OF THE INVENTION

It is an object of the present invention to provide substances which are suitable for the treatment of a variety of diseases, in particular preterm labor, premature birth, dysmenorrhea, inappropriate secretion of vasopressin, congestive heart failure, arterial hypertension, liver cirrhosis, nephrotic syndrome and ocular hypertension.

It is notably an object of the present invention to provide chemical compounds which are able to down-regulate, including to antagonize, the function of OT and/or V1a in disease states in animals, preferably mammals, especially in humans.

It is also an object of the present invention to provide small molecule chemical compounds for the modulation, preferably the down-regulation or antagonization of the oxytocin receptor.

Moreover, it is an object of the present invention to provide methods for preparing said small molecule chemical compounds. It is furthermore an object of the present invention to provide a new category of pharmaceutical formulations for the treatment of preterm labor and dysmenorrhea, and/or diseases mediated by the oxytocin receptor.

It is finally an object of the present invention to provide a method for the treatment and/or prevention of disorders mediated by the oxytocin receptor, like preterm labor, inappropriate secretion of vasopressin, congestive heart failure, arterial hypertension, liver cirrhosis, nephrotic syndrome, dysmenorrhea and ocular hypertension with oxytocin and/or vasopressin antagonists, acting for example by antagonizing the binding of oxytocin and/or vasopressin to their receptor.

In a first aspect, the invention provides compounds of formula I:

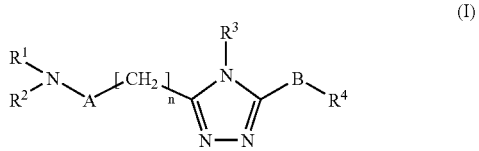

(I)

wherein:

$R^1$ and $R^2$ are independently selected from the group consisting of H, $C_1$-$C_6$-alkyl, aryl $C_1$-$C_6$-alkyl, heteroaryl$C_1$-$C_6$-alkyl, $C_3$-$C_6$-cycloalkyl $C_1$-$C_6$-alkyl and heterocycloalkyl $C_1$-$C_6$-alkyl; or $R^1$ and $R^2$, together with the nitrogen atom they are linked to, form a substituted or unsubstituted 5-8-membered saturated, partially unsaturated or aromatic ring containing optionally one or more additional heteroatoms selected from O, N, S;

A is selected from the group consisting of C(O) and $SO_2$;

$R^3$ is selected from a the group consisting of H, $C_1$-$C_6$-aklyl, aryl $C_1$-$C_6$-alkyl, heteroaryl $C_1$-$C_6$-alkyl, aryl, heteroaryl, $C_3$-$C_6$cycloalkyl $C_1$-$C_6$-alkyl, heterocycloalkyl $C_1$-$C_6$-alkyl, $C_2$-$C_6$-alkenyl;

B is selected from the group consisting of S, O and $NR^5$;

$R^4$ and $R^5$ are independently selected from the group consisting of H, $C_1$-$C_6$-alkyl, aryl $C_1$-$C_6$-alkyl, heteroaryl $C_1$-$C_6$-alkyl, acyl, aryl acyl, heteroaryl acyl $C_3$-$C_6$-cycloalkyl $C_1$-$C_6$-alkyl, heterocycloalkyl $C_1$-$C_6$-alkyl, $C_2$-$C_6$-alkenyl; and n is an integer from 2 to 10;

In a second aspect, the invention provides a compound according to formula I for the treatment of disease.

In a third aspect, the invention provides a compound of formula L for the preparation of a pharmaceutical composition.

In a fourth aspect, the invention provides a compound according to formula I for the modulation of the function of OT and/or V1a receptors.

In a fifth aspect, the invention provides a method of synthesis of a compound according to formula I.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"$C_3$-$C_6$-cycloalkyl" refers to saturated or partially unsaturated carbocyclic rings having 3 to 6 carbon atoms. Examples include cyclopropyl, cyclobutyl, cyclopentyl, cyclohexyl, cyclohexenyl and the like.

"$C_3$-$C_6$-heterocycloalkyl" refers to saturated or partially unsaturated rings having 3 to 6 atoms and containing at least one heterotom selected from N, S and O. Examples include pyrrolidinyl, piperidinyl, piperazinyl, imidazolidinyl, morpholinyl and the like.

"$C_3$-$C_6$cycloalkyl $C_1$-$C_6$-alkyl" refers to $C_1$-$C_6$-alkyl groups having an $C_3$-$C_6$-cycloalkyl substituent, such as, for example methyl-cyclopropane, ethyl-cyclohexane and the like.

"$C_3$-$C_6$-heterocycloalkyl $C_1$-$C_6$-alkyl" refers to $C_1$-$C_6$-alkyl groups having an $C_3$-$C_6$-heterocycloalkyl substituent, such as, for example methyl-pyrrolidine, methyl piperidine, ethyl-tetrahydro-furan and the like.

"Aryl" refers to an unsaturated aromatic carbocyclic group of from 6 to 14 carbon atoms having a single ring (e.g. phenyl) or multiple condensed rings (e.g. naphthyl). Examples of aryl include phenyl, naphthyl, phenanthrenyl and the like.

"aryl $C_1$-$C_6$-alkyl" refers to $C_1$-$C_6$-alkyl groups having an aryl substituent, such as, for example, benzyl, phenethyl and the like.

"Heteroaryl" refers to a monocyclic heteromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"heteroaryl $C_1$-$C_6$-alkyl" refers to $C_1$-$C_6$-alkyl groups having a heteroaryl substituent, such as, for example, 2-furylmethyl, 2-thienylmethyl, 2-(1H-indol-3-yl)ethyl and the like.

"Alkenyl" refers to alkenyl groups preferably having from 2 to 6 carbon atoms and having one or more sites of alkenyl unsaturation. Example of alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having one or more sites of alkynyl unsaturation. Examples of alkynyl groups include ethynyl (—C≡CH), propargyl (—$CH_2$C≡CH), and the like.

"Acyl" refers to the group (O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —R where R includes "$C_1$-$C_6$-alkyl" or "aryl" or "heteroaryl" or "$C_1$-$C_6$-alkyl aryl" or "$C_1$-$C_6$-alkyl heteroaryl". Examples of alkoxy groups include by way of example, methoxy, ethoxy, phenoxy and the like.

"Alkoxycarbonyl" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to a group "—$SO_2$—R" wherein R is selected from H, "$C_1$-$C_6$-alkyl", "$C_1$-$C_6$-alkyl" optionally substituted with halogens, such as, for example, an —$SO_2$—$CF_3$ group, e"aryl", "heteroaryl", "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" optionally substituted with halogens, such as, for example, an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Examples of thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactones, cyclic anhydrides, but also acetals, thioacetals, aminals formed by ring closure for instance in an effort to obtain a protective group.

"Pharmaceutically acceptable salts or complexes" refers to salts or complexes of the identified compounds of Formula I that retain the desired biological activity and are not toxic. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disul-fonic acid, and poly-galacturonic acid. Said compounds can also be administered as pharmaceutically acceptable quaternary salts known by a person skilled in the art, which specifically include the quaternary ammonium salt of the Formula —NR, R',R"+Z−, wherein R, R', R" is independently hydrogen, alkyl, or benzyl, and Z is a counterion, including chloride, bromide, iodide, —O-alkyl, toluenesulfonate, methylsulfonate, sulfonate, phos-phate, or carboxylate (such as benzoate, succinate, acetate, glycolate, maleate, malate, sate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers-to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have an activity as OT-R antagonists.

The term "preterm labor" or the term "premature labor" shall mean expulsion from the uterus of an infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "caesarean delivery" shall mean incision through the abdominal and uterine walls for delivery of a foetus.

The present invention also includes the geometrical isomers, the optical active forms, enantiomers, diastereomers of compounds according to formula L mixtures of these, as well as their racemates and also pharmaceutically acceptable salts.

Preferred $R^1$ and $R^2$ in compounds according to formula I are those that are independently selected from the group consisting of H, methyl, ethyl, propyl and butyl, optionally substituted by substituted or unsubstituted $C_1$-$C_6$-alkoxy, preferably methoxy, substituted or unsubstituted $C_2$-$C_6$-alkenyl, preferably ethenyl, substituted or unsubstituted aryl or heteroaryl, preferably mono- or poly-halogen substituted phenyl, methoxyphenyl, pyrrolidinone, furanyl, benzodioxolyl, substituted or unsubstituted $C_3$-$C_6$-cycloalkyl or 5-6-membered heterocycle, preferably cyclopropyl, tetahydrofuryl and pyrrolidinone.

Preferred $R^3$ in compounds according to formula I are those that are independently selected from the group consisting of H, methyl, ethyl, propyl, butyl optionally substituted by substituted or unsubstituted $C_1$-$C_6$-alkoxy, preferably methoxy, substituted or unsubstituted $C_2$-$C_6$-alkenyl, preferably ethenyl, substituted or unsubstituted aryl or heteroaryl, preferably mono- or poly-halogen substituted phenyl, methoxyphenyl, pyrrolidinone, furanyl, benzodioxolyl, substituted or unsubstituted $C_3$-$C_6$-cycloalkyl or 5-6-membered heterocycle, preferably cyclopropyl, tetahydrofuryl and pyrrolidinone and aryl, optionally substituted by substituted or unsubstituted $C_1$-$C_6$-alkyl, preferably methyl, halogen, substituted or unsubstituted $C_1$-$C_6$-alkoxy, preferably methoxy.

Preferred $R^4$ and $R^5$ in compounds according to formula I are those that are independently selected from the group consisting of H, methyl, ethyl, propyl and butyl, optionally substituted by substituted or unsubstituted $C_1$-$C_6$-alkoxy, preferably methoxyphenyl, substituted or unsubstituted $C_2$-$C_6$-alkenyl, preferably ethenyl, ethenylphenyl, substituted or unsubstituted acyl aryl, preferably, carbonyl aryl, substituted or unsubstituted aryl or heteroaryl, preferably mono- or poly-halogen substituted phenyl, cyanophenyl, methylphenyl, tri-halo-methylphenyl, substituted or unsubstituted $C_3$-$C_6$-cycloalkyl or 5-6-membered heterocycle, preferably cyclohexyl.

A particularly preferred embodiment of the present invention is a triazole derivative according to formula I wherein A is C(O), B is S and n is 2, 3 or 4.

Compounds of formula I may be used for the treatment of a disease.

Specifically, the compounds of formula I are suitable for use in treating disorders such as preterm labor, premature birth, dysmenorrhea, inappropriate secretion of vasopressin, congestive heart failure, arterial hypertension, liver cirrhosis, nephrotic syndrome, ocular hypertension and for stopping labor prior to cesarean delivery. The compounds of the present invention are in particular useful for the treatment of preterm labor, premature birth and dysmenorrhea.

Preferably, the compounds according to Formula I alone or in a form of a pharmaceutical composition are suitable for the modulation of oxytocin and/or vasopressin (in particular $V_{1a}$) function(s), thus specifically allowing the treatment and/or prevention of disorders which are mediated by the oxytocin and/or vasopressin receptors. Such modulation preferably involves the inhibition of OT-R function(s), notably by the antagonization of the oxytocin receptor in mammals, and in particular in humans.

Abnormal activity or hyperactivity of the oxytocin and/or vasopressin receptors are frequently involved in various disorders including the above enumerated disorders and disease states. Hence, the compounds according to the invention may be used for the treatment of disorders by modulating OT-R function or pathways. The modulation of the OT-R function or pathways may involve the down-regulation and/or inhibition of the oxytocin receptor. The compounds of the invention may be employed alone or in combination with further pharmaceutical agents, e.g. with a further OT-R modulator.

When employed as pharmaceuticals, the triazole derivatives of the present invention are typically administered in the form of a pharmaceutical composition. Hence, pharmaceutical compositions comprising a compound of Formula I and a pharmaceutically acceptable carrier, diluent or excipient are also within the scope of the present invention. A person skilled in the art is aware of a whole variety of such carriers, diluents or excipients suitable to formulate a pharmaceutical composition.

The compounds of the invention, together with a conventionally employed adjuvant, carrier, diluent or excipient may be formulated as pharmaceutical compositions and unit dosages thereof, and in such form may be employed as solids, such as tablets or filled capsules, or liquids such as solutions, suspensions, emulsions, elixir, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the triazole derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably Formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the triazole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint; methyl salicylate, or orange flavoring.

Injectable compositions are typically based upon injectable sterile saline or phosphate-buffered saline or other injectable carriers known in the art. As above mentioned, the triazole derivatives of Formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of in (8).

The compounds of this invention can also be administered in sustained release forms or from sustained release drug delivery systems. A description of representative sustained release materials can also be found in the incorporated materials in (8).

Still a further object of the present invention is a process for preparing preparing [1,2,4]triazole derivatives according to Formula I.

The triazole derivatives exemplified in this invention may be prepared from readily available or previously described starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Synthesis of Compounds of the Invention:

Generally, the [1,2,4]triazole derivatives according to the general Formula I may be obtained by several processes, using both solution-phase and solid-phase chemistry protocols. Depending on the nature of $R^1$-$R^4$, A, B and n, certain processes will, in some instances, be preferred over others, and it is assumed that the choice of the most suitable process will be known to the practitioner skilled in the art.

Five examples of synthetic pathways for compounds of formula I will be described.

The following abbreviations refer respectively to the definitions below:
ACN (Acetonitrile)
AMEBA (Acid-sensitive Methoxy benzaldehyde)
$CDCl_3$ (deuterated chloroform)
cHex (Cyclohexanes)
DCM (Dichloromethane)
DECP (Diethylcyanophosphonate)
DIC (Diisopropyl carbodiimide)
DMAP (4-Dimethylaminopyridine)
DMF (Dimethylform-amide)
DMSO (Dimethylsulfoxide)
DMSO-$d_6$ (deuterated dimethylsul-foxide)
EDC (1-(3-Dimethyl-amino-propyl)-3-ethylcarbodiimide)
EtOAc (Ethyl acetate)
$Et_2O$ (Diethyl ether)
HOBt (1-Hydroxybenzotriazole)
$K_2CO_3$ (potassium carbonate)
NaH (Sodium hydride)
$NaHCO_3$ (Sodium bicarbonate)
nBuLi (n Butyllithium)
TBTU (O-Benzotriazolyl-N,N,N',N'-tetramethyluronium-tetrafluoroborate)
TEA (Triethyl amine)
TFA (Trifluoro-acetic acid)
THF (Tetrahydrofuran)
$MgSO_4$ (Magnesium sulfate)
PetEther (Petroleum ether)
rt (room temperature).

Protocol I:

A preferred pathway for preparing [1,2,4]triazole derivatives according to the general Formula I, wherein B is a sulphur moiety (Formula Ia), with $R^1$, $R^2$, $R^3$ and $R^4$, A and n being defined as above, consists in the alkylation of the corresponding mercaptotriazole precursor of formula II in presence of an appropriate alkylating agent $R^4X$ (formula m) in which $R^4$ is as defined above and X is a leaving group such as chloro, bromo, iodo, methanesulfonate or p-toluenesulfonate. This alkylation follows solution-phase chemistry protocols well known to those skilled in the art such as shown in Scheme I. The alkylation is conducted in any of a variety of solvents, including methanol, ethanol, 2-methoxyethanol, tetrahydrofuran, N,N-dimethylformamide, dichloromethane and water, depending on the properties of the particular substituents, in the presence of a base, such as a trialkylamine, alkoxide or hydroxide. The alkylation reaction is generally run at a temperature comprised between 0° C. and 125° C., depending on the reactivity of the alkylating agent.

Scheme I:

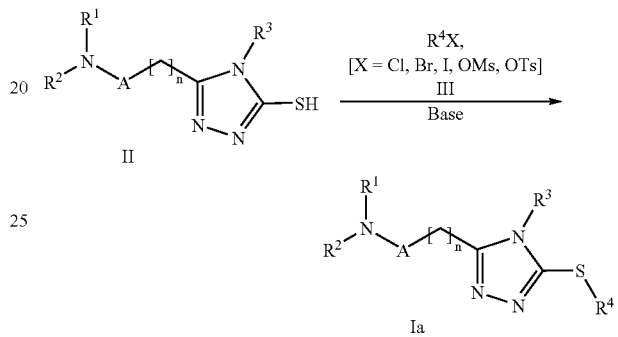

Mercaptotriazole derivatives of Formula II, used for the preparation of triazoles derivatives of compounds of formula Ia according to scheme I can be prepared from an appropriate amine IV, using a variety of synthetic strategies, of which some selected examples are shown in Scheme II (9-14).

Scheme II:

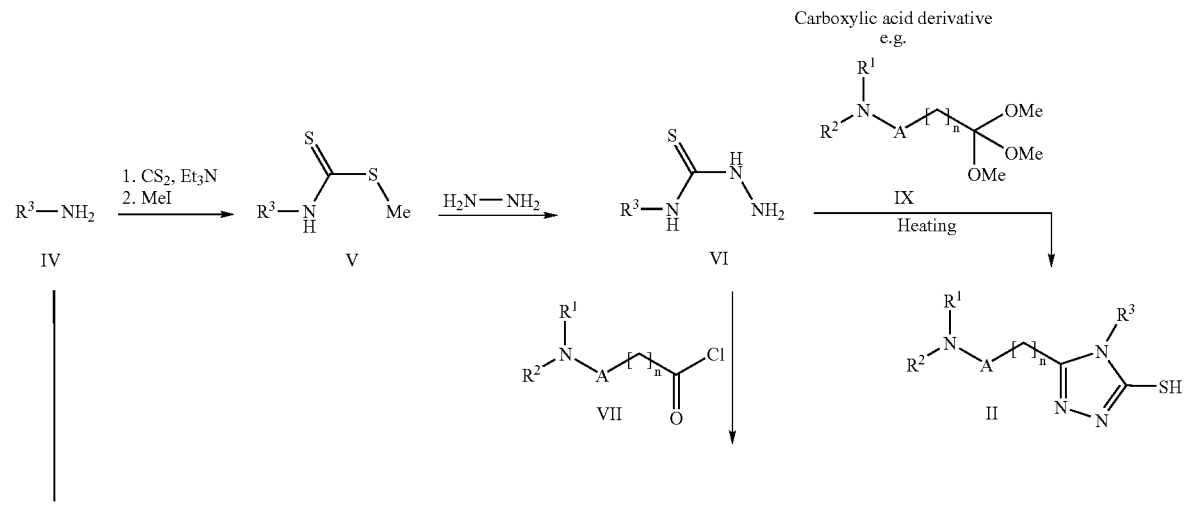

-continued

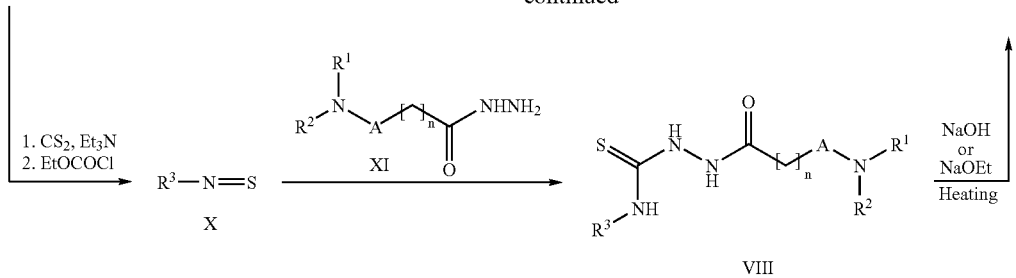

First, an amine of formula IV may be converted to a dithiocarbamate ester of formula V in a one-pot two-step sequence involving treatment with carbon disulfide in the presence of a base such as triethylamine followed by alkylation with methyl iodide. Treatment of a dithiocarbamate ester of formula V with hydrazine affords a 4-substituted thiosemicarbazide of formula VI (scheme II).

Then, reaction of a thiosemicarbazide of formula VI with the appropriate acid chloride of formula VII leads to an acylthiosemicarbazide of formula VIII (scheme II).

Finally, mercaptotriazoles of formula II may be obtained either by direct reaction of the thiosemicarbazide derivative of formula VI with an appropriate acid derivative of formula IX (for example reaction with a trimethyl orthoester at elevated temperature in a suitable solvent, such as 2-methoxyethanol at reflux) or by cylization of an acylthiosemicarbazide of formula VIII in presence of hydroxide or alkoxide (scheme II).

An alternative way of obtaining an acylthiosemicarbazide of formula VIII is first reacting an amine of formula IV following standard reaction conditions widely described in the literature (9-14) to obtain an isothiocyanate of formula X which is then added to an acid hydrazide of formula XI to lead to an acylthiosemicarbazide of formula VIII (scheme II). Acid hydrazides of formula XI can be readily obtained from the corresponding ester which is either commercial or can be prepared from available starting materials according to standard protocols well known to the practitioner skilled in the art.

Derivatives of mecaptotriazoles of formula II can be prepared using known modifications to the Scheme II reaction sequences.

Protocol II:

An another preferred pathway for preparing [1,2,4]triazole derivatives according to the general Formula I wherein, wherein B can be S (formula Ia), NR$^5$ (formula Ib) or O (formula Ic), with R$^1$, R$^2$, R$^3$, R$^4$ and R$^5$, A and n being defined as above, consists in the displacement of a leaving group on the triazole, e.g. chlorotriazole of formula XII or methanesulfonyltriazole of formula XIII. The leaving group on the triazole can be displaced by an appropriate nucleophile of formula respectively XIV, XV or XVI under reaction conditions well known to the person skilled in the art and as described in Scheme III.

For example, S-substituted mercaptotriazoles of formula Ia (general Formula I, wherein B is a Sulphur moiety) can be prepared by addition of a thiol R$^4$SH (formula XIV), wherein R$^4$ is defined as above, on a chlorotriazole of formula XII or a methylsulfonyltriazole XIII in the presence of a base such as N,N-diisopropylethylamine, at elevated temperature (for example, in DMF at reflux).

Aminotriazoles of formula Ib (general Formula I, wherein B is NR$^5$) can be obtained by heating a chlorotriazole of formula XIII or a methanesulfonyltriazole of formula XIII with an amine of formula R$^4$R$^5$NH (XV), where R$^4$ and R$^5$ are defined as above.

Alkoxy and aryloxytriazole of formula Ic (general Formula I, wherein B is Oxygen) can be prepared by heating a chlorotriazole XII or a methanesulfonyltriazole XIII with the appropriate alkoxyde or phenoxide anion R$_4$O$^-$ (formula XVI), where R$_4$ is defined as above.

Scheme III:

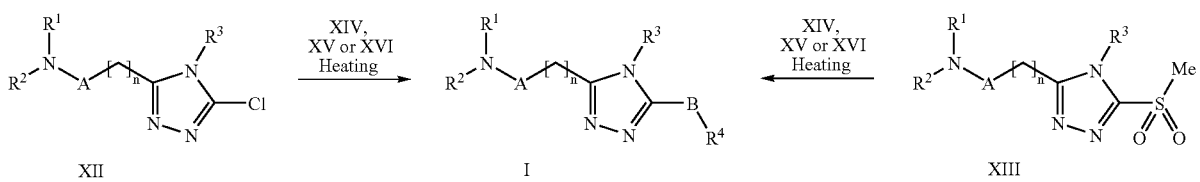

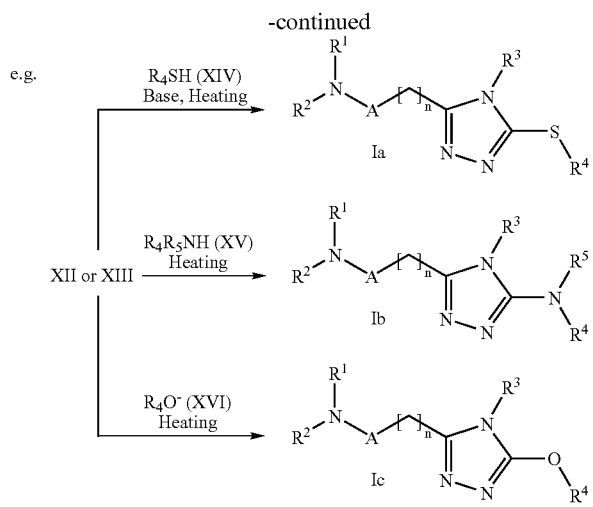

The chlorotriazoles of formula XII used for the preparation of triazoles of formula Ia, Ib or Ic according to scheme III may be prepared by treatment of a mercaptotriazole precursor of formula II with chlorine under anhydrous conditions in a solvent such as chloroform or dichloromethane, as shown in Scheme IV.

The methylsulfonylthiotriazoles of formula XIII used for the preparation of triazoles of formula Ia, Ib or Ic according to scheme III may be prepared by alkylation of the same mercaptotriazole precursor of formula II with methyl iodide to lead to a methylthiotriazole of formula XVII which is then oxidized into the methylsulfunonyltriazole of formula XIII using hydrogen peroxide in acetic acid or similar methods known to the person skilled in the art and as described in Scheme IV.

Scheme IV:

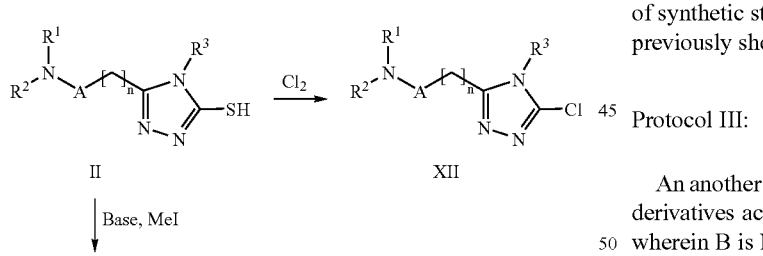

Mercaptotriazole derivatives of Formula II, used for the preparation of chlorotriazoles of formula XII and methylsulfonylthiotriazoles of formula XIII according to scheme IV can be prepared from an appropriate amine IV, using a variety of synthetic strategies, of which some selected examples are previously shown in Scheme II (see protocol I).

Protocol III:

An another preferred pathway for preparing [1,2,4]triazole derivatives according to the formula Id (formula I wherein, wherein B is NR$^5$ and R$^5$=H) can be prepared following the synthetic route described in Scheme V.

Scheme V:

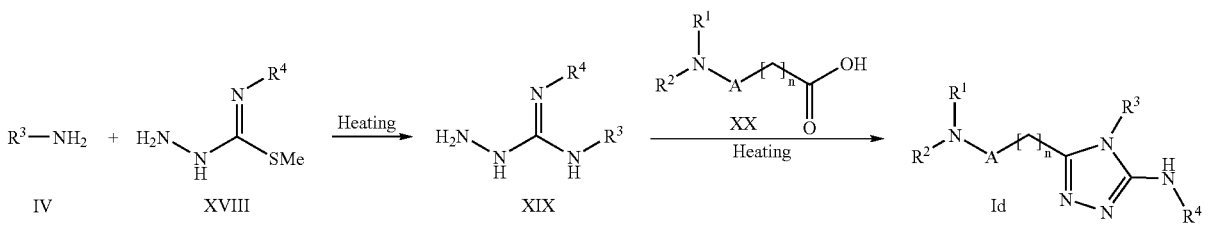

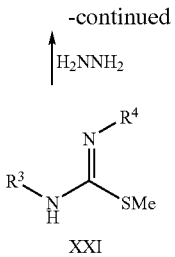

An appropriate amine of formula IV is heated together with a S-methyl thiosemicarbyzide derivative of formula XVIII to give an aminoguanidine of formula XIX. Heating an aminoguanidine of formula XIX with an appropriate carboxylic acid of formula XX provides an aminotriazole of formula Id. Aminoguanidines of formula XIX can be also obtained by an hydrazine treatment of isothioureas of formula XXI.

Protocol IV:

An another preferred pathway for the preparation of [1,2,4]triazole derivatives according to the formula Id (formula I wherein, wherein B is $NR^5$ and $R^5$=H) consists in the condensation of an aminotriazole of structure Ie (formula I wherein, wherein B is $NR^5$ and $R^4$=$R^5$=H) with an aromatic aldehyde under suitable reaction conditions well known to the person skilled in the art. Reduction of the resulting Schiff base of formula XXII with a suitable agent such as sodium borohydride leads the [1,2,4]triazole derivatives according to the formula Id (Scheme VI).

Scheme VI:

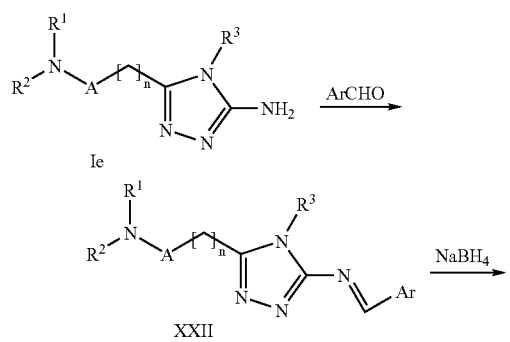

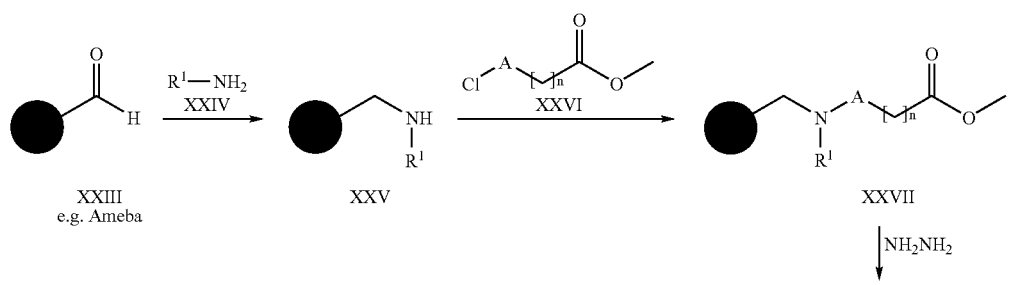

Aminotriazole of formula Ie used to prepare triazoles of formula Id according to the above scheme VI can be prepared by different synthetic routes, including the one described in Scheme V, starting with the suitable S-methyl thiosemicarbazide derivative XVIII with $R^4$=H.

[1,2,4]Triazole derivatives according to the general Formula I, whereby the substituents $R^1$-$R^4$, A, B and n are as above defined, can be prepared using modifications to Schemes I to VI reaction sequences or by other current methods or procedures according to published literature well known to the practitioner skilled in the art (9-14).

Protocol V:

According to yet another preferred process, [1,2,4]triazole derivatives according to the general Formula I, whereby the substituents $R^1$, $R^2$, $R^3$, $R^4$ and $R^5$, A, B and n are as above defined, are prepared by solid-phase and/or mixed solid-/solution-phase synthesis protocols such as, e.g., those described in the Example I and shown in Scheme VII.

It will be appreciated by the practitioner skilled in the art that basically the same conditions, methods and reagents as above described in Schemes I to VI for the sollution-phase synthesis of compounds of Formula I can be applied to the solid-phase and/or mixed solid-/solution-phase synthesis of said compounds.

Scheme VII:

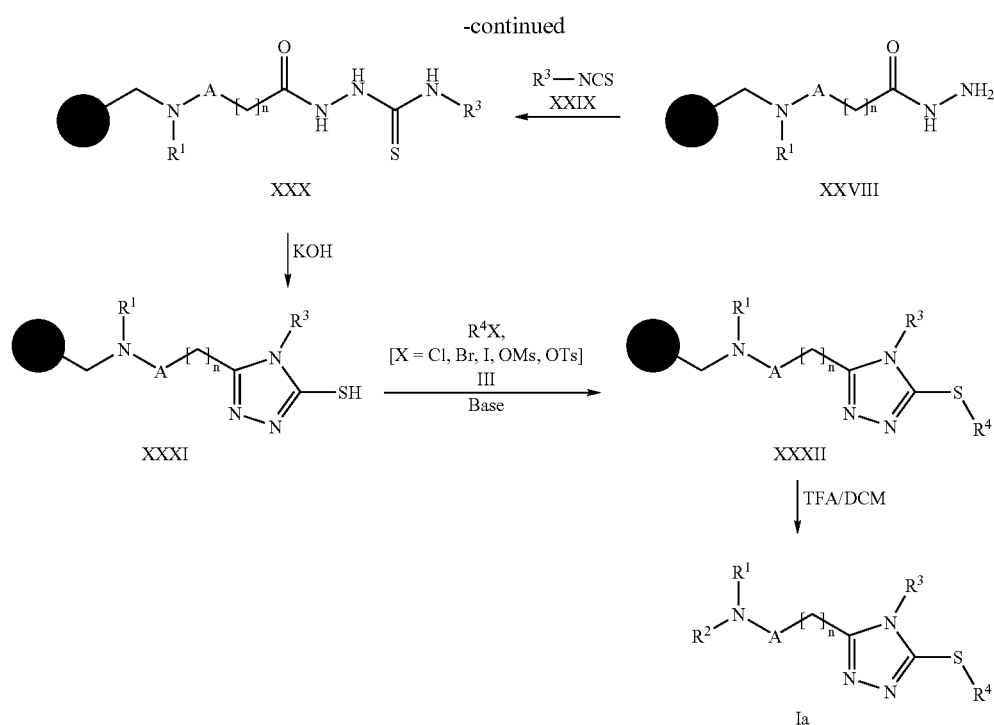

In the context of such a solid-phase and/or mixed solid-/solution-phase synthesis protocol (Protocol V, Scheme VII), the $R^1$ or $R^2$-groups of compounds II, VII-IX, XI-XIII, XVII, XX and XXII shown in Schemes I-VI, are found on a suitable resin comprising the appropriate cleavable linker. The circles within the Scheme VII illustrate the resin beads to which the corresponding compounds are linked during the solid phase synthesis. It is to be understood that further to the mentioned resin types, other suitable reagents, notably resins, known to a person skilled in the art, could be employed for the solid-phase synthesis of compounds of general Formula I.

Thus, in one preferred scenario, an amino-derivatised resin of formula XXV is obtained by coupling of an appropriate amine of formula XXV with a suitable resin carrying an aldehyde moiety (e.g., AMEBA II (15) or ArgoGel-CHO resin) of formula XXIII, using standard reductive amination conditions well known to the practitioner skilled in the art (15).

According to the methods outlined in Scheme VII and described hereinafter in the Examples I, this intermediate of formula XXV can then be reacted with an acyl or sulfonyl chloride of formula XXVI containing an ester moiety, in the presence of a base, (e.g., N-ethyldiisopropylamine) to lead to a compound of formula XXVII.

Then, addition of an excess of hydrazine to a compound of formula XXVII at 50° C. leads to the corresponding acid hydrazide of formula XXVIII. This acid hydrazide of formula XXVIII is then converted into semicarbazide corresponding to a structure of formula XXX by addition of a isothiocyanate of formula XXIX at room temperature.

The semicarbazide of formula XXX is then cyclised into a triazole derivative of formula XXXI under basic conditions (e.g., 0.3 M KOH), at elevated temperature, such as 65° C. The resulting cyclized derivative of formula XXXI can be further functionalized in the presence of a base (e.g. N-ethyldiisopropylamine) by an appropriate alkylating agent $R^4X$ of formula IIII wherein $R^4$ is defined as above and "X" is a leaving group such as chloro, bromo, iodo, methanesulfonate or p-toluenesulfonate. The resulting product of formula XXXII can be cleaved from the resin under acidic conditions (e.g. in a TFA/DCM solution), affording the corresponding [1,2,4]triazole of formula Ia (formula I wherein B is a Sulphur moiety) as described hereinafter in the Example I.

Amines of formula XV used according to scheme VII are either commercial, e.g., 1-(3-amino-propyl)-pyrrolidin-2-one, cyclopropyl-methylamine, phenethylamine, furan-2-yl-methylamine, 2-methoxy-ethylamine, butylamine, 3-methoxy-propylamine, benzo[1,3]dioxol-5-yl-methylamine, propylamine, 4-fluoro-benzylamine, (tetrahydrofuran-2-yl)-methylamine, 2-methoxy-benzylamine, 4-methoxy-benzylamine, benzylamine, isobutylamine, allylamine, or can be prepared from readily available starting material according published literature procedures and methods well known to the practioner skilled in the art.

Compounds of formula XXVI may also be either commercial, e.g., methyl 3-(chloroformyl)-propionate, methyl 4-(chloroformyl)-butyrate, methyl 5-(chloroformyl)-pentanoate, or can be prepared from readily available starting material according published literature procedures and current methods well known to the practioner skilled in the art.

Isothiocyanates of formula XXI are either commercial, e.g., 1-isothiocyanato-3-methyl-benzene, 1-chloro-4-isothiocyanato-benzene, 1-isothiocyanato-4-methyl-benzene, 2-isothiocyanatomethyl-tetrahydro-furan, (2-isothiocyanato-ethyl)-benzene, 1-isothiocyanato-methyl-4-methyl-benzene, 3-isothiocyanato-propene, isothiocyanato-methane, 1-isothiocyanato-2-methyl-propane, 1-fluoro-4-isothiocyanato-benzene, isothio-cyanato-methyl-benzene, isothiocyanato-benzene, 1-chloro-3-isothiocyanato-benzene, 1-isothio-cyanato-3-methoxy-propane, 1-isothiocyanato-3-methoxy-benzene, or can be prepared from readily available starting material according published literature procedures and methods well known to the practioner skilled in the art.

Alkylating agent $R^4X$ of formula III are either commercial, e.g., benzylbromide, (3-bromo-propenyl)-benzene, allylbromide, bromomethyl-cyclohexane, 1-bromomethyl-3-methyl-benzene, 1-bromomethyl-4-fluoro-benzene, 1-bromomethyl-3,5-dimethyl-benzene, 1-bromomethyl-3-fluoro-benzene, 1-bromomethyl-4-trifluoromethyl-benzene, (2-bromo-ethoxy)-benzene, bromoethane, 1-bromo-2-methoxy-ethane, 1-bromomethyl-4-methyl-benzene, 2-bromomethyl-tetrahydro-pyran, 2-bromo-1-phenyl-ethanone, bromo-acetic acid ethyl ester, 1-bromomethyl-2,3,4,5,6-pentafluoro-benzene, (2-bromo-ethyl)-benzene, 1-bromomethyl-2-methyl-benzene, 1-bromomethyl-2-fluoro-benzene, 1-bromomethyl-3-chloro-benzene, 1-bromomethyl-2-chloro-4-fluoro-benzene, 3-bromomethyl-benzonitile, 1-bromo-butane, or can be prepared from readily available starting material according published literature procedures and current methods well known to the practioner skilled in the art.

The reaction sequences outlined in the above Schemes (I to VI) provide enantiomerically pure compounds of general Formula I, if enantiomerically pure starting materials are used. (R) as well as (S) enantiomers can be obtained depending upon whether (R) or (S) forms of commercially available starting materials are used.

According to a further general process, compounds of Formula I can be converted to alternative compounds of Formula I, employing suitable interconversion techniques.

If the above set out general synthetic methods are not applicable for obtaining compounds according to Formula I and/or necessary intermediates for the synthesis of compounds of Formula I, suitable methods of preparation known by a person skilled on the art should be used. In general, the synthesis pathways for any individual compound of Formula I will depend on the specific substitutents of each molecule and upon the ready availability of intermediates necessary; again such factors being appreciated by those of ordinary skill in the art. For all the protection, de-protection methods, see (16) and (17).

Compounds of this invention can be isolated in association with solvent molecules by crystallization. The pharmaceutically acceptable acid addition salts of the compounds of Formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula I with a suitable base. Both types of salt may be formed or interconverted using ion-exchange resin techniques.

EXAMPLES

The invention will be illustrated by means of the following examples which are not to be construed as limiting the scope of the invention.

The compounds of the present invention may be synthesized according to the different synthesis pathways provided above. The following examples illustrate preferred methods for synthesizing the compounds according to formula I and determining their activities.

Example 1

3-[5-[(3-chlorobenzyl)sulfanyl]-4-(3-methoxyphenyl)-4H-1,2,4-triazol-3-yl]-N-(2-methoxybenzyl) propanamide (1) (Compound of Formula Ia) See Protocol V, Scheme VII

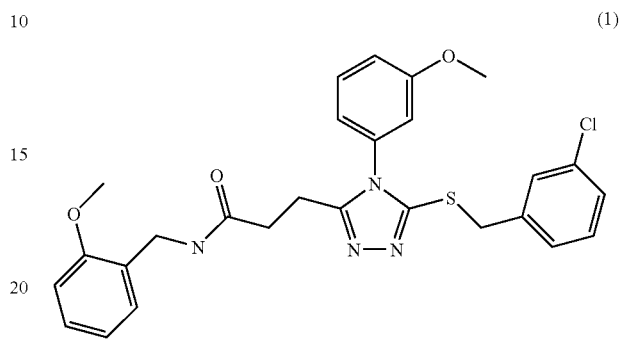

(1)

Protocol V:

Step 1: Reductive Amination (Compound of Formula XXV):

In a round bottomed flask, fitted with stirrer and nitrogen inlet, was suspended AMEBA II (15) resin of formula XXIII (50 g, 0.048 mol, 0.96 mmol/g), in mixture 9:1 of THF/TMOF (500 mL). Primary amine (compound of formula XXIV), e.g. 2-methyoxy benzylamine (0.072 mol, 7.9 mL, 1.5 eq), followed by acetic acid (2.75 mL, 1.5 eq) were sequentially added. The resulting mixture was stirred for 1 hour (imine formation). Sodium triacetoxyborohydride (15.25 g, 0.072 mol, 1.5 eq) was added to the flask and the reaction stirred overnight at room temperature under nitrogen. The excess of hydride was neutralized with a 2 N NaOH solution (20 mL). The resin was recovered on a sintered funnel and was washed sequentially with DMF (250 mL), water (250 mL), DMF (250 mL), water (250 mL), acetone (250 mL), methanol (250 mL), acetone (250 mL) and methanol (250 nm). The resin was first dried by flusing air for 1 hour, then in vacuo at 60° C.

Step 2: Reaction of the Resin with an Acylor Sulfonyl Chloride (Compound of Formula XXVII The resulting Amino-derivatised AMEBA II resin of formula XXV obtained from Step 1 (0.75 mmol/g of resin), was suspended in dichloromethane (10 mL/g of resin) in a round bottomed flask. An acid chloride or sulfonyl chloride of formula XXVI (3 eq), e.g. methyl 3-(chloroformyl)-propionate, was added, followed by N-ethyldiisopropylamine (3 eq). The reaction mixture was shaken at room temperature for 18 hours. The resin was filtered and washed sequentially with DCM, DMF, DCM and MeOH before being dried in vacuo.

Step 3: Hydrazine Addition (Compound of Formula XXVIII):

Ester derivatised AMEBA II resin of formula XXVII obtained from Step 2 (~0.7 mmol/g), was put into a round bottomed flask with a magnetic stirrer. To the flask was added N,N-dimethylformamide (5 mL/g of resin), hydrazine hydrate (5 mL/g of resin). A water condenser was fitted and the reaction was stirred slowly at 50° C. for 18 hours. The reaction was allowed to cool to room temperature, filtered and the resin washed five times with water and the waste disposed of accordingly. The resin was then washed sequentially with DMF, DCM and MeOH before being dried in vacuo.

Step 4: Isocyanate Addition (Compound of Formula XXX):

The resin linked to the resulting acid hydrazide of formula XXVIII and recovered from above Step 3 (1.5 g, ~0.7 mmol/g), was weighed into boiling tubes. Standard solutions of the isothiocyanates of formula XXIX, e.g. 1-isothiocyanate-3-methoxy-benzene, were made up (0.42 M in anhydrous ml). These standard solutions (25 mL, 10.5 mmol, 10 eq) were then added to the boiling tubes, which were sealed with a pressure releasing septum. The tubes were shaken at room temperature for 66 hours. The resin of each tube was filtered and washed with 2×DMF and the waste disposed of accordingly. The resin was then washed sequentially with DCM and MeOH before being dried in vacuo.

Step 5: Cyclization (Compound of Formula XXXI):

The resins resulting from the previous Step 4 and of formula X, were transferred to a clean boiling tube and a 3:2 mixture of 1,4-dioxane and 0.3M KOH (20 mL) was added. The tubes were heated to 65° C. and shaken for 18 hours. The reactions were allowed to cool to room temperature. The resin was washed with 3× water, 2×MeOH, 2×DCM and 2×MeOH before being dried in vacuo.

Step 6: Alkylation (Compound of Formula XXXII:

The resin-bound compound of formula XXXI obtained from Step 5, was transferred into a 96-well filter-plate (approximatively 50 mg of dry resin/well) and each well treated with 1 ml of alkyl bromide (formula III) solution (0.21 mmol/ml of 1,4-dioxane), e.g. 1-Bromomethyl-3-chloro-benzene. N-ethyldiisoprpylamine (50 μl) was added to each well, the plate sealed and shaken at room temperature for 18 hours. The resin was filtered and washed with 2×DMF and the waste disposed of accordingly. The resin was then washed sequentially with DMF, DCM, MeOH and finally DCM before being dried in vacuo.

Step 7: Cleavageform the Resin (Compound of Formula Ia):

A standard solution of 60% TFA/DCM was prepared. This solution (3×0.5 ml) was dripped through each well of the filter plate containing the resin-bound compound of formula XXXII obtained from Step 6, collecting in a 2 ml plate. The solvents were evaporated. This procedure was repeated once (3×0.5 ml of 60% TFA/DCM solution) and the solvents were removed in vacuo. Dry THF (0.5 mL) and MeOH (0.5 mL) were finally dripped through and the solvent removed in vacuo. The final compound (formula Ia) obtained after purification by two successive flash chromatography processes (first column using 100% ethyl acetate progressing to 5% methanol/ethyl acetate as eluent; second column performed with a mixture 50% hexane/ethyl acetate progressing to 100% ethyl acetate over 1 hour as eluent) is 3-[5-[(3-chlorobenzyl)sulfanyl]-4-(3-methoxyphenyl)-4H 1,2,4-triazol-3-yl]-N-(2-methoxybenzyl)propanamide (1) ($^1$H NMR (400 MHz, CDCl$_3$): 2.5 (m, 2H), 2.6 (m, 2H), 3.6 (s, 3H), 3.7 (s, 3H), 4.1-4.3 (m, 4H), 5.3 (m, 1H), 5.4 (m, 2H), 5.7 (m, 2H), 5.8 (m, 1H), 6.9-7.1 (m, 6H), 7.2 (m, 1H). M$^+$(ESI$^+$): 523).

The below listed compounds in Table 2 (designated by example numbers) were prepared in a similar way by following the general method as outlined in Example 1 and using the corresponding starting amines (Table 1).

TABLE 1

| Chemical Structure | FMWT |
|---|---|
| H$_2$N-CH$_2$CH$_2$CH$_2$-N-pyrrolidinone | 142.20 |
| cyclopropyl-CH$_2$-NH$_2$ | 71.12 |
| phenyl-CH$_2$CH$_2$-NH$_2$ | 121.18 |
| furan-2-yl-CH$_2$-NH$_2$ | 97.12 |
| H$_2$N-CH$_2$CH$_2$-O-CH$_3$ | 75.11 |
| H$_3$C-CH$_2$CH$_2$CH$_2$-NH$_2$ | 73.14 |
| H$_3$C-O-CH$_2$CH$_2$CH$_2$CH$_2$-NH$_2$ | 89.14 |
| benzo[1,3]dioxol-5-yl-CH$_2$-NH$_2$ | 151.17 |
| H$_3$C-CH$_2$-NH$_2$ | 59.11 |
| 4-F-phenyl-CH$_2$-NH$_2$ | 125.15 |
| H$_2$N-CH$_2$-tetrahydrofuran-2-yl | 101.15 |
| 2-methoxyphenyl-CH$_2$-NH$_2$ | 137.18 |

TABLE 1-continued

| Chemical Structure | FMWT |
|---|---|
| 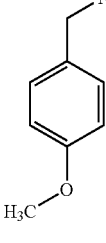 | 137.18 |
| 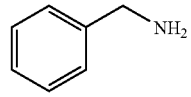 | 107.16 |

TABLE 1-continued

| Chemical Structure | FMWT |
|---|---|
| 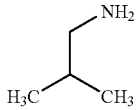 | 73.14 |
| 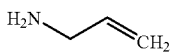 | 57.10 |

TABLE 2

| Example No. | Chemical Structure | M.W. | IUPAC-Name | M+(ESI+) |
|---|---|---|---|---|
| 2 | 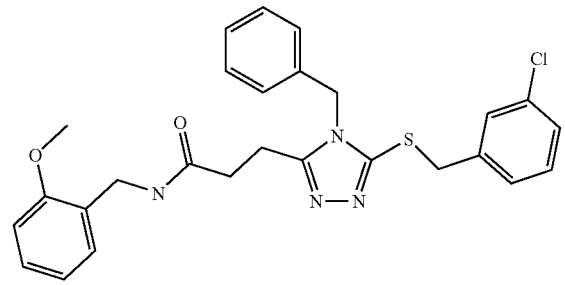 | 507.06 | 2-{4-benzyl-5-[(3-chlorobenzyl)sulfanyl]-4H-1,2,4-triazol-3-yl}-N-(2-methylbenzyl)propanamide | 507 |
| 3 | 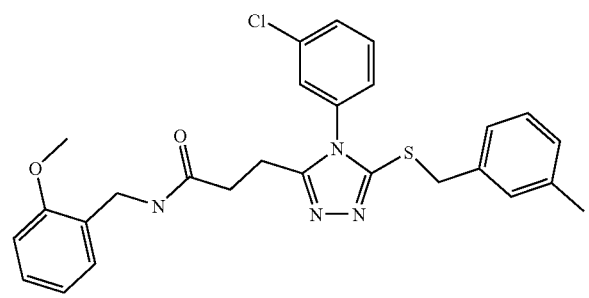 | 507.06 | 3-{4-(3-chlorophenyl)-5-[(3-methylbenzyl)sulfanyl]-4H-1,2,4-triazol-3-yl}-N-(2-methoxybenzyl)propanamide | 507 |
| 4 | 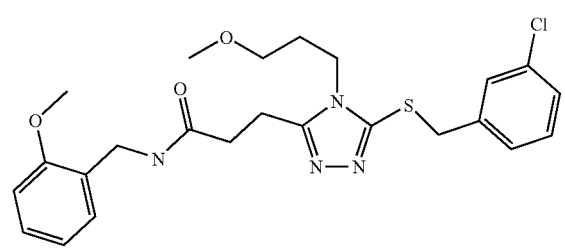 | 489.04 | 3-[5-[(3-chlorobenzyl)sulfanyl]-4-(3-methoxypropyl)-4H-1,2,4-triazol-3-yl]-N-(2-methoxybenzyl)propanamide | 489 |

TABLE 2-continued

| Example No. | Chemical Structure | M.W. | IUPAC-Name | M⁺(ESI⁺) |
|---|---|---|---|---|
| 5 | 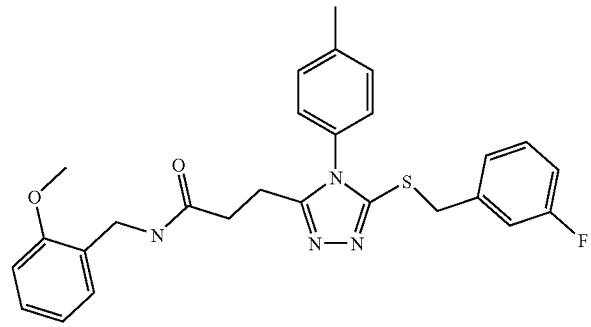 | 490.60 | 3-[5-[(3-fluorobenzyl)sulfanyl]-4-(4-methylphenyl)-4H-1,2,4-triazol-3-yl]-N-(2-methoxybenzyl)propanamide | 491 |
| 6 | 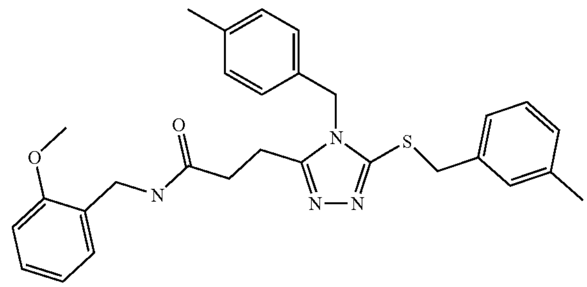 | 500.66 | N-(2-methoxybenzyl)-3-{4-(4-methylbenzyl)-5-[3-methylbenzyl)sulfanyl]-4H-1,2,4-triazol-3-yl}propanamide | 501 |
| 7 | 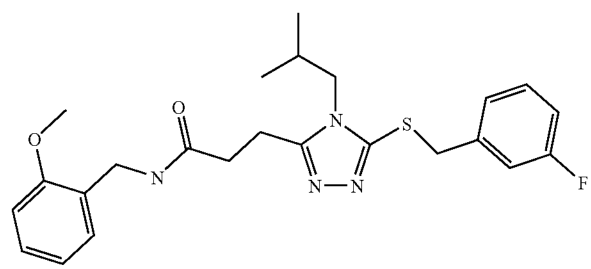 | 456.58 | 3-{5-[(3-fluorobenzyl)sulfanyl]-4-isobutyl-4H-1,2,4-triazol-3-yl}-N-(2-methoxybenzyl)propanamide | 457 |
| 8 | 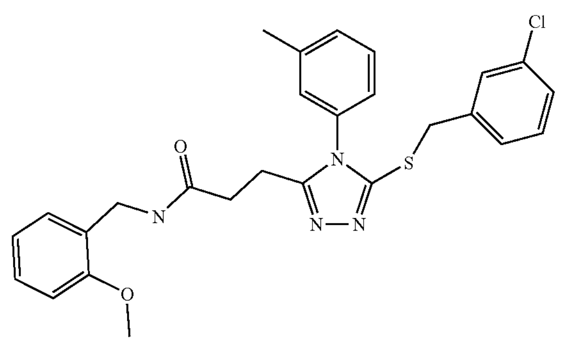 | 507.06 | 3-[5-[(3-chlorobenzyl)sulfanyl]-4-(3-methylphenyl)-4H-1,2,4-triazol-3-yl]-N-(2-methoxybenzyl)propanamide | 507 |
| 9 | 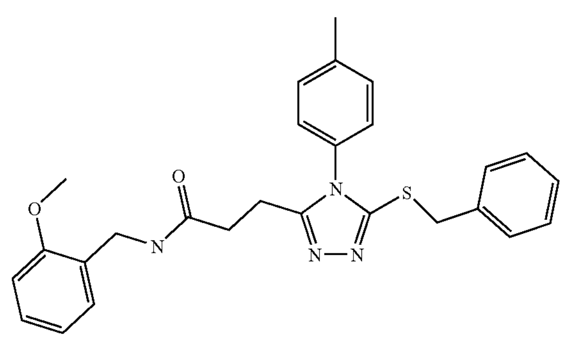 | 472.61 | 3-[5-(benzylsulfanyl)-4-(4-methylphenyl)-4H-1,2,4-triazol-3-yl]-N-(2-methoxybenzyl)propanamide | 473 |

TABLE 2-continued

| Example No. | Chemical Structure | M.W. | IUPAC-Name | M+(ESI+) |
|---|---|---|---|---|
| 10 | 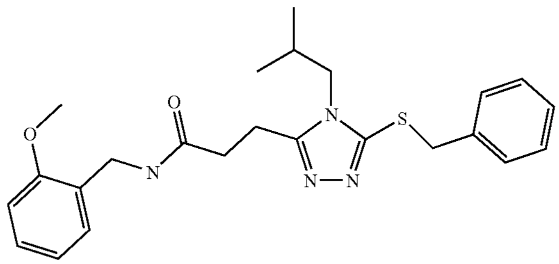 | 438.59 | 3-[5-(benzylsulfanyl)-4-isobutyl-4H-1,2,4-triazol-3-yl]-N-(2-methoxybenzyl)propanamide | 439 |
| 11 | 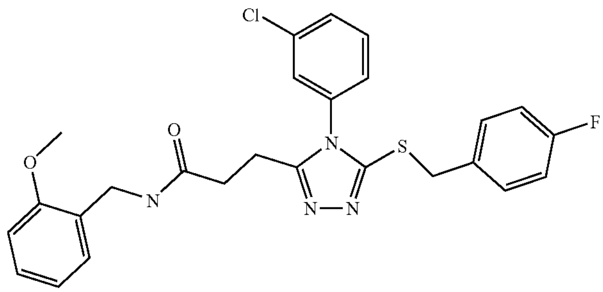 | 511.02 | 3-{4-(3-chlorophenyl)-5-[(4-fluorobenzyl)sulfanyl]-4H-1,2,4-triazol-3-yl}-N-(2-methoxybenzyl)propanamide | 511 |
| 12 | 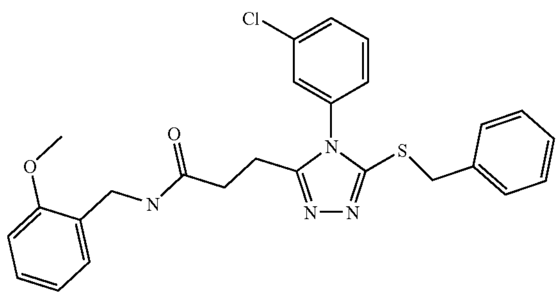 | 493.03 | 3-[5-(benzylsulfanyl)-4-(3-chlorophenyl)-4H-1,2,4-triazol-3-yl]-N-(2-methoxybenzyl)propanamide | 493 |
| 13 | 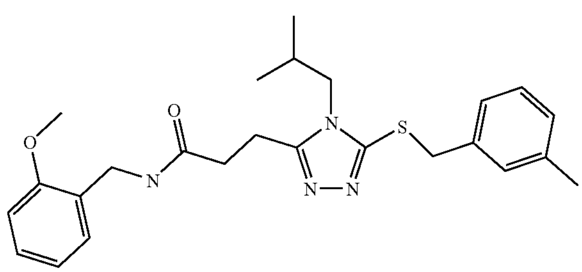 | 452.62 | 3-{4-isobutyl-5-[(3-methylbenzyl)sulfanyl]-4H-1,2,4-triazol-3-yl}-N-(2-methoxybenzyl)propanamide | 453 |
| 14 | 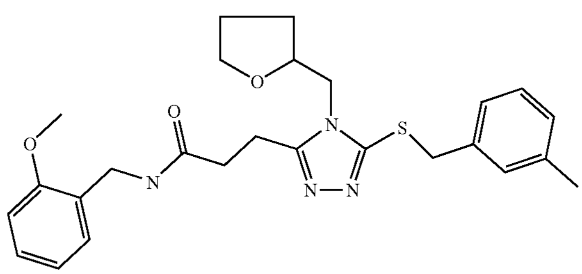 | 480.63 | N-(2-methoxybenzyl)-3-[5-[(3-methylbenzyl)sulfanyl]-4-(tetrahydro-2-furanylmethyl)-4H-1,2,4-triazol-3-yl]propanamide | 481 |

TABLE 2-continued

| Example No. | Chemical Structure | M.W. | IUPAC-Name | M+(ESI+) |
|---|---|---|---|---|
| 15 | 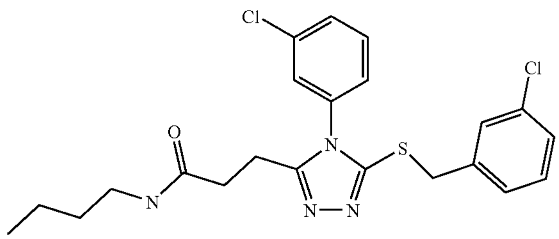 | 463.43 | N-butyl-3-[5-[(3-chlorobenzyl)sulfanyl]-4-(3-chlorophenyl)-4H-1,2,4-triazol-3-yl]propanamide | 463 |
| 16 | 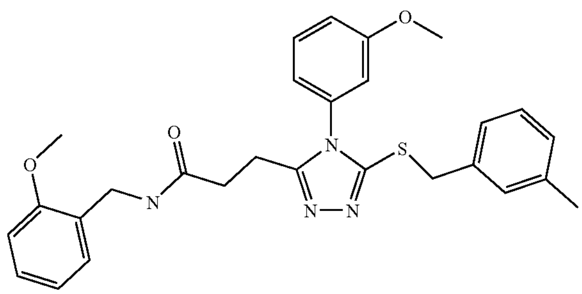 | 502.64 | N-(2-methoxybenzyl)-3-{4-(3-methoxyphenyl)-5-[(3-methylbenzyl)sulfanyl]-4H-1,2,4-triazol-3-yl}propanamide | 503 |
| 17 | 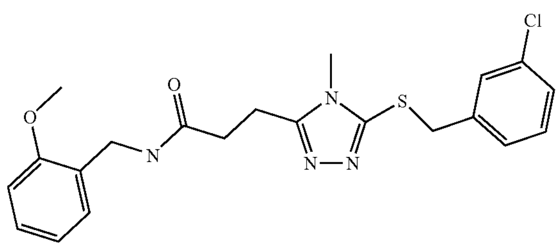 | 430.96 | 3-{5-[(3-chlorobenzyl)sulfanyl]-4-methyl-4H-1,2,4-triazol-3-yl}-N-(2-methoxybenzyl)propanamide | 431 |
| 18 | 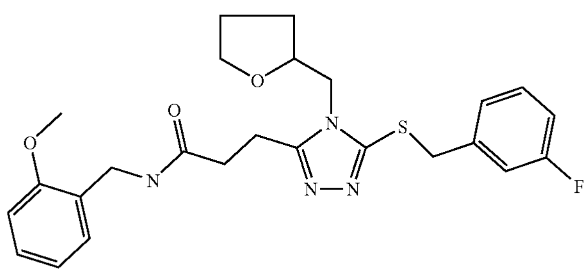 | 484.59 | 3-[5-[(3-fluorobenzyl)sulfanyl]-4-(tetrahydro-2-furanylmethyl)-4H-1,2,4-triazol-3-yl]-N-(2-methoxybenzyl)propanamide | 485 |
| 19 | 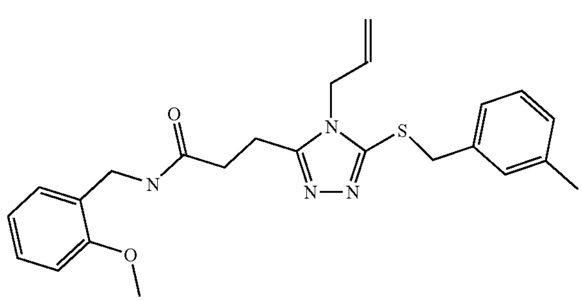 | 436.58 | 3-{4-allyl-5-[(3-methylbenzyl)sulfanyl]-4H-1,2,4-triazol-3-yl}-N-(2-methoxybenzyl)propanamide | 437 |

TABLE 2-continued

| Example No. | Chemical Structure | M.W. | IUPAC-Name | M⁺(ESI⁺) |
|---|---|---|---|---|
| 20 | 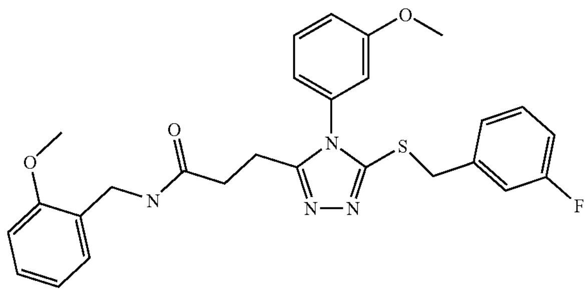 | 506.60 | 3-[5-[(3-fluorobenzyl)sulfanyl]-4-(3-methoxyphenyl)-4H-1,2,4-triazol-3-yl]-N-(2-methoxybenzyl)propanamide | 507 |
| 21 | 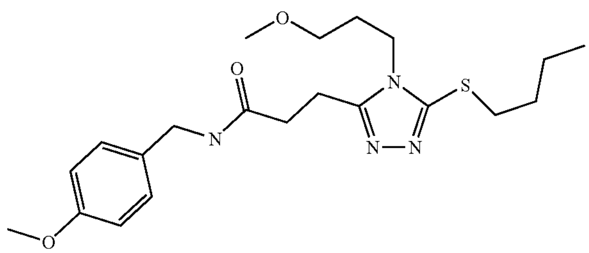 | 420.58 | 3-[5-(butylsulfanyl)-4-(3-methoxypropyl)-4H-1,2,4-triazol-3-yl]-N-(4-methoxybenzyl)propanamide | 421 |
| 22 | 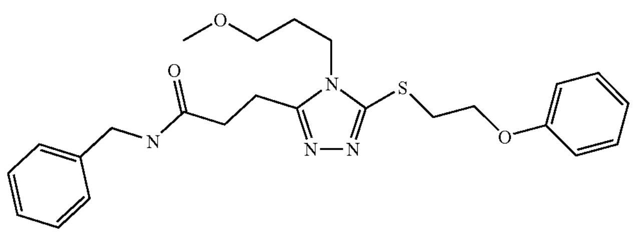 | 454.59 | N-benzyl-3-{4-(3-methoxypropyl)-5-[(2-phenoxyethyl)sulfanyl]-4H-1,2,4-triazol-3-yl}propanamide | 455 |
| 23 | 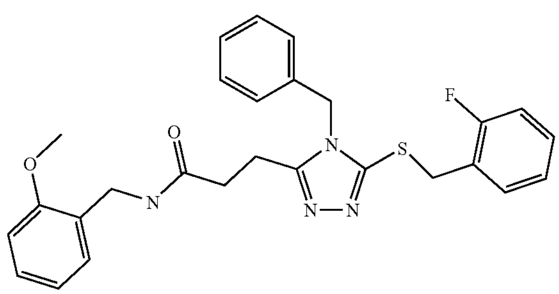 | 490.60 | 3-{4-benzyl-5-[(2-fluorobenzyl)sulfanyl]-4H-1,2,4-triazol-3-yl)-N-(2-methoxybenzyl)propanamide | 491 |
| 24 | 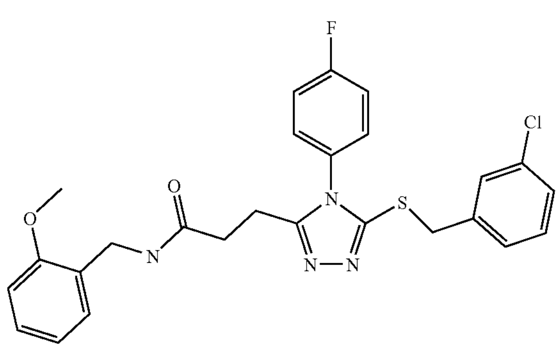 | 511.02 | 3-[5-[(3-chlorobenzyl)sulfanyl]-4-(4-fluorophenyl)-4H-1,2,4-triazol-3-yl]-N-(2-methoxybenzyl)propanamide | 511 |

TABLE 2-continued

| Example No. | Chemical Structure | M.W. | IUPAC-Name | M+(ESI+) |
|---|---|---|---|---|
| 25 | 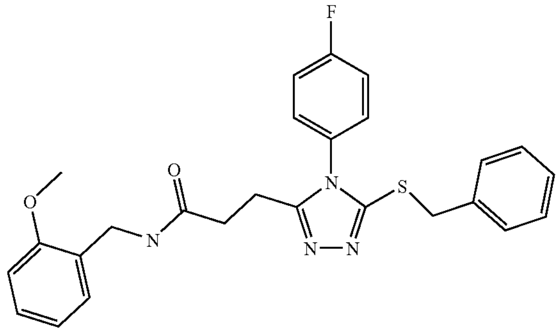 | 476.57 | 3-[5-(benzylsulfanyl}-4-(4-fluorophenyl)-4H-1,2,4-triazol-3-yl]-N-(2-methoxybenzyl)propanamide | 477 |
| 26 | 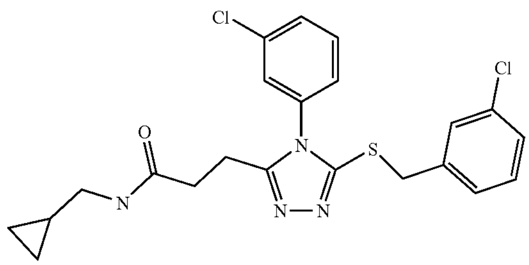 | 461.41 | 3-[5-[(3-chlorophenyl)-4H-1,2,4-(3-chlorophenyl)-4H-1,2,4-triazol-3-yl]-N-(cyclopropylmethyl)propanamide | 461 |
| 27 | 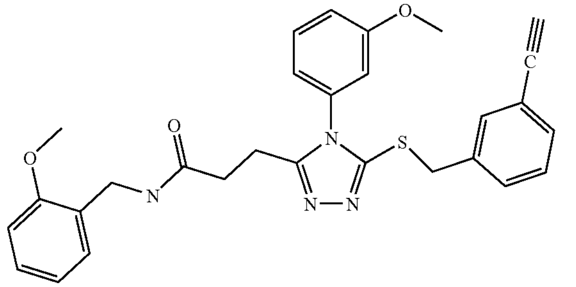 | 513.62 | 3-[5-[(3-cyanobenzyl)sulfanyl]-4-(3-methoxyphenyl)-4H-1,2,4-triazol-3-yl]-N-(2-methoxybenzyl)propanamide | 514 |
| 28 | 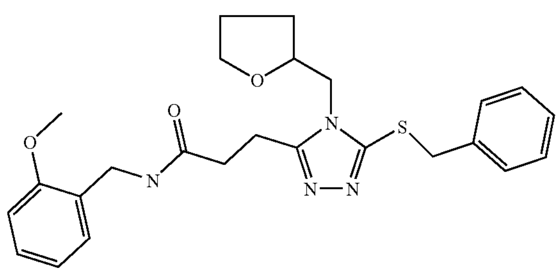 | 466.60 | 3-[5-(benzylsulfanyl)-4-(tetrahydro-2-furanylmethyl)-4H-1,2,4-triazol-3-yl]-N-(2-methoxybenzyl)propanamide | 467 |
| 29 | 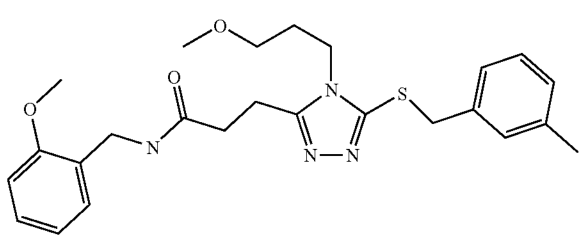 | 468.62 | N-(2-methoxybenzyl)-3-{4-(3-methoxypropyl)-5-[(3-methylbenzyl)sulfanyl]-4H-1,2,4-triazol-3-yl}propanamide | 469 |

TABLE 2-continued

| Example No. | Chemical Structure | M.W. | IUPAC-Name | M+(ESI+) |
|---|---|---|---|---|
| 30 | 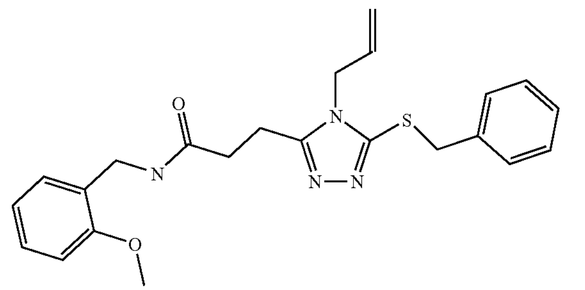 | 422.55 | 3-[4-allyl-5-(benzylsulfanyl)-4H-1,2,4-triazol-3-yl]-N-(2-methoxybenzyl)propanamide | 423 |
| 31 | 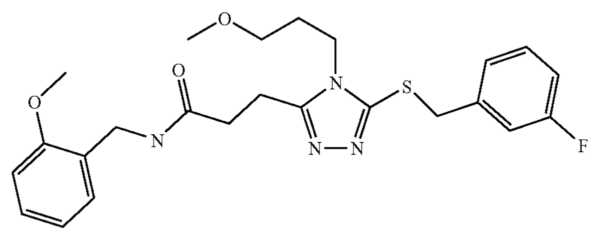 | 472.58 | 3-[5-[(3-fluorobenzyl)sulfanyl]-4-(3-methoxypropyl)-4H-1,2,4-triazol-3-yl]-N-(2-methoxybenzyl)propanamide | 473 |
| 32 | 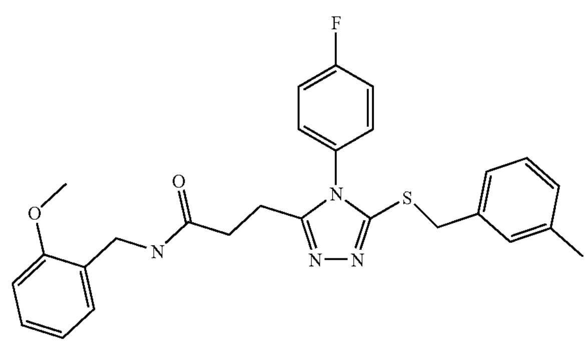 | 490.60 | 3-{4-(4-fluorophenyl)-5-[(3-methylbenzyl)sulfanyl]-4H-1,2,4-triazol-3-yl}-N-(2-methoxybenzyl)propanamide | 491 |
| 33 | 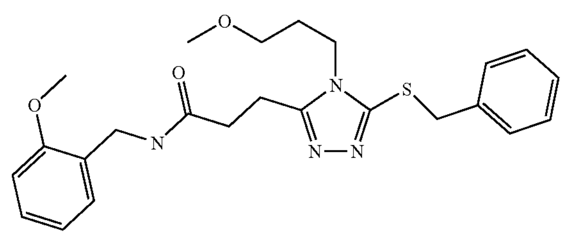 | 454.59 | 3-[5-(benzylsulfanyl)-4-(3-methoxypropyl)-4H-1,2,4-triazol-3-yl]-N-(2-methoxybenzyl)propanamide | 455 |
| 34 | 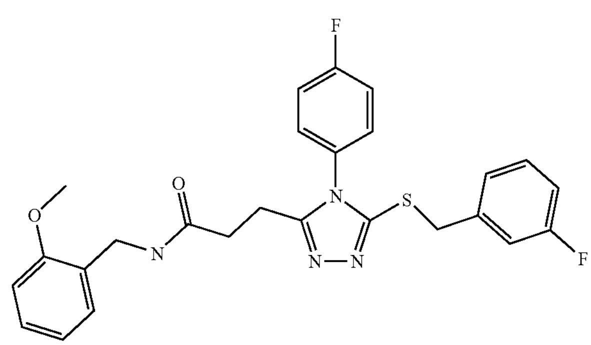 | 494.57 | 3-[5-[(3-fluorobenzyl)sulfanyl]-4-(4-fluorophenyl)-4H-1,2,4-triazol-3-yl]-N-(2-methoxybenzyl)propanamide | 495 |

TABLE 2-continued

| Example No. | Chemical Structure | M.W. | IUPAC-Name | M⁺(ESI⁺) |
|---|---|---|---|---|
| 35 | 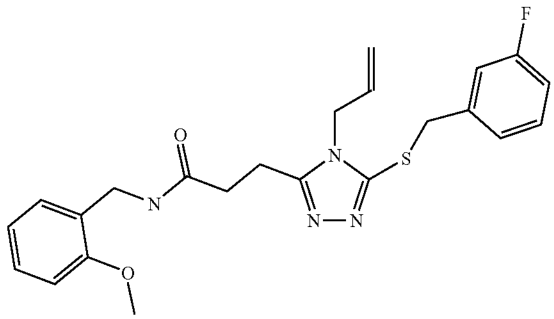 | 440.54 | 3-{4-allyl-5-[(3-fluorobenzyl)sulfanyl]-4H-1,2,4-triazol-3-yl}-N-(2-methoxybenzyl)propanamide | 441 |
| 36 | 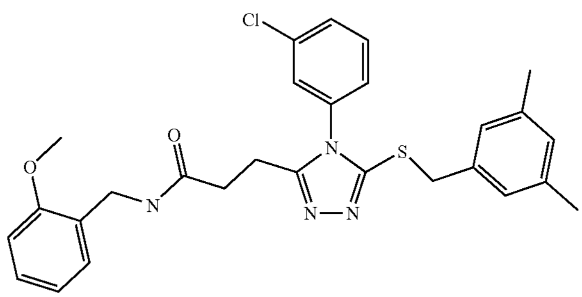 | 521.08 | 3-{4-(3-chlorophenyl)-5-[(3,5-dimethylbenzyl)sulfanyl]-4H-1,2,4-triazol-3-yl}-N-(2-methoxybenzyl)propanamide | 521 |
| 37 | 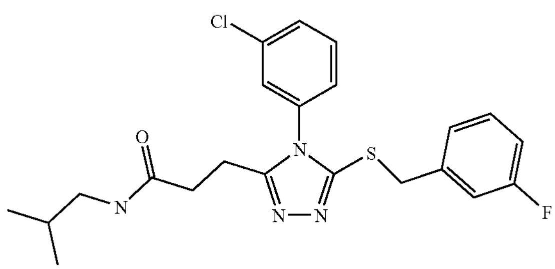 | 446.98 | 3-{4-(3-chlorophenyl)-5-[(3-fluorobenzyl)sulfanyl]-4H-1,2,4-triazol-3-yl}-N-isobutylpropanamide | 447 |
| 38 | 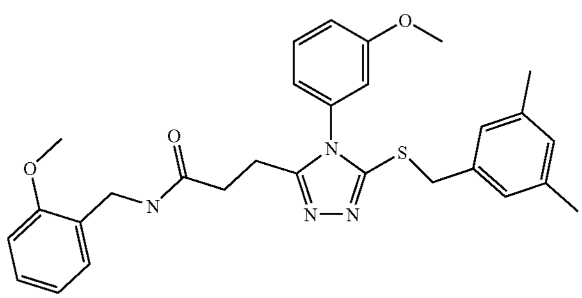 | 516.66 | 3-[5-[(3,5-dimethylbenzyl)sulfanyl]-4-(3-methoxyphenyl)-4H-1,2,4-triazol-3-yl]-N-(2-methoxybenzyl)propanamide | 517 |
| 39 | 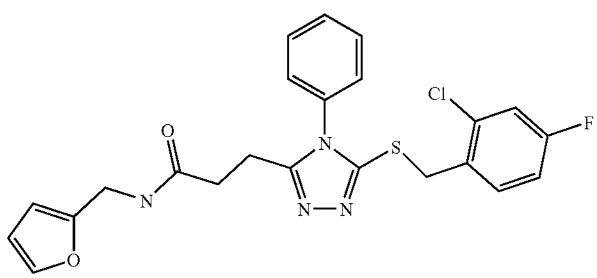 | 470.95 | 3-{5-[(2-chloro-4-fluorobenzyl)sulfanyl]-4-phenyl-4H-1,2,4-triazol-3-yl}-N-(2-furylmethyl)propanamide | 471 |

TABLE 2-continued

| Example No. | Chemical Structure | M.W. | IUPAC-Name | M⁺(ESI⁺) |
|---|---|---|---|---|
| 40 | 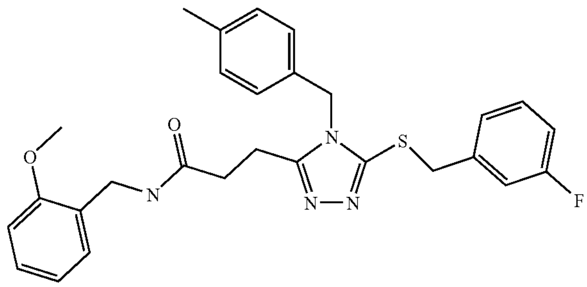 | 504.63 | 3-[5-[(3-fluorobenzyl)sulfanyl]4-(4-methylbenzyl)-4H-1,2,4-triazol-3-yl]-N-(2-methoxybenzyl)propanamide | 505 |
| 41 | 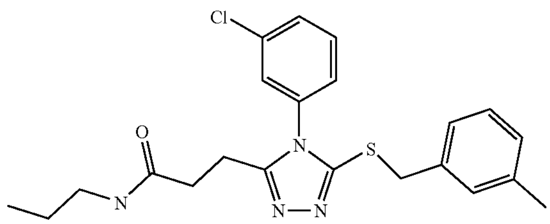 | 428.99 | 3-{4-(3-chlorophenyl)-5-[(3-methylbenzyl)sulfanyl]-4H-1,2,4-triazol-3-yl}-N-propylpropanamide | 429 |
| 42 | 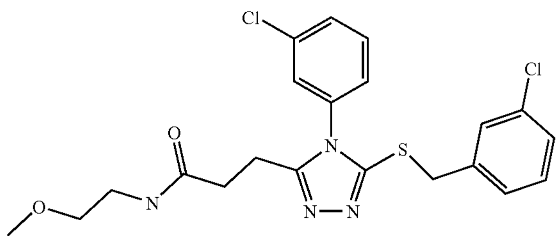 | 465.40 | 3-[5-[(3-chlorobenzyl)sulfanyl]-4-(3-chlorophenyl)-4H-1,2,4-triazol-3-yl]-N-(2-methoxyethyl)propanamide | 465 |
| 43 | 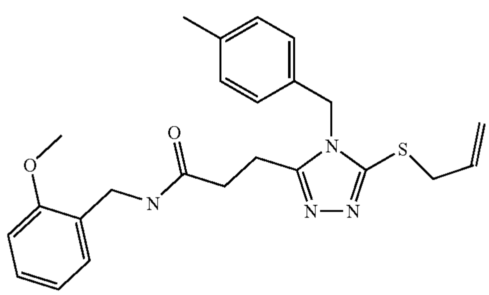 | 436.58 | 3-[5-(allylsulfanyl)-4-(4-methylbenzyl)-4H-1,2,4-triazol-3-yl]-N-(2-methoxybenzyl)propanamide | 437 |
| 44 | 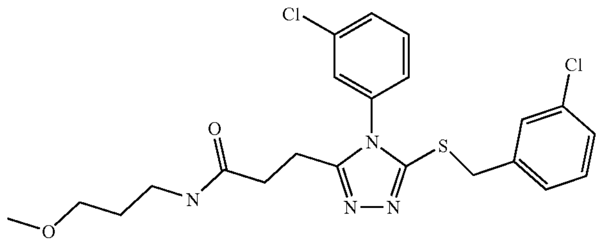 | 479.43 | 3-[5-[(3-chlorobenzyl)sulfanyl]-4-(3-chlorophenyl)-4H-1,2,4-triazol-3-yl]-N-(3-methoxypropyl)propanamide | 479 |

TABLE 2-continued

| Example No. | Chemical Structure | M.W. | IUPAC-Name | M+(ESI+) |
|---|---|---|---|---|
| 45 | 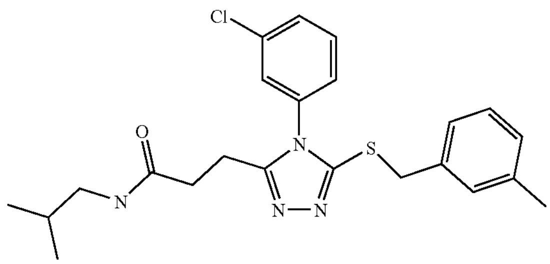 | 443.01 | 3-{4-(3-chlorophenyl)-5-[(3-methylbenzyl)sulfanyl]-4H-1,2,4-triazol-3-yl}-N-isobutylpropanamide | 443 |
| 46 | 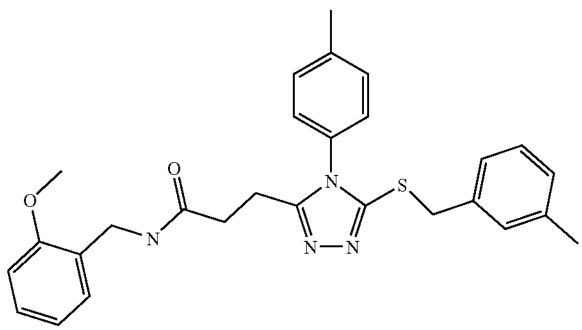 | 486.64 | N-(2-methoxybenzyl)-3-[5-[(3-methylbenzyl)sulfanyl]-4-(4-methylphenyl)-4H-1,2,4-triazol-3-yl]propanamide | 487 |
| 47 | 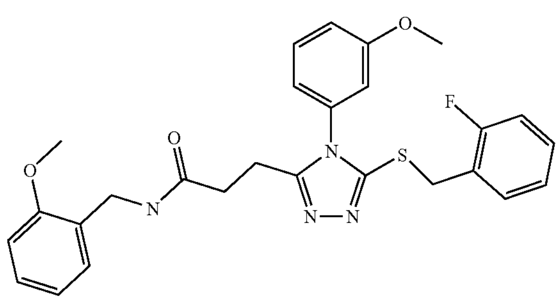 | 506.60 | 3-[5-[(2-fluorobenzyl)sulfanyl]-4-(3-methoxyphenyl)-4H-1,2,4-triazol-3-yl]-N-(2-methoxybenzyl)propanamide | 507 |
| 48 | 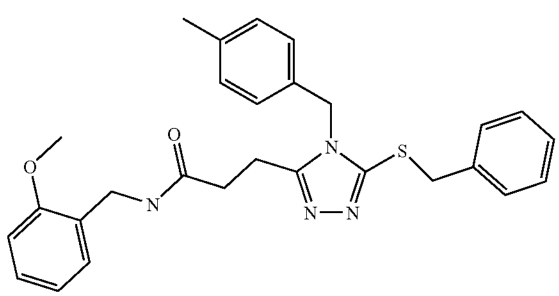 | 486.64 | 3-[5-(benzylsulfanyl)-4-(4-methylbenzyl)-4H-1,2,4-triazol-3-yl]-N-(2-methoxybenzyl)propanamide | 487 |
| 49 | 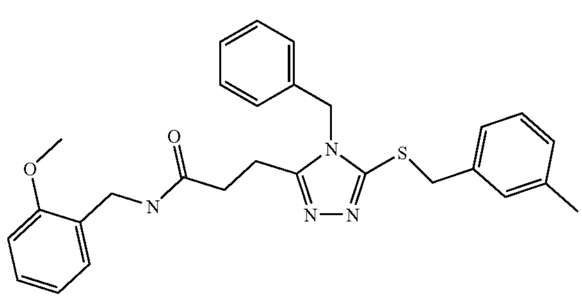 | 486.64 | 3-{4-benzyl-5-[(3-methylbenzyl)sulfanyl]-4H-1,2,4-triazol-3-yl}-N-(2-methoxybenzyl)propanamide | 487 |

TABLE 2-continued

| Example No. | Chemical Structure | M.W. | IUPAC-Name | M+(ESI+) |
|---|---|---|---|---|
| 50 | 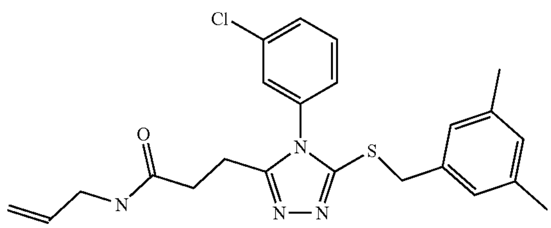 | 441.00 | N-allyl-3-{4-(3-chlorophenyl)-5-[(3,5-dimethylbenzyl)sulfanyl]-4H-1,2,4-triazol-3-yl}propanamide | 441 |
| 51 | 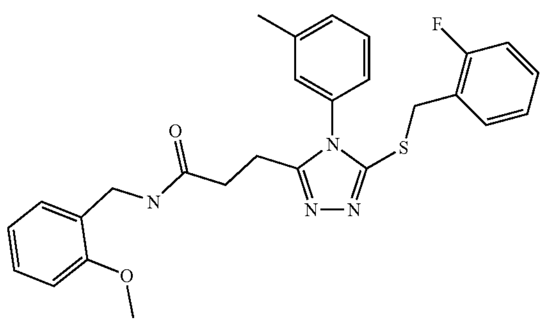 | 490.60 | 3-[5-[(2-fluorobenzyl)sulfanyl]-4-(3-methylphenyl)-4H-1,2,4-triazol-3-yl]-N-(2-methoxybenzyl)propanamide | 491 |
| 52 | 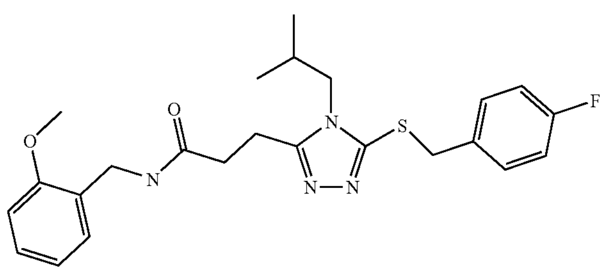 | 456.58 | 3-{5-[(4-fluorobenzyl)sulfanyl]-4-isobutyl-4H-1,2,4-triazol-3-yl}-N-(2-methoxybenzyl)propanamide | 457 |
| 53 | 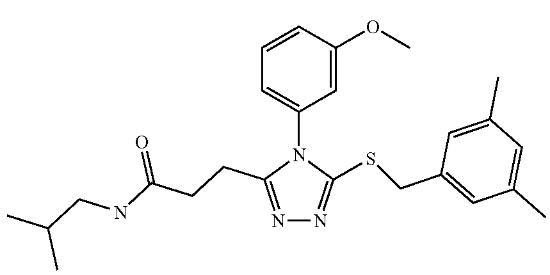 | 452.62 | 3-[5-[(3,5-dimethylbenzyl)sulfanyl]-4-(3-methoxyphenyl)-4H-1,2,4-triazol-3-yl]-N-isobutylpropanamide | 453 |
| 54 | 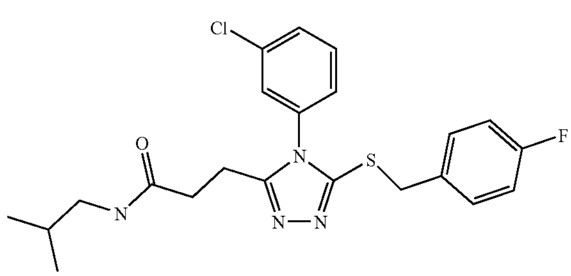 | 446.98 | 3-{4-(3-chlorophenyl)-5-[(4-fluorobenzyl)sulfanyl]-4H-1,2,4-triazol-3-yl}-N-isobutylpropanamide | 447 |

TABLE 2-continued

| Example No. | Chemical Structure | M.W. | IUPAC-Name | M+(ESI+) |
|---|---|---|---|---|
| 55 | 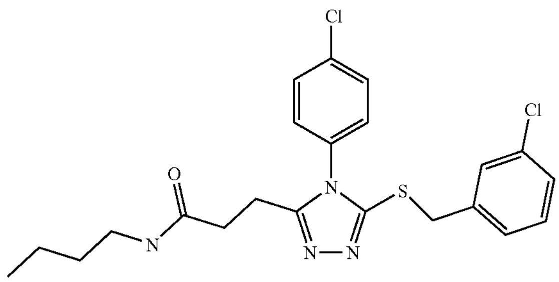 | 463.43 | N-butyl-3-[5-[(3-chlorobenzyl)sulfanyl]-4-(4-chlorophenyl)-4H-1,2,4-triazol-3-yl]propanamide | 463 |
| 56 | 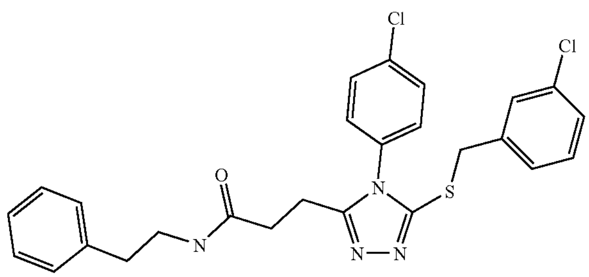 | 511.47 | 3-[5-[(3-chlorobenzyl)-sulfanyl]-4-(4-chlorophenyl)-4H-1,2,4-triazol-3-yl]-N-(2-phenylethyl)propanamide | 511 |
| 57 | 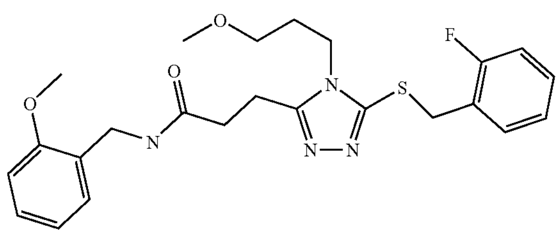 | 472.58 | 3-[5-[(2-fluorobenzyl)-sulfanyl]-4-(3-methoxypropyl)-4H-1,2,4-triazol-3-yl]-N-(2-methoxybenzyl)propanamide | 473 |
| 58 | 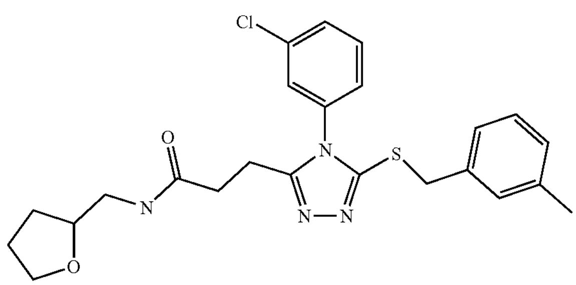 | 471.02 | 3-{4-(3-chlorophenyl)-5-[(3-methylbenzyl)sulfanyl]-4H-1,2,4-triazol-3-yl}-N-(tetrahydro-2-furanylmethyl)propanamide | 471 |
| 59 | 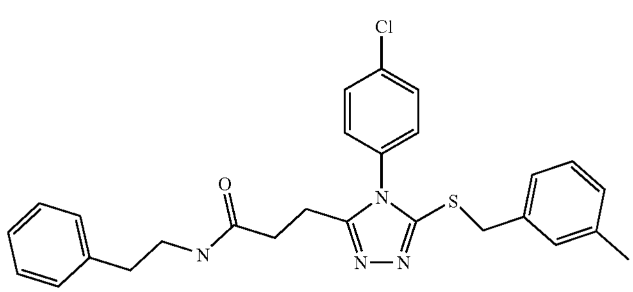 | 491.06 | 3-{4-(4-chlorophenyl)-5-[(3-methylbenzyl)sulfanyl]-4H-1,2,4-triazol-3-yl}-N-(2-phenylethyl)propanamide | 491 |

TABLE 2-continued

| Example No. | Chemical Structure | M.W. | IUPAC-Name | M+(ESI+) |
|---|---|---|---|---|
| 60 | 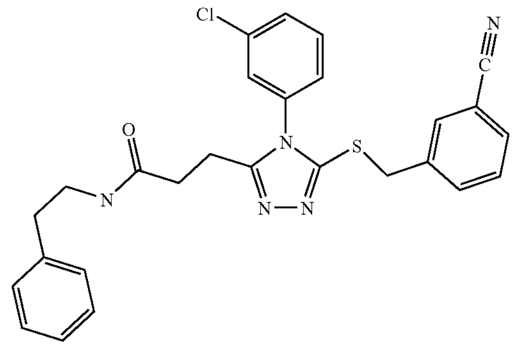 | 502.04 | 3-{4-(3-chlorophenyl)-5-[(3-cyanobenzyl)sulfanyl]-4H-1,2,4-triazol-3-yl}-N-(2-phenylethyl)propanamide | 502 |
| 61 | 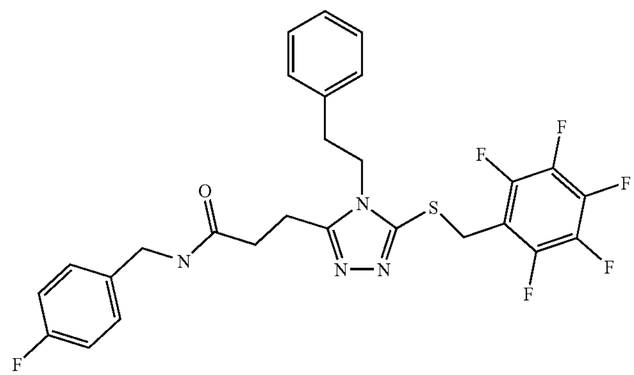 | 564.55 | N-(4-fluorobenzyl)-3-[5-[(2,3,4,5,6-pentafluorobenzyl)sulfanyl]-4-(2-phenylethyl)-4H-1,2,4-triazol-3-yl]propanamide | 565 |
| 62 | 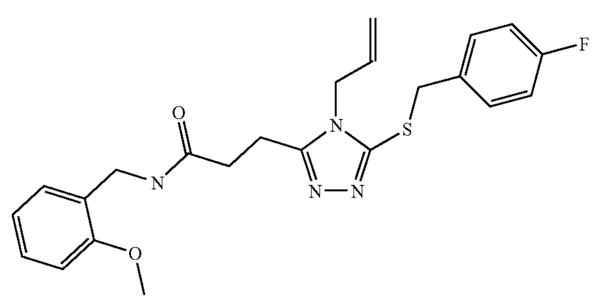 | 440.54 | 3-{4-allyl-5-[(4-fluorobenzyl)sulfanyl]-4H-1,2,4-triazol-3-yl}-N-(2-methoxybenzyl)propanamide | 441 |
| 63 | 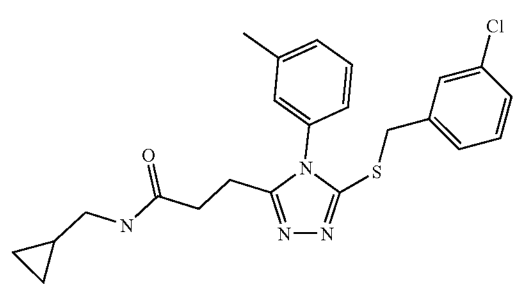 | 441.00 | 3-[5-[(3-chlorobenzyl)sulfanyl]-4-(3-methylphenyl)-4H-1,2,4-triazol-3-yl]-N-(cyclopropylmethyl)propanamide | 441 |

TABLE 2-continued

| Example No. | Chemical Structure | M.W. | IUPAC-Name | M+(ESI+) |
|---|---|---|---|---|
| 64 | 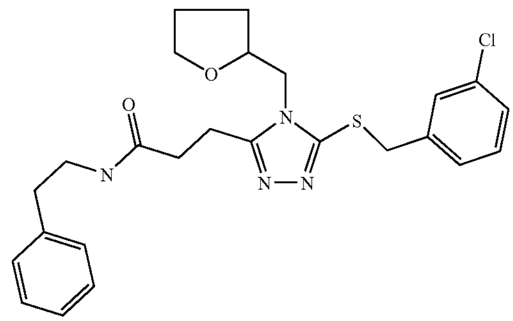 | 485.05 | 3-[5-[(3-chlorobenzyl)sulfanyl]-4-(tetrahydro-2-furanylmethyl)-4H-1,2,4-triazol-3-yl]-N-(2-phenylethyl)propanamide | 485 |
| 65 | 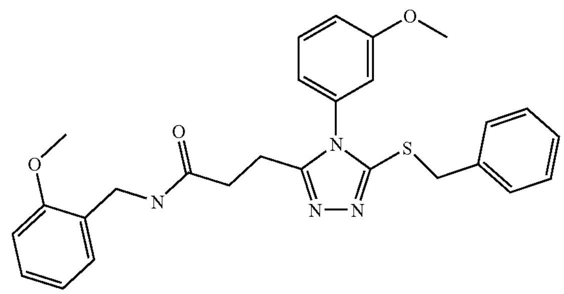 | 488.61 | 3-[5-(benzylsulfanyl)-4-(3-methoxyphenyl)-4H-1,2,4-triazol-3-yl]-N-(2-methoxybenzyl)propanamide | 489 |
| 66 | 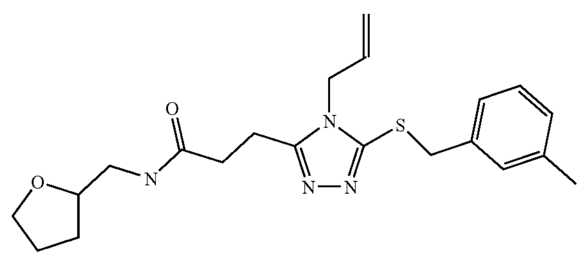 | 400.55 | 3-{4-allyl-5-[(3-methylbenzyl)sulfanyl]-4H-1,2,4-triazol-3-yl}-N-(tetrahydro-2-furanylmethyl)propanamide | 401 |
| 67 | 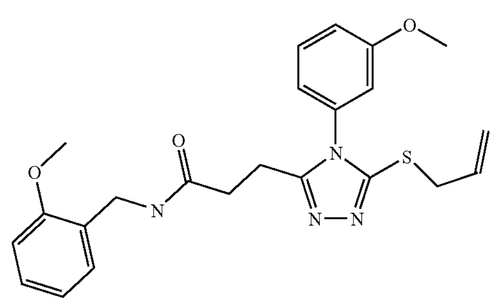 | 438.55 | 3-[5-(allylsulfanyl)-4-(3-methoxyphenyl)-4H-1,2,4-triazol-3-yl]-N-(2-methoxybenzyl)propanamide | 439 |
| 68 | 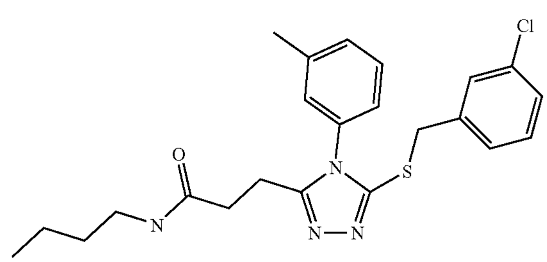 | 443.01 | N-butyl-3-(5-[(3-chlorobenzyl)sulfanyl]-4-(3-methylphenyl)-4H-1,2,4-triazol-3-yl]propanamide | 443 |

TABLE 2-continued

| Example No. | Chemical Structure | M.W. | IUPAC-Name | M⁺(ESI⁺) |
|---|---|---|---|---|
| 69 | 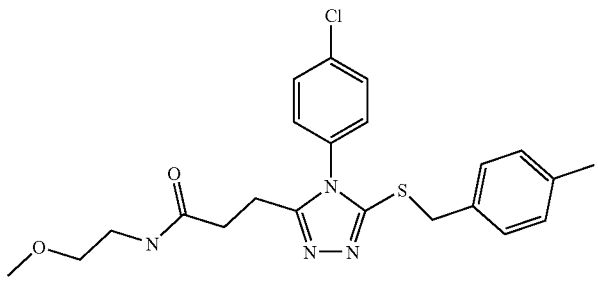 | 444.99 | 3-{4-(4-chlorophenyl)-5-[(4-methylbenzyl)sulfanyl]-4H-1,2,4-triazol-3-yl}-N-(2-methoxyethyl)propanamide | 445 |
| 70 | 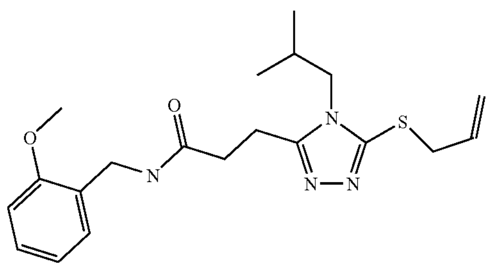 | 388.55 | 3-[5-(allylsulfanyl)-4-isobutyl-4H-1,2,4-triazol-3-yl]-N-(2-methoxybenzyl)propanamide | 389 |
| 71 | 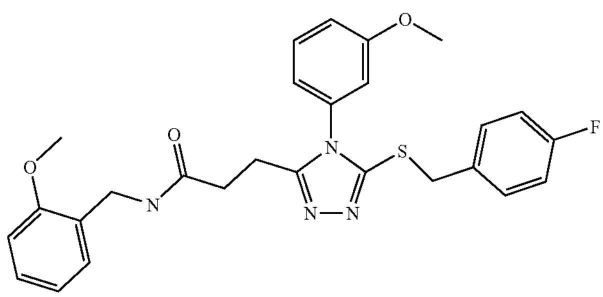 | 506.60 | 3-[5-[(4-fluorobenzyl)sulfanyl]-4-(3-methoxyphenyl)-4H-1,2,4-triazol-3-yl]-N-(2-methoxybenzyl)propanamide | 507 |
| 72 | 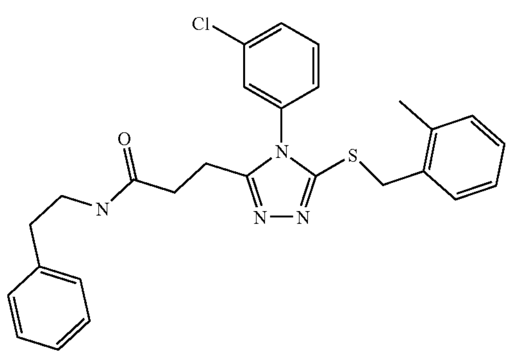 | 491.06 | 3-{4-(3-chlorophenyl)-5-[(2-methylbenzyl)sulfanyl]-4H-1,2,4-triazol-3-yl}-N-(2-phenylethyl)propanamide | 491 |
| 73 | 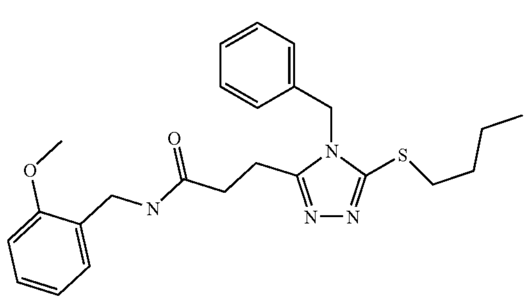 | 438.59 | 3-[4-benzyl-5-(butylsulfanyl)-4H-1,2,4-triazol-3-yl]-N-(2-methoxybenzyl)propanamide | 439 |

TABLE 2-continued

| Example No. | Chemical Structure | M.W. | IUPAC-Name | M+(ESI+) |
|---|---|---|---|---|
| 74 | 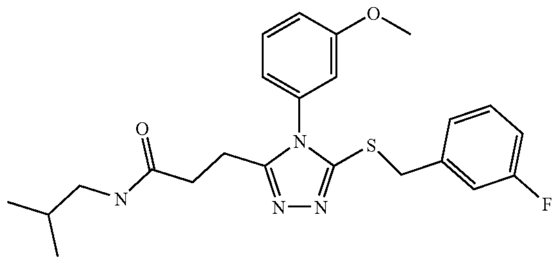 | 442.56 | 3-[5-[(3-fluorobenzyl)sulfanyl]-4-(3-methoxyphenyl)-4H-1,2,4-triazol-3-yl]-N-isobutylpropanamide | 443 |
| 75 | 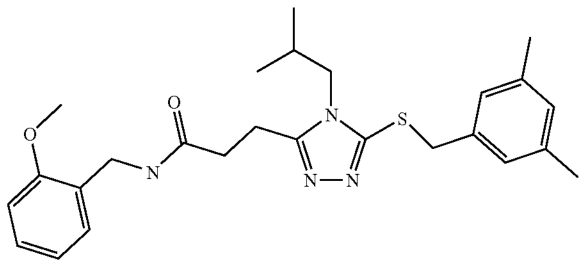 | 466.65 | 3-{5-[(3,5-dimethylbenzyl)sulfanyl]-4-isobutyl-4H-1,2,4-triazol-3-yl}-N-(2-methoxybenzyl)propanamide | 467 |
| 76 | 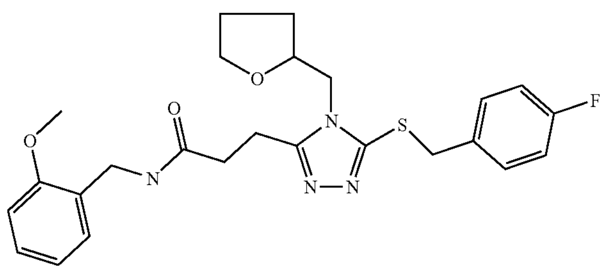 | 484.59 | 3-[5-[(4-fluorobenzyl)sulfanyl]4-(tetrahydro-2-furanylmethyl)-4H-1,2,4-triazol-3-yl]-N-(2-methoxybenzyl)propanamide | 485 |
| 77 | 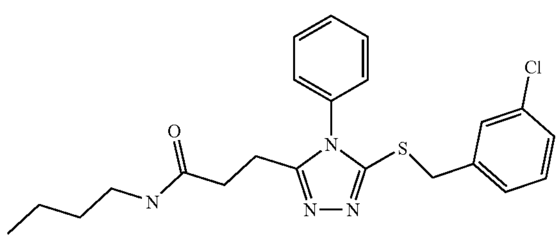 | 428.99 | N-butyl-3-{5-[(3-chlorobenzyl)sulfanyl]-4-phenyl-4H-1,2,4-triazol-3-yl}propanamide | 429 |
| 78 | 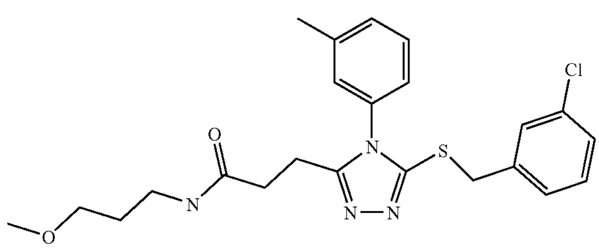 | 459.01 | 3-[5-[(3-chlorobenzyl)sulfanyl]-4-(3-methylphenyl)-4H-1,2,4-triazol-3-yl]-N-(3-methoxypropyl)propanamide | 459 |
| 79 | 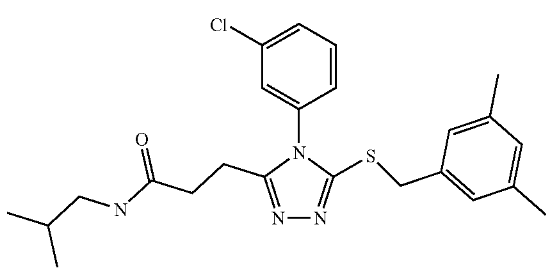 | 457.04 | 3-{4-(3-chlorophenyl)-5-[(3,5-dimethylbenzyl)sulfanyl]-4H-1,2,4-triazol-3-yl}-N-isobutylpropanamide | 457 |

TABLE 2-continued

| Example No. | Chemical Structure | M.W. | IUPAC-Name | M⁺(ESI⁺) |
|---|---|---|---|---|
| 80 | 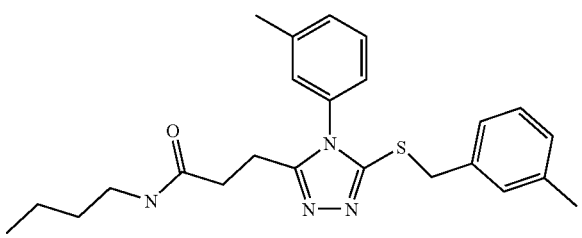 | 422.59 | N-butyl-3-[5-[(3-methylbenzyl)sulfanyl]-4-(3-methylphenyl)-4H-1,2,4-triazol-3-yl]propanamide | 423 |
| 81 | 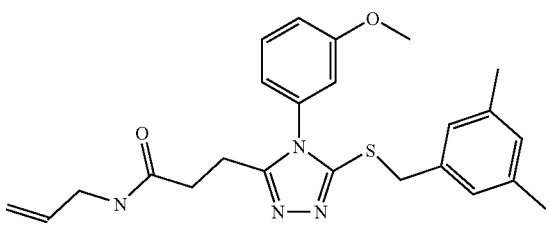 | 436.58 | N-allyl-3-[5-[(3,5-dimethylbenzyl)sulfanyl]-4-(3-methoxyphenyl)-4H-1,2,4-triazol-3-yl]propanamide | 437 |
| 82 | 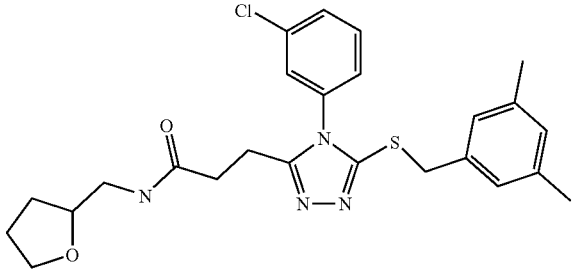 | 485.05 | 3-{4-(3-chlorophenyl)-5-[(3,5-dimethylbenzyl)sulfanyl]-4H-1,2,4-triazol-3-yl}-N-(tetrahydro-2-furanylmethyl)propanamide | 485 |
| 83 | 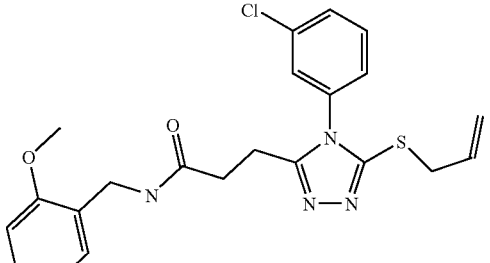 | 442.97 | 3-[5-(allylsulfanyl)-4-(3-chlorophenyl)-4H-1,2,4-triazol-3-yl]-N-(2-methoxybenzyl)propanamide | 443 |
| 84 | 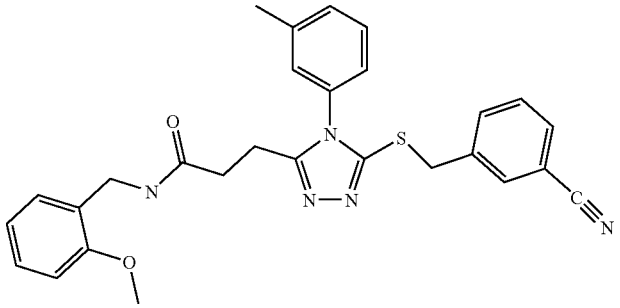 | 497.62 | 3-[5-[(3-cyanobenzyl)sulfanyl]-4-(3-methylphenyl)-4H-1,2,4-triazol-3-yl]-N-(2-methoxybenzyl)propanamide | 498 |

TABLE 2-continued

| Example No. | Chemical Structure | M.W. | IUPAC-Name | M+(ESI+) |
|---|---|---|---|---|
| 85 | 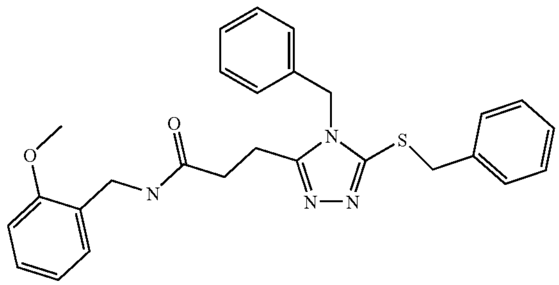 | 472.61 | 3-[4-benzyl-5-(benzylsulfanyl)-4H-1,2,4-triazol-3-yl]-N-(2-methoxybenzyl)propanamide | 473 |
| 86 | 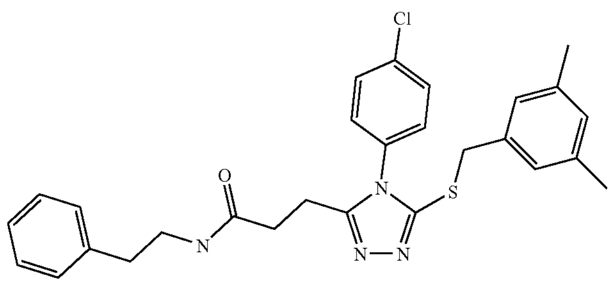 | 505.08 | 3-{4-(4-chlorophenyl)-5-[(3,5-dimethylbenzyl)sulfanyl]-4H-1,2,4-triazol-3-yl}-N-(2-phenylethyl)propanamide | 505 |
| 87 | 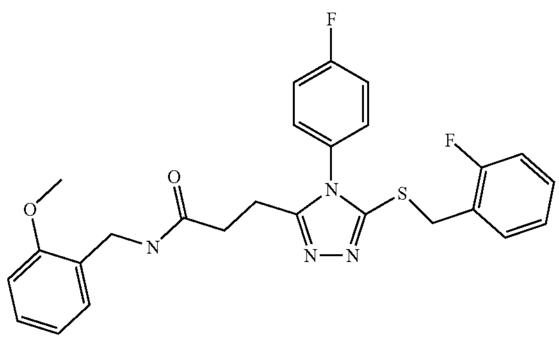 | 494.57 | 3-[5-[(2-fluorobenzyl)sulfanyl]4-(4-fluorophenyl)-4H-1,2,4-triazol-3-yl]-N-(2-methoxybenzyl)propanamide | 495 |
| 88 | 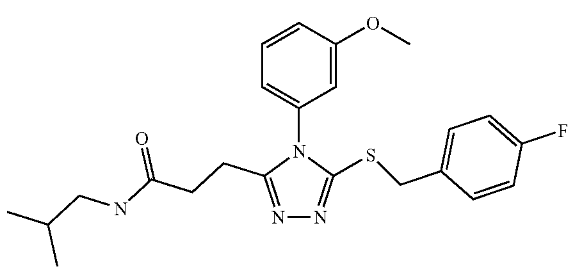 | 442.56 | 3-[5-[(4-fluorobenzyl)sulfanyl]-4-(3-methoxyphenyl)-4H-1,2,4-triazol-3-yl]-N-isobutylpropanamide | 443 |
| 89 | 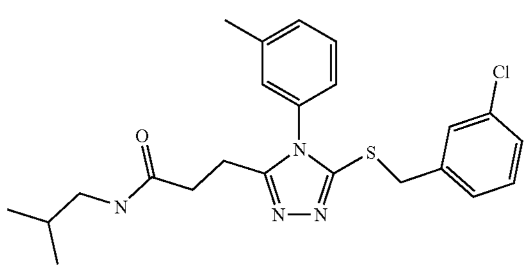 | 443.01 | 3-[5-[(3-chlorobenzyl)sulfanyl]-4-(3-methylphenyl)-4H-1,2,4-triazol-3-yl]-N-isobutylpropanamide | 443 |

TABLE 2-continued

| Example No. | Chemical Structure | M.W. | IUPAC-Name | M⁺(ESI⁺) |
|---|---|---|---|---|
| 90 | 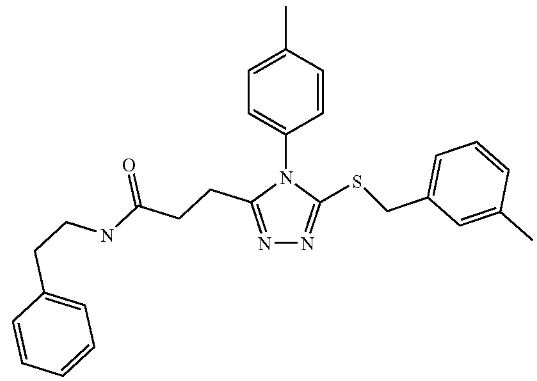 | 470.64 | 3-[5-[(3-methylbenzyl)sulfanyl]-4-(4-methylphenyl)-4H-1,2,4-triazol-3-yl]-N-(2-phenylethyl)propanamide | 471 |
| 91 | 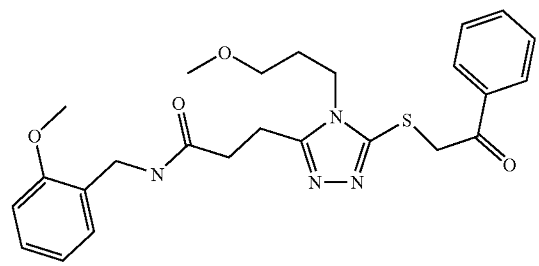 | 482.60 | N-(2-methoxybenzyl)-3-{4-(3-methoxypropyl)-5-[2-oxo-2-phenylethyl)sulfanyl]-4H-1,2,4-triazol-3-yl}propanamide | 483 |
| 92 | 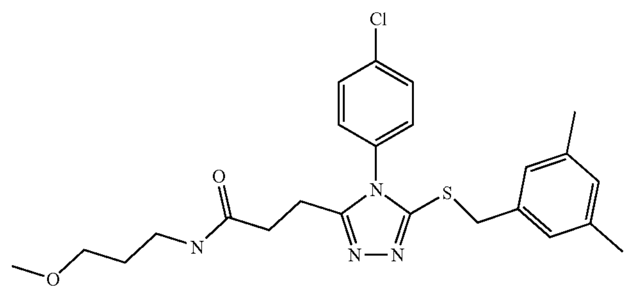 | 473.04 | 3-{4-(4-chlorophenyl)-5-[(3,5-dimethylbenzyl)sulfanyl]-4H-1,2,4-triazol-3-yl}-N-(3-methoxypropyl)propanamide | 473 |
| 93 | 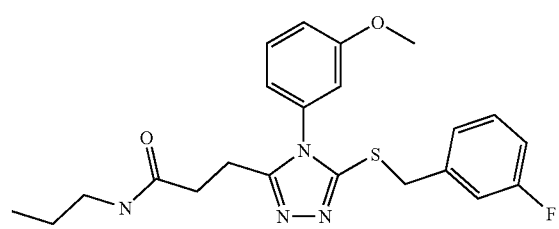 | 428.53 | 3-[5-[(3-fluorobenzyl)sulfanyl]-4-(3-methoxyphenyl)-4H-1,2,4-triazol-3-yl]-N-propylpropanamide | 429 |
| 94 | 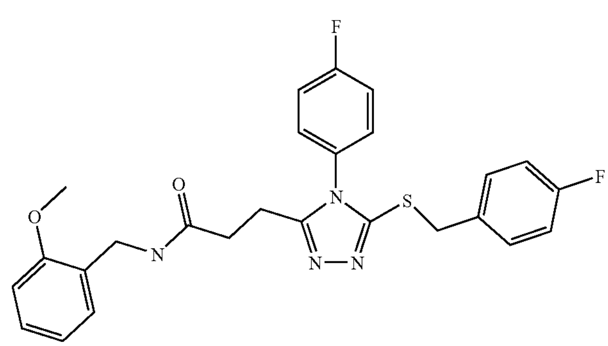 | 494.57 | 3-[5-[(4-fluorobenzyl)sulfanyl]-4-(4-fluorophenyl)-4H-1,2,4-triazol-3-yl]-N-(2-methoxybenzyl)propanamide | 495 |

TABLE 2-continued

| Example No. | Chemical Structure | M.W. | IUPAC-Name | M+(ESI+) |
|---|---|---|---|---|
| 95 | 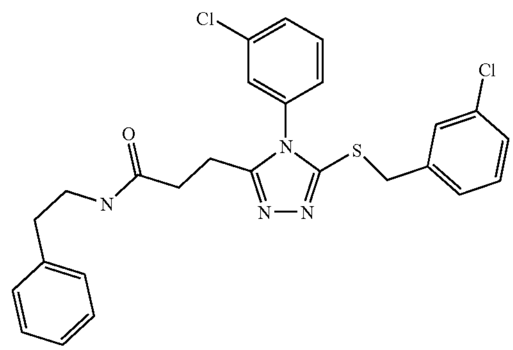 | 511.47 | 3-[5-[(3-chlorobenzyl)sulfanyl]-4-(3-chlorophenyl)-4H-1,2,4-triazol-3-yl]-N-(2-phenylethyl)propanamide | 511 |
| 96 | 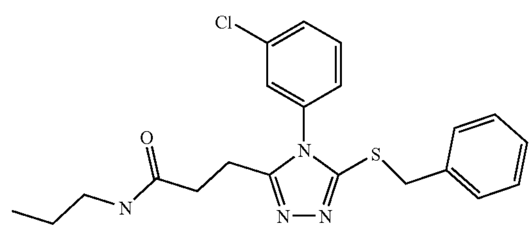 | 414.96 | 3-[5-(benzylsulfanyl)-4-(3-chlorophenyl)-4H-1,2,4-triazol-3-yl]-N-propylpropanamide | 415 |
| 97 | 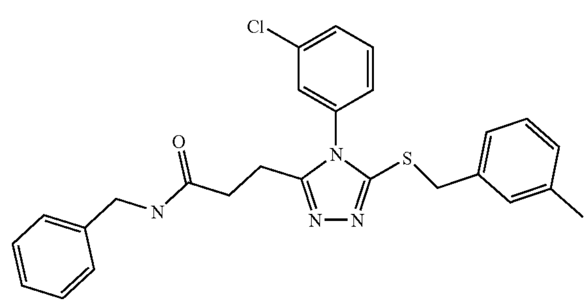 | 477.03 | N-benzyl-3-{4-(3-chlorophenyl)-5-[(3-methylbenzyl)sulfanyl]-4H-1,2,4-triazol-3-yl}propanamide | 477 |
| 98 | 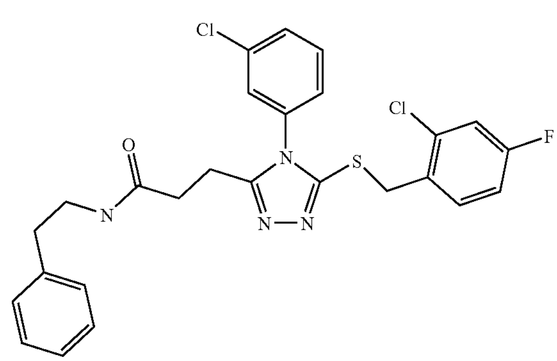 | 529.46 | 3-[5-[(2-chloro-4-fluorobenzyl)sulfanyl]-4-(3-chlorophenyl)-4H-1,2,4-triazol-3-yl]-N-(2-phenylethyl)propanamide | 529 |

TABLE 2-continued

| Example No. | Chemical Structure | M.W. | IUPAC-Name | M⁺(ESI⁺) |
|---|---|---|---|---|
| 99 | 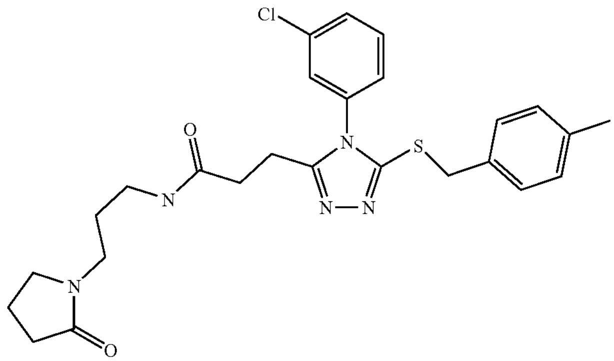 | 512.08 | 3-{4-(3-chlorophenyl)-5-[4-methylbenzyl)sulfanyl]-4H-1,2,4-triazol-3-yl}-N-[3-(2-oxo-1-pyrrolidinyl)propyl]propanamide | 512 |
| 100 | 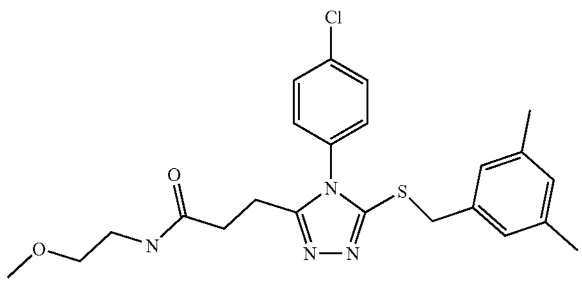 | 459.01 | 3-{4-(4-chlorophenyl)-5-[(3,5-dimethylbenzyl)sulfanyl]-4H-1,2,4-triazol-3-yl}-N-(2-methoxyethyl)propanamide | 459 |
| 101 | 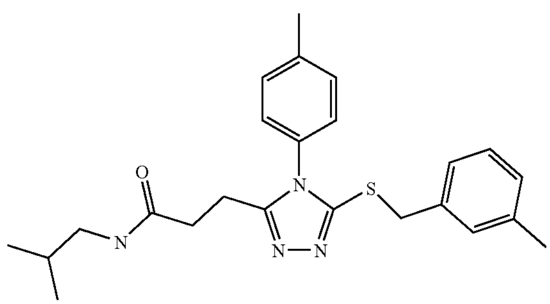 | 422.59 | N-isobutyl-3-[5-[(3-methylbenzyl)sulfanyl]-4-(4-methylphenyl)-4H-1,2,4-triazol-3-yl]propanamide | 423 |
| 102 | 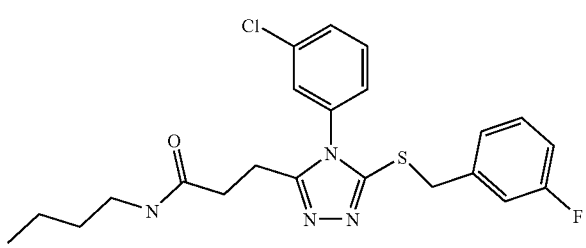 | 446.98 | N-butyl-3-{4-(3-chlorophenyl)-5-[(3-fluorobenzyl)sulfanyl]-4H-1,2,4-triazol-3-yl}propanamide | 447 |
| 103 | 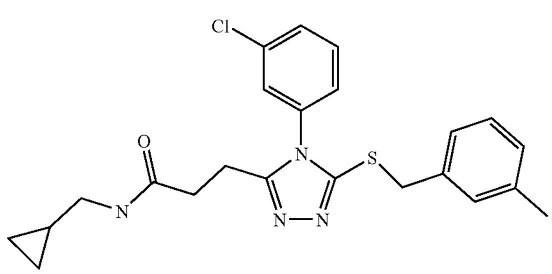 | 441.00 | 3-{4-(3-chlorophenyl)-5-[3-methylbenzyl)sulfanyl]-4H-1,2,4-triazol-3-yl}-N-(cyclopropylmethyl)propanamide | 441 |

TABLE 2-continued

| Example No. | Chemical Structure | M.W. | IUPAC-Name | M+(ESI+) |
|---|---|---|---|---|
| 104 | 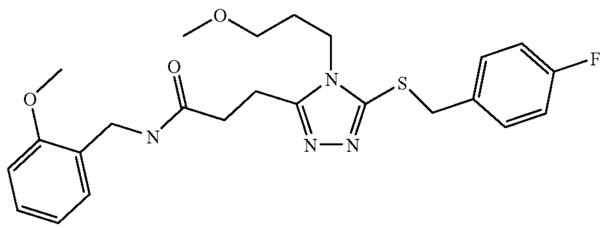 | 472.58 | 3-[5-[(4-fluorobenzyl)sulfanyl]-4-(3-methoxypropyl)-4H-1,2,4-triazol-3-yl]-N-(2-methoxybenzyl)propanamide | 473 |
| 105 | 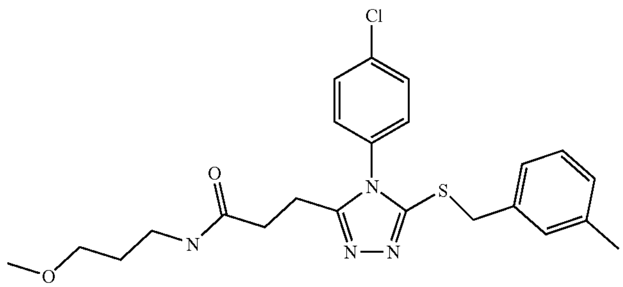 | 459.01 | 3-{4-(4-chlorophenyl)-5-[(3-methylbenzyl)sulfanyl]-4H-1,2,4-triazol-3-yl]-N-(3-methoxypropyl)propanamide | 459 |
| 106 | 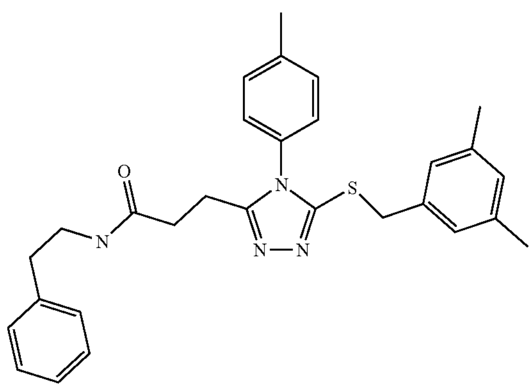 | 484.67 | 3-[5-[(3,5-dimethylbenzyl)sulfanyl]-4-(4-methylphenyl)-4H-1,2,4-triazol-3-yl]-N-(2-phenylethyl)propanamide | 485 |
| 107 | 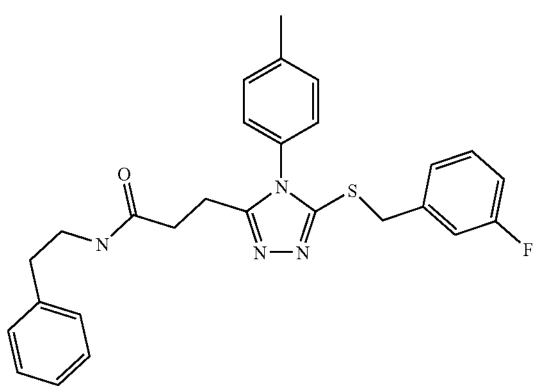 | 474.60 | 3-[5-[(3-fluorobenzyl)sulfanyl]-4-(4-methylphenyl)-4H-1,2,4-triazol-3-yl]-N-(2-phenylethyl)propanamide | 475 |

TABLE 2-continued

| Example No. | Chemical Structure | M.W. | IUPAC-Name | M⁺(ESI⁺) |
|---|---|---|---|---|
| 108 | 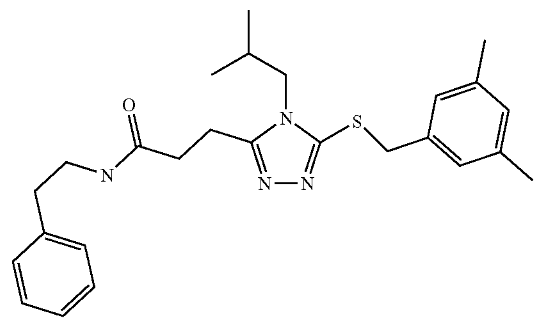 | 450.65 | 3-{5-[(3,5-dimethylbenzyl)sulfanyl]-4-isobutyl-4H-1,2,4-triazol-3-yl}-N-(2-phenylethyl)propanamide | 451 |
| 109 | 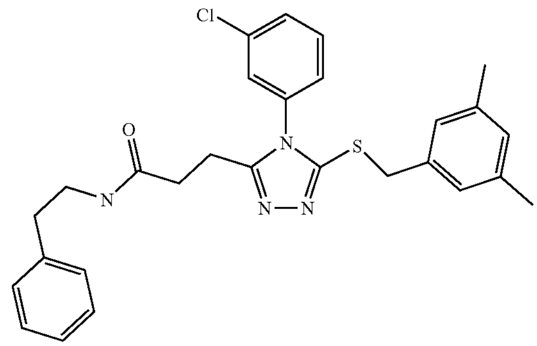 | 505.08 | 3-{4-(3-chlorophenyl)-5-[(3,5-dimethylbenzyl)sulfanyl]-4H-1,2,4-triazol-3-yl}-N-(2-phenylethyl)propanamide | 505 |
| 110 | 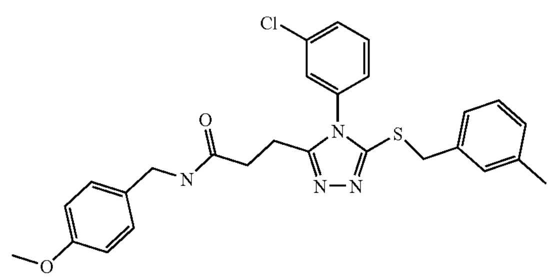 | 507.06 | 3-{4-(3-chlorophenyl)-5-[(3-methylbenzyl)sulfanyl]-4H-1,2,4-triazol-3-yl}-N-(4-methoxybenzyl)propanamide | 507 |
| 111 | 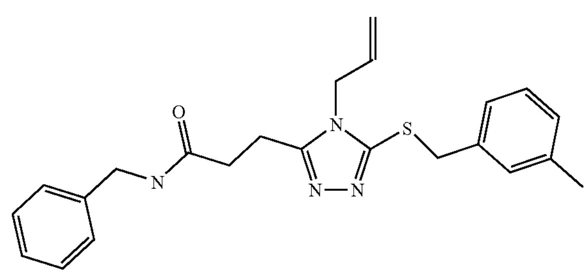 | 406.55 | 3-{4-allyl-5-[(3-methylbenzyl)sulfanyl]-4H-1,2,4-triazol-3-yl}-N-benzylpropanamide | 407 |
| 112 | 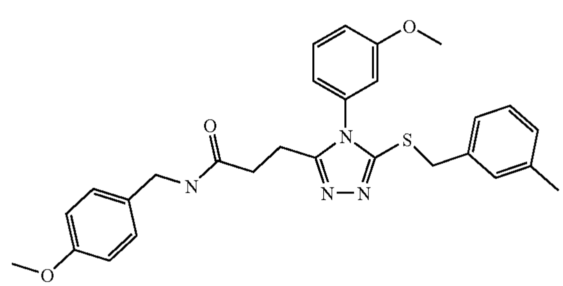 | 502.64 | N-(4-methoxybenzyl)-3-{4-(3-methoxyphenyl)-5-[(3-methylbenzyl)sulfanyl]-4H-1,2,4-triazol-3-yl}propanamide | 503 |

TABLE 2-continued

| Example No. | Chemical Structure | M.W. | IUPAC-Name | M+(ESI+) |
|---|---|---|---|---|
| 113 | 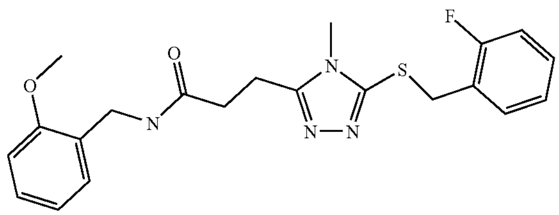 | 414.50 | 3-{5-[(2-fluorobenzyl)sulfanyl]4-methyl-4H-1,2,4-triazol-3-yl}-N-(2-methoxybenzyl)propanamide | 415 |
| 114 | 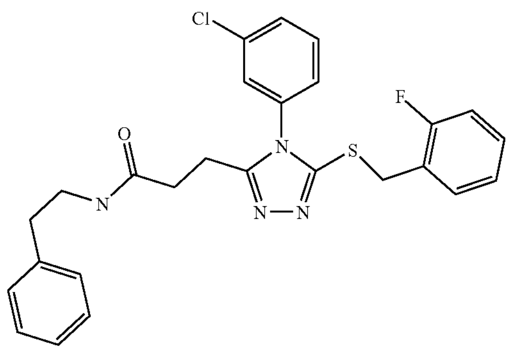 | 495.02 | 3-{4-(3-chlorophenyl)-5-[(2-fluorobenzyl)sulfanyl]-4H-1,2,4-triazol-3-yl}-N-(2-phenylethyl)propanamide | 495 |
| 115 | 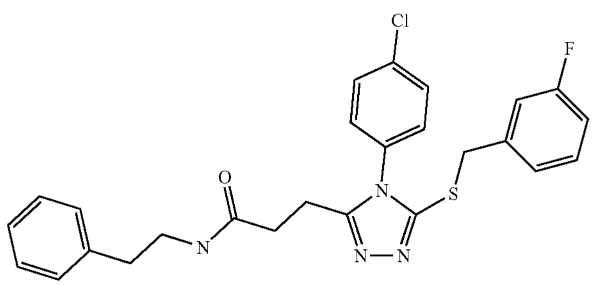 | 495.02 | 3-{4-(4-chlorophenyl)-5-[(3-fluorobenzyl)sulfanyl]-4H-1,2,4-triazol-3-yl}-N-(2-phenylethyl)propanamide | 495 |
| 116 | 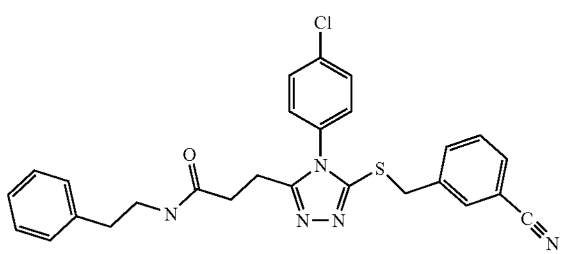 | 502.04 | 3-{4-(4-chlorophenyl)-5-[(3-cyanobenzyl)sulfanyl]-4H-1,2,4-triazol-3-yl)-N-(2-phenylethyl)propanamide | 502 |
| 117 | 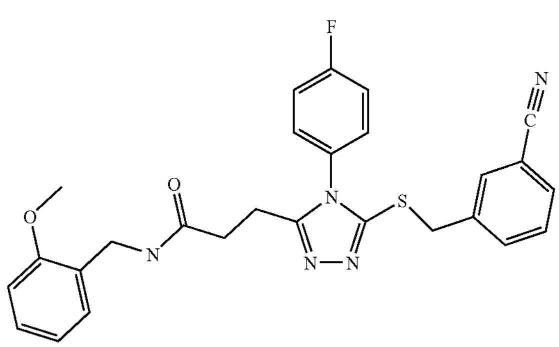 | 501.58 | 3-[5-[(3-cyanobenzyl)sulfanyl]4-(4-fluorophenyl)-4H-1,2,4-triazol-3-yl]-N-(2-methoxybenzyl)propanamide | 502 |

TABLE 2-continued

| Example No. | Chemical Structure | M.W. | IUPAC-Name | M+(ESI+) |
|---|---|---|---|---|
| 118 | 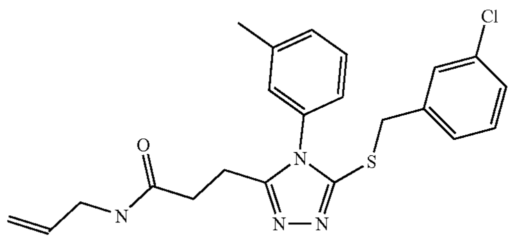 | 426.97 | N-allyl-3-[5-[(3-chlorobenzyl)sulfanyl]-4-(3-methylphenyl)-4H-1,2,4-triazol-3-yl]propanamide | 427 |
| 119 | 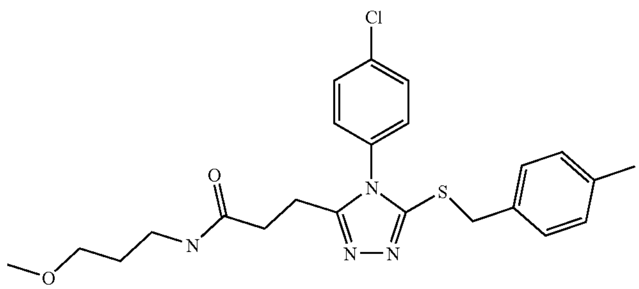 | 459.01 | 3-{4-(4-chlorophenyl)-5-[(4-methylbenzyl)sulfanyl]-4H-1,2,4-triazol-3-yl}-N-(3-methoxypropyl)propanamide | 459 |
| 120 | 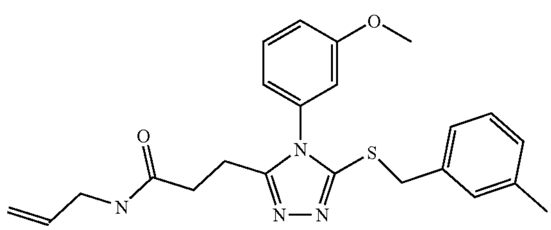 | 422.55 | N-allyl-3-{4-(3-methoxyphenyl)-5-[(3-methylbenzyl)sulfanyl]-4H-1,2,4-triazol-3-yl}propanamide | 423 |
| 121 | 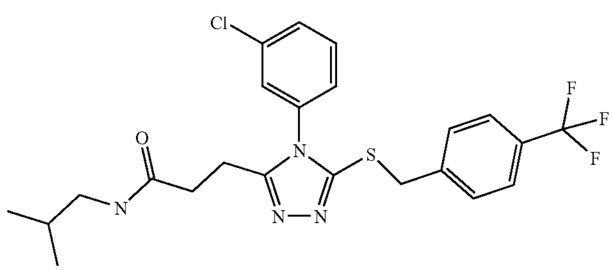 | 496.98 | 3-(4-(3-chlorophenyl)-5-{[4-(trifluoromethyl)benzyl]sulfanyl}-4H-1,2,4-triazol-3-yl)-N-isobutylpropanamide | 497 |
| 122 | 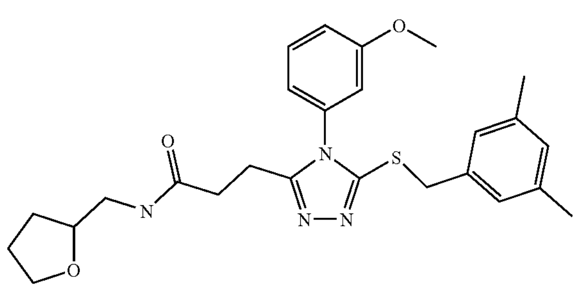 | 480.63 | 3-[5-[(3,5-dimethylbenzyl)sulfanyl]-4-(3-methoxyphenyl)-4H-1,2,4-triazol-3-yl]-N-(tetrahydro-2-furanylmethyl)propanamide | 481 |

TABLE 2-continued

| Example No. | Chemical Structure | M.W. | IUPAC-Name | M+(ESI+) |
|---|---|---|---|---|
| 123 | 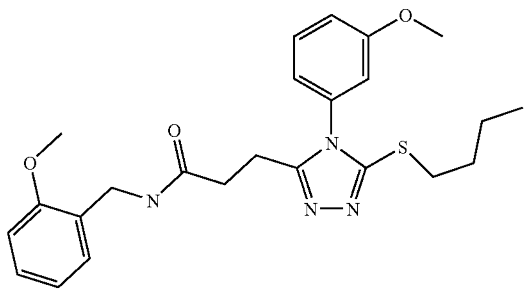 | 454.59 | 3-[5-(butylsulfanyl)-4-(3-methoxyphenyl)-4H-1,2,4-triazol-3-yl]-N-(2-methoxybenzyl)propanamide | 455 |
| 124 | 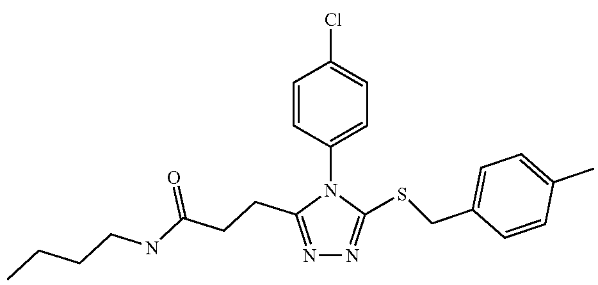 | 443.01 | N-butyl-3-{4-(4-chlorophenyl)-5-[(4-methylbenzyl)sulfanyl)-4H-1,2,4-triazol-3-yl]propanamide | 443 |
| 125 | 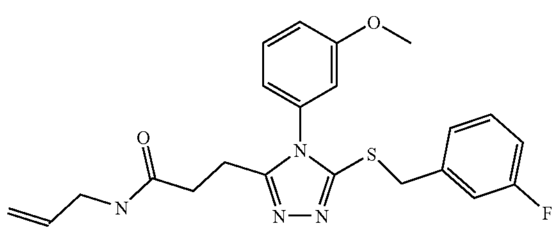 | 426.51 | N-allyl-3-[5-[(3-fluorobenzyl)sulfanyl]-4-(3-methoxyphenyl)-4H-1,2,4-triazol-3-yl]propanamide | 427 |
| 126 | 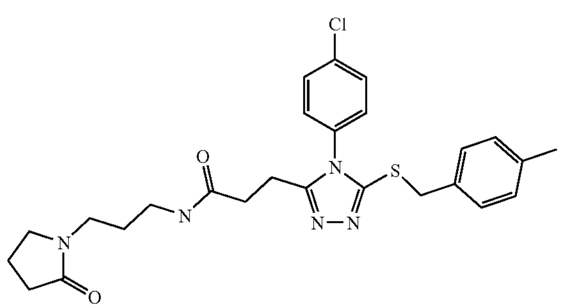 | 512.08 | 3-{4-(4-chlorophenyl)-5-[(4-methylbenzyl)sulfanyl]-4H-1,2,4-triazol-3-yl}-N-[3-(2-oxo-1-pyrrolidinyl)propyl]propananmide | 512 |
| 127 | 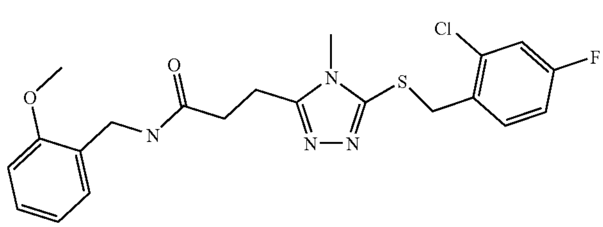 | 448.95 | 3-{5-[(2-chloro-4-fluorobenzyl)sulfanyl]-4-methyl-4H-1,2,4-triazol-3-yl}-N-(2-methoxybenzyl)propanamide | 449 |

TABLE 2-continued

| Example No. | Chemical Structure | M.W. | IUPAC-Name | M+(ESI+) |
|---|---|---|---|---|
| 128 | 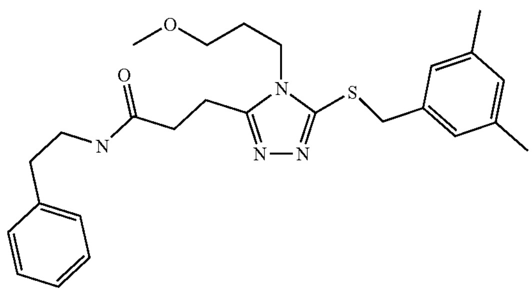 | 466.65 | 3-[5-[(3,5-dimethylbenzyl)sulfanyl]-4-(3-methoxypropyl)-4H-1,2,4-triazol-3-yl]-N-(2-phenylethyl)propanamide | 467 |
| 129 | 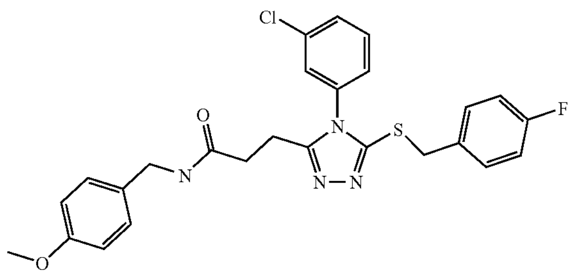 | 511.02 | 3-{4-(3-chlorophenyl)-5-[(4-fluorobenzyl)sulfanyl]-4H-1,2,4-triazol-3-yl}-N-(4-methoxybenzyl)propanamide | 511 |
| 130 | 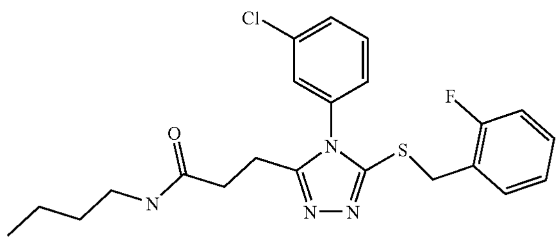 | 446.98 | N-butyl-3-{4-(3-chlorophenyl)-5-[(2-fluorobenzyl)sulfanyl]-4H-1,2,4-triazol-3-yl}propanamide | 447 |
| 131 | 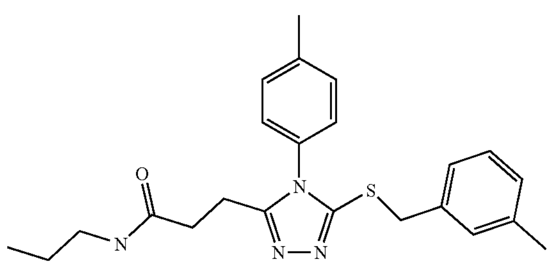 | 408.57 | 3-[5-[(3-methylbenzyl)sulfanyl]-4-(4-methylphenyl)-4H-1,2,4-triazol-3-yl]-N-propylpropanamide | 409 |
| 132 | 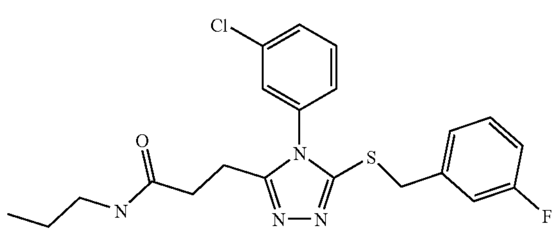 | 432.95 | 3-{4-(3-chlorophenyl)-5-[(3-fluorobenzyl)sulfanyl]-4H-1,2,4-triazol-3-yl}-N-propylpropanamide | 433 |

TABLE 2-continued

| Example No. | Chemical Structure | M.W. | IUPAC-Name | M+(ESI+) |
|---|---|---|---|---|
| 133 | 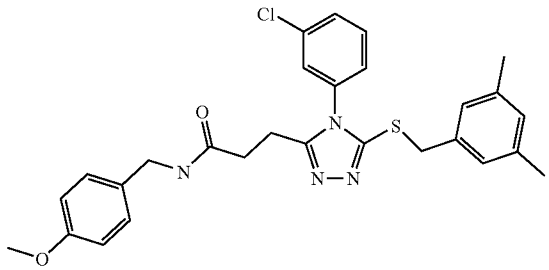 | 521.08 | 3-{4-(3-chlorophenyl)-5-[3,5-dimethylbenzyl)sulfanyl]-4H-1,2,4-triazol-3-yl}-N-(4-methoxybenzyl)propanamide | 521 |
| 134 | 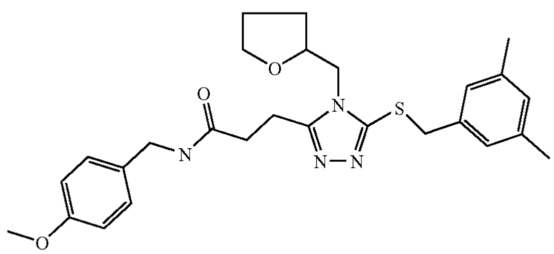 | 494.66 | 3-[5-[(3,5-dimethylbenzyl)sulfanyl]-4-(tetrahydro-2-furanylmethyl)-4H-1,2,4-triazol-3-yl]-N-(4-methoxybenzyl)propanamide | 495 |
| 135 | 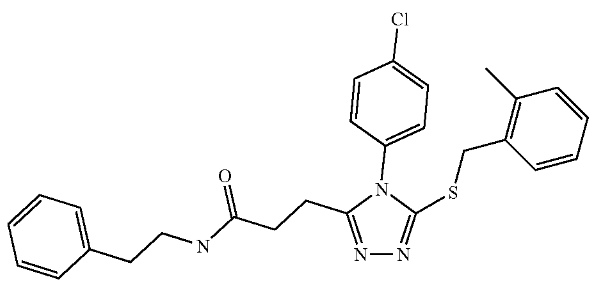 | 491.06 | 3-{4-(4-chlorophenyl)-5-[(2-methylbenzyl)sulfanyl]-4H-1,2,4-triazol-3-yl}-N-(2-phenylethyl)propanamide | 491 |
| 136 | 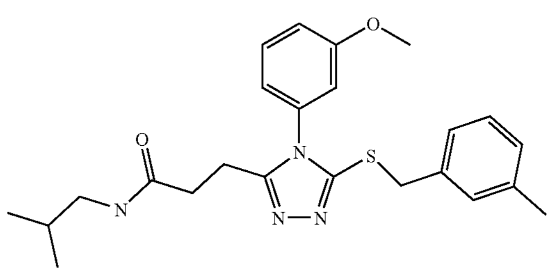 | 438.59 | N-isobutyl-3-{4-(3-methoxyphenyl)-5-[(3-methylbenzyl)sulfanyl]-4H-1,2,4-triazol-3-yl}propanamide | 439 |
| 137 | 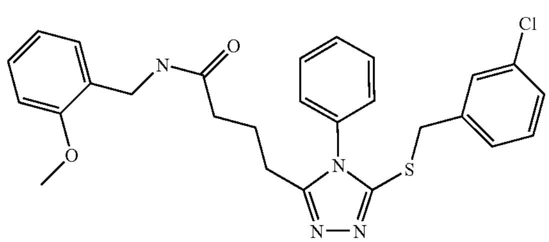 | 507.06 | 4-{5-[(3-chlorobenzyl)sulfanyl]-4-phenyl-4H-1,2,4-triazol-3-yl}-N-(2-methoxybenzyl)butanamide | 507 |

TABLE 2-continued

| Example No. | Chemical Structure | M.W. | IUPAC-Name | M+(ESI+) |
|---|---|---|---|---|
| 138 | 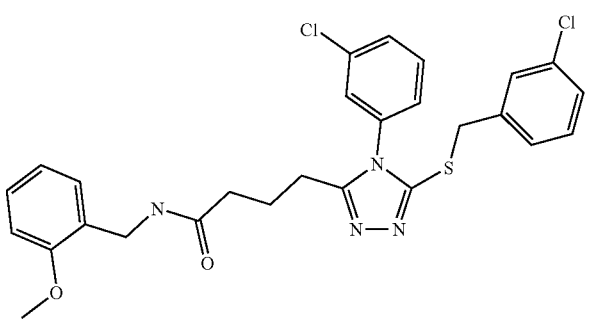 | 541.50 | 4-[5-[(3-chlorobenzyl)sulfanyl]-4-(3-chlorophenyl)-4H-1,2,4-triazol-3-yl]-N-(2-methoxybenzyl)butanamide | 542 |
| 139 | 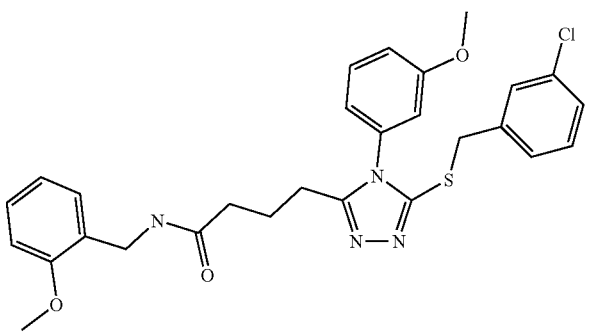 | 537.08 | 4-[5-[(3-chlorobenzyl)sulfanyl]-4-(3-methoxyphenyl)-4H-1,2,4-triazol-3-yl]-N-(2-methoxybenzyl)butanamide | 537 |
| 140 | 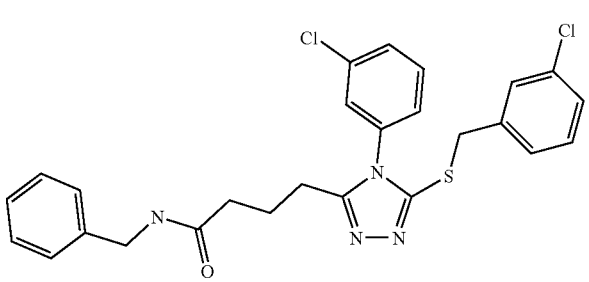 | 511.47 | N-benzyl-4-[5-[(3-chlorobenzyl)sulfanyl]-4-(3-chlorophenyl)-4H-1,2,4-triazol-3-yl]butanamide | 511 |
| 141 | 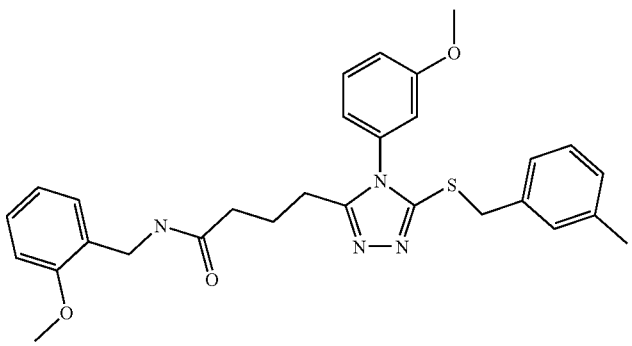 | 516.66 | N-(2-methoxybenzyl)-4-{4-(3-methoxyphenyl)-5-[(3-methylbenzyl)sulfanyl]-4H-1,2,4-triazol-3-yl}butanamide | 517 |

TABLE 2-continued

| Example No. | Chemical Structure | M.W. | IUPAC-Name | M+(ESI+) |
|---|---|---|---|---|
| 142 | 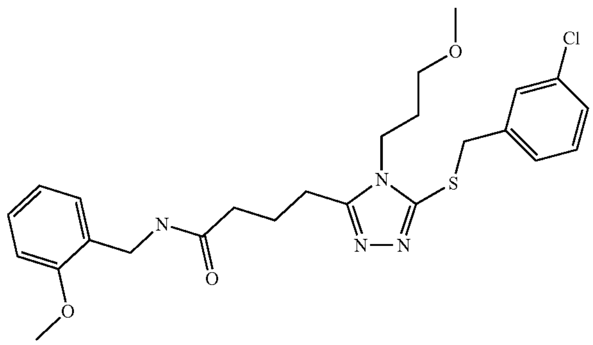 | 503.07 | 4-([5-[{(3-chlorobenzyl)sulfanyl]-4-(3-methoxypropyl)-4H-1,2,4-triazol-3-yl]-N-(2-methoxybenzyl)butanamide | 503 |
| 143 | 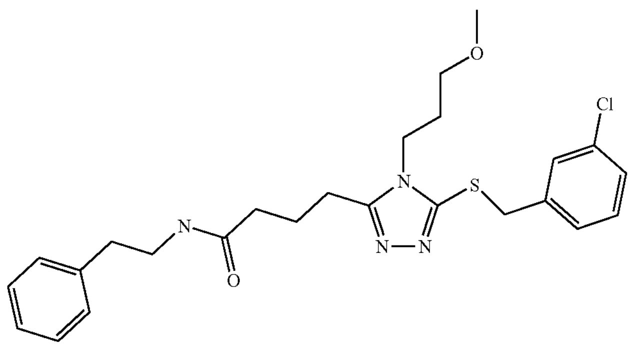 | 487.07 | 4-[5-[(3-chlorobenzyl)sulfanyl]-4-(3-methoxypropyl)-4H-1,2,4-triazol-3-yl]-N-(2-phenylethyl)butanamide | 487 |
| 144 | 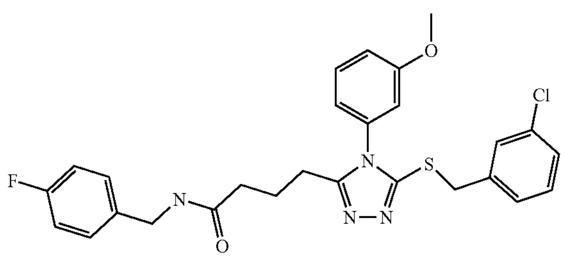 | 525.05 | 4-[5-[(3-chlorobenzyl)sulfanyl]-4-(3-methoxyphenyl)-4H-1,2,4-triazol-3-yl]-N-(4-fluorobenzyl)butanamide | 525 |
| 145 | 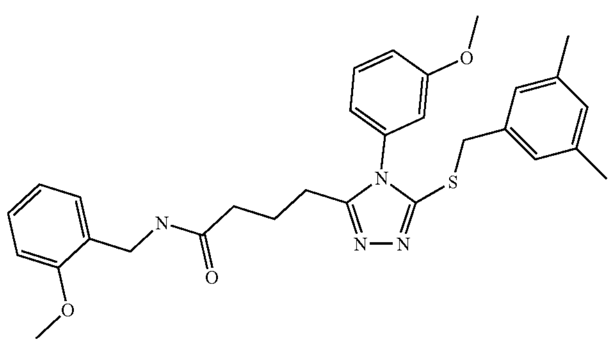 | 530.69 | 4-[5-[(3,5-dimethylbenzyl)sulfanyl]-4-(3-methoxyphenyl)-4H-1,2,4-triazol-3-yl]-N-(2-methoxybenzyl)butanamide | 531 |
| 146 | 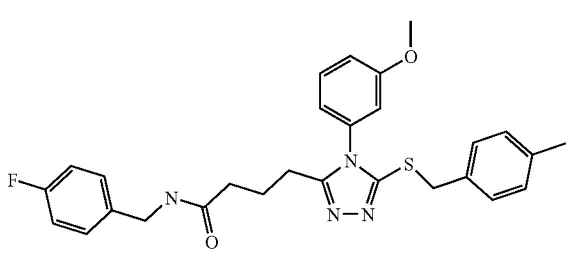 | 504.63 | N-(4-fluorobenzyl)-4-{4-(3-methoxyphenyl)-5-[(4-methylbenzyl)sulfanyl]-4H-1,2,4-triazol-3-yl}butanamide | 505 |

TABLE 2-continued

| Example No. | Chemical Structure | M.W. | IUPAC-Name | M⁺(ESI⁺) |
|---|---|---|---|---|
| 147 | 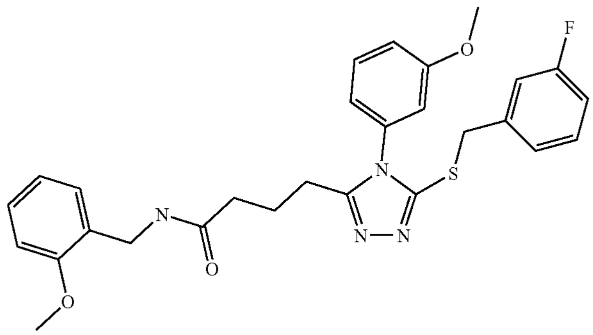 | 520.63 | 4-[5-[(3-fluorobenzyl)sulfanyl]-4-(3-methoxyphenyl)-4H-1,2,4-triazol-3-yl]-N-(2-methoxybenzyl)butanamide | 521 |
| 148 | 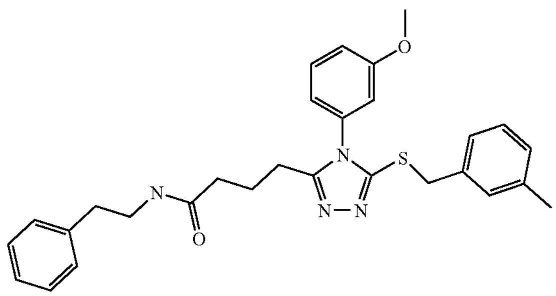 | 500.66 | 4-{4-(3-methoxyphenyl)-5-[(3-methylbenzyl)sulfanyl]-4H-1,2,4-triazol-3-yl}-N-(2-phenylethyl)butanamide | 501 |
| 149 | 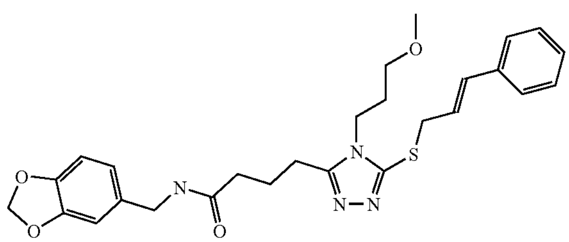 | 508.64 | N-(1,3-benzodioxol-5-ylmethyl)-4-(4-(3-methoxypropyl)-5-{[(2E)-3-phenyl-2-propenyl]sulfanyl}-4H-1,2,4-triazol-3-yl)butanamide | 509 |
| 150 | 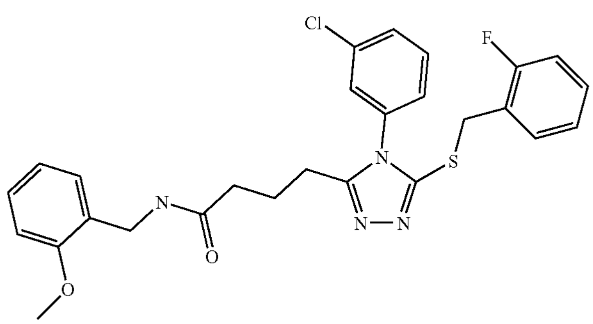 | 525.05 | 4-{4-(3-chlorophenyl)-5-[(2-fluorobenzyl)sulfanyl]-4H-1,2,4-triazol-3-yl}-N-(2-methoxybenzyl)butanamide | 525 |
| 151 | 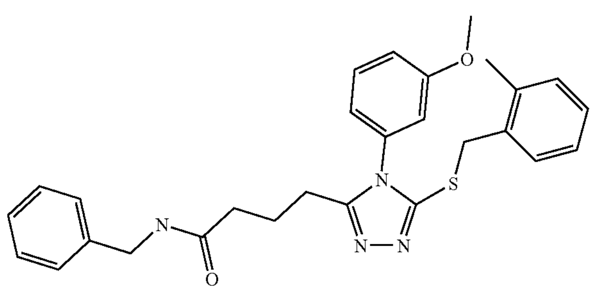 | 486.64 | N-benzyl-4-{4-(3-methoxyphenyl)-5-[(2-methylbenzyl)sulfanyl]-4H-1,2,4-triazol-3-yl}butanamide | 487 |

TABLE 2-continued

| Example No. | Chemical Structure | M.W. | IUPAC-Name | M+(ESI+) |
|---|---|---|---|---|
| 152 | 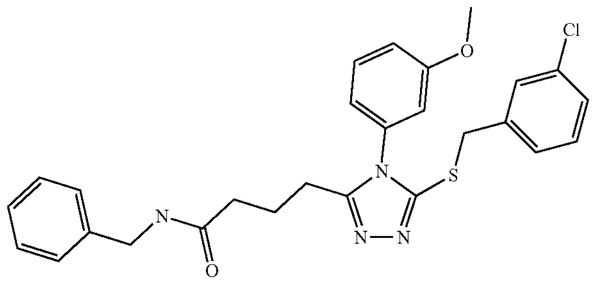 | 507.06 | N-benzyl-4-[5-[(3-chlorobenzyl)sulfanyl]-4-(3-methoxyphenyl)-4H-1,2,4-triazol-3-yl]butanamide | 570 |
| 153 | 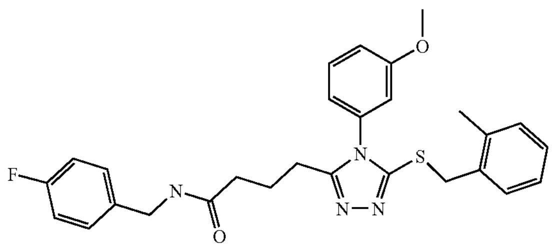 | 504.63 | N-(4-fluorobenzyl)-4-{4-(3-methoxyphenyl)-5-[(2-methylbenzyl)sulfanyl]-4H-1,2,4-triazol-3-yl}butanamide | 505 |
| 154 | 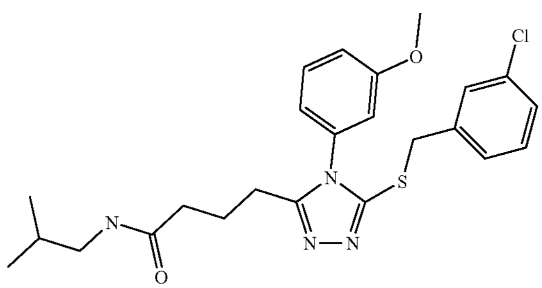 | 473.04 | 4-[5-[(3-chlorobenzyl)sulfanyl]-4-(3-methoxyphenyl)-4H-1,2,4-triazol-3-yl]-N-isobutylbutanamide | 473 |
| 155 | 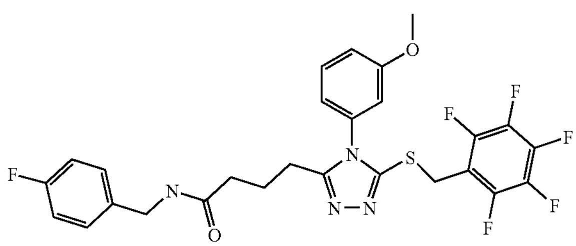 | 580.55 | N-(4-fluorobenzyl)-4-{4-(3-methoxyphenyl)-5-[(2,3,4,5,6-pentafluorobenzyl)sulfanyl]-4H-1,2,4-triazol-3-yl}butanamide | 581 |
| 156 | 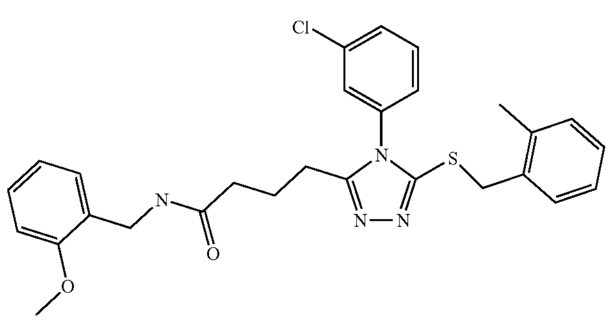 | 521.08 | 4-{4-(3-chlorophenyl)-5-[(2-methylbenzyl)sulfanyl]-4H-1,2,4-triazol-3-yl}-N-(2-methoxybenzyl)butanamide | 521 |

TABLE 2-continued

| Example No. | Chemical Structure | M.W. | IUPAC-Name | M⁺(ESI⁺) |
|---|---|---|---|---|
| 157 | 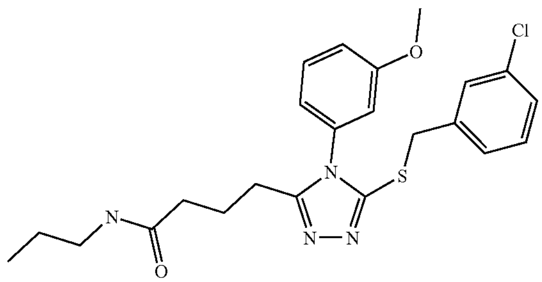 | 459.01 | 4-[5-[(3-chlorobenzyl)sulfanyl]-4-(3-methoxyphenyl)-4H-1,2,4-triazol-3-yl]-N-propylbutanamide | 459 |
| 158 | 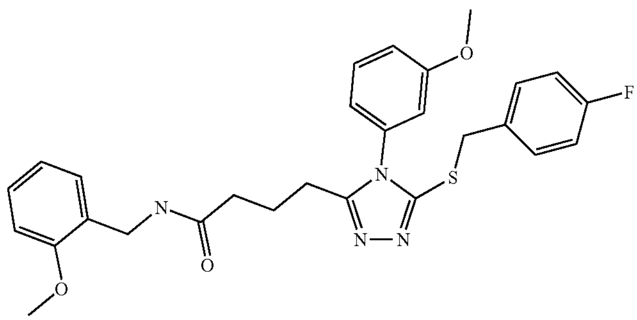 | 520.63 | 4-[5-[(4-fluorobenzyl)sulfanyl]-4-(3-methoxyphenyl)-4H-1,2,4-triazol-3-yl]-N-(2-methoxybenzyl)butanamide | 521 |
| 159 | 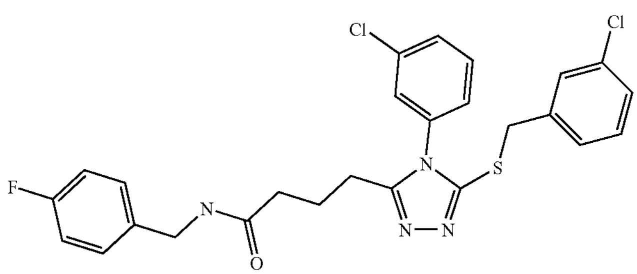 | 529.46 | 4-[5-[(3-chlorobenzyl)sulfanyl]-4-(3-chlorophenyl)-4H-1,2,4-triazol-3-yl]-N-(4-fluorobenzyl)butanamide | 529 |
| 160 | 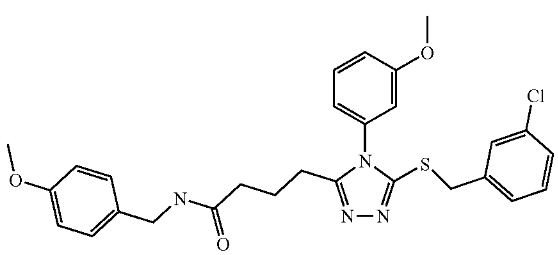 | 537.08 | 4-[5-[(3-chlorobenzyl)sulfanyl]-4-(3-methoxyphenyl)-4H-1,2,4-triazol-3-yl]-N-(4-methoxybenzyl)butanamide | 537 |
| 161 | 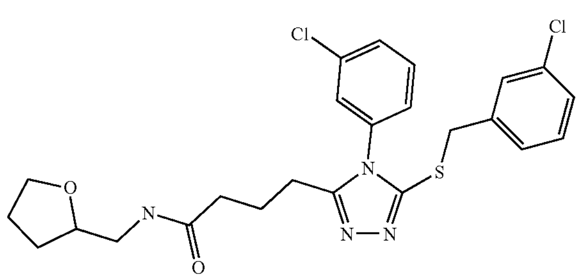 | 505.47 | 4-[5-[(3-chlorobenzyl)sulfanyl]-4-(3-chlorophenyl)-4H-1,2,4-triazol-3-yl]-N-(tetrahydro-2-furanylmethyl)butanamide | 505 |

TABLE 2-continued

| Example No. | Chemical Structure | M.W. | IUPAC-Name | M+(ESI+) |
|---|---|---|---|---|
| 162 | 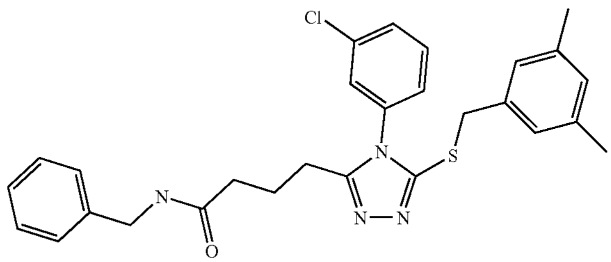 | 505.08 | N-benzyl-4-{4-(3-chlorophenyl)-5-[(3,5-dimethylbenzyl)sulfanyl]-4H-1,2,4-triazol-3-yl}butanamide | 505 |
| 163 | 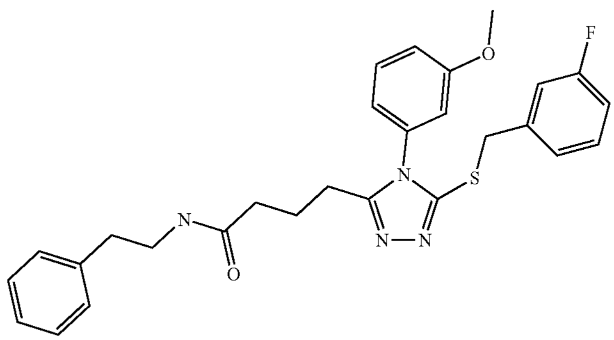 | 504.63 | 4-[5-[(3-fluorobenzyl)sulfanyl]-4-(3-methoxyphenyl)-4H-1,2,4-triazol-3-yl]-N-(2-phenylethyl)butanamide | 505 |
| 164 | 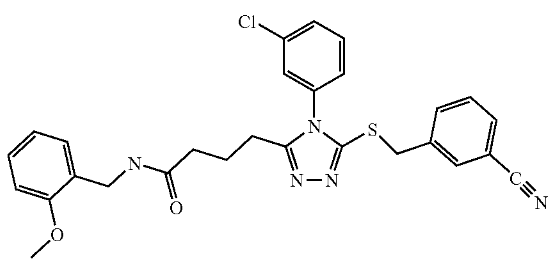 | 532.07 | 4-[3-chlorophenyl)-5-[(3-cyanobenzyl)sulfanyl]-4H-1,2,4-triazol-3-yl}-N-(2-methoxybenzyl)butanamide | 532 |
| 165 | 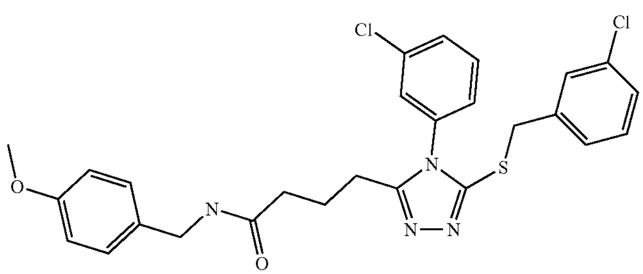 | 541.50 | 4-[5-[(3-chlorobenzyl)sulfanyl]-4-(3-chlorophenyl)-4H-1,2,4-triazol-3-yl]-N-(4-methoxybenzyl)butanamide | 542 |
| 166 | 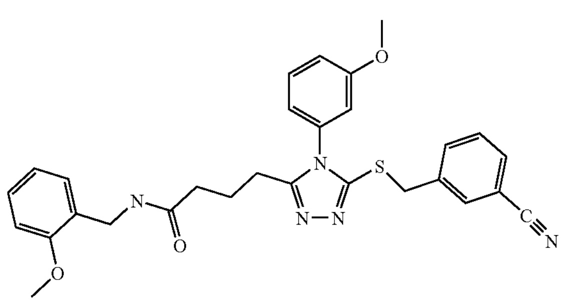 | 527.65 | 4-[5-[(3-cyanobenzyl)sulfanyl]-4-(3-methoxyphenyl)-4H-1,2,4-triazol-3-yl]-N-(2-methoxybenzyl)butanamide | 528 |

TABLE 2-continued

| Example No. | Chemical Structure | M.W. | IUPAC-Name | M+(ESI+) |
|---|---|---|---|---|
| 167 | 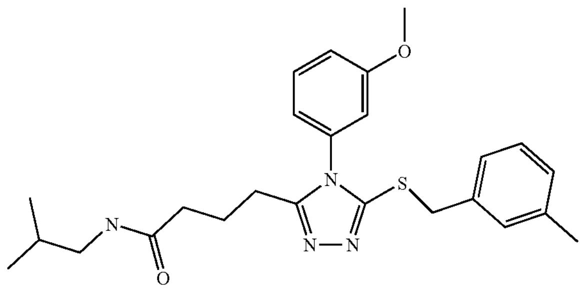 | 452.62 | N-isobutyl-4-{4-(3-methoxyphenyl)-5-[(3-methylbenzyl)sulfanyl]-4H-1,2,4-triazol-3-yl}butanamide | 453 |
| 168 | 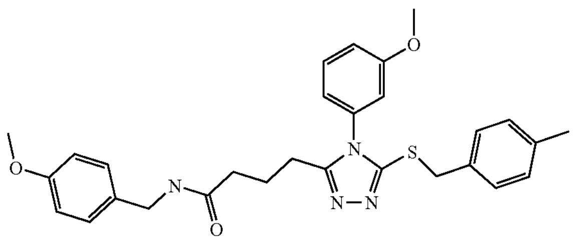 | 516.66 | N-(4-methoxybenzyl)-4-{4-(3-methoxyphenyl)-5-[(4-methylbenzyl)sulfanyl]-4H-1,2,4-triazol-3-yl}butanamide | 517 |
| 169 | 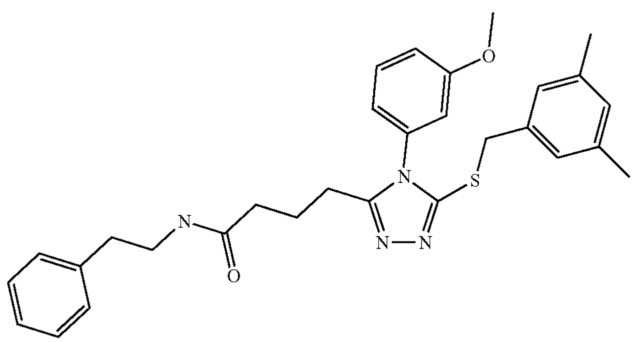 | 514.69 | 4-[5-[(3,5-dimethylbenzyl)sulfanyl]-4-(3-methoxyphenyl)-4H-1,2,4-triazol-3-yl]-N-(2-phenylethyl)butanamide | 515 |
| 170 | 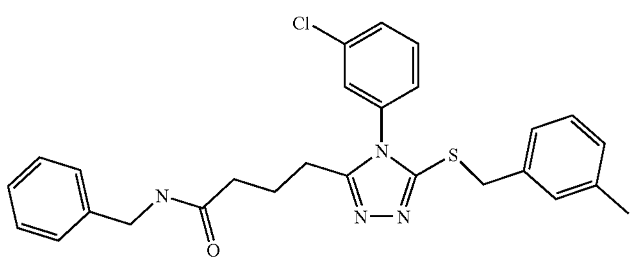 | 491.06 | N-benzyl-4-{4-(3-chlorophenyl)-5-[(3-methylbenzyl)sulfanyl]-4H-1,2,4-triazol-3-yl}butanamide | 491 |
| 171 | 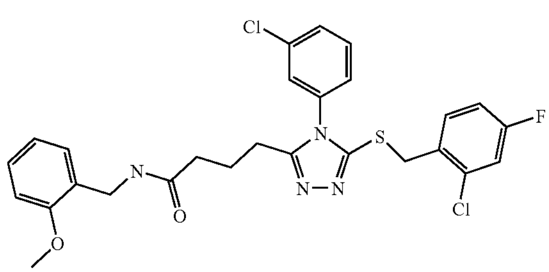 | 559.49 | 4-[5-[(2-chloro-4-fluorobenzyl)sulfanyl]-4-(3-chlorophenyl)-4H-1,2,4-triazol-3-yl]-N-(2-methoxybenzyl)butanamide | 559 |

US 7,468,385 B2

TABLE 2-continued

| Example No. | Chemical Structure | M.W. | IUPAC-Name | M+(ESI+) |
|---|---|---|---|---|
| 172 | 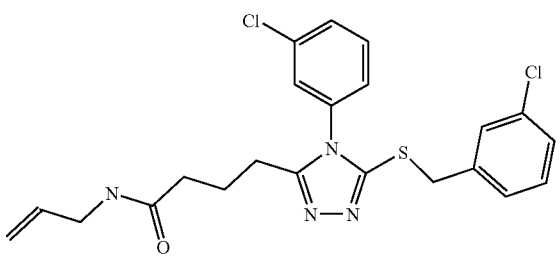 | 461.41 | N-allyl-4-[5-[(3-chlorobenzyl)sulfanyl]-4-(3-chlorophenyl)-4H-1,2,4-triazol-3-yl]butanamide | 461 |
| 173 | 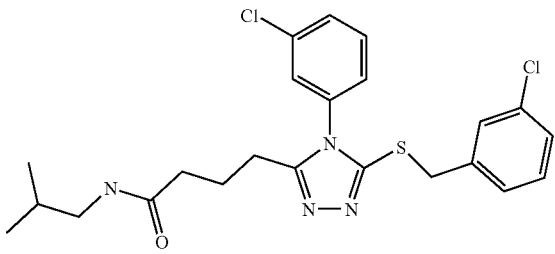 | 477.46 | 4-[5-[(3-chlorobenzyl)sulfanyl]-4-(3-chlorophenyl)-4H-1,2,4-triazol-3-yl]-N-isobutylbutanamide | 477 |
| 174 | 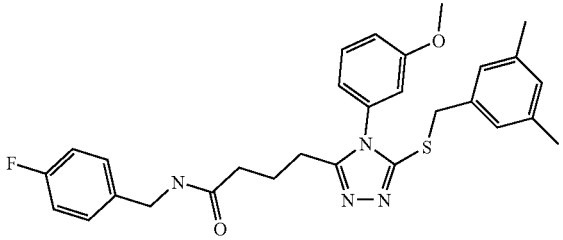 | 518.66 | 4-[5-[(3,5-dimethylbenzyl)sulfanyl]-4-(3-methoxyphenyl)-4H-1,2,4-triazol-3-yl]-N-(4-fluorobenzyl)butanamide | 519 |
| 175 | 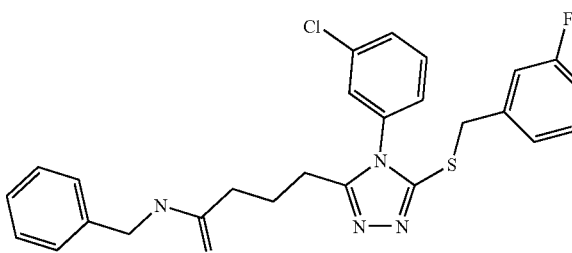 | 495.02 | N-benzyl-4-{4-(3-chlorophenyl)-5-[(3-fluorobenzyl)sulfanyl]-4H-1,2,4-triazol-3-yl}butanamide | 495 |
| 176 | 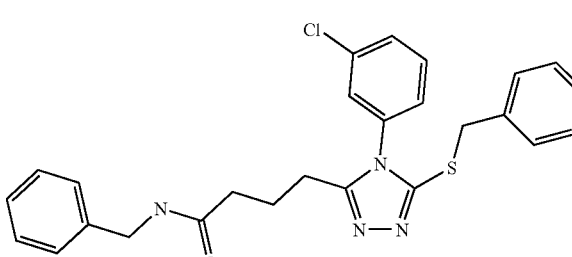 | 477.03 | N-benzyl-4-{5-(benzylsulfanyl)-4-(3-chlorophenyl)-4H-1,2,4-triazol-3-yl]butanamide | 477 |

TABLE 2-continued

| Example No. | Chemical Structure | M.W. | IUPAC-Name | M+(ESI+) |
|---|---|---|---|---|
| 177 | 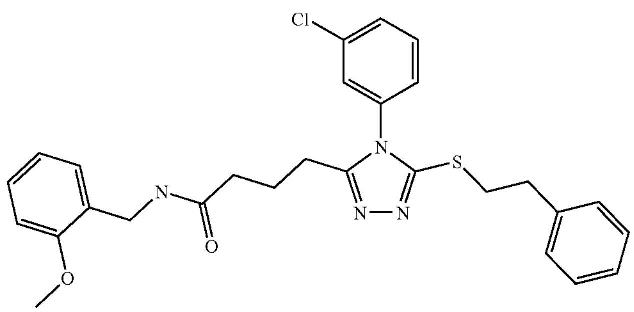 | 521.08 | 4-{4-(3-chlorophenyl)-5-[(2-phenylethyl)sulfanyl]-4H-1,2,4-triazol-3-yl]-N-(2-methoxybenzyl)butanamide | 521 |
| 178 | 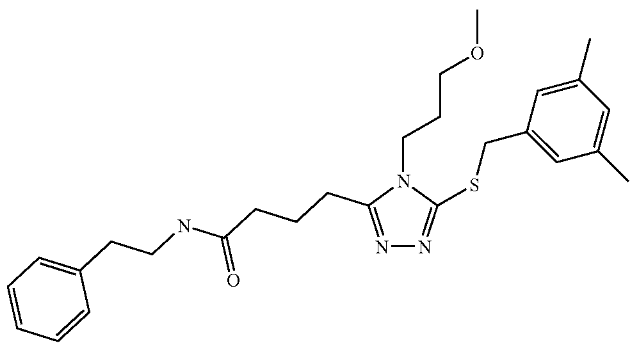 | 480.67 | 4-[5-[(3,5-dimethylbenzyl)sulfanyl]-4-(3-methoxypropyl)-4H-1,2,4-triazol-3-yl]-N-(2-phenylethyl)butanamide | 481 |
| 179 | 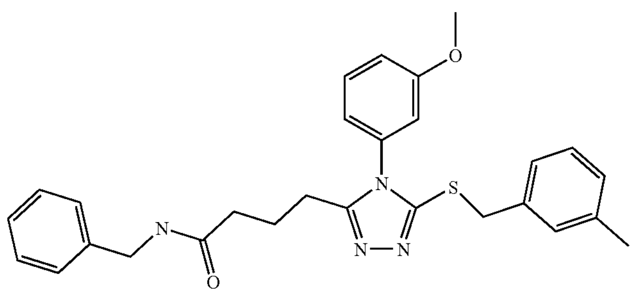 | 486.64 | N-benzyl-4-{4-(3-methoxyphenyl)-5-[(3-methylbenzyl)sulfanyl]-4H-1,2,4-triazol-3-yl}butanamide | 487 |
| 180 | 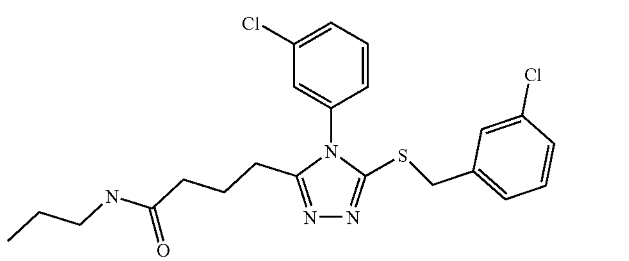 | 463.43 | 4-[5-{(3-chlorobenzyl)sulfanyl]-4-(3-chlorophenyl)-4H-1,2,4-triazol-3-yl]-N-propylbutanamide | 463 |
| 181 | 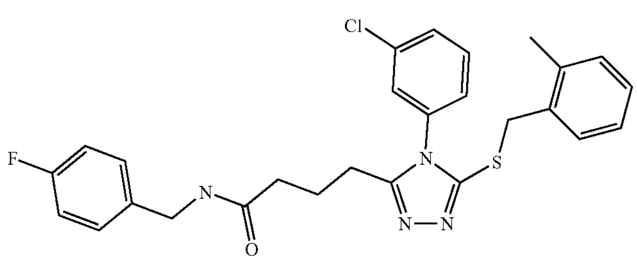 | 509.05 | 4-{4-(3-chlorophenyl)-5-[(2-methylbenzyl)sulfanyl]-4H-1,2,4-triazol-3-yl}-N-(4-fluorobenzyl)butanamide | 509 |

TABLE 2-continued

| Example No. | Chemical Structure | M.W. | IUPAC-Name | M+(ESI+) |
|---|---|---|---|---|
| 182 | 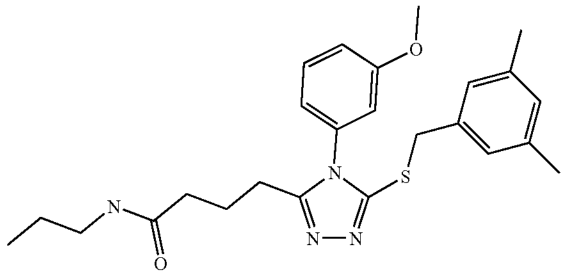 | 452.62 | 4-[5-[(3,5-dimethylbenzyl) sulfanyl]-4-(3-methoxyphenyl)-4H-1,2,4-triazol-3-yl]-N-propylbutanamide | 453 |
| 183 | 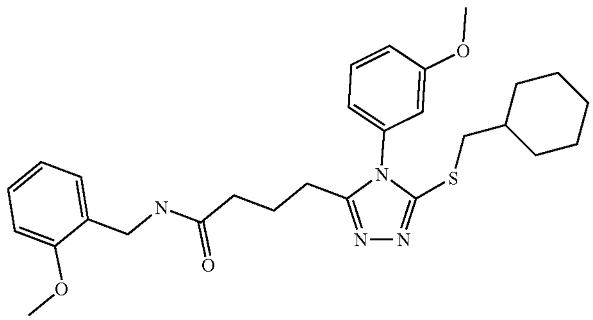 | 508.69 | 4-[5-[(cyclohexylmethyl) sulfanyl]-4-(3-methoxyphenyl)-4H-1,2,4-triazol-3-yl]-N-(2-methoxybenzyl)butanamide | 509 |
| 184 | 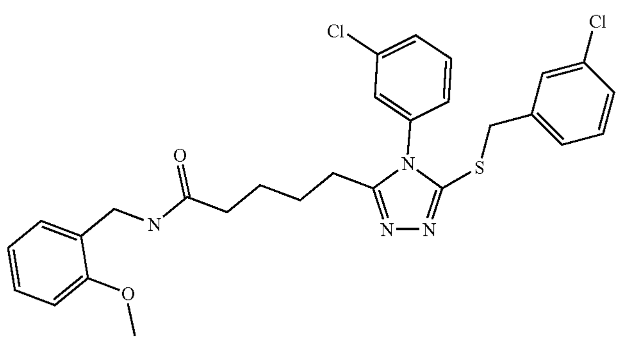 | 555.53 | 5-[5-[(3-chlorobenzyl) sulfanyl]-4-(3-chlorophenyl)-4H-1,2,4-triazol-3-yl]-N-(2-methoxybenzyl)pentanamide | 555 |
| 185 | 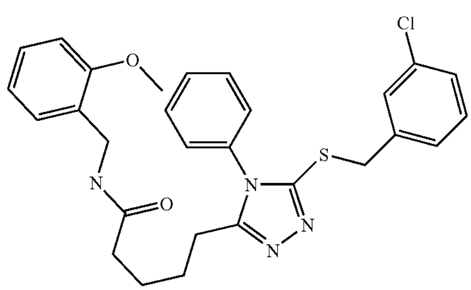 | 521.08 | 4-{5-[(3-chlorobenzyl) sulfanyl]-4-phenyl-4H-1,2,4-triazol-3-yl}-N-(2-methoxybenzyl)pentanamide | 521 |
| 186 | 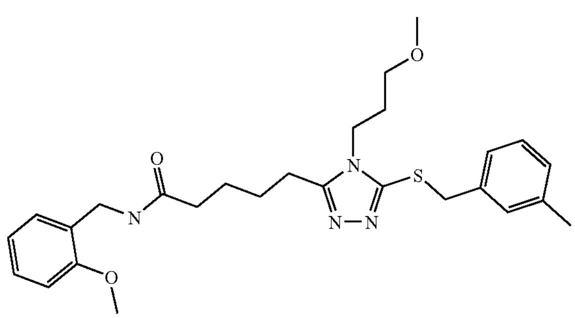 | 496.67 | N-(2-methoxybenzyl)-5-{4-(3-methoxypropyl)-5-[(3-methylbenzyl) sulfanyl]-4H-1,2,4-triazol-3-yl}pentanamide | 497 |

TABLE 2-continued

| Example No. | Chemical Structure | M.W. | IUPAC-Name | M+(ESI+) |
|---|---|---|---|---|
| 187 | 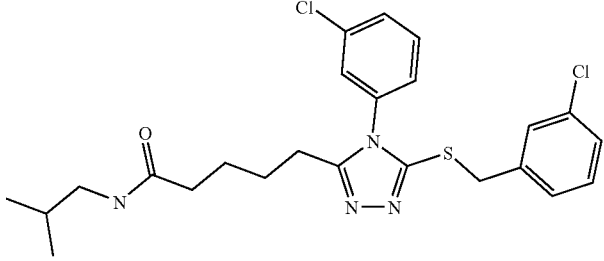 | 491.48 | 5-[5-[(3-chlorobenzyl)sulfanyl]-4-(3-chlorophenyl)-4H-1,2,4-triazol-3-yl]-N-isobutylpentanamide | 491 |
| 188 | 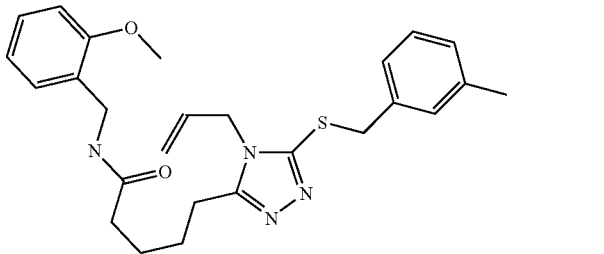 | 464.63 | 4-{4-allyl-5-[(3-methylbenzyl)sulfanyl]-4H-1,2,4-triazol-3-yl}-N-(2-methoxybenzyl)pentanamide | 465 |
| 189 | 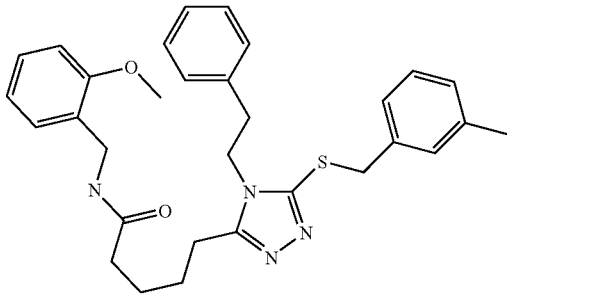 | 528.72 | N-(2-methoxybenzyl)-5-[5-[(3-methylbenzyl)sulfanyl]-4-(2-phenylethyl)-4H-1,2,4-triazol-3-yl]pentanamide | 529 |
| 190 | 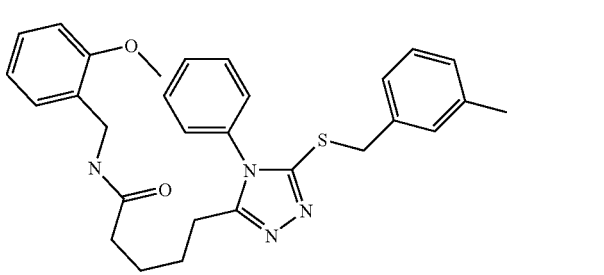 | 500.66 | N-(2-methoxybenzyl)-5-{5-[3-methylbenzyl)sulfanyl]-4-phenyl-4H-1,2,4-triazol-3-yl}pentanamide | 501 |
| 191 | 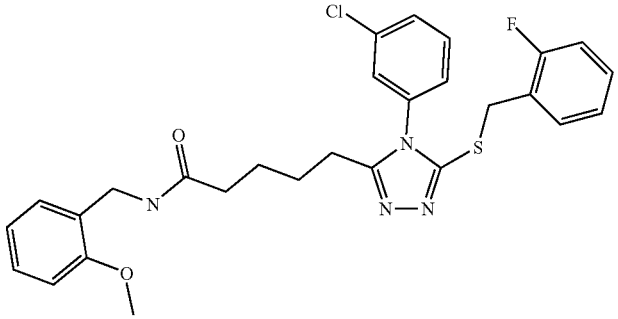 | 539.07 | 5-{4-(3-chlorophenyl)-5-[(2-fluorobenzyl)sulfanyl]-4H-1,2,4-triazol-3-yl}-N-(2-methoxybenzyl)pentanamide | 539 |

TABLE 2-continued

| Example No. | Chemical Structure | M.W. | IUPAC-Name | M+(ESI+) |
|---|---|---|---|---|
| 192 | 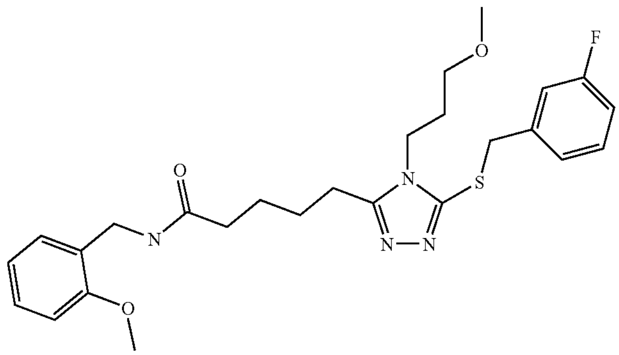 | 500.64 | 5-[5-[(3-fluorobenzyl)sulfanyl]-4-(3-methoxypropyl)-4H-1,2,4-triazol-3-yl]-N-(2-methoxybenzyl)pentanamide | 501 |
| 193 | 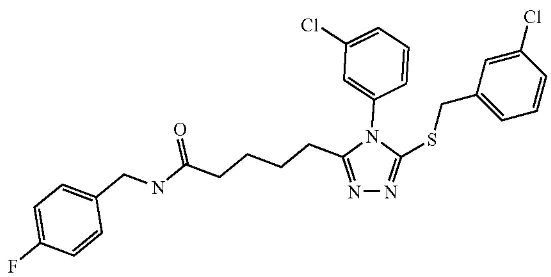 | 543.49 | 5-[5-[(3-chlorobenzyl)sulfanyl]-4-(3-chlorophenyl)-4H-1,2,4-triazol-3-yl]-N-(4-fluorobenzyl)pentanamide | 543 |
| 194 | 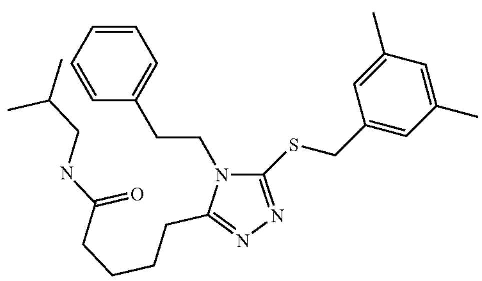 | 478.70 | 5-[5-[(3,5-dimethylbenzyl)sulfanyl]-4-(2-phenylethyl)-4H-1,2,4-triazol-3-yl]-N-isobutylpentanamide | 479 |
| 195 | 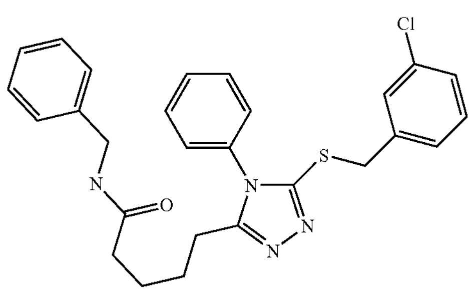 | 491.06 | N-benzyl-5-{5-[(3-chlorobenzyl)sulfanyl]-4-phenyl-4H-1,2,4-triazol-3-yl}pentanamide | 491 |
| 196 | 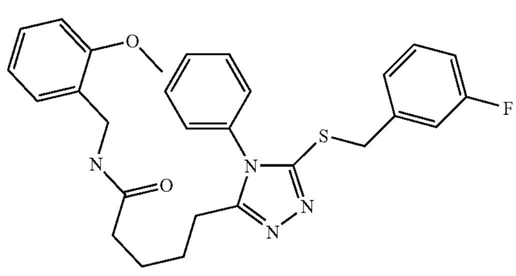 | 504.63 | 5-{5-[(3-fluorobenzyl)sulfanyl]-4-phenyl-4H-1,2,4-triazol-3-yl}-N-(2-methoxybenzyl)pentanamide | 505 |

TABLE 2-continued

| Example No. | Chemical Structure | M.W. | IUPAC-Name | M⁺(ESI⁺) |
|---|---|---|---|---|
| 197 | 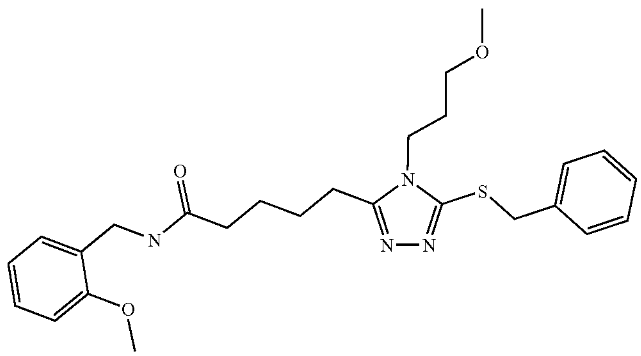 | 482.65 | 5-[5-(benzylsulfanyl)-4-(3-methoxypropyl)-4H-1,2,4-triazol-3-yl]-N-(2-methoxypropyl)pentanamide | 483 |
| 198 | 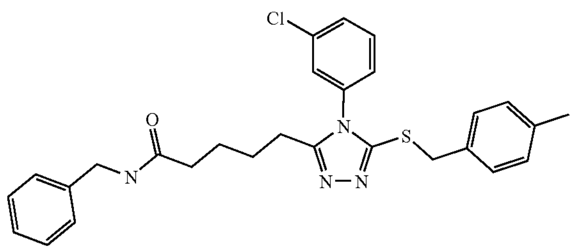 | 505.08 | N-benzyl-5-{4-(3-chlorophenyl)-5-[(4-methylbenzyl)sulfanyl]-4H-1,2,4-triazol-3-yl}pentanamide | 505 |
| 199 | 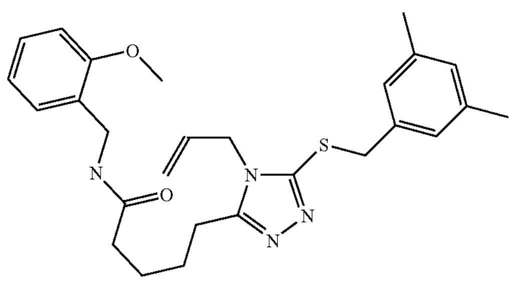 | 478.66 | 5-{4-allyl-5-[(3,5-dimethylbenzyl)sulfanyl]-4H-1,2,4-triazol-3-yl}-N-(2-methoxybenzyl)pentanamide | 479 |
| 200 | 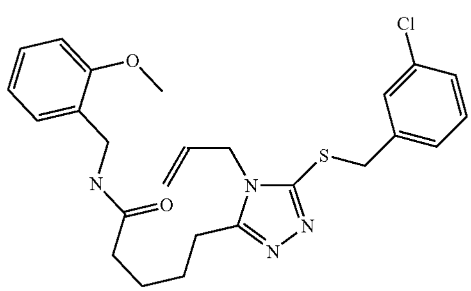 | 485.05 | 5-{4-allyl-5-[(3-chlorobenzyl)sulfanyl]-4H-1,2,4-triazol-3-yl}-N-(2-methoxybenzyl)pentanamide | 485 |
| 201 | 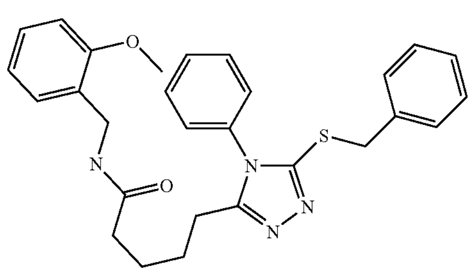 | 486.64 | 5-[5-(benzylsulfanyl)-4-phenyl-4H-1,2,4-triazol-3-yl]-N-(2-methoxybenzyl)pentanamide | 487 |

TABLE 2-continued

| Example No. | Chemical Structure | M.W. | IUPAC-Name | M+(ESI+) |
|---|---|---|---|---|
| 202 | 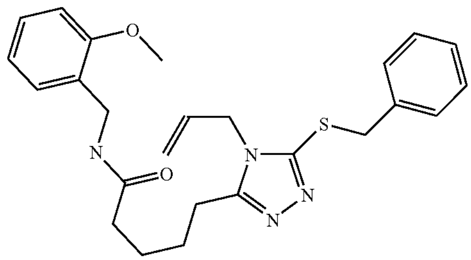 | 450.61 | 5-[4-allyl-5-(benzyl-sulfanyl)-4H-1,2,4-triazol-3-yl]-N-(2-methoxybenzyl)pentanamide | 451 |
| 203 | 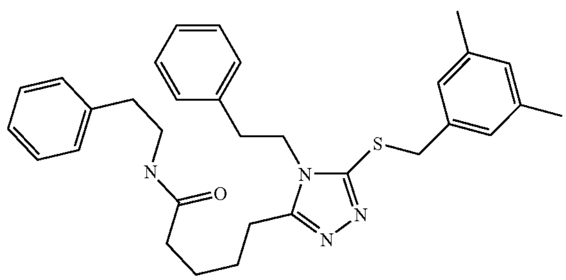 | 526.75 | 5-[5-[(3,5-dimethylbenzyl)sulfanyl]-4-(2-phenylethyl)-4H-1,2,4-triazol-3-yl]-N-(2-phenylethyl)pentanamide | 527 |
| 204 | 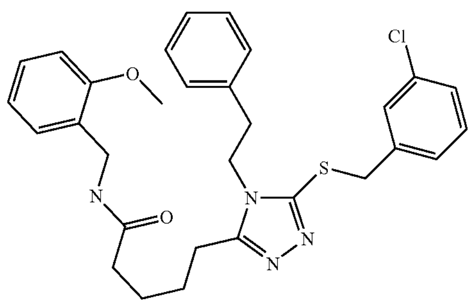 | 549.14 | 5-[5-[(3-chlorobenzyl)sulfanyl]-4-(2-phenylethyl)-4H-1,2,4-triazol-3-yl]-N-(2-methoxybenzyl)pentanamide | 549 |
| 205 | 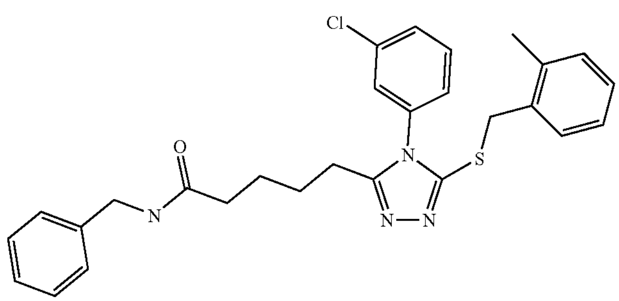 | 505.08 | N-benzyl-5-{4-(3-chlorophenyl)-5-[(2-methylbenzyl)sulfanyl]-4H-1,2,4-triazol-3-yl}pentanamide | 505 |
| 206 | 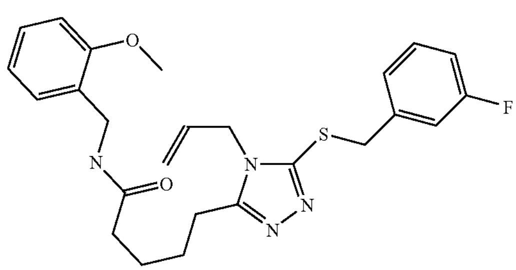 | 468.60 | 4-allyl-5-[(3-fluorobenzyl)sulfanyl]-4H-1,2,4-triazol-3-yl}-N-(2-methoxybenzyl)pentanamide | 469 |

TABLE 2-continued

| Example No. | Chemical Structure | M.W. | IUPAC-Name | M⁺(ESI⁺) |
|---|---|---|---|---|
| 207 | 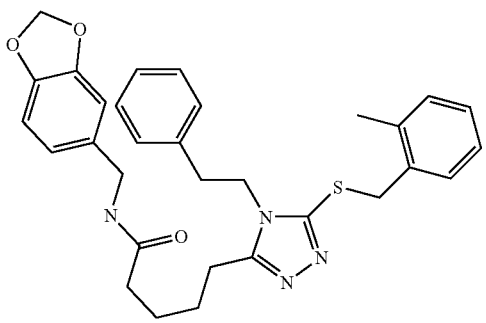 | 542.70 | N-(1,3-benzodioxol-5-ylmethyl)-5-[5-[(2-methylbenzyl)sulfanyl]-4-(2-phenylethyl)-4H-1,2,4-triazol-3-yl]pentanamide | 543 |
| 208 | 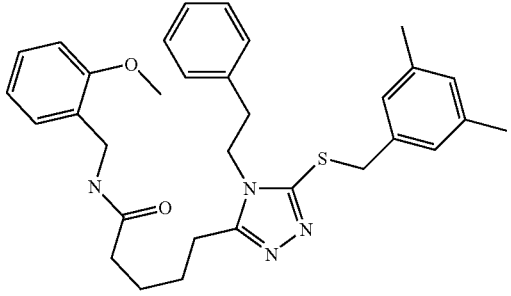 | 542.75 | 5-[5-[(3,5-dimethylbenzyl)sulfanyl]-4-(2-phenylethyl)-4H-1,2,4-triazol-3-yl]-N-(2-methoxybenzyl)pentanamide | 543 |
| 209 | 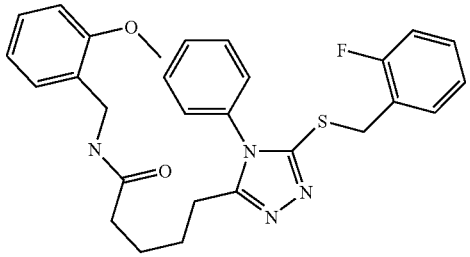 | 504.63 | 5-{5-[(2-fluorobenzyl)sulfanyl]-4-phenyl-4H-1,2,4-triazol-3-yl}-N-(2-methoxybenzyl)pentanamide | 505 |
| 210 | 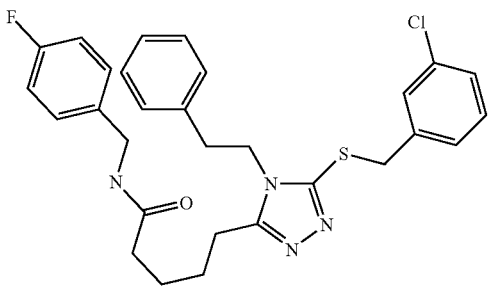 | 537.10 | 5-[5-[(3-chlorobenzyl)sulfanyl]-4-(2-phenylethyl)-4H-1,2,4-triazol-3-yl]-N-(4-fluorobenzyl)pentanamide | 537 |
| 211 | 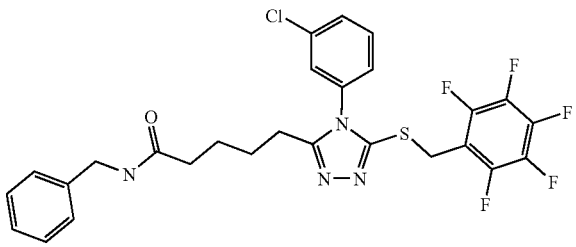 | 581.01 | N-benzyl-5-{4-(3-chlorophenyl)-5-[(2,3,4,5,6-pentafluorobenzyl)sulfanyl]-4H-1,2,4-triazol-3-yl}pentanamide | 581 |

TABLE 2-continued

| Example No. | Chemical Structure | M.W. | IUPAC-Name | M+(ESI+) |
|---|---|---|---|---|
| 212 | 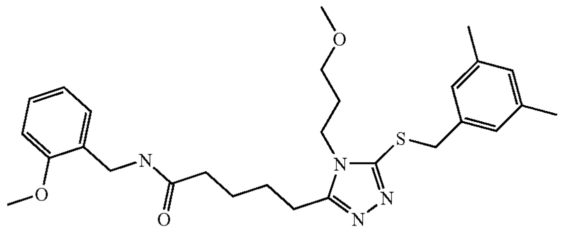 | 510.70 | 5-[5-[(3,5-dimethylbenzyl)sulfanyl]-4-(3-methoxypropyl)-4H-1,2,4-triazol-3-yl]-N-(2-methoxybenzyl)pentanamide | 511 |
| 213 | 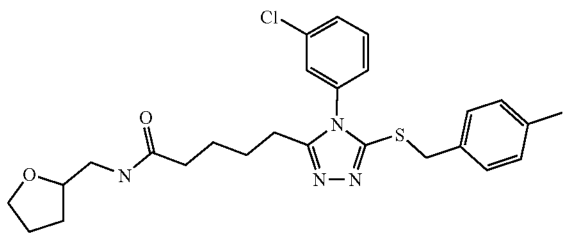 | 499.08 | 5-{4-(3-chlorophenyl)-5-[(4-methylbenzyl)sulfanyl]-4H-1,2,4-triazol-3-yl}-N-(tetrahydro-2-furanylmethyl)pentanamide | 499 |
| 214 | 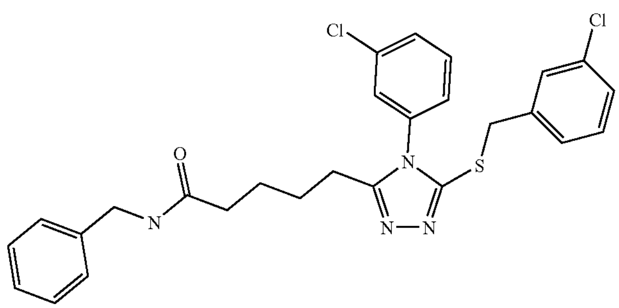 | 525.50 | N-benzyl-5-[5-[(3-chlorobenzyl)sulfanyl]-4-(3-chlorophenyl)-4H-1,2,4-triazol-3-yl]pentanamide | 526 |
| 215 | 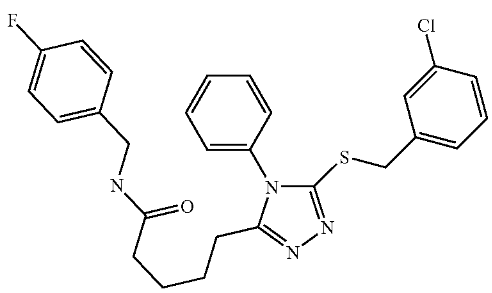 | 509.05 | 5-{5-[(3-chlorobenzyl)sulfanyl]-4-phenyl-4H-1,2,4-triazol-3-yl}-N-(4-fluorobenzyl)pentanamide | 509 |
| 216 | 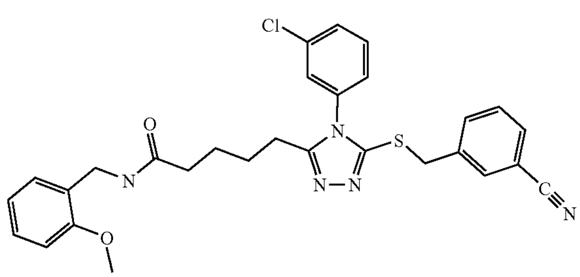 | 546.09 | 5-{4-(3-chlorophenyl)-5-[(3-cyanobenzyl)sulfanyl]-4H-1,2,4-triazol-3-yl}-N-(2-methoxybenzyl)pentanamide | 546 |

TABLE 2-continued

| Example No. | Chemical Structure | M.W. | IUPAC-Name | M+(ESI+) |
|---|---|---|---|---|
| 217 | 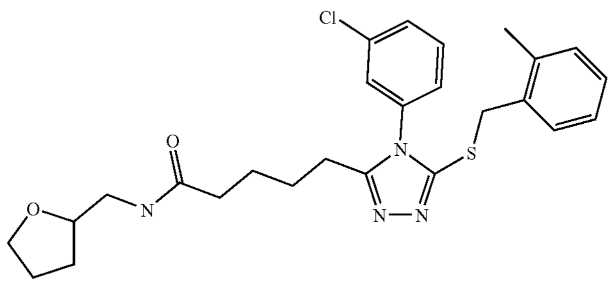 | 499.08 | 5-{4-(3-chlorophenyl)-5-[(2-methylbenzyl)sulfanyl]-4H-1,2,4-triazol-3-yl}-N-(tetrahydro-2-furanylmethyl)pentanamide | 499 |
| 218 | 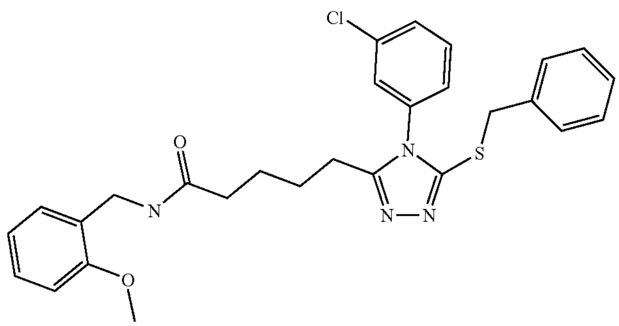 | 521.08 | 5-[5-(benzylsulfanyl)-4-(3-chlorophenyl)-4H-1,2,4-triazol-3-yl]-N-(2-methoxybenzyl)pentanamide | 521 |
| 219 | 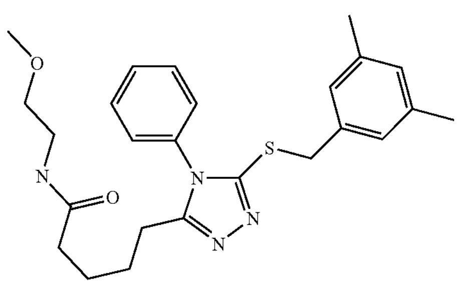 | 452.62 | 5-{5-[(3,5-dimethylbenzyl)sulfanyl]-4-phenyl-4H-1,2,4-triazol-3-yl}-N-(2-methoxyethyl)pentanamide | 453 |
| 220 | 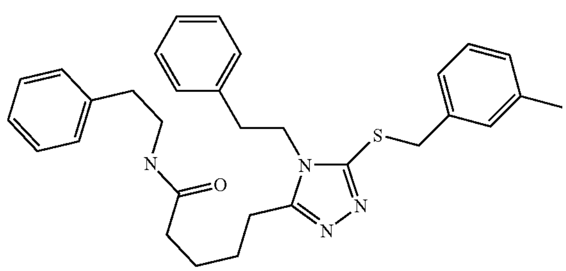 | 512.72 | 5-[5-[(3-methylbenzyl)sulfanyl]-4-(2-phenylethyl)-4H-1,2,4-triazol-3-yl]-N-(2-phenylethyl)pentanamide | 513 |
| 221 | 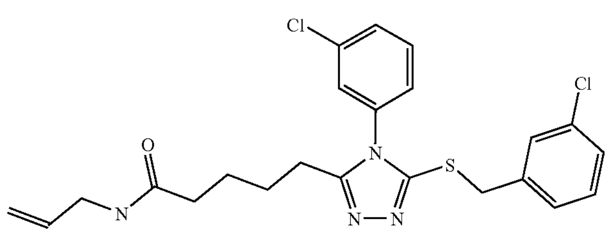 | 475.44 | N-allyl-5-[5-[(3-chlorobenzyl)sulfanyl]-4-(3-chlorophenyl)-4H-1,2,4-triazol-3-yl]pentanamide | 475 |

TABLE 2-continued

| Example No. | Chemical Structure | M.W. | IUPAC-Name | M+(ESI+) |
|---|---|---|---|---|
| 222 | 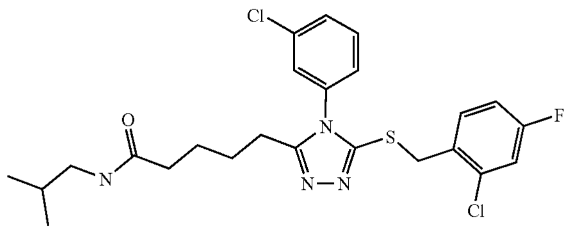 | 509.47 | 5-[5-[(2-chloro-4-fluorobenzyl)sulfanyl]-4-(3-chlorophenyl)-4H-1,2,4-triazol-3-yl]-N-isobutylpentanamide | 509 |
| 223 | 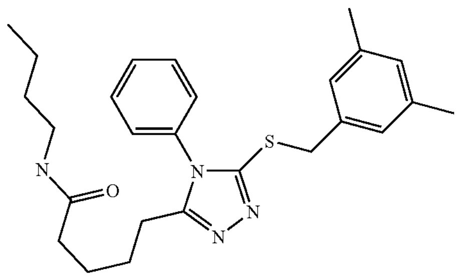 | 450.65 | N-butyl-5-{5-[(3,5-dimethylbenzyl)sulfanyl]-4-phenyl-4H-1,2,4-triazol-3-yl}pentanamide | 451 |
| 224 | 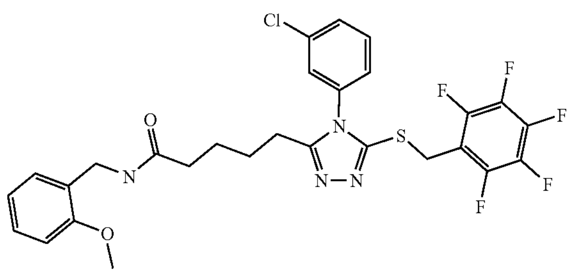 | 611.04 | 5-{4-(3-chlorophenyl)-5-[(2,3,4,5,6-pentafluorobenzyl)sulfanyl]-4H-1,2,4-triazol-3-yl]-N-(2-methoxybenzyl)pentanamide | 611 |
| 225 | 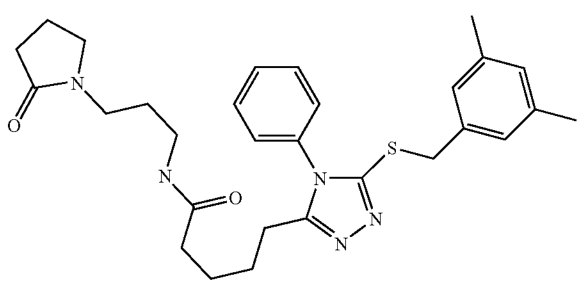 | 519.71 | 5-{5-[(3,5-dimethylbenzyl)sulfanyl]-4-phenyl-4H-1,2,4-triazol-3-yl}-N-[3-(2-oxo-1-pyrrolidinyl)propyl]pentanamide | 520 |
| 226 | 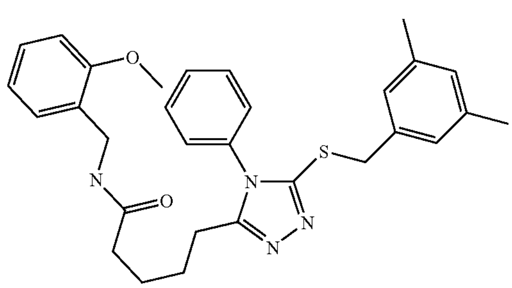 | 514.69 | 5-{5-[(3,5-dimethylbenzyl)sulfanyl]-4-phenyl-4H-1,2,4-triazol-3-yl}-N-(2-methoxybenzyl)pentanamide | 515 |

TABLE 2-continued

| Example No. | Chemical Structure | M.W. | IUPAC-Name | M+(ESI+) |
|---|---|---|---|---|
| 227 | 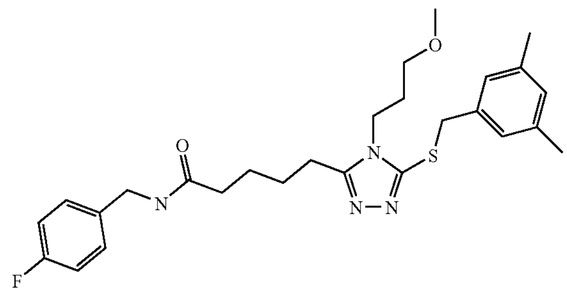 | 498.67 | 5-[5-[(3,5-dimethylbenzyl)sulfanyl]-4-(3-methoxypropyl)-4H-1,2,4-triazol-3-yl]-N-(4-fluorobenzyl)pentanamide | 499 |
| 228 | 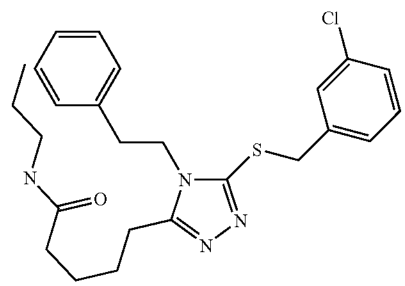 | 471.07 | 5-[5-[(3-chlorobenzyl)sulfanyl]-4-(2-phenylethyl)-4H-1,2,4-triazol-3-yl]-N-propylpentanamide | 471 |
| 229 | 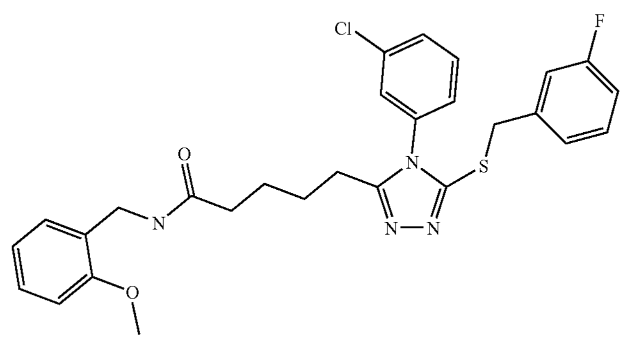 | 539.07 | 5-{4-(3-chlorophenyl)-5-[(3-fluorobenzyl)sulfanyl]-4H-1,2,4-triazol-3-yl}-N-(2-methoxybenzyl)pentanamide | 539 |
| 230 | 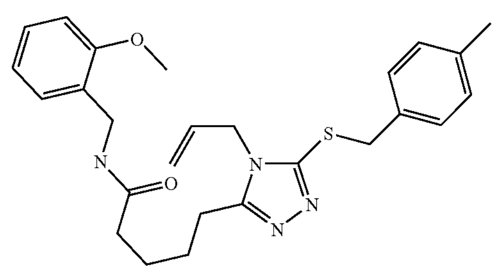 | 464.63 | 5-{4-allyl-5-[(4-methylbenzyl)sulfanyl]-4H-1,2,4-triazol-3-yl}-N-(2-methoxybenzyl)pentanamide | 465 |
| 231 | 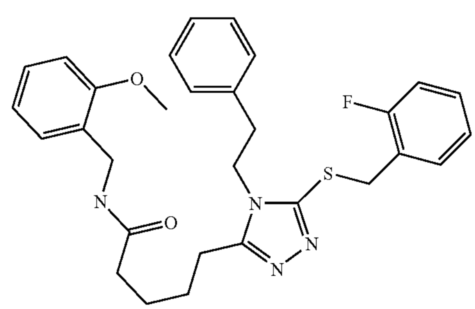 | 532.68 | 5-[5-[(2-fluorobenzyl)sulfanyl]-4-(2-phenylethyl)-4H-1,2,4-triazol-3-yl]-N-(2-methoxybenzyl)pentanamide | 533 |

TABLE 2-continued

| Example No. | Chemical Structure | M.W. | IUPAC-Name | M+(ESI+) |
|---|---|---|---|---|
| 232 | 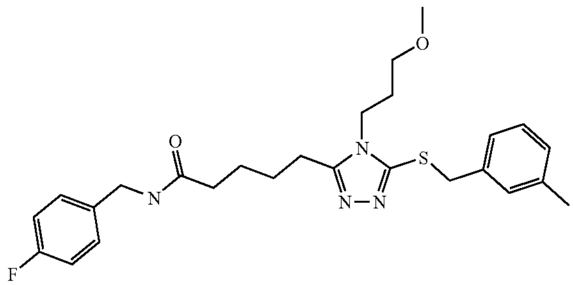 | 484.64 | N-(4-fluorobenzyl)-5-{4-(3-methoxypropyl)-5-[(3-methylbenzyl)sulfanyl]-4H-1,2,4-triazol-3-yl}pentanamide | 485 |
| 233 | 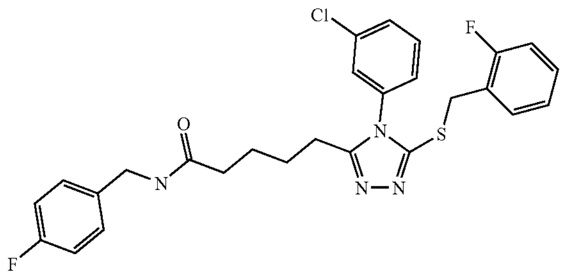 | 527.04 | 5-{4-(3-chlorophenyl)-5-[(2-fluorobenzyl)sulfanyl]-4H-1,2,4-triazol-3-yl}-N-(4-fluorobenzyl)pentanamide | 527 |
| 234 | 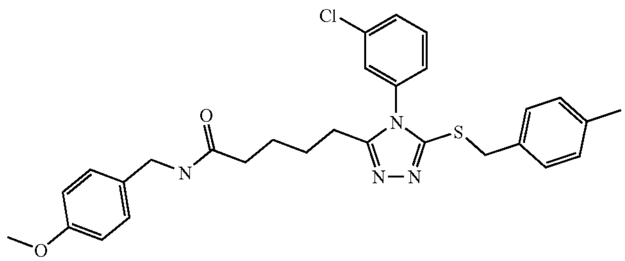 | 535.11 | 5-{4-(3-chlorophenyl)-5-[(4-methylbenzyl)sulfanyl]-4H-1,2,4-triazol-3-yl}-N-(4-methoxybenzyl)pentanamide | 535 |
| 235 | 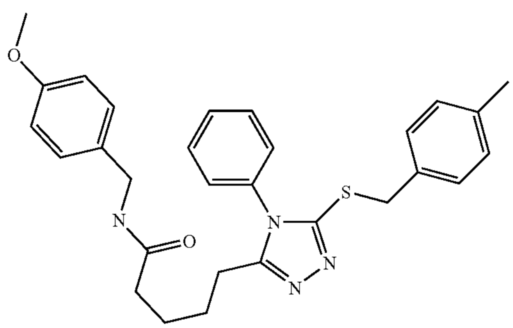 | 500.66 | N-(4-methoxybenzyl)-5-{5-[(4-methylbenzyl)sulfanyl]-4-phenyl-4H-1,2,4-triazol-3-yl}pentanamide | 501 |
| 236 | 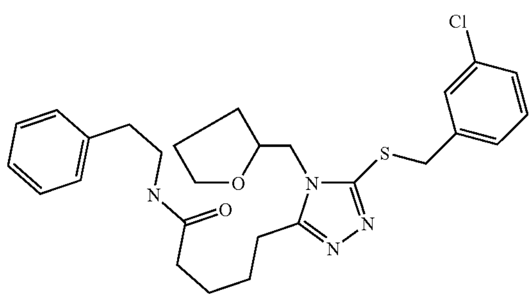 | 513.10 | 5-[5-[(3-chlorobenzyl)sulfanyl]-4-(tetrahydro-2-furanylmethyl)-4H-1,2,4-triazol-3-yl]-N-(2-phenylethyl)pentanamide | 513 |

TABLE 2-continued

| Example No. | Chemical Structure | M.W. | IUPAC-Name | M+(ESI+) |
|---|---|---|---|---|
| 237 | 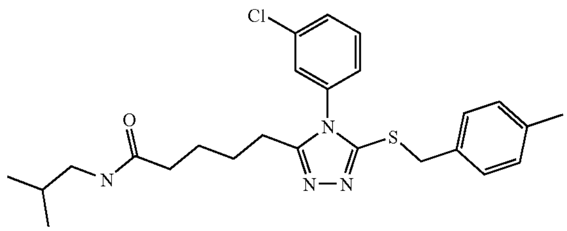 | 471.07 | 5-{4-(3-chlorophenyl)-5-[(4-methylbenzyl)sulfanyl]-4H-1,2,4-triazol-3-yl}-N-isobutylpentanamide | 471 |
| 238 | 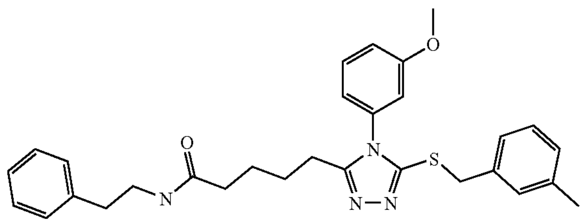 | 514.69 | 5-{4-(3-methoxyphenyl)-5-[(3-methylbenzyl)sulfanyl]-4H-1,2,4-triazol-3-yl}-N-(2-phenylethyl)pentanamide | 515 |
| 239 | 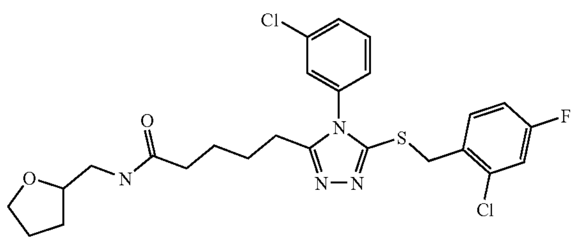 | 537.48 | 5-[5-[(2-chloro-4-fluorobenzyl)sulfanyl]-4-(3-chlorophenyl)-4H-1,2,4-triazol-3-yl]-N-(tetrahydro-2-furanylmethyl)pentanamide | 537 |
| 240 | 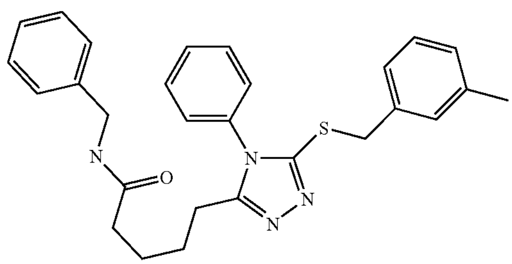 | 470.64 | N-benzyl-5-{5-[(3-methylbenzyl)sulfanyl]-4-phenyl-4H-1,2,4-triazol-3-yl}pentanamide | 471 |
| 241 | 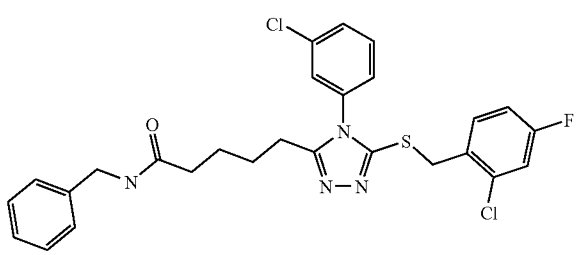 | 543.49 | N-benzyl-5-[5-[(2-chloro-4-fluorobenzyl)sulfanyl]4-(3-chlorophenyl)-4H-1,2,4-triazol-3-yl]pentanamide | 543 |
| 242 | 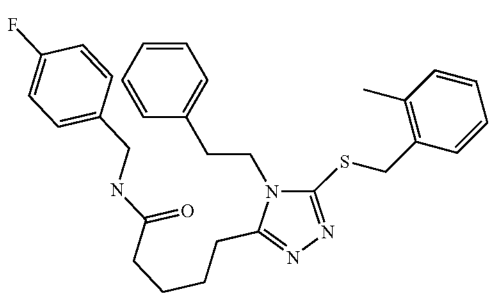 | 516.68 | N-(4-fluorobenzyl)-5-[5-[(2-methylbenzyl)sulfanyl]-4-(2-phenylethyl)-4H-1,2,4-triazol-3-yl]pentanamide | 517 |

TABLE 2-continued

| Example No. | Chemical Structure | M.W. | IUPAC-Name | M+(ESI+) |
|---|---|---|---|---|
| 243 | 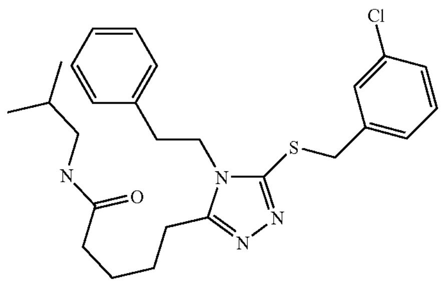 | 485.09 | 5-[5-[(3-chlorobenzyl)sulfanyl]-4-(2-phenylethyl)-4H-1,2,4-triazol-3-yl]-N-isobutylpentanamide | 485 |
| 244 | 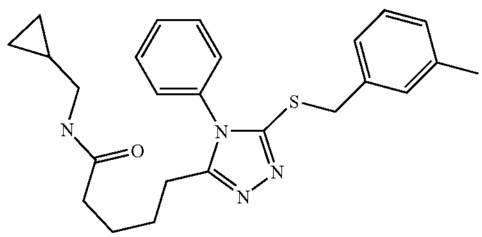 | 434.61 | N-(cyclopropylmethyl)-5-{5-[(3-methylbenzyl)sulfanyl]-4-phenyl-4H-1,2,4-triazol-3-yl}pentanamide | 435 |
| 245 | 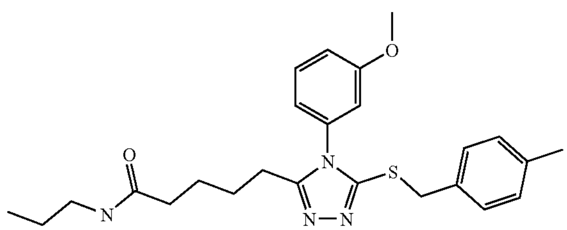 | 452.62 | 5-{4-(3-methoxyphenyl)-5-[(4-methylbenzyl)sulfanyl]-4H-1,2,4-triazol-3-yl}-N-propylpentanamide | 453 |
| 246 | 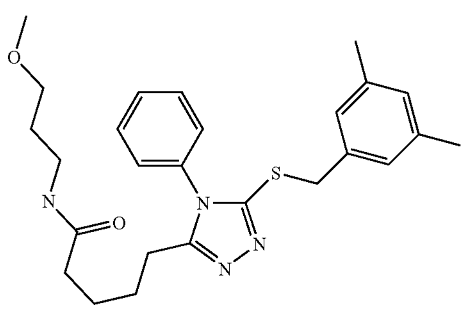 | 466.65 | 5-{5-[(3,5-dimethylbenzyl)sulfanyl]-4-phenyl-4H-1,2,4-triazol-3-yl}-N-(3-methoxypropyl)pentanamide | 467 |
| 247 | 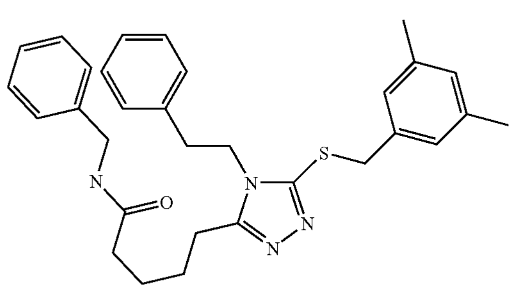 | 512.72 | N-benzyl-5-[5-[(3,5-dimethylbenzyl)sulfanyl]-4-(2-phenylethyl)-4H-1,2,4-triazol-3-yl]pentanamide | 513 |

TABLE 2-continued

| Example No. | Chemical Structure | M.W. | IUPAC-Name | M⁺(ESI⁺) |
|---|---|---|---|---|
| 248 | 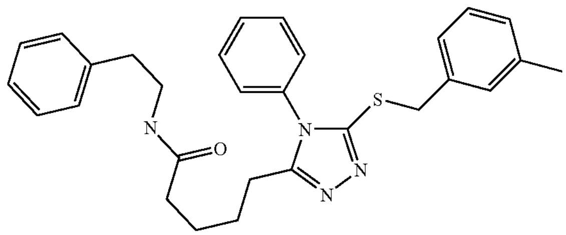 | 484.67 | 5-{5-[(3-methylbenzyl)sulfanyl]-4-phenyl-4H-1,2,4-triazol-3-yl}-N-(2-phenylethyl)pentanamide | 485 |
| 249 | 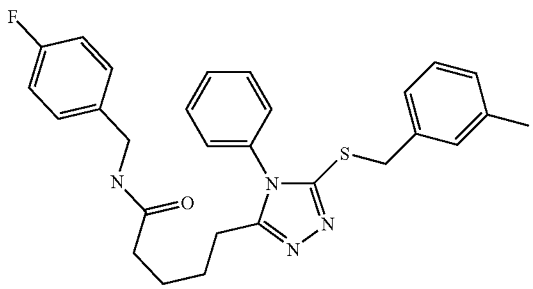 | 488.63 | N-(4-fluorobenzyl)-5-{5-[(3-methylbenzyl)sulfanyl]-4-phenyl-4H-1,2,4-triazol-3-pentanamide | 489 |
| 250 | 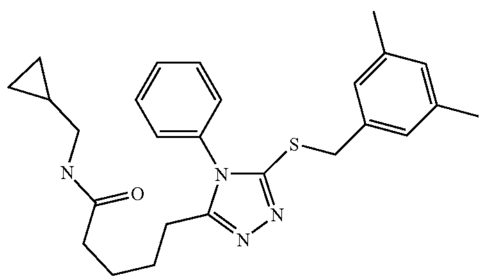 | 448.63 | N-(cyclopropylmethyl)-5-{5-[(3,5-dimethylbenzyl)sulfanyl]-4-phenyl-4H-1,2,4-triazol-3-yl}pentanamide | 449 |
| 251 | 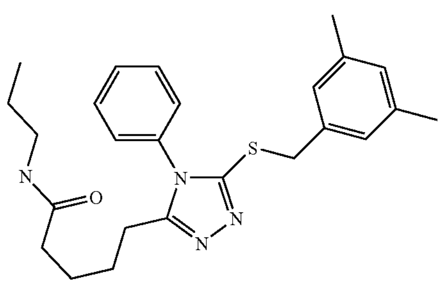 | 436.62 | 5-{5-[(3,5-dimethylbenzyl)sulfanyl]-4-phenyl-4H-1,2,4-triazol-3-yl}-N-propylpentanamide | 437 |
| 252 | 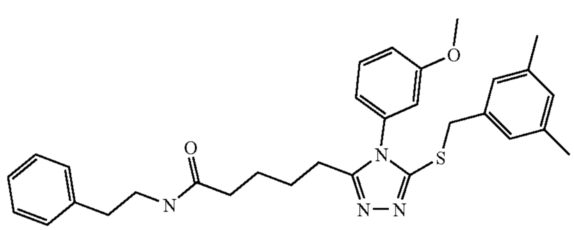 | 528.72 | 5-[5-[(3,5-dimethylbenzyl)sulfanyl]-4-(3-methoxyphenyl)-4H-1,2,4-triazol-3-yl]-N-(2-phenylethyl)pentanamide | 529 |
| 253 | 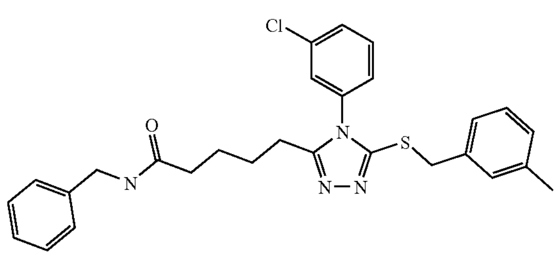 | 505.08 | N-benzyl-5-{4-(3-chlorophenyl)-5-[(3-methylbenzyl)sulfanyl]-4H-1,2,4-triazol-3-yl}pentanamide | 505 |

TABLE 2-continued

| Example No. | Chemical Structure | M.W. | IUPAC-Name | M+(ESI+) |
|---|---|---|---|---|
| 254 | 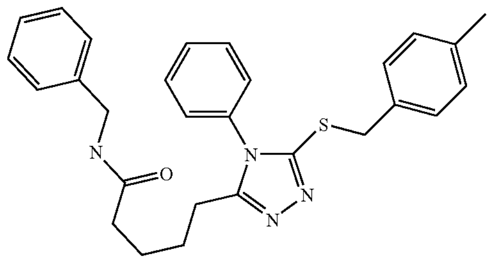 | 470.64 | N-benzyl-5-{5-[(4-methylbenzyl)sulfanyl]-4-phenyl-4H-1,2,4-triazol-3-yl}pentanamide | 471 |
| 255 | 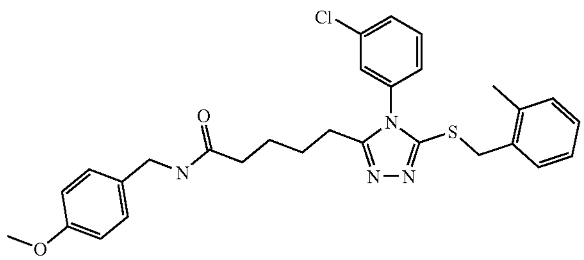 | 535.11 | 5-{4-(3-chlorophenyl)-5-[(2-methylbenzyl)sulfanyl]-4H-1,2,4-triazol-3-yl}-N-(4-methoxybenzyl)pentanamide | 535 |
| 256 | 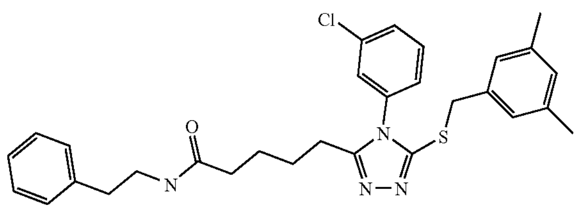 | 533.14 | 5-{4-(3-chlorophenyl)-5-[(3,5-dimethylbenzyl)sulfanyl]-4H-1,2,4-triazol-3-yl}-N-(2-phenylethyl)pentanamide | 533 |
| 257 | 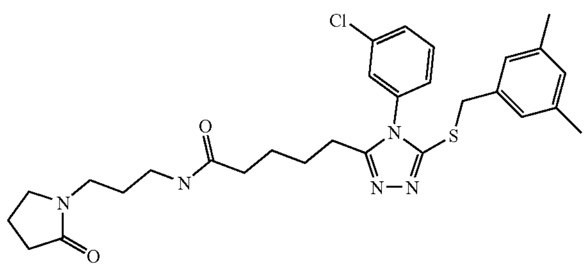 | 554.16 | 5-{4-(3-chlorophenyl)-5-[(3,5-dimethylbenzyl)sulfanyl]-4H-1,2,4-triazol-3-yl}-N-[3-(2-oxo-1-pyrrolidinyl)propyl]pentanamide | 554 |
| 258 | 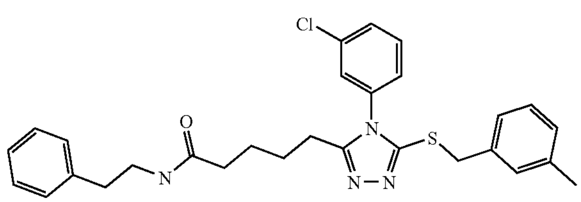 | 519.11 | 5-{4-(3-chlorophenyl)-5-[(3-methylbenzyl)sulfanyl]-4H-1,2,4-triazol-3-yl}-N-(2-phenylethyl)pentanamide | 519 |
| 259 | 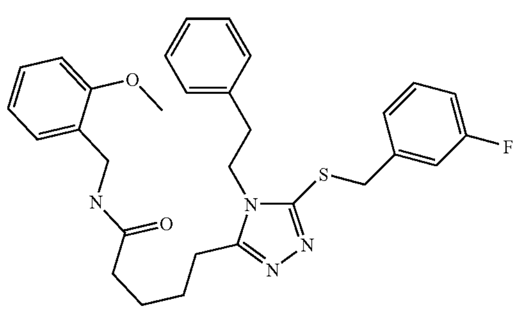 | 532.68 | 5-[5-[(3-fluorobenzyl)sulfanyl]-4-(2-phenylethyl)-4H-1,2,4-triazol-3-yl]-N-(2-methoxybenzyl)pentanamide | 533 |

TABLE 2-continued

| Example No. | Chemical Structure | M.W. | IUPAC-Name | M+(ESI+) |
|---|---|---|---|---|
| 260 | 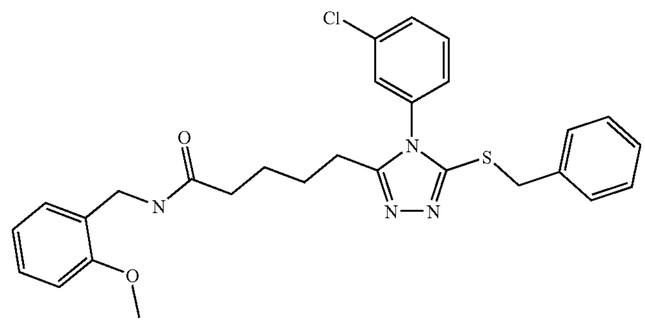 | 535.11 | 5-{4-(3-chlorophenyl)-5-[(2-methylbenzyl)sulfanyl]-4H-1,2,4-triazol-3-yl}-N-(2-methoxybenzyl)pentanamide | 535 |
| 261 | 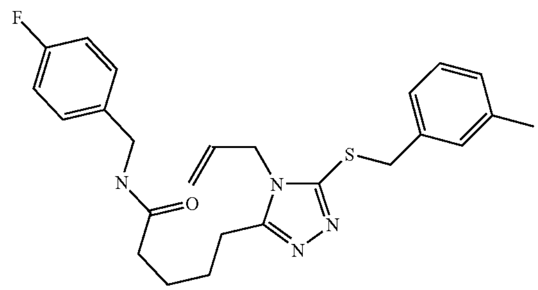 | 452.60 | 5-{4-allyl-5-[(3-methylbenzyl)sulfanyl]-4H-1,2,4-triazol-3-yl}-N-(4-fluorobenzyl)pentanamide | 453 |
| 262 | 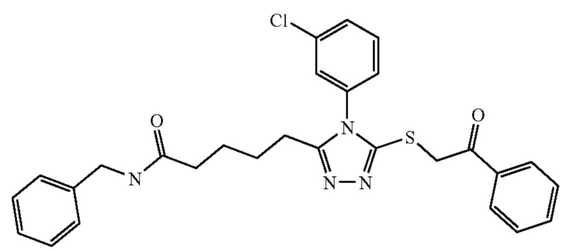 | 519.07 | N-benzyl-5-{4-(3-chlorophenyl)-5-[(2-oxo-2-phenylethyl)sulfanyl]-4H-1,2,4-triazol-3-yl}pentanamide | 519 |
| 263 | 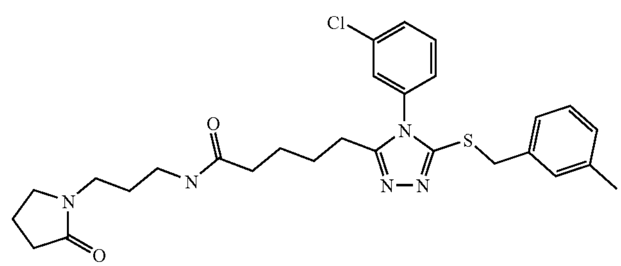 | 540.13 | 5-{4-(3-chlorophenyl)-5-[(3-methylbenzyl)sulfanyl]-4H-1,2,4-triazol-3-yl}-N-[3-(2-oxo-1-pyrrolidinyl)propyl]pentanamide | |
| 264 | 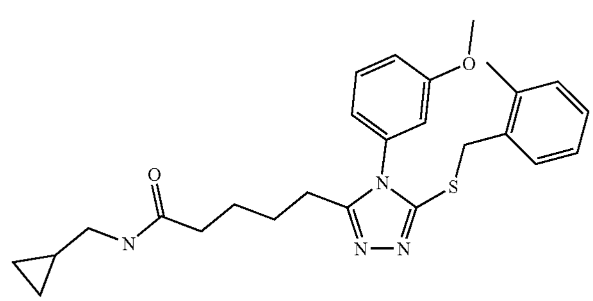 | 464.63 | N-(cyclopropylmethyl)-5-{4-(3-methoxyphenyl)-5-[(2-methylbenzyl)sulfanyl]-4H-1,2,4-triazol-3-yl}pentanamide | 465 |

TABLE 2-continued

| Example No. | Chemical Structure | M.W. | IUPAC-Name | M+(ESI+) |
|---|---|---|---|---|
| 265 | 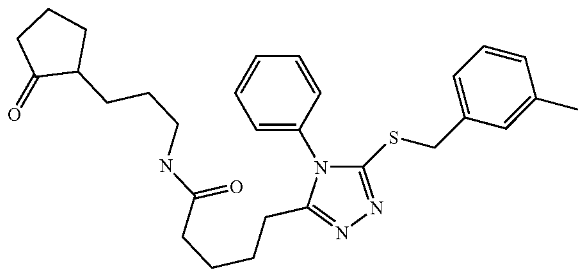 | 505.68 | 5-{5-[(3-methylbenzyl)sulfanyl]-4-phenyl-4H-1,2,4-triazol-3-yl}-N-[3-(2-oxo-1-pyrrolidinyl)propyl]pentanamide | 506 |
| 266 | 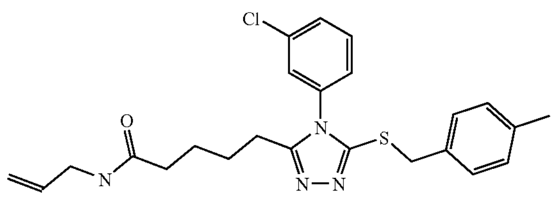 | 455.02 | N-allyl-5-{4-(3-chlorophenyl)-5-[(4-methylbenzyl)sulfanyl]-4H-1,2,4-triazol-3-yl}pentanamide | 455 |
| 267 | 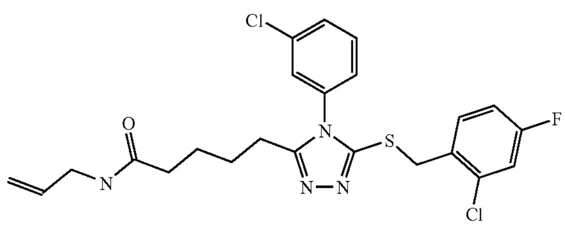 | 493.43 | N-allyl-5-[5-[(2-chloro-4-fluorobenzyl)sulfanyl]-4-(3-chlorophenyl)-4H-1,2,4-triazol-3-yl]pentanamide | 493 |
| 268 | 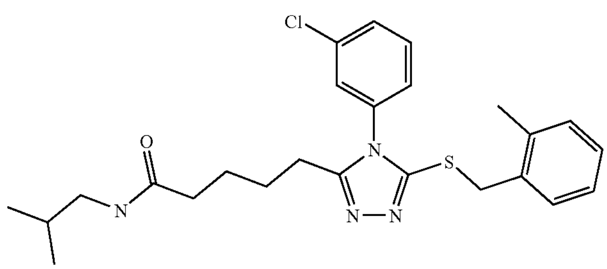 | 471.07 | 5-{4-(3-chlorophenyl)-5-[(2-methylbenzyl)sulfanyl]-4H-1,2,4-triazol-3-yl}-N-isobutylpentanamide | 471 |
| 269 | 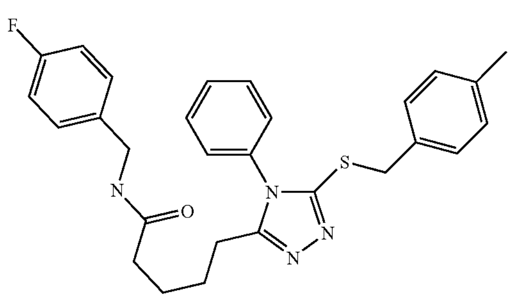 | 488.63 | N-(4-fluorobenzyl)-5-{5-[(4-methylbenzyl)sulfanyl]-4-phenyl-4H-1,2,4-triazol-3-yl}pentanamide | 489 |
| 270 | 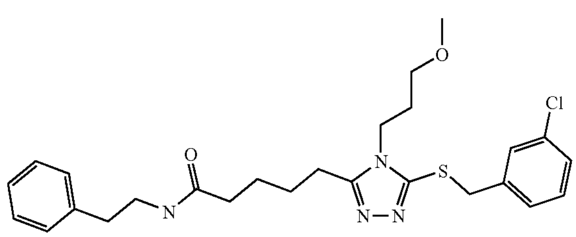 | 501.09 | 5-[5-[(3-chlorobenzyl)sulfanyl]-4-(3-methoxypropyl)-4H-1,2,4-triazol-3-yl]-N-(2-phenylethyl)pentanamide | 501 |

TABLE 2-continued

| Example No. | Chemical Structure | M.W. | IUPAC-Name | M+(ESI+) |
|---|---|---|---|---|
| 271 | 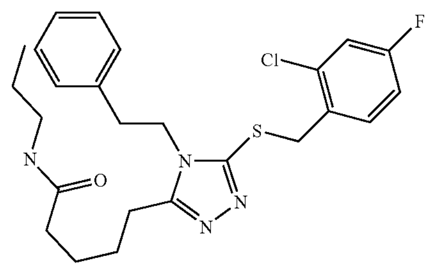 | 489.06 | 5-[5-[(2-chloro-4-fluorobenzyl)sulfanyl]-4-(2-phenylethyl)-4H-1,2,4-triazol-3-yl]-N-propylpentanamide | 489 |
| 272 | 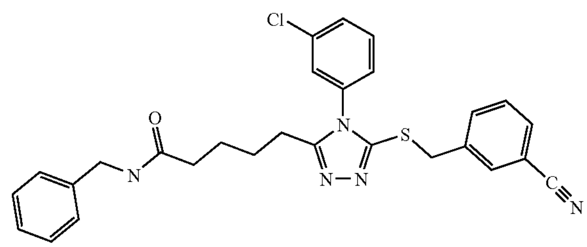 | 516.07 | N-benzyl-5-{4-(3-chlorophenyl)-5-[(3-cyanobenzyl)sulfanyl]-4H-1,2,4-triazol-3-yl}pentanamide | 516 |
| 273 | 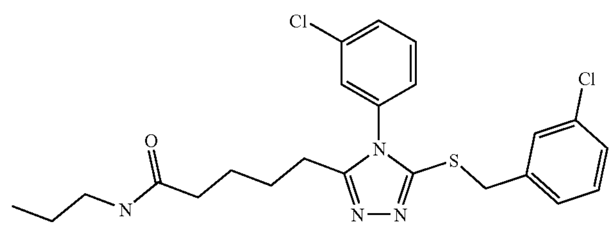 | 477.46 | 5-[5-[(3-chlorobenzyl)sulfanyl]-4-(3-chlorophenyl)-4H-1,2,4-triazol-3-yl]-N-propylpentanamide | 477 |
| 274 | 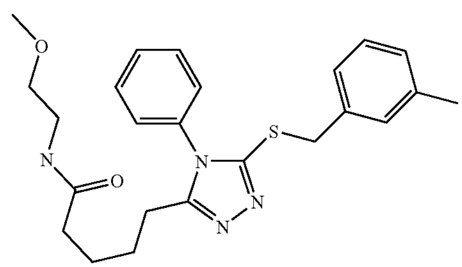 | 438.59 | N-(2-methoxyethyl)-5-{5-[(3-methylbenzyl)sulfanyl]-4-phenyl-4H-1,2,4-triazol-3-yl}pentanamide | 439 |
| 275 | 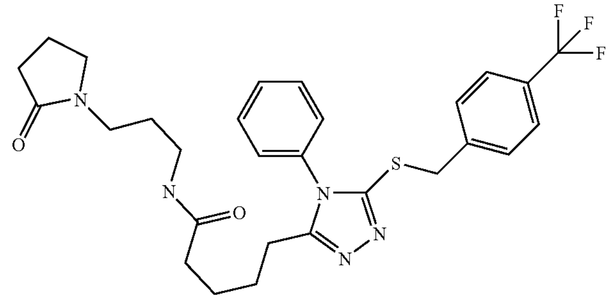 | 559.66 | N-[3-(2-oxo-1-pyrrolidinyl)propyl]-5-(4-phenyl-5-{[4-(trifluoromethyl)benzyl]sulfanyl}-4H-1,2,4-triazol-3-yl)pentanamide | 560 |

TABLE 2-continued

| Example No. | Chemical Structure | M.W. | IUPAC-Name | M+(ESI+) |
|---|---|---|---|---|
| 276 | 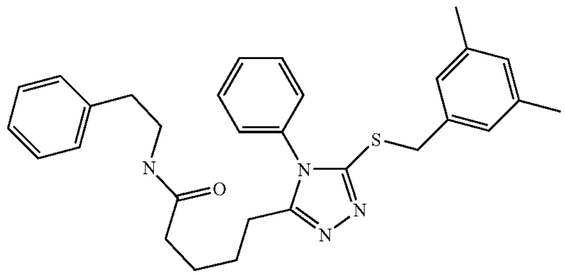 | 498.69 | 5-{5-[(3,5-dimethylbenzyl)sulfanyl]-4-phenyl-4H-1,2,4-triazol-3-yl}-N-(2-phenylethyl)pentanamide | 499 |
| 277 | 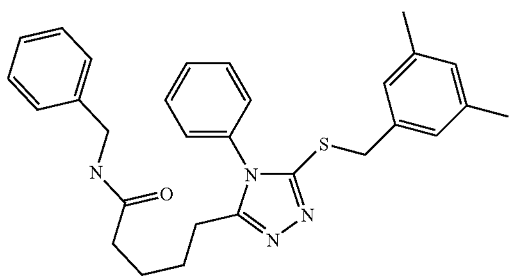 | 484.67 | N-benzyl-5-{5-[(3,5-dimethylbenzyl)sulfanyl]-4-phenyl-4H-1,2,4-triazol-3-yl}pentanamide | 485 |
| 278 | 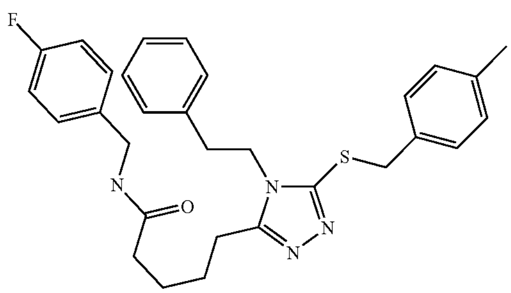 | 516.68 | N-(4-fluorobenzyl)-5-[5-[(4-methylbenzyl)sulfanyl]-4-(2-phenylethyl)-4H-1,2,4-triazol-3-yl]pentanamide | 517 |
| 279 | 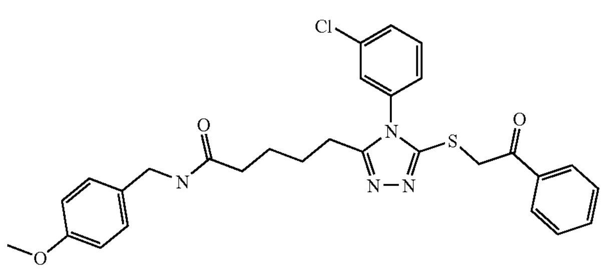 | 549.09 | 5-{4-(3-chlorophenyl)-5-[(2-oxo-2-phenylethyl)sulfanyl]-4H-1,2,4-triazol-3-yl}-N-(4-methoxybenzyl)pentanamide | 549 |
| 280 | 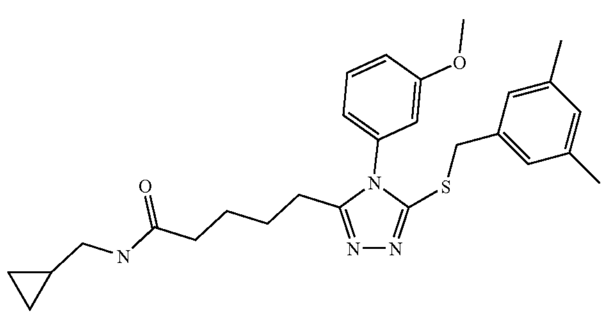 | 478.66 | N-(cyclopropylmethyl)-5-[5-[(3,5-dimethylbenzyl)sulfanyl]-4-(3-methoxyphenyl)-4H-1,2,4-triazol-3-yl]pentanamide | 479 |

TABLE 2-continued

| Example No. | Chemical Structure | M.W. | IUPAC-Name | M+(ESI+) |
|---|---|---|---|---|
| 281 | 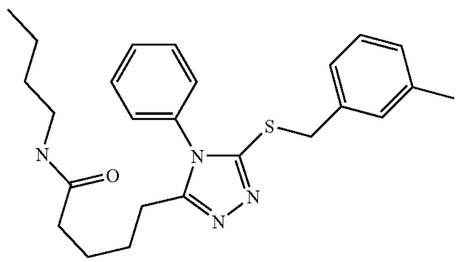 | 436.62 | N-butyl-5-{5-[(3-methylbenzyl)sulfanyl]-4-phenyl-4H-1,2,4-triazol-3-yl}pentanamide | 437 |
| 282 | 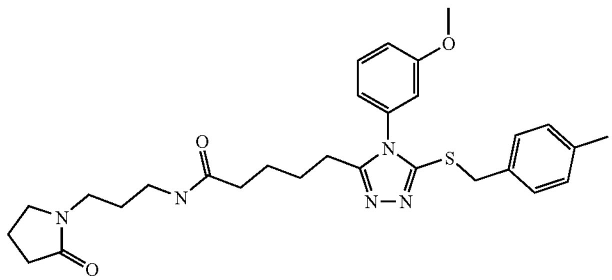 | 535.71 | 5-{4-(3-methoxyphenyl)-5-[(4-methylbenzyl)sulfanyl]-4H-1,2,4-triazol-3-yl}-N-[3-(2-oxo-1-pyrrolidinyl)propyl]pentanamide | 536 |
| 283 | 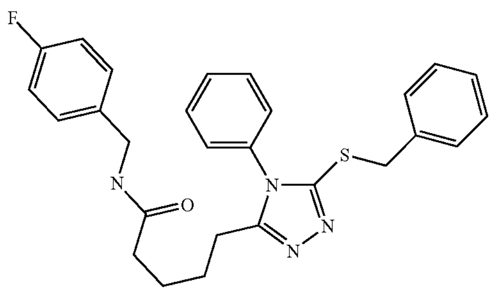 | 474.60 | 5-[5-(benzylsulfanyl)-4-phenyl-4H-1,2,4-triazol-3-yl]-N-(4-fluorobenzyl)pentanamide | 475 |
| 284 | 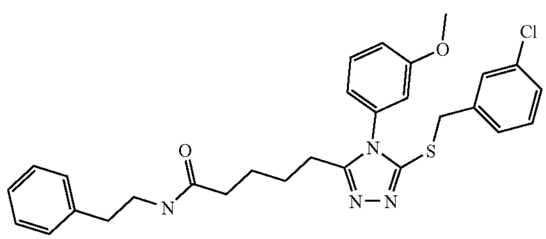 | 535.11 | 5-[5-[(3-chlorobenzyl)sulfanyl]-4-(3-methoxyphenyl)-4H-1,2,4-triazol-3-yl]-N-(2-phenylethyl)pentanamide | 535 |
| 285 | 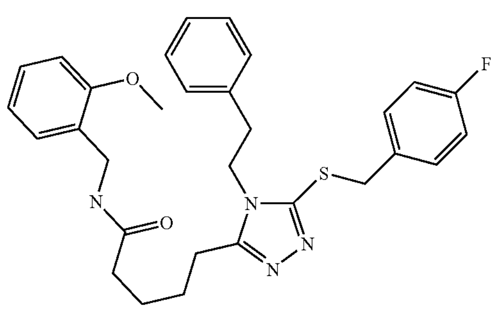 | 532.68 | 5-[5-[(4-fluorobenzyl)sulfanyl]-4-(2-phenylethyl)-4H-1,2,4-triazol-3-yl]-N-(2-methoxybenzyl)pentanamide | 533 |

TABLE 2-continued

| Example No. | Chemical Structure | M.W. | IUPAC-Name | M⁺(ESI⁺) |
|---|---|---|---|---|
| 286 | 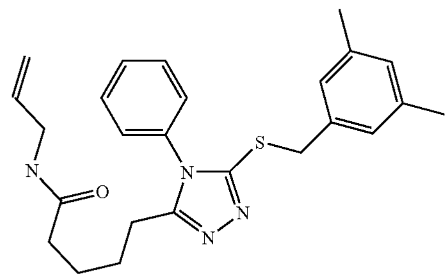 | 434.61 | N-allyl-5-{5-[(3,5-dimethylbenzyl)sulfanyl]-4-phenyl-4H-1,2,4-triazol-3-yl}pentanamide | 435 |
| 287 | 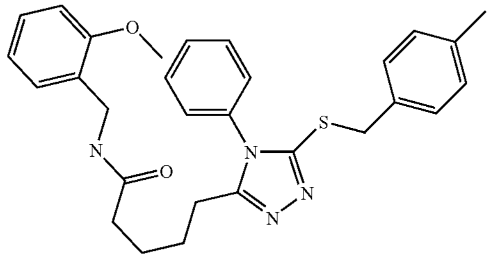 | 500.66 | N-(2-methoxybenzyl)-5-{5-[(4-methylbenzyl)sulfanyl]-4-phenyl-4H-1,2,4-triazol-3-yl}pentanamide | 501 |
| 288 | 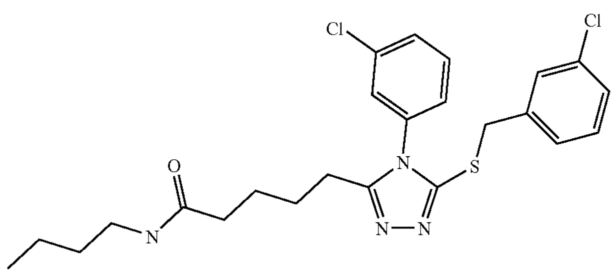 | 491.48 | N-butyl-5-[5-[(3-chlorobenzyl)sulfanyl]-4-(3-chlorophenyl)-4H-1,2,4-triazol-3-yl}pentanamide | 491 |
| 289 | 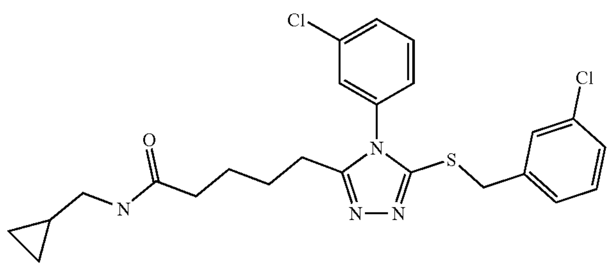 | 489.47 | 5-[5-[(3-chlorobenzyl)sulfanyl]-4-(3-chlorophenyl)-4H-1,2,4-triazol-3-yl]-N-(cyclopropylmethyl)pentanamide | 489 |
| 290 | 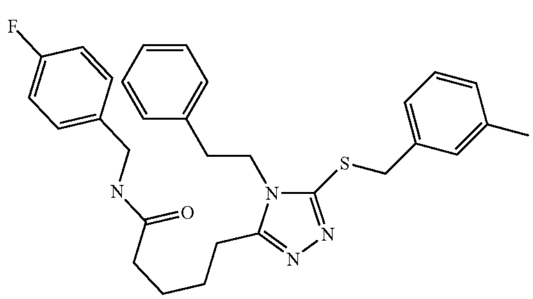 | 516.68 | N-(4-fluorobenzyl)-5-[5-[(3-methylbenzyl)sulfanyl]-4-(2-phenylethyl)-4H-1,2,4-triazol-3-yl]pentanamide | 517 |

TABLE 2-continued

| Example No. | Chemical Structure | M.W. | IUPAC-Name | M+(ESI+) |
|---|---|---|---|---|
| 291 | 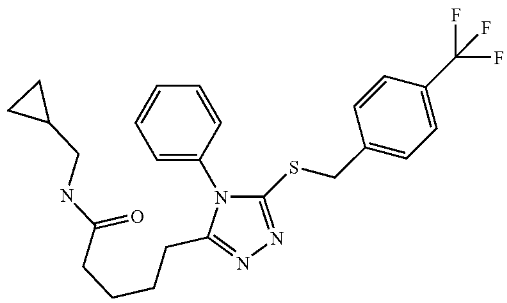 | 488.58 | N-(cyclopropylmethyl)-5-(4-phenyl-5-{[4-(trifluoromethyl)benzyl]sulfanyl}-4H-1,2,4-triazol-3-yl)pentanamide | 489 |
| 292 | 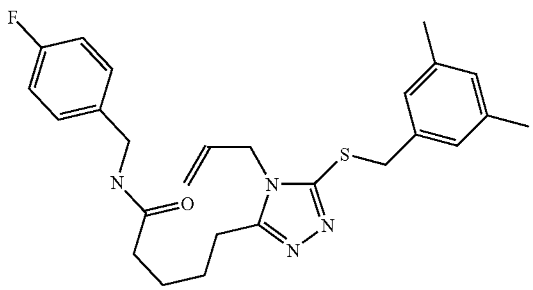 | 466.62 | 5-{4-allyl-5-[(3,5-dimethylbenzyl)sulfanyl]-4H-1,2,4-triazol-3-yl]-N-(4-fluorobenzyl)pentanamide | 467 |
| 293 | 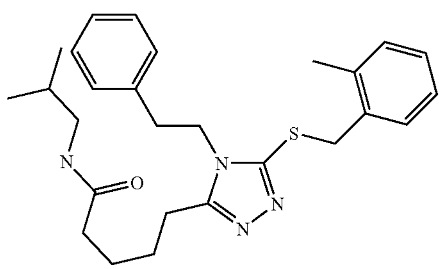 | 464.68 | N-isobutyl-5-[5-[(2-methylbenzyl)sulfanyl]-4-(2-phenylethyl)-4H-1,2,4-triazol-3-yl]pentanamide | 465 |
| 294 | 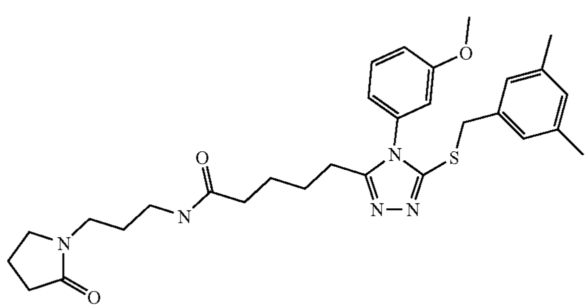 | 549.74 | 5-[5-[(3,5-dimethylbenzyl)sulfanyl]-4-(3-methoxyphenyl)-4H-1,2,4-triazol-3-yl]-N-[3-(2-oxo-1-pyrrolidinyl)propyl]pentanamide | 550 |
| 295 | 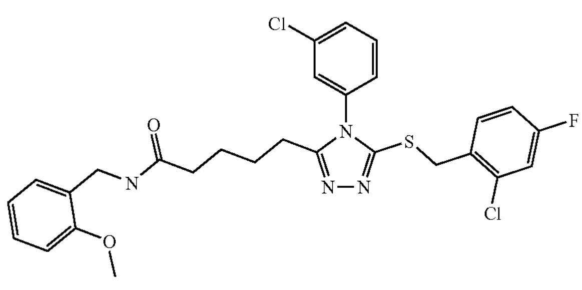 | 573.52 | 5-[5-[(2-chloro-4-fluorobenzyl)sulfanyl]-4-(3-chlorophenyl)-4H-1,2,4-triazol-3-yl]-N-(2-methoxybenzyl)pentanamide | 574 |

TABLE 2-continued

| Example No. | Chemical Structure | M.W. | IUPAC-Name | M+(ESI+) |
|---|---|---|---|---|
| 296 | 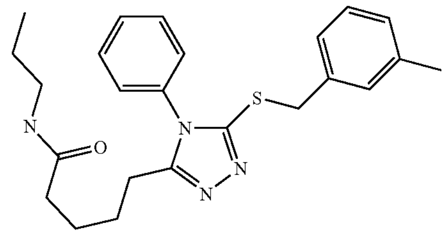 | 422.59 | 5-{5-[(3-methylbenzyl)sulfanyl]-4-phenyl-4H-1,2,4-triazol-3-yl}-N-propylpentanamide | 423 |
| 297 | 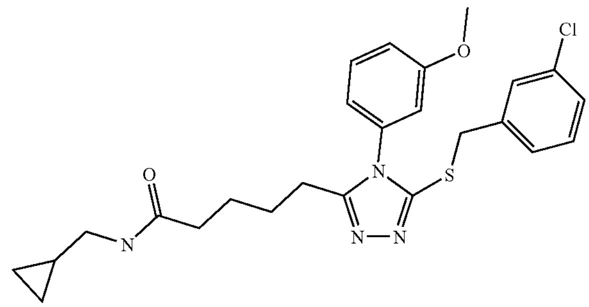 | 485.05 | 5-[5-[(3-chlorobenzyl)sulfanyl]-4-(3-methoxyphenyl)-4H-1,2,4-triazol-3-yl]-N-(cyclopropylmethyl)pentanamide | 485 |
| 298 | 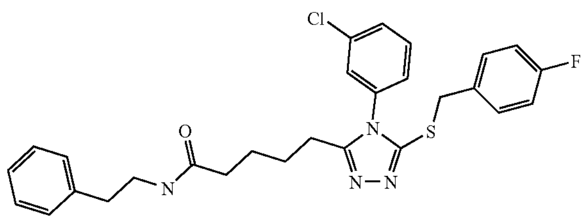 | 523.07 | 5-{4-(3-chlorophenyl)-5-[(4-fluorobenzyl)sulfanyl]-4H-1,2,4-triazol-3-yl}-N-(2-phenylethyl)pentanamide | 523 |
| 299 | 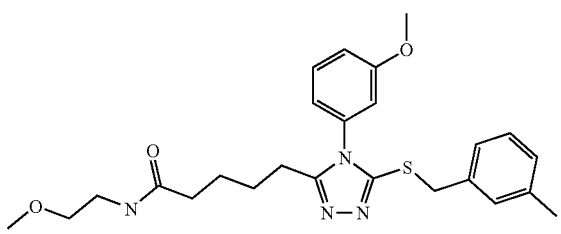 | 468.62 | N-(2-methoxyethyl)-5-{4-(3-methoxyphenyl)-5-[3-methylbenzyl)sulfanyl]-4H-1,2,4-triazol-3-yl}pentanamide | 469 |
| 300 | 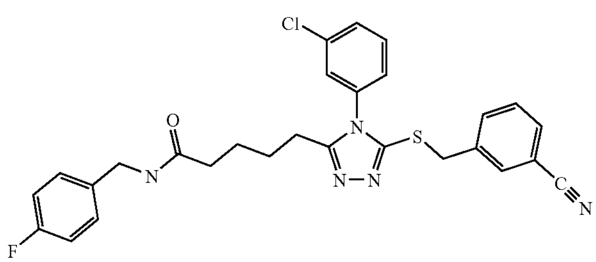 | 534.06 | 5-{4-(3-chlorophenyl)-5-[3-cyanobenzyl)sulfanyl]-4H-1,2,4-triazol-3-yl}-N-(4-fluorobenzyl)pentanamide | 534 |
| 301 | 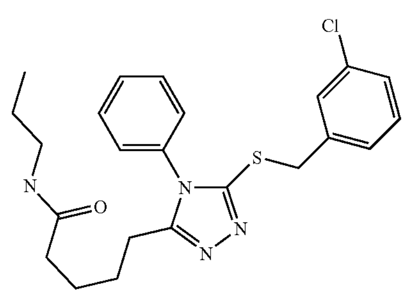 | 457.04 | 5-{5-[(3-chlorobenzyl)sulfanyl]-4-phenyl-4H-1,2,4-triazol-3-yl}-N-isobutylpentanamide | 457 |

TABLE 2-continued

| Example No. | Chemical Structure | M.W. | IUPAC-Name | M+(ESI+) |
|---|---|---|---|---|
| 302 | 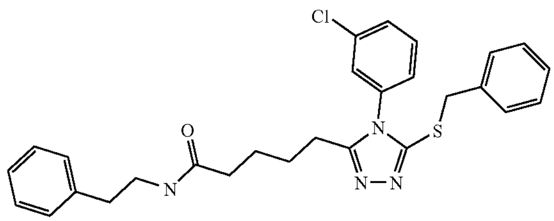 | 505.08 | 5-[5-(benzylsulfanyl)-4-(3-chlorophenyl)-4H-1,2,4-triazol-3-yl]-N-(2-phenylethyl)pentanamide | 505 |
| 303 | 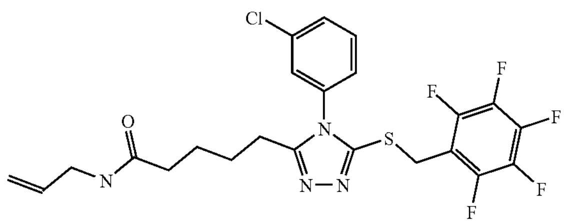 | 530.95 | N-allyl-5-{4-(3-chlorophenyl)-5-[(2,3,4,5,6-pentafluorobenzyl)sulfanyl]-4H-1,2,4-triazol-3-yl}pentanamide | 531 |
| 304 | 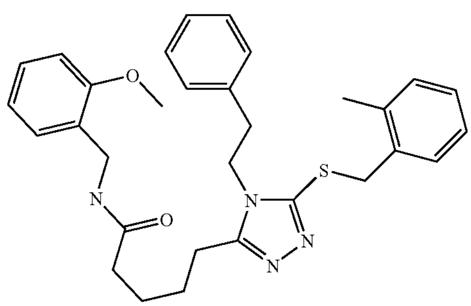 | 528.72 | N-(2-methoxybenzyl)-5-[5-[(2-methylbenzyl)sulfanyl]-4-(2-phenylethyl)-4H-1,2,4-triazol-3-yl]pentanamide | 529 |
| 305 | 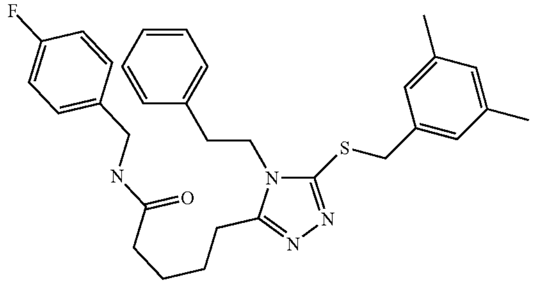 | 530.71 | 5-[5-[(3,5-dimethylbenzyl)sulfanyl]-4-(2-phenylethyl)-4H-1,2,4-triazol-3-yl]-N-(4-fluorobenzyl)pentanamide | 531 |
| 306 | 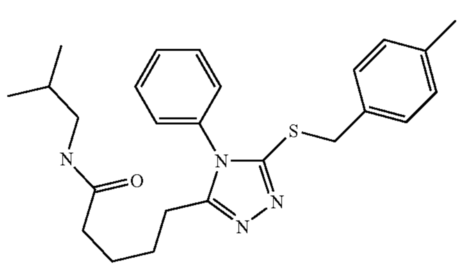 | 436.62 | N-isobutyl-5-{5-[(4-methylbenzyl)sulfanyl]-4-phenyl-4H-1,2,4-triazol-3-yl}pentanamide | 437 |
| 307 | 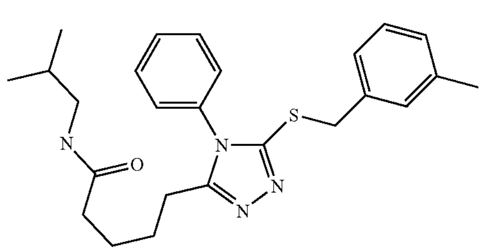 | 436.62 | N-isobutyl-5-{5-[(3-methylbenzyl)sulfanyl]-4-phenyl-4H-1,2,4-triazol-3-yl}pentanamide | 437 |

TABLE 2-continued

| Example No. | Chemical Structure | M.W. | IUPAC-Name | M+(ESI+) |
|---|---|---|---|---|
| 308 | 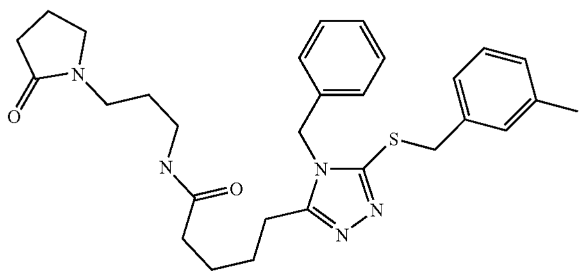 | 519.71 | 5-{4-benzyl-5-[(3-methylbenzyl)sulfanyl]-4H-1,2,4-triazol-3-yl}-N-[3-(2-oxo-1-pyrrolidinyl)propyl]pentanamide | 520 |
| 309 | 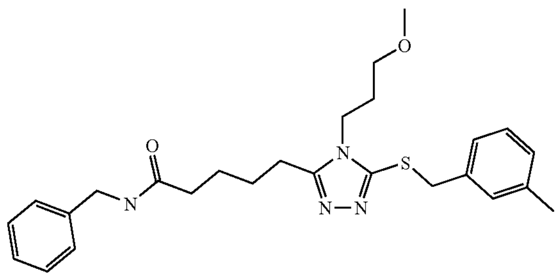 | 466.65 | N-benzyl-5-{4-(3-methoxypropyl)-5-[(3-methylbenzyl)sulfanyl]-4H-1,2,4-triazol-3-yl}pentanamide | 467 |
| 310 | 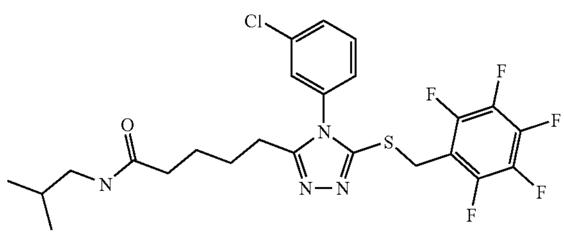 | 546.99 | 5-{4-(3-chlorophenyl)-5-[(2,3,4,5,6-pentafluorobenzyl)sulfanyl]-4H-1,2,4-triazol-3-yl}-N-isobutylpentanamide | 547 |
| 311 | 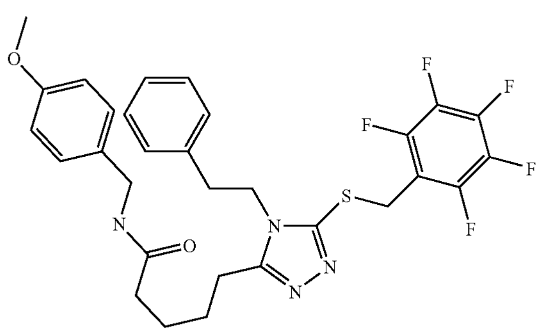 | 604.64 | N-(4-methoxybenzyl)-5-[5-[(2,3,4,5,6-pentafluorobenzyl)sulfanyl]-4-(2-phenylethyl)-4H-1,2,4-triazol-3-yl]pentanamide | 605 |
| 312 | 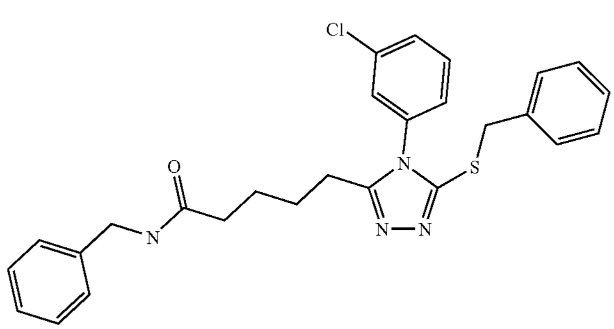 | 491.06 | N-benzyl-5-[5-(benzylsulfanyl)-4-(3-chlorophenyl)-4H-1,2,4-triazol-3-yl]pentanamide | 491 |

TABLE 2-continued

| Example No. | Chemical Structure | M.W. | IUPAC-Name | M+(ESI+) |
|---|---|---|---|---|
| 313 | 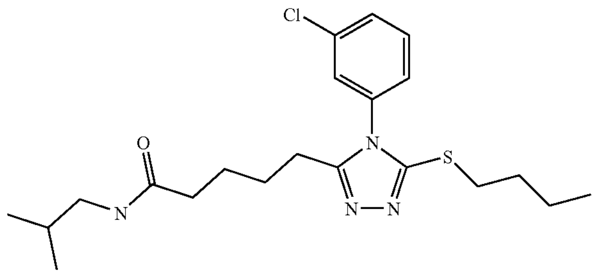 | 423.02 | 5-[5-(butylsulfanyl)-4-(3-chlorophenyl)-4H-1,2,4-triazol-3-yl]-N-isobutylpentanamide | 423 |
| 314 | 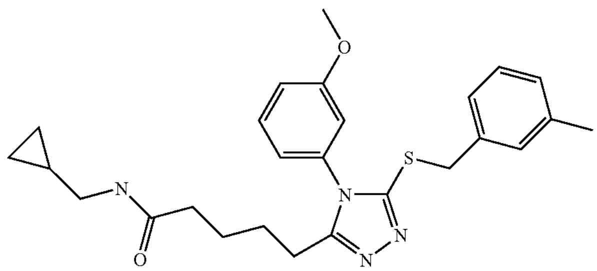 | 464.63 | N-(cyclopropylmethyl)-5-{4-(3-methoxyphenyl)-5-[(3-methylbenzyl)sulfanyl]-4H-1,2,4-triazol-3-yl}pentanamide | 465 |
| 315 | 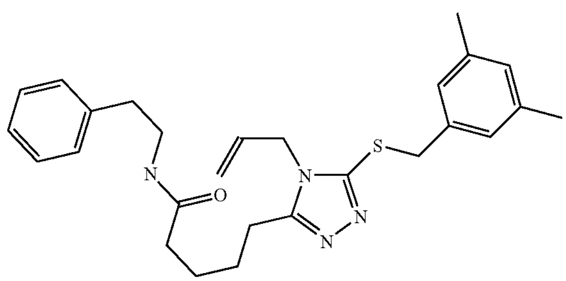 | 462.66 | 5-{4-allyl-5-[3,5-dimethylbenzyl)sulfanyl]-4H-1,2,4-triazol-3-yl}-N-(2-phenylethyl)pentanamide | 463 |
| 316 | 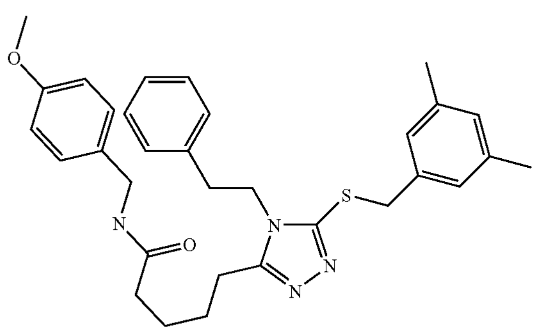 | 542.75 | 5-[5-[(3,5-dimethylbenzyl)sulfanyl]-4-(2-phenylethyl)-4H-1,2,4-triazol-3-yl]-N-(4-methoxybenzyl)pentanamide | 543 |
| 317 | 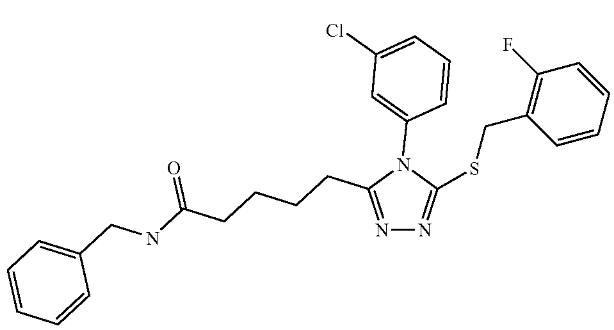 | 509.05 | N-benzyl-5-{4-(3-chlorophenyl)-5-[(2-fluorobenzyl)sulfanyl]-4H-1,2,4-triazol-3-yl}pentanamide | 509 |

TABLE 2-continued

| Example No. | Chemical Structure | M.W. | IUPAC-Name | M+(ESI+) |
|---|---|---|---|---|
| 318 | 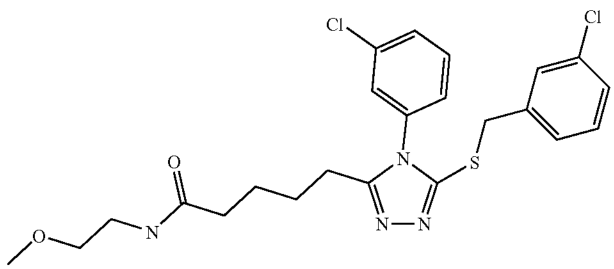 | 493.46 | 5-[5-[(3-chlorobenzyl)sulfanyl]-4-(3-chlorophenyl)-4H-1,2,4-triazol-3-yl]-N-(2-methoxyethyl)pentanamide | 493 |
| 319 | 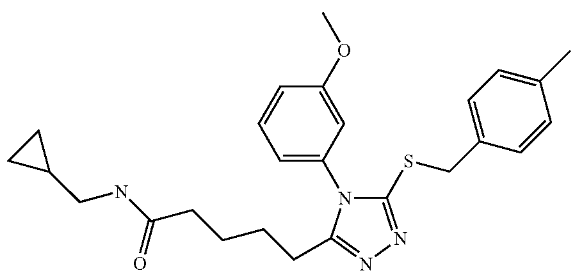 | 464.63 | N-(cyclopropylmethyl)-5-{4-(3-methoxyphenyl)-5-[(4-methylbenzyl)sulfanyl]-4H-1,2,4-triazol-3-yl}pentanamide | 465 |
| 320 | 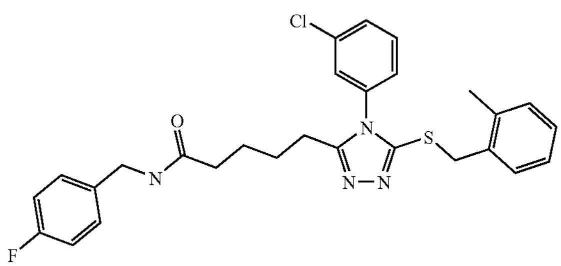 | 523.07 | 5-{4-(3-chlorophenyl)-5-[(2-methylbenzyl)sulfanyl]-4H-1,2,4-triazol-3-yl)-N-(4-fluorobenzyl)pentanamide | 523 |
| 321 | 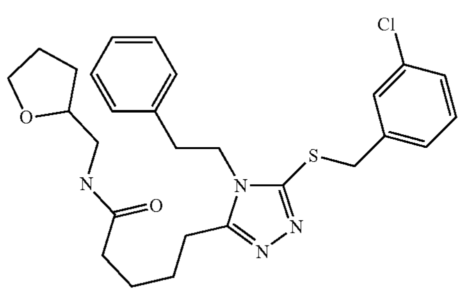 | 513.10 | 5-[5-[(3-chlorobenzyl)sulfanyl]-4-(2-phenylethyl)-4H-1,2,4-triazol-3-yl]-N-(tetrahydro-2-furanylmethylpentanamide | 513 |
| 322 | 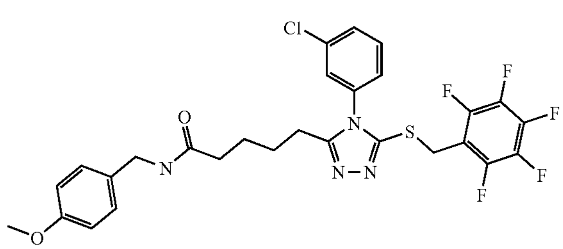 | 611.04 | 5-{4-(3-chlorophenyl)-5-[(2,3,4,5,6-pentafluorobenzyl)sulfanyl]-4H-1,2,4-triazol-3-yl}-N-(4-methoxybenzyl)pentanamide | 611 |

TABLE 2-continued

| Example No. | Chemical Structure | M.W. | IUPAC-Name | M+(ESI+) |
|---|---|---|---|---|
| 323 | 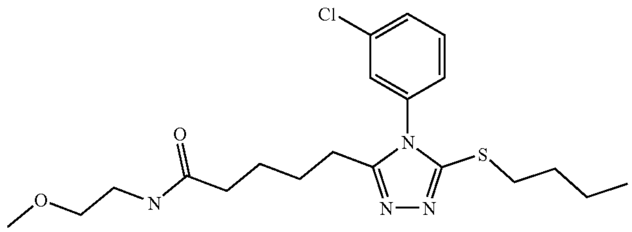 | 424.99 | 5-[5-(butylsulfanyl)-4-(3-chlorophenyl)-4H-1,2,4-triazol-3-yl]-N-(2-methoxyethyl)pentanamide | 425 |
| 324 | 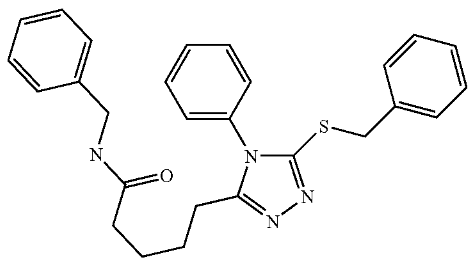 | 456.61 | N-benzyl-5-[5-(benzylsulfanyl)-4-phenyl-4H-1,2,4-triazol-3-yl]pentanamide | 457 |
| 325 | 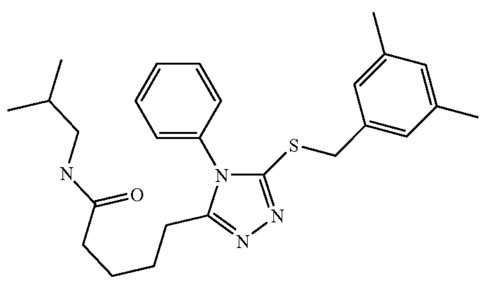 | 450.65 | 5-{5-[(3,5-dimethylbenzyl)sulfanyl]-4-phenyl-4H-1,2,4-triazol-3-yl}-N-isobutylpentanamide | 451 |
| 326 | 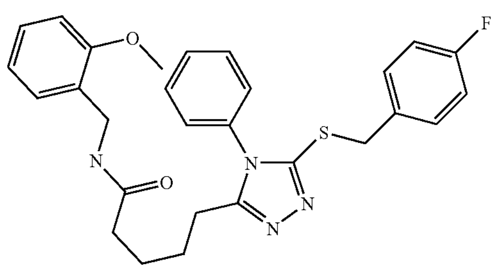 | 504.63 | 5-{5-[(4-fluorobenzyl)sulfanyl]-4-phenyl-4H-1,2,4-triazol-3-yl}-N-(2-methoxybenzyl)pentanamide | 505 |
| 327 | 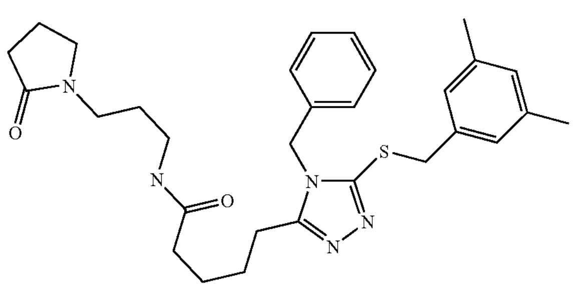 | 533.74 | 5-{4-benzyl-5-[(3,5-dimethylbenzyl)sulfanyl]-4H-1,2,4-triazol-3-yl}-N-[3-(2-oxo-1-pyrrolidinyl)propyl]pentanamide | 534 |

TABLE 2-continued

| Example No. | Chemical Structure | M.W. | IUPAC-Name | M+(ESI+) |
|---|---|---|---|---|
| 328 | 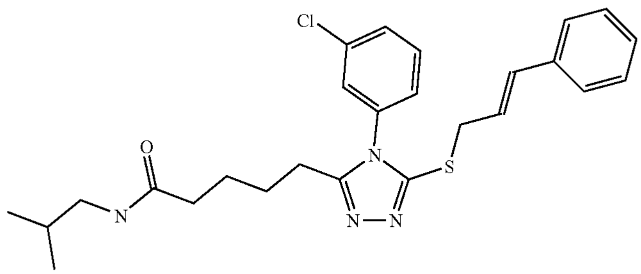 | 483.08 | 5-(4-(3-chlorophenyl)-5-{[(2E)-3-phenyl-2-propenyl]sulfanyl}-4H-1,2,4-triazol-3-yl)-N-isobutylpentanamide | 483 |
| 329 | 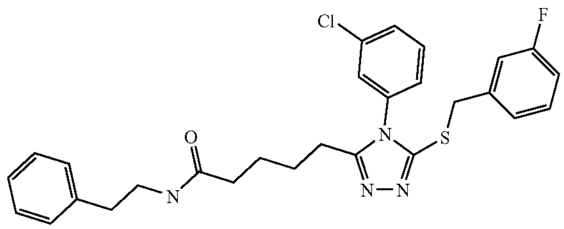 | 523.07 | 5-{4-(3-chlorophenyl)-5-[(3-fluorobenzyl)sulfanyl]-4H-1,2,4-triazol-3-yl]-N-(2-phenylethyl)pentanamide | 523 |
| 330 | 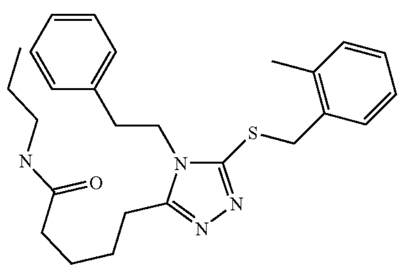 | 450.65 | 5-[5-[(2-methylbenzyl)sulfanyl]-4-(2-phenylethyl)-4H-1,2,4-triazol-3-yl]-N-propylpentanamide | 451 |
| 331 | 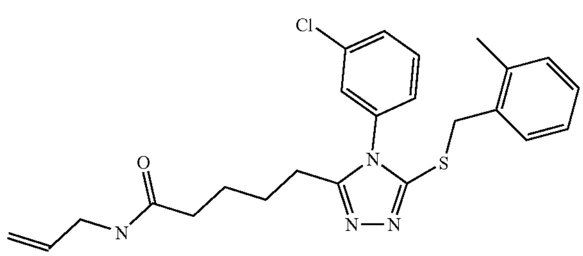 | 455.02 | N-allyl-5-{4-(3-chlorophenyl)-5-[(2-methylbenzyl)sulfanyl]-4H-1,2,4-triazol-3-yl}pentanamide | 455 |
| 332 | 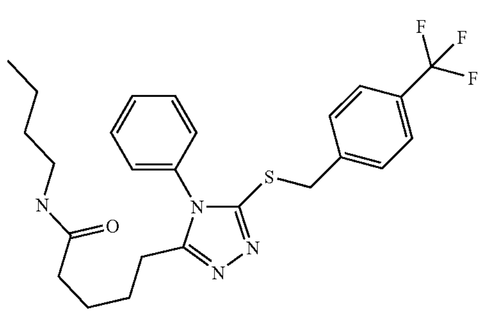 | 490.59 | N-butyl-5-(4-phenyl-5-{[4-(trifluoromethyl)benzyl]sulfanyl}-4H-1,2,4-triazol-3-yl)pentanamide | 491 |

TABLE 2-continued

| Example No. | Chemical Structure | M.W. | IUPAC-Name | M⁺(ESI⁺) |
|---|---|---|---|---|
| 333 | 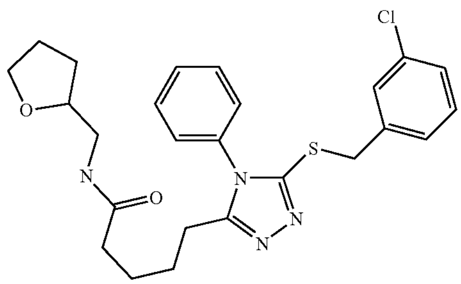 | 485.05 | 5-{5-[(3-chlorobenzyl)sulfanyl]-4-phenyl-4H-1,2,4-triazol-3-yl}-N-(tetrahydro-2-furanylmethyl)pentanamide | 485 |
| 334 | 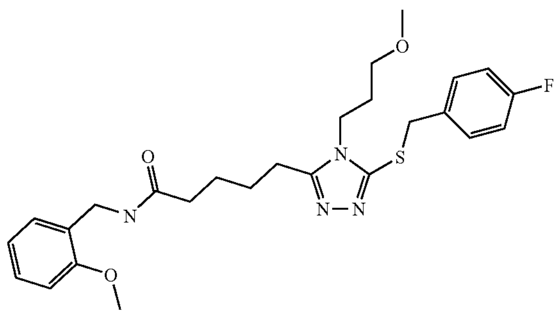 | 500.64 | 5-[5-[(4-fluorobenzyl)sulfanyl]-4-(3-methoxypropyl)-4H-1,2,4-triazol-3-yl]-N-(2-methoxybenzyl)pentanamide | 501 |
| 335 | 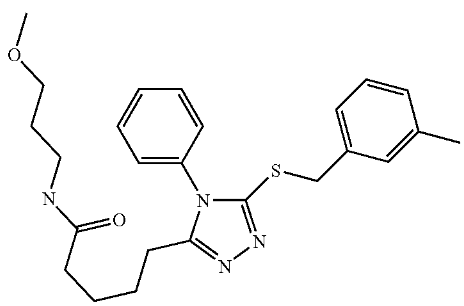 | 452.62 | N-(3-methoxypropyl)-5-{5-[(3-methylbenzyl)sulfanyl]-4-phenyl-4H-1,2,4-triazol-3-yl}pentanamide | 453 |
| 336 | 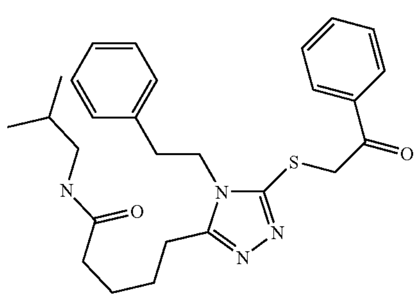 | 478.66 | N-isobutyl-5-[5-[(2-oxo-2-phenylethyl)sulfanyl]-4-(2-phenylethyl)-4H-1,2,4-triazol-3-yl]pentanamide | 479 |
| 337 | 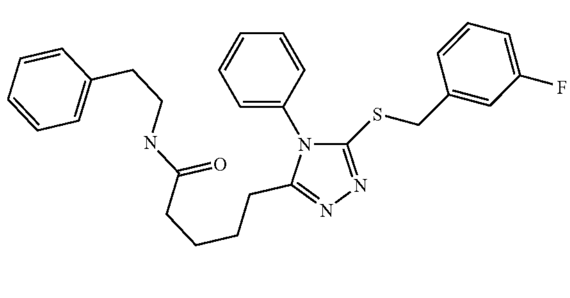 | 488.63 | 5-{5-[(3-fluorobenzyl)sulfanyl]-4-phenyl-4H-1,2,4-triazol-3-yl)-N-(2-phenylethyl)pentanamide | 489 |

TABLE 2-continued

| Example No. | Chemical Structure | M.W. | IUPAC-Name | M+(ESI+) |
|---|---|---|---|---|
| 338 | 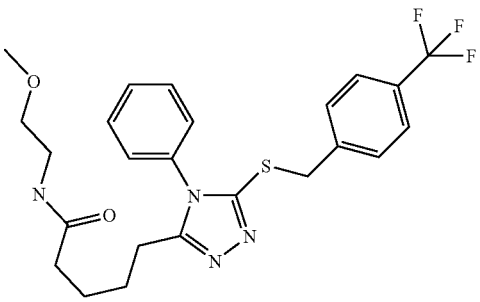 | 492.57 | N-(2-methoxyethyl)-5-(4-phenyl-5-{[4-(trifluoromethyl)benzyl]sulfanyl}-4H-1,2,4-triazol-3-yl)pentanamide | 493 |
| 339 | 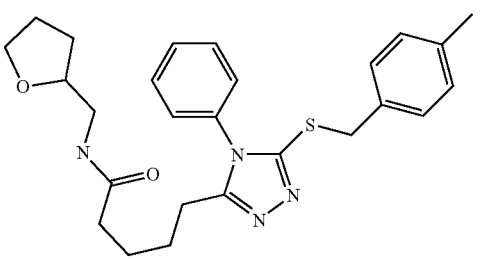 | 464.63 | 5-{5-[(4-methylbenzyl)sulfanyl]-4-phenyl-4H-1,2,4-triazol-3-yl}-N-(tetrahydro-2-furanylmethyl)pentanamide | 465 |
| 340 | 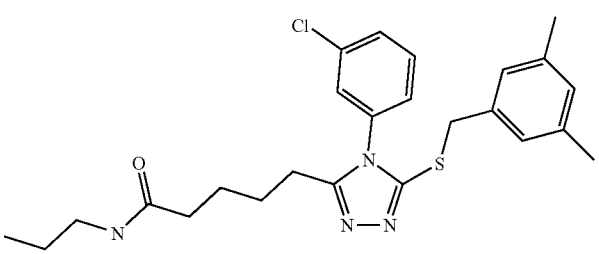 | 471.07 | 5-{4-(3-chlorophenyl)-5-[(3,5-dimethylbenzyl)sulfanyl]-4H-1,2,4-triazol-3-yl}-N-propylpentanamide | 471 |
| 341 | 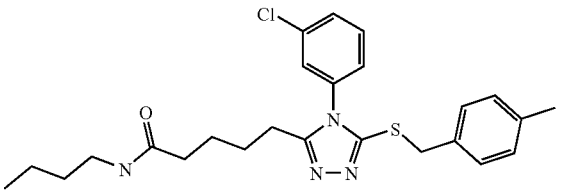 | 471.07 | N-butyl-5-{4-(3-chlorophenyl)-5-[(4-methylbenzyl)sulfanyl]-4H-1,2,4-triazol-3-yl}pentanamide | 471 |
| 342 | 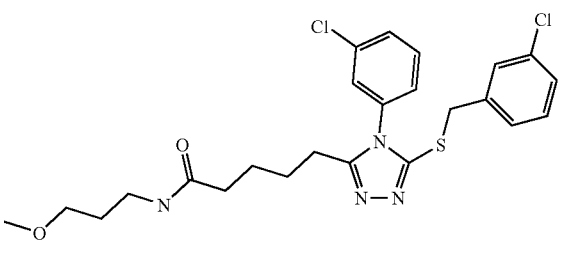 | 507.48 | 5-[5-[(3-chlorobenzyl)sulfanyl]-4-(3-chlorophenyl)-4H-1,2,4-triazol-3-yl]-N-(3-methoxypropyl)pentanamide | 507 |
| 343 | 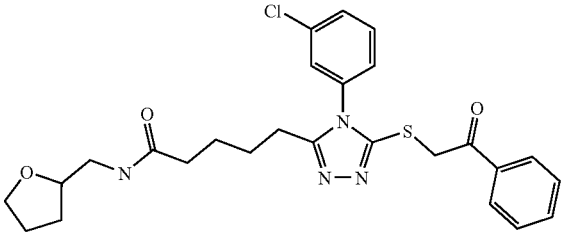 | 513.06 | 5-{4-(3-chlorophenyl)-5-[(2-oxo-2-phenylethyl)sulfanyl]-4H-1,2,4-triazol-3-yl}-N-(tetrahydro-2-furanylmethyl)pentanamide | 513 |

TABLE 2-continued

| Example No. | Chemical Structure | M.W. | IUPAC-Name | M+(ESI+) |
|---|---|---|---|---|
| 344 | 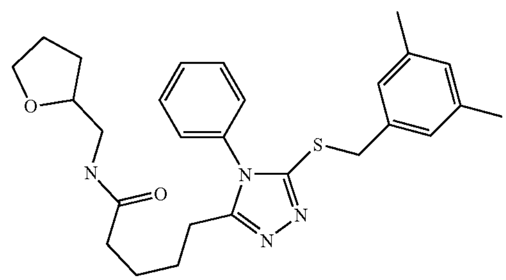 | 478.66 | 5-{5-[(3,5-dimethylbenzyl)sulfanyl]-4-phenyl-4H-1,2,4-triazol-3-yl)-N-(tetrahydro-2-furanylmethyl)pentanamide | 479 |
| 345 | 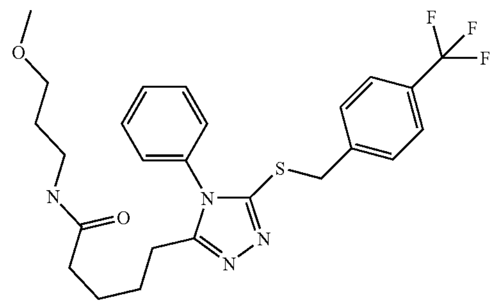 | 506.59 | N-(3-methoxypropyl)-5-(4-phenyl-5-{[4-(trifluoromethyl)benzyl]sulfanyl}-4H-1,2,4-triazol-3-yl)pentanamide | 507 |
| 346 | 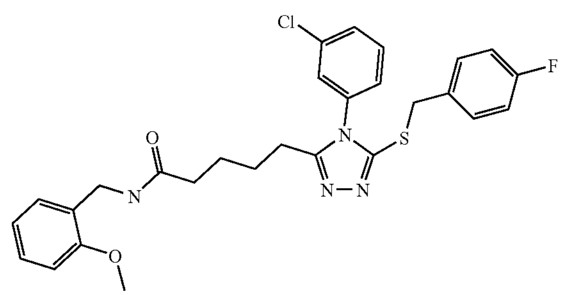 | 539.07 | 5-{4-(3-chlorophenyl)-5-](4-fluorobenzyl)sulfanyl]-4H-1,2,4-triazol-3-yl}-N-(2-methoxybenzyl)pentanamide | 539 |
| 347 | 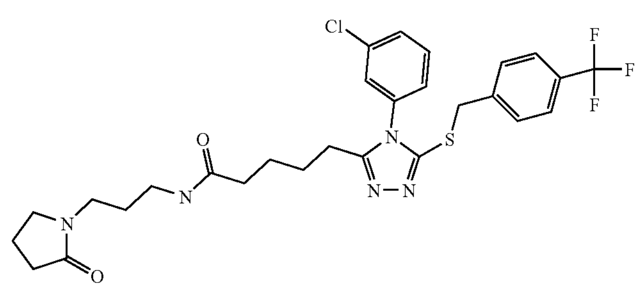 | 594.10 | 5-(4-(3-chlorophenyl)-5-{[4-(trifluoromethyl)benzyl]sulfanyl}-4H-1,2,4-triazol-3-yl)-N-[3-(2-oxo-1-pyrrolidinyl)propyl]pentanamide | 594 |
| 348 | 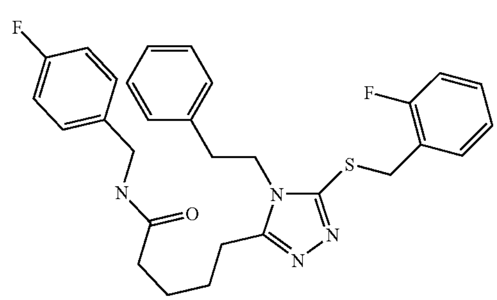 | 520.65 | N-(4-fluorobenzyl)-5-[5-[(2-fluorobenzyl)sulfanyl]-4-(2-phenylethyl)-4H-1,2,4-triazol-3-yl]pentanamide | 521 |

TABLE 2-continued

| Example No. | Chemical Structure | M.W. | IUPAC-Name | M+(ESI+) |
|---|---|---|---|---|
| 349 | 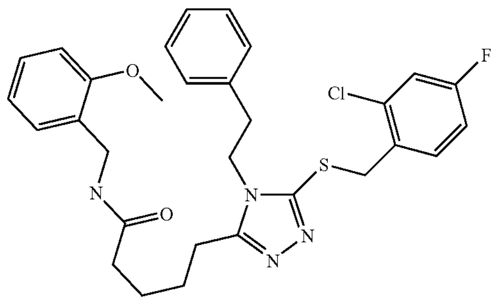 | 567.13 | 5-[5-[(2-chloro-4-fluorobenzyl)sulfanyl]-4-(2-phenylethyl)-4H-1,2,4-triazol-3-yl]-N-(2-methoxybenzyl)pentanamide | 567 |
| 350 | 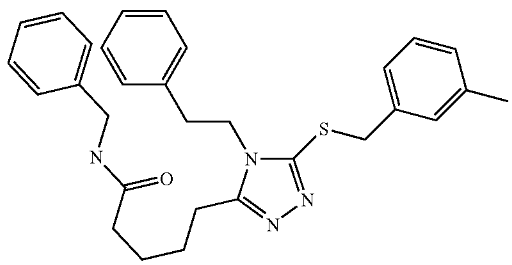 | 498.69 | N-benzyl-5-[5-[(3-methylbenzyl)sulfanyl]-4-(2-phenylethyl)-4H-1,2,4-triazol-3-yl]pentanamide | 499 |
| 351 | 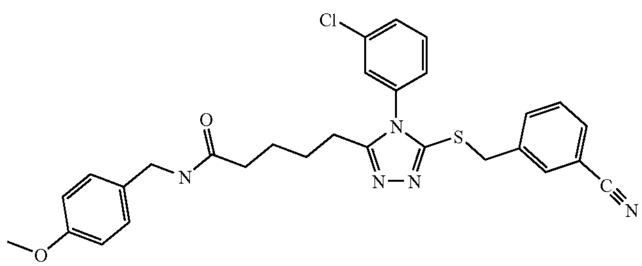 | 546.09 | 5-{4-(3-chlorophenyl)-5-[(3-cyanobenzyl)sulfanyl]-4H-1,2,4-triazol-3-yl}-N-(4-methoxybenzyl)pentanamide | 546 |
| 352 | 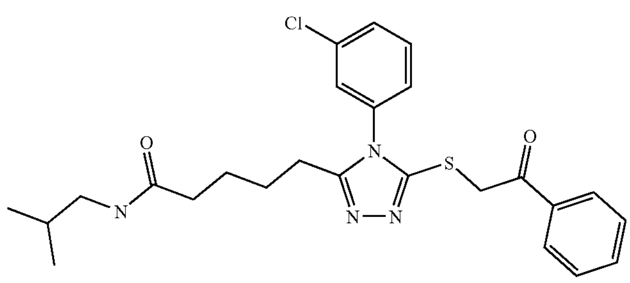 | 485.05 | 5-{4-(3-chlorophenyl)-5-[(2-oxo-2-phenylethyl)sulfanyl]-4H-1,2,4-triazol-3-yl)-N-isobutylpentanamide | 485 |
| 353 | 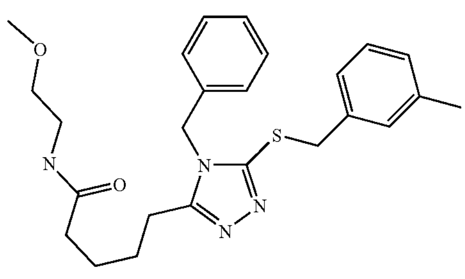 | 452.62 | 5-{4-benzyl-5-[(3-methylbenzyl)sulfanyl]-4H-1,2,4-triazol-3-yl}-N-(2-methoxyethyl)pentanamide | 453 |

TABLE 2-continued

| Example No. | Chemical Structure | M.W. | IUPAC-Name | M+(ESI+) |
|---|---|---|---|---|
| 354 | 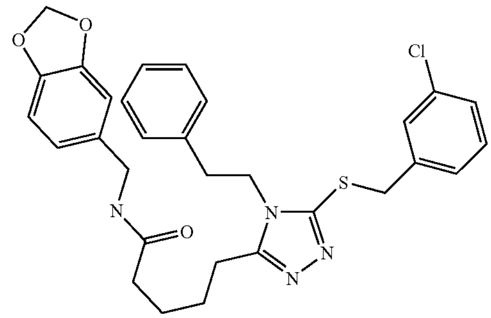 | 563.12 | N-(1,3-benzodioxol-5-ylmethyl)-5-[5-[(3-chlorobenzyl)sulfanyl]-4-(2-phenylethyl)-4H-1,2,4-triazol-3-yl]pentanamide | 563 |
| 355 | 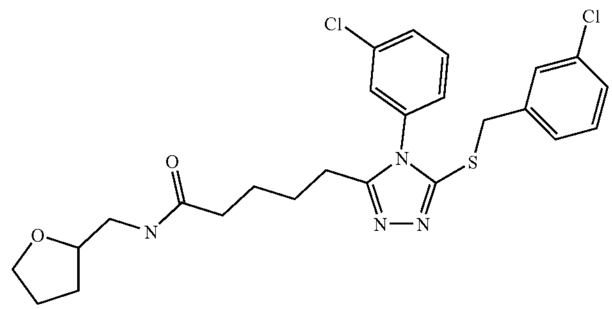 | 519.49 | 5-[5-[(3-chlorobenzyl)sulfanyl]-4-(3-chlorophenyl)-4H-1,2,4-triazol-3-yl]-N-(tetrahydro-2-furanylmethyl)pentanamide | 519 |
| 356 | 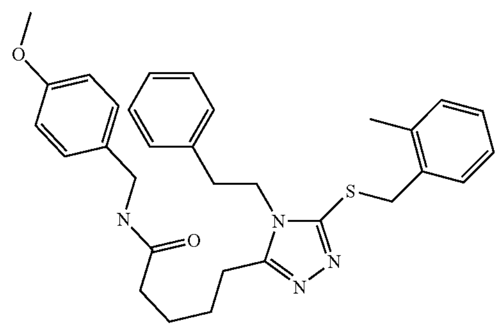 | 528.72 | N-(4-methoxybenzyl)-5-[5-[(2-methylbenzyl)sulfanyl]-4-(2-phenylethyl)-4H-1,2,4-triazol-3-yl]pentanamide | 529 |
| 357 | 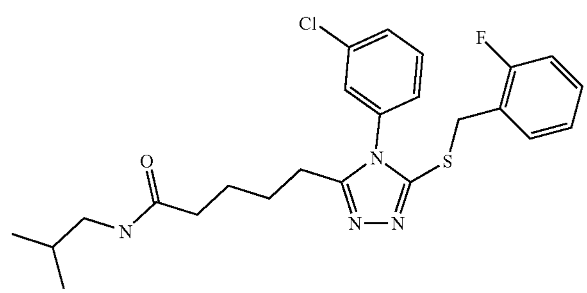 | 475.03 | 5-{4-(3-chlorophenyl)-5-[(2-fluorobenzyl)sulfanyl]-4H-1,2,4-triazol-3-yl}-N-isobutylpentanamide | 475 |
| 358 | 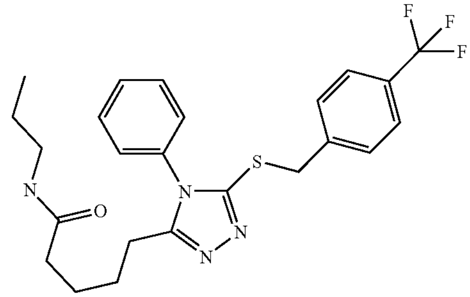 | 476.57 | 5-(4-phenyl-5-{[4-(trifluoromethyl)benzyl]sulfanyl}-4H-1,2,4-triazol-3-yl)-N-propylpentanamide | 477 |

TABLE 2-continued

| Example No. | Chemical Structure | M.W. | IUPAC-Name | M+(ESI+) |
|---|---|---|---|---|
| 359 | 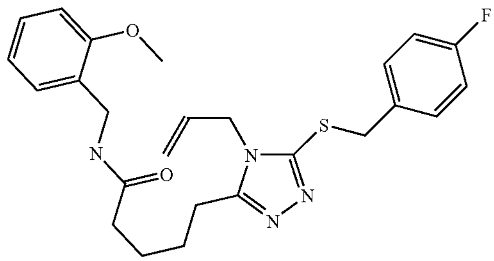 | 468.60 | 5-{4-allyl-5-[(4-fluorobenzyl)sulfanyl]-4H-1,2,4-triazol-3-yl}-N-(2-methoxybenzyl)pentanamide | 469 |
| 360 | 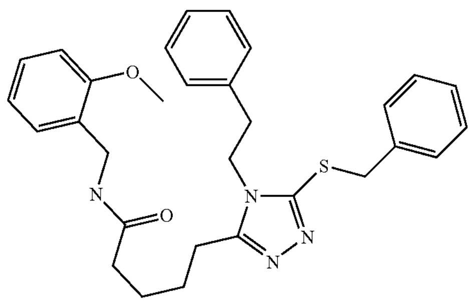 | 514.69 | 5-[5-(benzylsulfanyl)-4-(2-phenylethyl)-4H-1,2,4-triazol-3-yl]-N-(2-methoxybenzyl)pentanamide | 515 |
| 361 | 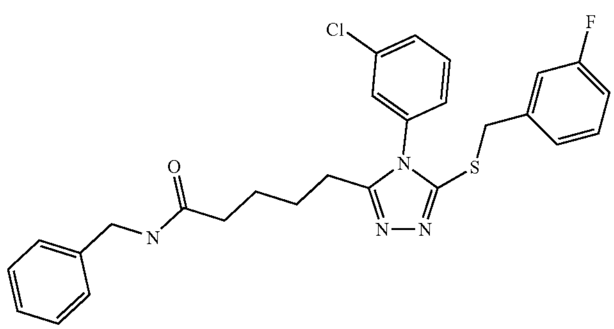 | 509.05 | N-benzyl-5-{4-(3-chlorophenyl)-5-[(3-fluorobenzyl)sulfanyl]-4H-1,2,4-triazol-3-yl}pentanamide | 509 |
| 362 | 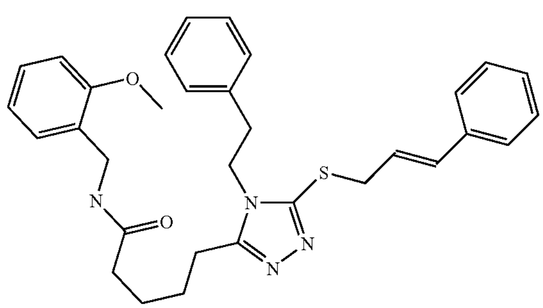 | 540.73 | N-(2-methoxybenzyl)-5-(4-(2-phenylethyl)-5-{[(2E)-3-phenyl-2-propenyl]sulfanyl}-4H-1,2,4-triazol-3-yl)pentanamide | 541 |
| 363 | 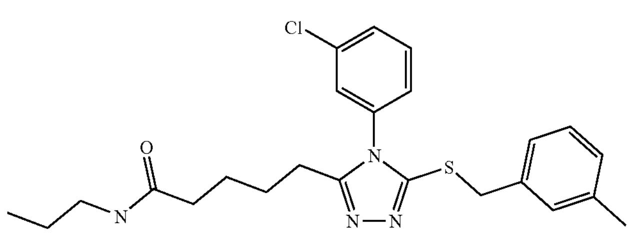 | 457.04 | 5-{4-(3-chlorophenyl)-5-[(3-methylbenzyl)sulfanyl]-4H-1,2,4-triazol-3-yl}-N-propylpentanamide | 457 |

TABLE 2-continued

| Example No. | Chemical Structure | M.W. | IUPAC-Name | M+(ESI+) |
|---|---|---|---|---|
| 364 | 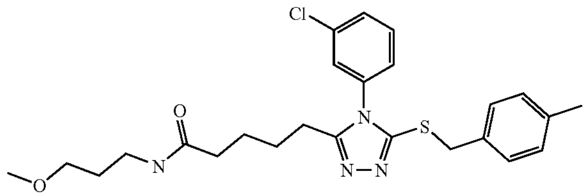 | 487.07 | 5-{4-(3-chlorophenyl)-5-[(4-methylbenzyl)sulfanyl]-4H-1,2,4-triazol-3-yl}-N-(3-methoxypropyl)pentanamide | 487 |
| 365 | 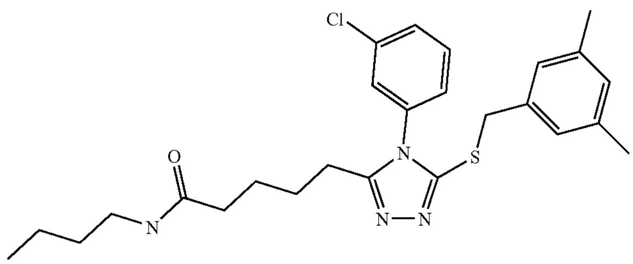 | 485.09 | N-butyl-5-{4-(3-chlorophenyl)-5-[(3,5-dimethylbenzyl)sulfanyl]-4H-1,2,4-triazol-3-yl}pentanamide | 485 |
| 366 | 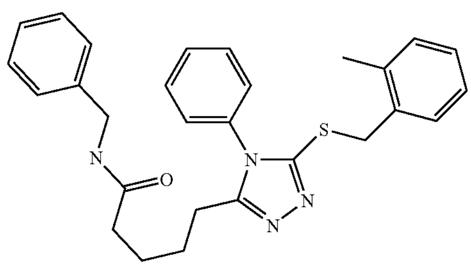 | 470.64 | N-benzyl-5-{5-[(2-methylbenzyl)sulfanyl]-4-phenyl-4H-1,2,4-triazol-3-yl}pentanamide | 471 |
| 367 | 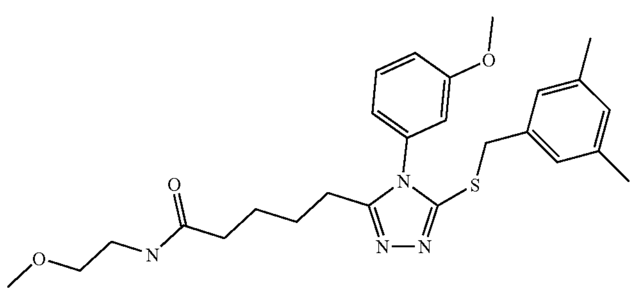 | 482.65 | 5-[5-[(3,5-dimethylbenzyl)sulfanyl]-4-(3-methoxyphenyl)-4H-1,2,4-triazol-3-yl]-N-(2-methoxyethyl)pentanamide | 483 |
| 368 | 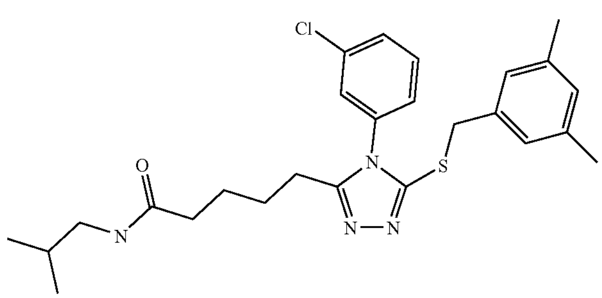 | 485.09 | 5-{4-(3-chlorophenyl)-5-[(3,5-dimethylbenzyl)sulfanyl]-4H-1,2,4-triazol-3-yl}-N-isobutylpentanamide | 485 |

TABLE 2-continued

| Example No. | Chemical Structure | M.W. | IUPAC-Name | M+(ESI+) |
|---|---|---|---|---|
| 369 | 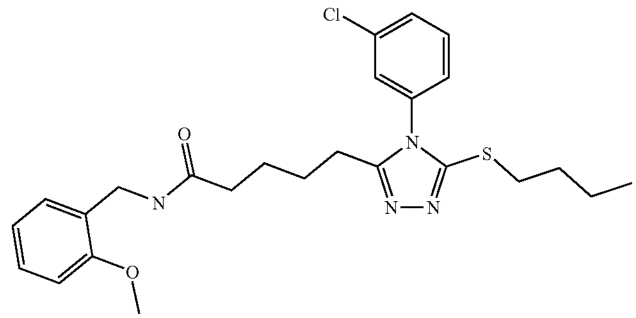 | 487.07 | 5-[5-(butylsulfanyl)-4-(3-chlorophenyl)-4H-1,2,4-triazol-3-yl]-N-(2-methoxybenzyl)pentanamide | 487 |
| 370 | 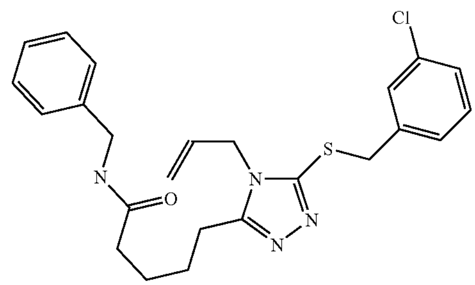 | 455.02 | 5-{4-allyl-5-[(3-chlorobenzyl)sulfanyl]-4H-1,2,4-triazol-3-yl}-N-benzylpentanamide | 455 |
| 371 | 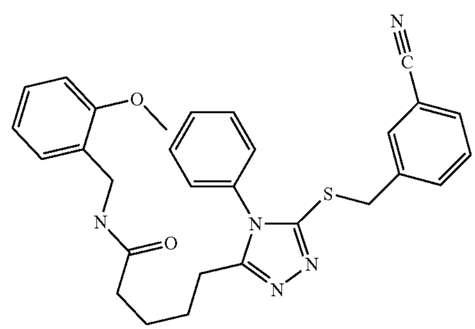 | 511.65 | 5-{5-[(3-cyanobenzyl)sulfanyl]-4-phenyl-4H-1,2,4-triazol-3-yl}-N-(2-methoxybenzyl)pentanamide | 512 |
| 372 | 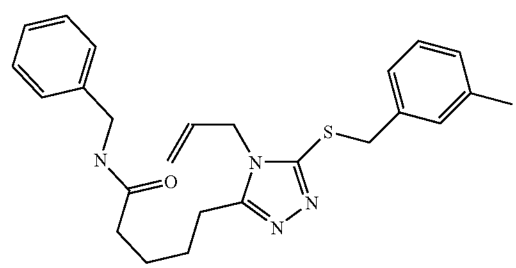 | 434.61 | 5-{4-allyl-5-[(3-methylbenzyl)sulfanyl]-4H-1,2,4-triazol-3-yl}-N-benzylpentanamide | 435 |
| 373 | 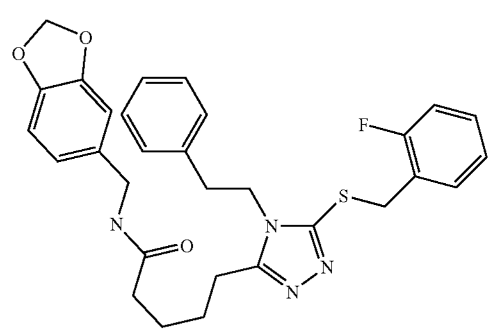 | 546.67 | N-(1,3-benzodioxol-5-ylmethyl)-5-[5-[(2-fluorobenzyl)sulfanyl]-4-(2-phenylethyl)-4H-1,2,4-triazol-3-yl]pentanamide | 547 |

TABLE 2-continued

| Example No. | Chemical Structure | M.W. | IUPAC-Name | M+(ESI+) |
|---|---|---|---|---|
| 374 | 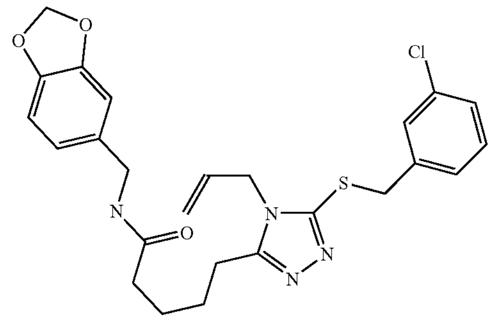 | 499.03 | 5-{4-allyl-5-[(3-chlorobenzyl)sulfanyl]-4H-1,2,4-triazol-3-yl}-N-(1,3-benzodioxol-5-ylmethyl)pentanamide | 499 |
| 375 | 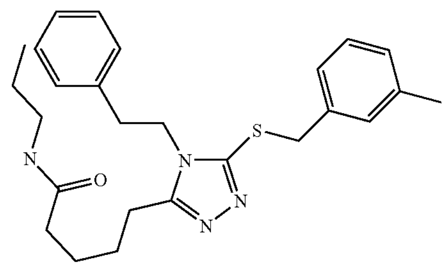 | 450.65 | 5-[5-[(3-methylbenzyl)sulfanyl]-4-(2-phenylethyl)-4H-1,2,4-triazol-3-yl]-N-propylpentanamide | 451 |
| 376 | 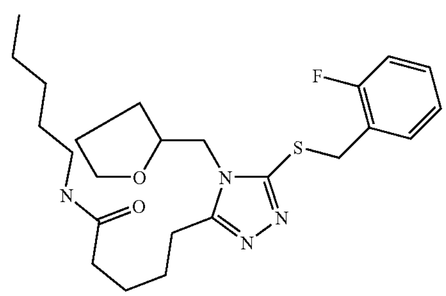 | 464.60 | 5-[5-[(2-fluorobenzyl)sulfanyl]-4-(tetrahydro-2-furanylmethyl)-4H-1,2,4-triazol-3-yl]-N-(3-methoxypropyl)pentanamide | 465 |
| 377 | 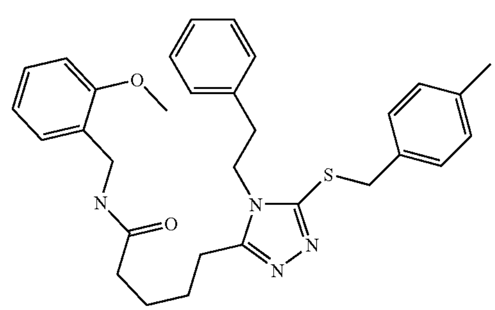 | 528.72 | N-(2-methoxybenzyl)-5-[5-[(4-methylbenzyl)sulfanyl]-4-(2-phenylethyl)-4H-1,2,4-triazol-3-yl]pentanamide | 529 |
| 378 | 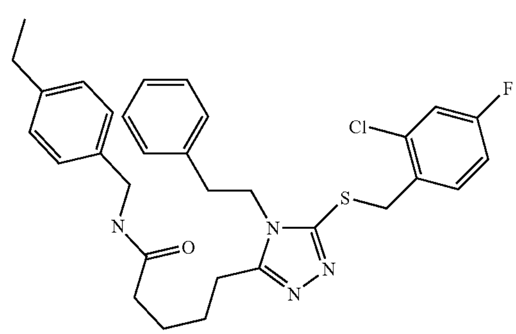 | 567.13 | 5-[5-[(2-chloro-4-fluorobenzyl)sulfanyl]-4-(2-phenylethyl)-4H-1,2,4-triazol-3-yl]-N-(4-methoxybenzyl)pentanamide | 567 |

TABLE 2-continued

| Example No. | Chemical Structure | M.W. | IUPAC-Name | M⁺(ESI⁺) |
|---|---|---|---|---|
| 379 | 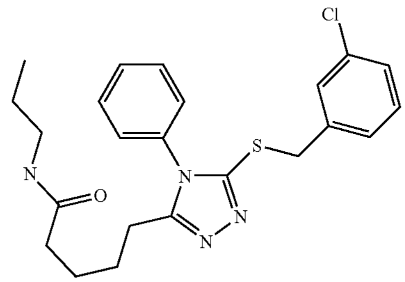 | 443.01 | 5-{5-[(3-chlorobenzyl)sulfanyl]-4-phenyl-4H-1,2,4-triazol-3-yl}-N-propylpentanamide | 443 |
| 380 | 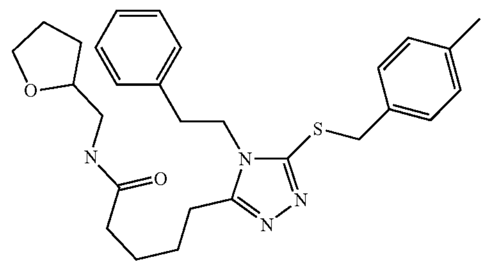 | 492.69 | 5-[5-[(4-methylbenzyl)sulfanyl]-4-(2-phenylethyl)-4H-1,2,4-triazol-3-yl]-N-(tetrahydro-2-furanylmethyl)pentanamide | 493 |
| 381 | 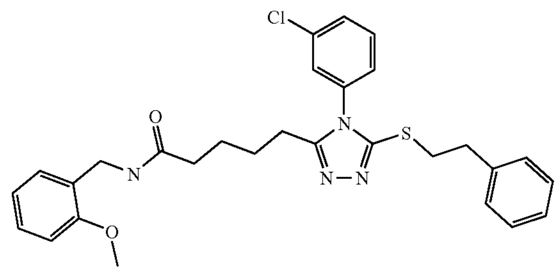 | 535.11 | 5-{4-(3-chlorophenyl)-5-[(2-phenylethyl)sulfanyl]-4H-1,2,4-triazol-3-yl}-N-(2-methoxybenzyl)pentanamide | 535 |
| 382 | 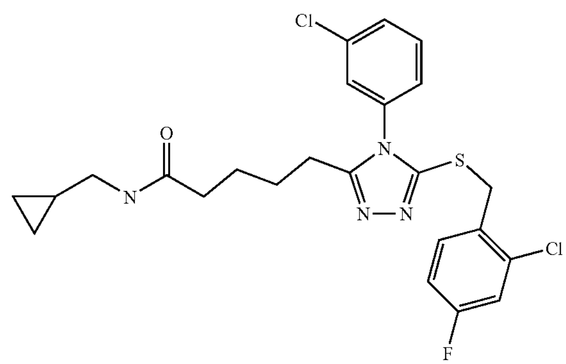 | 507.46 | 5-[5-[(2-chloro-4-fluorobenzyl)sulfanyl]-4-(3-chlorophenyl)-4H-1,2,4-triazol-3-yl]-N-(cyclopropylmethyl)pentanamide | 507 |

Example 383

Preparation of a Pharmaceutical Formulation

The following Formulation examples illustrate representative pharmaceutical compositions according to the present invention being.

Formulation 1—Tablets

A triazole compound of Formula I is admixed as a dry powder with a dry gelatin binder in an approximate 1:2 weight ration. A minor amount of magnesium stearate is added as a lubricant. The mixture is formed into 240-270 mg tablets (80-90 mg of active triazole compound per tablet) in a tablet press.

Formulation 2—Capsules

A triazole compound of Formula I is admixed as a dry powder with a starch diluent in an approximate 1:1 weight ratio. The mixture is filled into 250 mg capsules (125 mg of active triazole compound per capsule).

Formulation 3—Liquid

A triazole compound of Formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A triazole compound of Formula I is admixed as a dry powder with a dry gelatin binder in an approximate 1:2 weight ratio. A minor amount of magnesium stearate is added as a lubricant. The mixture is formed into 450-900 mg tablets (150-300 mg of active triazole compound) in a tablet press.

Formulation 5—Injection

A triazole compound of Formula I is dissolved in a buffered sterile saline injectable aqueous medium to a concentration of approximately 5 mg/ml.

Example 384

Biological Assays

The compounds according to Formula I may be subjected to the following assays:

a) In vitro Competition Binding Assay on hOT Receptor with Scintillation Proximity Assay (18).

This assay allows to determine the affinity of the test compounds for the human Oxytocin (hOT) receptor. Membranes from HEK293EBNA (cells expressing the hOT receptor) were suspended in buffer containing 50 mM Tris-HCl, pH 7.4, 5 mM MgCl2 and 0.1% BSA (w/v). The membranes (2-4 fg) were mixed with 0.1 mg SPA bead coated with wheat-germ aglutinin (WGA-PVT-Polyethylene Imine beads from Amersham) and 0.2 DM of the radiolabelled [$^{125}$I]-OVTA (OVTA being Omithin Vasoactive, an analogue of OT for competitive binding experiments). Non-specific binding was determined in the presence of 1 μM Oxytocin. The total assay volume was 100 μL. The plates (Corning® NBS plate) were incubated at room temperature for 30 min and counted on a Mibrobeta® plate scintillation counter. Competitive binding was performed in presence of compounds of formula (1) at the following concentrations: 30 μM, 10 μM, 1 μM, 300 nM, 100 nM 10 nM, 1 nM, 100 pM, 10 pM. The competitive binding data were analysed using the iterative, nonlinear, curve-fitting program, "Prism" (GraphPad Software, Inc).

The ability of triazole derivatives of formula (I) to inhibit the binding of $^{125}$I-OVTA to the OT-receptor was assessed using the above described in vitro biological assay. Representative values for some example compounds are given in Table 3 where the binding affinity of the compounds is expressed by the inhibition constant (Ki; μM). From these values, it can be derived that said test compounds according to formula I do show a significant binding to the oxytocin receptor.

TABLE 3

| Example No. | IUPAC-Name | Binding Affinity hOT-R (Ki [μM]) |
|---|---|---|
| 1 | 3-[5-[(3-chlorobenzyl)sulfanyl]-4-(3-methoxyphenyl)-4H-1,2,4-triazol-3-yl]-N-(2-methoxybenzyl)propanamide | 0.045 |
| 5 | 3-[5-[(3-fluorobenzyl)sulfanyl]-4-(4-methylphenyl)-4H-1,2,4-triazol-3-yl]-N-(2-methoxybenzyl)propanamide | 0.127 |

TABLE 3-continued

| Example No. | IUPAC-Name | Binding Affinity hOT-R (Ki [μM]) |
|---|---|---|
| 3 | 3-{4-(3-chlorophenyl)-5-[(3-methylbenzyl)sulfanyl]-4H-1,2,4-triazol-3-yl}-N-(2-methoxybenzyl)propanamide | 0.134 |
| 16 | N-(2-methoxybenzyl)-3-{4-(3-methoxyphenyl)-5-[(3-methylbenzyl)sulfanyl]-4H-1,2,4-triazol-3-yl}propanamide | 0.197 |
| 9 | 3-[5-(benzylsulfanyl)-4-(4-methylphenyl)-4H-1,2,4-triazol-3-yl]-N-(2-methoxybenzyl)propanamide | 0.205 |
| 8 | 3-[5-[(3-chlorobenzyl)sulfanyl]-4-(3-methylphenyl)-4H-1,2,4-triazol-3-yl]-N-(2-methoxybenzyl)propanamide | 0.229 |
| 15 | N-butyl-3-[5-[(3-chlorobenzyl)sulfanyl]-4-(3-chlorophenyl)-4H-1,2,4-triazol-3-yl]propanamide | 0.245 |
| 6 | N-(2-methoxybenzyl)-3-{4-(4-methylbenzyl)-5-[(3-methylbenzyl)sulfanyl]-4H-1,2,4-triazol-3-yl}propanamide | 0.246 |
| 4 | 3-[5-[(3-chlorobenzyl)sulfanyl]-4-(3-methoxypropyl)-4H-1,2,4-triazol-3-yl]-N-(2-methoxybenzyl)propanamide | 0.326 |
| 11 | 3-{4-(3-chlorophenyl)-5-[(4-fluorobenzyl)sulfanyl]-4H-1,2,4-triazol-3-yl}-N-(2-methoxybenzyl)propanamide | 0.329 |
| 12 | 3-[5-(benzylsulfanyl)-4-(3-chlorophenyl)-4H-1,2,4-triazol-3-yl]-N-(2-methoxybenzyl)propanamide | 0.439 |
| 184 | 5-[5-[(3-chlorobenzyl)sulfanyl]-4-(3-chlorophenyl)-4H-1,2,4-triazol-3-yl]-N-(2-methoxybenzyl)pentanamide | 0.481 |
| 189 | N-(2-methoxybenzyl)-5-[5-[(3-methylbenzyl)sulfanyl]-4-(2-phenylethyl)-4H-1,2,4-triazol-3-yl]pentanamide | 0.515 |
| 185 | 5-{5-[(3-chlorobenzyl)sulfanyl]-4-phenyl-4H-1,2,4-triazol-3-yl}-N-(2-methoxybenzyl)pentanamide | 0.603 |
| 137 | 4-{5-[(3-chlorobenzyl)sulfanyl]-4-phenyl-4H-1,2,4-triazol-3-yl}-N-(2-methoxybenzyl)butanamide | 2.550 | b) In vitro Competition Binding Assay on hV1a Receptor with Scintillation Proximity Assay (18)

This assay allows the determination of the affinity of the test compounds for the V1a receptor. Membranes from CHO cells expressing the hV1a receptor are suspended in buffer containing 50 mM Tris-HCl, pH 7.4, 5 mM MgCl$_2$ and 0.1% BSA (w/v). The membranes (5-10 μg) are mixed with 0.2 mg SPA bead coated with wheat-germ aglutinin (WGA beads from Amersham) and 0.03 nM of the radiolabelled [$^{125}$I]-LVA (LVA being Linear Vasopressin Antagonist and is an analogue of AVP for competitive binding experiments). Non-specific binding is determined in the presence of 1 μM AVP. The total assay volume is 100 μl. The plates (Corning® NBS plate) are incubated at room temperature for 2 hours and counted on a Mibrobeta® plate scintillation counter. Competitive binding can be performed in presence of test compounds at the following concentrations: 30 μM, 10 μM, 1 μM, 300 nM, 100 nM, 10 nM, 1 nM, 100 pM, 10 pM. The competitive binding data can then be analysed using the iterative, nonlinear, curve-fitting program, "Prism" (GraphPad Software, Inc).

The binding affinities to the $V_{1a}$ receptor of the triazole derivatives claimed in the formula I can be measured using the above described in vitro biological assay.

c) Functional Assay No. 1: Inhibition of Oxytocin Mediated $Ca^{2+}$-mobilization by FLIPR® (Fluorimetric Imaging Plate Reader)

The action of OT on the OT-receptor triggers a complex cascade of events in the cell which leads to an increase in the intra-cytoplasmic $Ca^{2+}$ concentration. This increase in $Ca^{2+}$ concentration results from both calcium release from the sarcoplasmic reticulum (calcium stores) into the cytoplasm and from calcium influx from the extracellular space through $Ca^{2+}$ channels. This $Ca^{2+}$ mobilization into the cytoplasm triggers the contractile machinery of the myometrial cells which leads to uterine contractions (4 and 19).

This assay allows the measurement of the inhibition of OT/OT-R mediated calcium mobilization by test compounds of formula (1).

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates were pre-coated with PLL (Poly-L-Lysine) 10 µg/ml+0.1% gelatine to attach HEK293EBNA cells (Human Embryonic Kidney cells expressing the hOT receptor) and incubated for 30 min up to 2 days at 37° C. The cells were plated out into 96-well-plates (60000 cells/well).

Labelling with fluo-4: 50 µg of fluo-4 (Ca2+ sensitive fluorescent dye) were dissolved in 20 µl pluronic acid (20% in DMSO). The dissolved fluo-4 was then diluted in 10 ml DMEM (Dubecco's Minimal Essential Medium)-F12 culture medium. The plates were washed one time with DMEM-F12 medium 100 µl of the fluo-4 containing-DMEM-F12 medium were added to the HEK-cells which were incubated for 1.5-2 h in this fluorescent medium. Fluo-4 is taken up by the cytoplasm of the cells.

Buffer: 145 mM NaCl, 5 mM KCl, 1 mM $MgCl_2$, 10 mM Hepes, 10 mM Glucose, EGTA Ethylene-bis oxyethylene nitrilo tetraacetic acid). The pH was adjusted to 7.4.

Performance of the assay: A minimum of 80 µl/well of compounds of formula (I) (5x) in the above buffer (1x) were prepared (96-well-plates). The compounds of formula (I) were added to the 96-well-plates at different concentrations (30 µM, 10 µM, 1 µM, 300 nM, 100 nM, 10 nM, 1 nM, 100 pM, 10 pM). OT was added at a concentration of 40 nM.

The relative fluorescence of Fluo ($\lambda_{ex}$=488 nm, $\lambda_{em}$=590 nm) is then measured by the FLIPR in presence or absence of compounds of formula (I). The fluorescence of the marker being sensitive to the amount of $Ca^{2+}$, the $Ca^{2+}$ movements can be detected. Then, it can be determined the ability of compounds of formula (I) to antagonize the oxytocin-induced intracellular $Ca^{2+}$-mobilization mediated by the oxytocin receptor.

The activities of the triazole derivatives according to formula I were assessed using the above described in vitro biological assay. Representative values for some example compounds are given in Table 4. The values refer to the concentration of the test compounds according to formula I necessary to antagonize by 50% the OT/OTR intracellular $Ca^{2+}$-mobilization. From the values, it can be derived that said example compounds according to formula I do exhibit a significant activity as oxytocin receptor antagonists.

TABLE 4

| Chemical Structure | IUPAC-Name | Inhibition of Ca2+ mobilisation; hOT-R IC50 [µM] |
| --- | --- | --- |
| 1 | 3-[5-[(3-chlorobenzyl)sulfanyl]-4-(3-methoxyphenyl)-4H-1,2,4-triazol-3-yl]-N-(2-methoxybenzyl)propanamide | 0.026 |

TABLE 4-continued

| Chemical Structure | IUPAC-Name | Inhibition of Ca2+ mobilisation; hOT-R IC50 [µM] |
| --- | --- | --- |
| 185 | 5-{5-[(3-chlorobenzyl)sulfanyl]-4-phenyl-4H-1,2,4-triazol-3-yl}-N-(2-methoxybenzyl)pentanamide | 0.058 |
| 137 | 4-{5-[(3-chlorobenzyl)sulfanyl]-4-phenyl-4H-1,2,4-triazol-3-yl}-N-(2-methoxybenzyl)butanamide | 0.486 | d) Functional Assay No. 1: Inhibition of Vasopressin-Mediated $Ca^{2+}$-Mobilization by FLIPR® (Fluorimetric Imaging Plate Reader)

The action of AVP on the $V_1$-receptor triggers a complex cascade of events in the cell which leads to an increase in the intra-cytoplasmic $Ca^{2+}$ concentration. This increase in $Ca^{2+}$ concentration results from both calcium release from the sarcoplasmic reticulum (calcium stores) into the cytoplasm and from calcium influx from the extracellular space through $Ca^{2+}$ channels. This $Ca^{2+}$ mobilization into the cytoplasm triggers the contractile machinery of the myometrial cells which leads to uterine contractions (4 and 19).

This assay can be used to measure the inhibition of AVP/$V_{1a}$-R mediated calcium mobilization by test compounds of formula (I).

FLIPR® is a fluorimetric imaging device using a laser (Argon-ion laser) for simultaneous illumination and reading (cooled CCD camera) of each well of a 96-well-plate, thus enabling rapid measurements on a large number of samples.

Preparing the plates: FLIPR-plates are pre-coated with PLL (Poly-L-Lysine) 10 µg/ml+0.1% gelatine to attach the CHO cells (expessing $hV_{1a}$) and incubated for 30 min up to 2 days at 37° C. The cells are plated out into 96-well plates (60000 cells/well).

Labelling with fluo-4: 50 µg fluo-4 (fluorescent marker) is dissolved in 20 µl pluronic acid (20% in DMSO). The dissolved fluo-4 is then diluted in 10 ml DMEM (Dubecco's Minimal Essential Medium-F12 medium. The medium is removed from the plates, followed by one wash with DMEM-F12 medium. 100 µl of the DMEM-F12 medium containing fluo-4 are added and the cells incubated for 1-1.5 h (CHO-cells).

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). Adjust to pH 7.4.

Performance of the assay: A minimum of 80 µl/well of antagonists (5x) in the above buffer (1x) is prepared (96-well plates). The antagonists can be added to the well-plates at different concentrations (30 µM, 10 µM, 1 µM, 300 nK 100 nM, 10 nK, 1 nM 100 pM, 10 pM). AVP is added at a concentration of 40 nM.

The relative fluorescence of Fluo-4 ($\lambda_{ex}$=488 nm, $\mu_{em}$=590 nm) can then be measured by the FLIPR in presence or absence of compounds of formula (1). The fluorescence of the marker being sensitive to the amount of $Ca^{2+}$, the $Ca^{2+}$ movements can be detected.

In the same way as for the FLIPR assay with OT receptor expressing cells, the capacity of the triazole derivatives according to formula I, to effectively antagonize AVP-induced intracellular $Ca^{2+}$-mobilization mediated by the action of AVP at the $V_{1a}$-receptor, can be assessed using the above described in vitro biological assay.

e) Functional Assay No. 2: Inhibition of IP3 (Inositol Tri-Phosphate)-Synthesis in HEK/EBNA-OTR Cells The interaction of OT on the OT-receptor leads to the IP3 synthesis, second messenger for $Ca^{2+}$ release from sarcoplasmic reticulum, involved in the uterine contraction triggering process (4).

This assay can be used to show the inhibition of the OT/OT-R mediated IP3 synthesis by using test compounds of formula (I).

Stimulation of the cells: HEK/EBNA OTR (rat or human) cells are plated out into costar 12-well plates, and equilibrated for 15-24 h with 4 µCi/ml radiolabelled [$^3$H]-Inositol with 1% FCS (0.5 ml/well) and without inositol supplement. The medium containing the label is aspirated. DMEM medium (without FCS, inositol), 20 mM Hepes (4-(2-hydroxyethyl)-1-piperazine-ethane-sulphonic acid), 1 mg/ml BSA containing 10 mM LiCl (freshly prepared), are added and incubated for 10-15 min at 37° C. The agonist (i.e. oxytocin used at a concentration of 10 nM) and the antagonists (i.e. the tests compounds of formula (1) can be used in a concentration of 10 µM, 1 µM, 300 nM, 100 nM, 10 nM, 1 nM, 100 pM, 10 pM, 3 pM) can be added at the required time (15-45 min), followed by aspiration of the medium In the presence of OT, the radiolabelled inositol is converted to radiolabelled IP3. Antagonizing OT at the OT-receptor inhibits the IP3 formation.

The amount of the radiolabelled IP3 may be determined through the ensuing work-up. The reaction is stopped with 1 ml STOP-solution (i.e. 0.4 M perchloric acid), and let sit for 5-10 min at Room Temperature. Then, 0.8 ml are transferred into tubes containing 0.4 ml of neutralizing solution (0.72 M KOH/0.6M $KHCO_3$), and the tubes vortexed and kept in the cold at least for 2 h.

Separation of IP's: The samples are spun in a table top centrifuge at 3000-4000 rpm for 15 min. 1 ml of the supernatant is transferred to new tubes containing 2.5 ml $H_2O$. Packed resin (Dowex AG1X8) is equilibrated with 20 ml $H_2O$, and the whole samples are poured onto the chromatography columns, thus separating the mixture. To remove free inositol, two washes with 10 ml $H_2O$ are carried out.

Elution of total IP's: Elution is achieved using 3 ml 1M ammonium formate/0.1M formic acid. The eluant is collected in scintillation counting tubes, after the addition of 7 ml of scintillation liquid. The amount of [$^3$H]-IP3 is determined by a scintillating counter.

The ability of compounds of formula(I) to effectively antagonize oxytocin-induced IP3-synthesis mediated by the oxytocin receptor, can be assessed using the above described in vitro biological assay.

f) In vivo Model for Inhibition of Uterine Contractions

The assay evaluates the biological effect of tested compounds in an in vivo model of preterm labor, premature birth.

Non-pregnant Charles River CD (SD) BR female rats (9-10 weeks old, 200-250 g) were treated at 18 and 24 hours before the experiment with 250 µg/kg, i.p. diethylstilbestrol (DES). For the assay, the animal was anaesthetised with urethane (1.75 g/kg, i.p.) and placed on a homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P23ID Gould Statham pressure transducer.

One jugular vein was isolated, cannulated with a PE60 tubing and connected to a butterfly needle to provide an i.v. route of administration of the test compounds via a dispensing syringe.

In the case of intraduodenal administration of the test compounds, the duodenum can be isolated and similarly cannulated through a small incision in its wall.

One carotid artery was also isolated and cannulated with PE60 catheter and connected to a suitable syringe for blood sample collection.

After a stabilization period and throughout the experiment, the same dose of oxytocin was repeatedly injected intravenously at 30-min intervals. When reproducible contractile responses of the uterus to the same OT stimulus (selected dose of oxytocin) were obtained, the dose of the test or of the reference (vehicle) was administered. Further injection cycles of the same dose of oxytocin, were continued (OT injections at 30-min intervals) for a suitable time after treatment to assess the inhibitory effects and the reversibility of these effects.

The contractile response of the uterus to oxytocin was quantified by measuring the intra-uterine pressure and the number of contractions. The effect of the reference and test compounds was evaluated by comparing pre- and post-treatment pressure values. In addition, at 2, 30, 90 and 210 minutes after test compound administration, a 0.5-ml blood sample was withdrawn from the cannulated carotid artery of each experimental animal. Plasma was obtained by standard laboratory procedure and the resulting samples were stored at −20° C.

The activities of the triazole derivatives claimed in the Formula I can be assessed using the above described in vivo biological assay. Representative values for one example compound are given in Table 5. The values refer to the capacity of the example compound according to Formula I to effectively antagonize oxytocin-induced uterine contractions in the rat. From the values shown in Table 5 it can be derived that said example test compound according to Formula I does exhibit a significant activity as tocolytic, i.e. uterine-relaxing, agent.

TABLE 5

| Chemical Structure | IUPAC-Name | % Reduction of Uterine Contraction | Doses [mg/kg] |
|---|---|---|---|
| 1 | 3-[5-[(3-chlorobenzyl)sulfanyl]-4-(3-methoxyphenyl)-4H-1,2,4-triazol-3-yl]-N-(2-methoxybenzyl)propanamide | 16.9 ± 5.1 | 10 |

REFERENCES

1. Thibonnier, M. et al. *Adv. Rev. Pharmacol. Toxicol.* 2001, 41, 175-202.
2. Brinbauer, M. *TEM* 2000, 11, 406-410.
3. Maggi, M. et al. *J. Clin. Endocrinol. Metabol.* 1990, 70, 1142-1154.
4. Mitchell, B. F. and Schmid, B. *J. Soc. Gynecol. Invest.* 2001, 8, 122-33.
5. Thibonnier et al. *Adv. Exp. Med. Biolog.* 1998, 449, 251-203.
6. Thorton, S. et al., *Experimental Physiology* 2001; 86, 297-302.
7. Evans B. E. et al. *J. Med. Chem.* 1992, 35, 3919-3927.
8. Gennaro, A. R. et al., Remington's Pharmaceutical Sciences. 18th ed. Easton: The Mack Publishing Company, 1995.
9. Moustafa, O. S. *Heterocycl. Commun.* 2000, 6, 465-471.
10. Ashton, W. T. et al. *Med. Chem.* 1993, 36, 591-609.
11. Ashton, W. T. at al. (1992) EP 505111.

12. Carey, Let al. (1982) EP 48555.
13. Bertin, J. et al. (2000) WO 0046220.
14. Ashton, W. T. et al. (1991) EP 409332.
15. Fritch, Paul C. et al. Solid-Phase Org. Synth. 2001, 1, 105-112
16. Philip J. Kocienski, in "*Protecting Groups*", Georg Thieme Verlag Stuttgart, New York, 1994.
17. Theodora W. Greene et al. in "*Protective Groups in Organic Synthesis*", Wiley-Interscience, 1991.
18. Cook, N. D. et al. *Pharmaceutical Manufacturing International* 1992; p. 49-53
19. Gimpl G. and Fahrenholz, F. *Physiological Reviews* 2001, 81, 629-683

The invention claimed is:
1. The triazole derivative of Formula I:

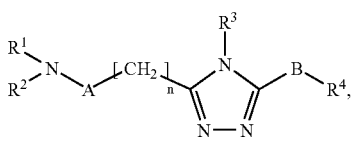

its geometrical isomers, its optically active forms as enantiomers, diastereomers, mixtures of these and its racemate forms, as well as salts thereof, wherein:

$R^1$ and $R^2$ are independently selected from the group consisting of H, $C_1$-$C_6$-alkyl, aryl $C_1$-$C_6$-alkyl, heteroaryl $C_1$-$C_6$-alkyl, $C_3$-$C_6$-cycloalkyl $C_1$-$C_6$-alkyl and $C_3$-$C_6$-heterocycloalkyl $C_1$-$C_6$-alkyl;

$R^1$ and $R^2$, together with the nitrogen atom they are linked to, form a substituted or unsubstituted 5-8-membered saturated, partially unsaturated or aromatic ring containing optionally one or more additional heteroatoms selected from O, N, S;

A is C(O);

$R^3$ is selected from the group consisting of H, $C_1$-$C_6$-alkyl, aryl $C_1$-$C_6$-alkyl, heteroaryl $C_1$-$C_6$-alkyl, aryl, heteroaryl, $C_3$-$C_6$-cycloalkyl $C_1$-$C_6$-alkyl, $C_3$-$C_6$-heterocycloalkyl $C_1$-$C_6$-alkyl, $C_2$-$C_6$-alkenyl;

B is S;

$R^4$ and $R^5$ are selected from the group consisting of H, $C_1$-$C_6$-alkyl, aryl $C_1$-$C_6$-alkyl, heteroaryl $C_1$-$C_6$-alkyl, acyl, aryl acyl, heteroaryl acyl, $C_3$-$C_6$-cycloalkyl $C_1$-$C_6$-alkyl, $C_3$-$C_6$-heterocycloalkyl $C_1$-$C_6$-alkyl, $C_2$-$C_6$-alkenyl;

n is an integer from 2 to 10.

2. The triazole derivative according to claim 1, wherein A is carbonyl.
3. The triazole derivative according to claim 1, wherein B is sulfur.
4. The triazole derivative according to claim 1, wherein n is an integer from 2, 3 or 4.
5. The triazole derivative according to claim 1, wherein A is carbonyl, B is sulfur and n is an integer from 2, 3 or 4.
6. A triazole derivative according to claim 1, selected from the group consisting of:

3-{4-benzyl-5-[(3-chlorobenzyl)sulfanyl]-4H-1,2,4-triazol-3-yl}-N-(2-methoxybenzyl)propanamide,
3-{4-(3-chlorophenyl)-5-[(3-methylbenzyl)sulfanyl]-4H-1,2,4-triazol-3-yl}-N-(2-methoxybenzyl)propanamide,
3-[5-[(3-chlorobenzyl)sulfanyl]-4-(3-methoxypropyl)-4H-1,2,4-triazol-3-yl]-N-(2-methoxybenzyl)propanamide,
3-[5-[(3-chlorobenzyl)sulfanyl]-4-(3-methoxyphenyl)-4H-1,2,4-triazol-3-yl]-N-(2-methoxybenzyl)propanamide,
3-[5-[(3-fluorobenzyl)sulfanyl]-4-(4-methylphenyl)-4H-1,2,4-triazol-3-yl]-N-(2-methoxybenzyl)propanamide,
N-(2-methoxybenzyl)-3-{4-(4-methylbenzyl)-5-[(3-methylbenzyl)sulfanyl]-4H-1,2,4-triazol-3-yl}propanamide,
3-{5-[(3-fluorobenzyl)sulfanyl]-4-isobutyl-4H-1,2,4-triazol-3-yl}-N-(2-methoxybenzyl)propanamide,
3-[5-[(3-chlorobenzyl)sulfanyl]-4-(3-methylphenyl)-4H-1,2,4-triazol-3-yl]-N-(2-methoxybenzyl)propanamide,
3-[5-(benzylsulfanyl)-4-(4-methylphenyl)-4H-1,2,4-triazol-3-yl]-N-(2-methoxybenzyl)propanamide,
3-[5-(benzylsulfanyl)-4-isobutyl-4H-1,2,4-triazol-3-yl]-N-(2-methoxybenzyl)propanamide,
3-{4-(3-chlorophenyl)-5-[(4-fluorobenzyl)sulfanyl]-4H-1,2,4-triazol-3-yl}-N-(2-methoxybenzyl)propanamide,
3-[5-(benzylsulfanyl)-4-(3-chlorophenyl)-4H-1,2,4-triazol-3-yl]-N-(2-methoxybenzyl)propanamide,
3-{4-isobutyl-5-[(3-methylbenzyl)sulfanyl]-4H-1,2,4-triazol-3-yl}-N-(2-methoxybenzyl)propanamide,
N-(2-methoxybenzyl)-3-[5-[(3-methylbenzyl)sulfanyl]-4-(tetrahydro-2-furanylmethyl)-4H-1,2,4-triazol-3-yl]propanamide,
N-butyl-3-[5-[(3-chlorobenzyl)sulfanyl]-4-(3-chlorophenyl)-4H-1,2,4-triazol-3-yl]propanamide,
N-(2-methoxybenzyl)-3-{4-(3-methoxyphenyl)-5-[(3-methylbenzyl)sulfanyl]-4H-1,2,4-triazol-3-yl}propanamide,
3-{5-[(3-chlorobenzyl)sulfanyl]-4-methyl-4H-1,2,4-triazol-3-yl}-N-(2-methoxybenzyl)propanamide,
3-[5-[(3-fluorobenzyl)sulfanyl]-4-(tetrahydro-2-furanylmethyl)-4H-1,2,4-triazol-3-yl]-N-(2-methoxybenzyl)propanamide,
3-{4-allyl-5-[(3-methylbenzyl)sulfanyl]-4H-1,2,4-triazol-3-yl}-N-(2-methoxybenzyl)propanamide,
3-[5-[(3-fluorobenzyl)sulfanyl]-4-(3-methoxyphenyl)-4H-1,2,4-triazol-3-yl]-N-(2-methoxybenzyl)propanamide,
3-[5-(butylsulfanyl)-4-(3-methoxypropyl)-4H-1,2,4-triazol-3-yl]-N-(4-methoxybenzyl)propanamide,
N-benzyl-3-{4-(3-methoxypropyl)-5-[(2-phenoxyethyl)sulfanyl]-4H-1,2,4-triazol-3-yl}propanamide,
3-{4-benzyl-5-[(2-fluorobenzyl)sulfanyl]-4H-1,2,4-triazol-3-yl}-N-(2-methoxybenzyl)propanamide,
3-[5-[(3-chlorobenzyl)sulfanyl]-4-(4-fluorophenyl)-4H-1,2,4-triazol-3-yl]-N-(2-methoxybenzyl)propanamide,
3-[5-(benzylsulfanyl)-4-(4-fluorophenyl)-4H-1,2,4-triazol-3-yl]-N-(2-methoxybenzyl)propanamide,
3-[5-[(3-chlorobenzyl)sulfanyl]-4-(3-chlorophenyl)-4H-1,2,4-triazol-3-yl]-N-(cyclopropylmethyl)propanamide,
3-[5-[(3-cyanobenzyl)sulfanyl]-4-(3-methoxyphenyl)-4H-1,2,4-triazol-3-yl]-N-(2-methoxybenzyl)propanamide,
3-[5-(benzylsulfanyl)-4-(tetrahydro-2-furanylmethyl)-4H-1,2,4-triazol-3-yl]-N-(2-methoxybenzyl)propanamide,
N-(2-methoxybenzyl)-3-{4-(3-methoxypropyl)-5-[(3-methylbenzyl)sulfanyl]-4H-1,2,4-triazol-3-yl}propanamide,
3-[4-allyl-5-(benzylsulfanyl)-4H-1,2,4-triazol-3-yl]-N-(2-methoxybenzyl)propanamide,
3-[5-[(3-fluorobenzyl)sulfanyl]-4-(3-methoxypropyl)-4H-1,2,4-triazol-3-yl]-N-(2-methoxybenzyl)propanamide, 3-{4-(4-fluorophenyl)-5-[(3-methylbenzyl)sulfanyl]-4H-1,2,4-triazol-3-yl}-N-(2-methoxybenzyl)propanamide,
3-[5-(benzylsulfanyl)-4-(3-methoxypropyl)-4H-1,2,4-triazol-3-yl]-N-(2-methoxybenzyl)propanamide,
3-[5-[(3-fluorobenzyl)sulfanyl]-4-(4-fluorophenyl)-4H-1,2,4-triazol-3-yl]-N-(2-methoxybenzyl)propanamide,
3-{4-allyl-5-[(3-fluorobenzyl)sulfanyl]-4H-1,2,4-triazol-3-yl}-N-(2-methoxybenzyl)propanamide,
3-{4-(3-chlorophenyl)-5-[(3,5-dimethylbenzyl)sulfanyl]-4H-1,2,4-triazol-3-yl}-N-(2-methoxybenzyl)propanamide,
3-{4-(3-chlorophenyl)-5-[(3-fluorobenzyl)sulfanyl]-4H-1,2,4-triazol-3-yl}-N-isobutylpropanamide,
3-[5-[(3,5-dimethylbenzyl)sulfanyl]-4-(3-methoxyphenyl)-4H-1,2,4-triazol-3-yl]-N-(2-methoxybenzyl)propanamide,
3-{5-[(2-chloro-4-fluorobenzyl)sulfanyl]-4-phenyl-4H-1,2,4-triazol-3-yl}-N-(2-furylmethyl)propanamide,
3-[5-[(3-fluorobenzyl)sulfanyl]-4-(4-methylbenzyl)-4H-1,2,4-triazol-3-yl]-N-(2-methoxybenzyl)propanamide,
3-{4-(3-chlorophenyl)-5-[(3-methylbenzyl)sulfanyl]-4H-1,2,4-triazol-3-yl}-N-propylpropanamide,
3-[5-[(3-chlorobenzyl)sulfanyl]-4-(3-chlorophenyl)-4H-1,2,4-triazol-3-yl]-N-(2-methoxyethyl)propanamide,
3-[5-(allylsulfanyl)-4-(4-methylbenzyl)-4H-1,2,4-triazol-3-yl]-N-(2-methoxybenzyl)propanamide,
3-[5-[(3-chlorobenzyl)sulfanyl]-4-(3-chlorophenyl)-4H-1,2,4-triazol-3-yl]-N-(3-methoxypropyl)propanamide,
3-{4-(3-chlorophenyl)-5-[(3-methylbenzyl)sulfanyl]-4H-1,2,4-triazol-3-yl}-N-isobutylpropanamide,
N-(2-methoxybenzyl)-3-[5-[(3-methylbenzyl)sulfanyl]-4-(4-methylphenyl)-4H-1,2,4-triazol-3-yl]propanamide,
3-[5-[(2-fluorobenzyl)sulfanyl]-4-(3-methoxyphenyl)-4H-1,2,4-triazol-3-yl]-N-(2-methoxybenzyl)propanamide,
3-[5-(benzylsulfanyl)-4-(4-methylbenzyl)-4H-1,2,4-triazol-3-yl]-N-(2-methoxybenzyl)propanamide,
3 {4-benzyl-5-[(3-methylbenzyl)sulfanyl]-4H-1,2,4-triazol-3-yl}-N-(2-methoxybenzyl)propanamide,
N-allyl-3-{4-(3-chlorophenyl)-5-[(3,5-dimethylbenzyl)sulfanyl]-4H-1,2,4-triazol-3-yl}propanamide,
3-[5-[(2-fluorobenzyl)sulfanyl]-4-(3-methylphenyl)-4H-1,2,4-triazol-3-yl]-N-(2-methoxybenzyl)propanamide,
3-{5-[(4-fluorobenzyl)sulfanyl]-4-isobutyl-4H-1,2,4-triazol-3-yl}-N-(2-methoxybenzyl)propanamide,
3-[5-[(3,5-dimethylbenzyl)sulfanyl]-4-(3-methoxyphenyl)-4H-1,2,4-triazol-3-yl]-N-isobutylpropanamide,
3-{4-(3-chlorophenyl)-5-[(4-fluorobenzyl)sulfanyl]-4H-1,2,4-triazol-3-yl}-N-isobutylpropanamide,
N-butyl-3-[5-[(3-chlorobenzyl)sulfanyl]-4-(4-chlorophenyl)-4H-1,2,4-triazol-3-yl]propanamide,
3-[5-[(3-chlorobenzyl)sulfanyl]-4-(4-chlorophenyl)-4H-1,2,4-triazol-3-yl]-N-(2-phenylethyl)propanamide,
3-[5-[(2-fluorobenzyl)sulfanyl]-4-(3-methoxypropyl)-4H-1,2,4-triazol-3-yl]-N-(2-methoxybenzyl)propanamide,
3-{4-(3-chlorophenyl)-5-[(3-methylbenzyl)sulfanyl]-4H-1,2,4-triazol-3-yl}-N-(tetrahydro-2-furanylmethyl)propanamide,
3-{4-(4-chlorophenyl)-5-[(3-methylbenzyl)sulfanyl]-4H-1,2,4-triazol-3-yl}-N-(2-phenylethyl)propanamide,
3-{4-(3-chlorophenyl)-5-[(3-cyanobenzyl)sulfanyl]-4H-1,2,4-triazol-3-yl}-N-(2-phenylethyl)propanamide,
N-(4-fluorobenzyl)-3-[5-[(2,3,4,5,6-pentafluorobenzyl)sulfanyl]-4-(2-phenylethyl)-4H-1,2,4-triazol-3-yl]propanamide,
3-{4-allyl-5-[(4-fluorobenzyl)sulfanyl]-4H-1,2,4-triazol-3-yl}-N-(2-methoxybenzyl)propanamide,
3-[5-[(3-chlorobenzyl)sulfanyl]-4-(3-methylphenyl)-4H-1,2,4-triazol-3-yl]-N-(cyclopropylmethyl)propanamide,
3-[5-[(3-chlorobenzyl)sulfanyl]-4-(tetrahydro-2-furanylmethyl)-4H-1,2,4-triazol-3-yl]-N-(2-phenylethyl)propanamide,
3-[5-(benzylsulfanyl)-4-(3-methoxyphenyl)-4H-1,2,4-triazol-3-yl]-N-(2-methoxybenzyl)propanamide,
3-{4-allyl-5-[(3-methylbenzyl)sulfanyl]-4H-1,2,4-triazol-3-yl}-N-(tetrahydro-2-furanylmethyl)propanamide,
3-[5-(allylsulfanyl)-4-(3-methoxyphenyl)-4H-1,2,4-triazol-3-yl]-N-(2-methoxybenzyl)propanamide,
N-butyl-3-[5-[(3-chlorobenzyl)sulfanyl]-4-(3-methylphenyl)-4H-1,2,4-triazol-3-yl]propanamide,
3-{4-(4-chlorophenyl)-5-[(4-methylbenzyl)sulfanyl]-4H-1,2,4-triazol-3-yl}-N-(2-methoxyethyl)propanamide,
3-[5-(allylsulfanyl)-4-isobutyl-4H-1,2,4-triazol-3-yl]-N-(2-methoxybenzyl)propanamide,
3-[5-[(4-fluorobenzyl)sulfanyl]-4-(3-methoxyphenyl)-4H-1,2,4-triazol-3-yl]-N-(2-methoxybenzyl)propanamide,
3-{4-(3-chlorophenyl)-5-[(2-methylbenzyl)sulfanyl]-4H-1,2,4-triazol-3-yl}-N-(2-phenylethyl)propanamide,
3-[4-benzyl-5-(butylsulfanyl)-4H-1,2,4-triazol-3-yl]-N-(2-methoxybenzyl)propanamide,
3-[5-[(3-fluorobenzyl)sulfanyl]-4-(3-methoxyphenyl)-4H-1,2,4-triazol-3-yl]-N-isobutylpropanamide,
3-{5-[(3,5-dimethylbenzyl)sulfanyl]-4-isobutyl-4H-1,2,4-triazol-3-yl}-N-(2-methoxybenzyl)propanamide.
3-[5-[(4-fluorobenzyl)sulfanyl]-4-(tetrahydro-2-furanylmethyl)-4H-1,2,4-triazol-3-yl]-N-(2-methoxybenzyl)propanamide,
N-butyl-3-{5-[(3-chlorobenzyl)sulfanyl]-4-phenyl-4H-1,2,4-triazol-3-yl}propanamide,
3-[5-[(3-chlorobenzyl)sulfanyl]-4-(3-methylphenyl)-4H-1,2,4-triazol-3-yl]-N-(3-methoxypropyl)propanamide,
3-{4-(3-chlorophenyl)-5-[(3,5-dimethylbenzyl)sulfanyl]-4H-1,2,4-triazol-3-yl}-N-isobutylpropanamide,
N-butyl-3-[5-[(3-methylbenzyl)sulfanyl]-4-(3-methylphenyl)-4H-1,2,4-triazol-3-yl]propanamide,
N-allyl-3-[5-[(3,5-dimethylbenzyl)sulfanyl]-4-(3-methoxyphenyl)-4H-1,2,4-triazol-3-yl]propanamide, 3-{4-(3-chlorophenyl)-5-[(3,5-dimethylbenzyl)sulfanyl]-4H-1,2,4-triazol-3-yl}-N-(tetrahydro-2-furanylmethyl)propanamide,
3-[5-(allylsulfanyl)-4-(3-chlorophenyl)-4H-1,2,4-triazol-3-yl]-N-(2-methoxybenzyl)propanamide,
3-[5-[(3-cyanobenzyl)sulfanyl]-4-(3-methylphenyl)-4H-1,2,4-triazol-3-yl]-N-(2-methoxybenzyl)propanamide,
3-[4-benzyl-5-(benzylsulfanyl)-4H-1,2,4-triazol-3-yl]-N-(2-methoxybenzyl)propanamide,
3-{4-(4-chlorophenyl)-5-[(3,5-dimethylbenzyl)sulfanyl]-4H-1,2,4-triazol-3-yl}-N-(2-phenylethyl)propanamide,
3-[5-[(2-fluorobenzyl)sulfanyl]-4-(4-fluorophenyl)-4H-1,2,4-triazol-3-yl]-N-(2-methoxybenzyl)propanamide,
3-[5-[(4-fluorobenzyl)sulfanyl]-4-(3-methoxyphenyl)-4H-1,2,4-triazol-3-yl]-N-isobutylpropanamide,
3-[5-[(3-chlorobenzyl)sulfanyl]-4-(3-methylphenyl)-4H-1,2,4-triazol-3-yl]-N-isobutylpropanamide,
3-[5-[(3-methylbenzyl)sulfanyl]-4-(4-methylphenyl)-4H-1,2,4-triazol-3-yl]-N-(2-phenylethyl)propanamide,
N-(2-methoxybenzyl)-3-{4-(3-methoxypropyl)-5-[(2-oxo-2-phenylethyl)sulfanyl]-4H-1,2,4-triazol-3-yl}propanamide, 3-{4-(4-chlorophenyl)-5-[(3,5-dimethylbenzyl)sulfanyl]-4H-1,2,4-triazol-3-yl}-N-(3-methoxypropyl)propanamide,
3-[5-[(3-fluorobenzyl)sulfanyl]-4-(3-methoxyphenyl)-4H-1,2,4-triazol-3-yl]-N-propylpropanamide,
3-[5-[(4-fluorobenzyl)sulfanyl]-4-(4-fluorophenyl)-4H-1,2,4-triazol-3-yl]-N-(2-methoxybenzyl)propanamide,
3-[5-[(3-chlorobenzyl)sulfanyl]-4-(3-chlorophenyl)-4H-1,2,4-triazol-3-yl]-N-(2-phenylethyl)propanamide,
3-[5-(benzylsulfanyl)-4-(3-chlorophenyl)-4H-1,2,4-triazol-3-yl]-N-propylpropanamide,
N-benzyl-3-{4-(3-chlorophenyl)-5-[(3-methylbenzyl)sulfanyl]-4H-1,2,4-triazol-3-yl}propanamide,
3-[5-[(2-chloro-4-fluorobenzyl)sulfanyl]-4-(3-chlorophenyl)-4H-1,2,4-triazol-3-yl]-N-(2-phenylethyl)propanamide,
3-{4-(3-chlorophenyl)-5-[(4-methylbenzyl)sulfanyl]-4H-1,2,4-triazol-3-yl}-N-[3-(2-oxo-1-pyrrolidinyl)propyl]propanamide,
3-{4-(4-chlorophenyl)-5-[(3,5-dimethylbenzyl)sulfanyl]-4H-1,2,4-triazol-3-yl}-N-(2-methoxyethyl)propanamide,
N-isobutyl-3-[5-[(3-methylbenzyl)sulfanyl]-4-(4-methylphenyl)-4H-1,2,4-triazol-3-yl]propanamide,
N-butyl-3-{4-(3-chlorophenyl)-5-[(3-fluorobenzyl)sulfanyl]-4H-1,2,4-triazol-3-yl}propanamide,
3-{4-(3-chlorophenyl)-5-[(3-methylbenzyl)sulfanyl]-4H-1,2,4-triazol-3-yl}-N-(cyclopropylmethyl)propanamide,
3-[5-[(4-fluorobenzyl)sulfanyl]-4-(3-methoxypropyl)-4H-1,2,4-triazol-3-yl]-N-(2-methoxybenzyl)propanamide,
3-{4-(4-chlorophenyl)-5-[(3-methylbenzyl)sulfanyl]-4H-1,2,4-triazol-3-yl}-N-(3-methoxypropyl)propanamide,
3-[5-[(3,5-dimethylbenzyl)sulfanyl]-4-(4-methylphenyl)-4H-1,2,4-triazol-3-yl]-N-(2-phenylethyl)propanamide,
3-[5-[(3-fluorobenzyl)sulfanyl]-4-(4-methylphenyl)-4H-1,2,4-triazol-3-yl]-N-(2-phenylethyl)propanamide,
3-{5-[(3,5-dimethylbenzyl)sulfanyl]-4-isobutyl-4H-1,2,4-triazol-3-yl}-N-(2-phenylethyl)propanamide,
3-{4-(3-chlorophenyl)-5-[(3,5-dimethylbenzyl)sulfanyl]-4H-1,2,4-triazol-3-yl}-N-(2-phenylethyl)propanamide,
3-{4-(3-chlorophenyl)-5-[(3-methylbenzyl)sulfanyl]-4H-1,2,4-triazol-3-yl}-N-(4-methoxybenzyl)propanamide,
3-{4-allyl-5-[(3-methylbenzyl)sulfanyl]-4H-1,2,4-triazol-3-yl}-N-benzylpropanamide,
N-(4-methoxybenzyl)-3-{4-(3-methoxyphenyl)-5-[(3-methylbenzyl)sulfanyl]-4H-1,2,4-triazol-3-yl}propanamide,
3-{5-[(2-fluorobenzyl)sulfanyl]-4-methyl-4H-1,2,4-triazol-3-yl}-N-(2-methoxybenzyl)propanamide,
3-{4-(3-chlorophenyl)-5-[(2-fluorobenzyl)sulfanyl]-4H-1,2,4-triazol-3-yl}-N-(2-phenylethyl)propanamide,
3-{4-(4-chlorophenyl)-5-[(3-fluorobenzyl)sulfanyl]-4H-1,2,4-triazol-3-yl}-N-(2-phenylethyl)propanamide,
3-{4-(4-chlorophenyl)-5-[(3-cyanobenzyl)sulfanyl]-4H-1,2,4-triazol-3-yl}-N-(2-phenylethyl)propanamide,
3-[5-[(3-cyanobenzyl)sulfanyl]-4-(4-fluorophenyl)-4H-1,2,4-triazol-3-yl]-N-(2-methoxybenzyl)propanamide,
N-allyl-3-[5-[(3-chlorobenzyl)sulfanyl]-4-(3-methylphenyl)-4H-1,2,4-triazol-3-yl]propanamide,
3-{4-(4-chlorophenyl)-5-[(4-methylbenzyl)sulfanyl]-4H-1,2,4-triazol-3-yl}-N-(3-methoxypropyl)propanamide,
N-allyl-3-{4-(3-methoxyphenyl)-5-[(3-methylbenzyl)sulfanyl]-4H-1,2,4-triazol-3-yl}propanamide,
3-(4-(3-chlorophenyl)-5-{[4-(trifluoromethyl)benzyl]sulfanyl}-4H-1,2,4-triazol-3-yl)-N-isobutylpropanamide,
3-[5-[(3,5-dimethylbenzyl)sulfanyl]-4-(3-methoxyphenyl)-4H-1,2,4-triazol-3-yl]-N-(tetrahydro-2-furanylmethyl)propanamide,
3-[5-(butylsulfanyl)-4-(3-methoxyphenyl)-4H-1,2,4-triazol-3-yl]-N-(2-methoxybenzyl)propanamide,
N-butyl-3-{4-(4-chlorophenyl)-5-[(4-methylbenzyl)sulfanyl]-4H-1,2,4-triazol-3-yl}propanamide,
N-allyl-3-[5-[(3-fluorobenzyl)sulfanyl]-4-(3-methoxyphenyl)-4H-1,2,4-triazol-3-yl]propanamide,
3-{4-(4-chlorophenyl)-5-[(4-methylbenzyl)sulfanyl]-4H-1,2,4-triazol-3-yl}-N-[3-(2-oxo-1-pyrrolidinyl)propyl]propanamide,
3-{5-[(2-chloro-4-fluorobenzyl)sulfanyl]-4-methyl-4H-1,2,4-triazol-3-yl}-N-(2-methoxybenzyl)propanamide,
3-[5-[(3,5-dimethylbenzyl)sulfanyl]-4-(3-methoxypropyl)-4H-1,2,4-triazol-3-yl]-N-(2-phenylethyl)propanamide,
3-{4-(3-chlorophenyl)-5-[(4-fluorobenzyl)sulfanyl]-4H-1,2,4-triazol-3-yl}-N-(4-methoxybenzyl)propanamide,
N-butyl-3-{4-(3-chlorophenyl)-5-[(2-fluorobenzyl)sulfanyl]-4H-1,2,4-triazol-3-yl}propanamide,
3-[5-[(3-methylbenzyl)sulfanyl]-4-(4-methylphenyl)-4H-1,2,4-triazol-3-yl]-N-propylpropanamide,
3-{4-(3-chlorophenyl)-5-[(3-fluorobenzyl)sulfanyl]-4H-1,2,4-triazol-3-yl}-N-propylpropanamide,
3-{4-(3-chlorophenyl)-5-[(3,5-dimethylbenzyl)sulfanyl]-4H-1,2,4-triazol-3-yl}-N-(4-methoxybenzyl)propanamide,
3-[5-[(3,5-dimethylbenzyl)sulfanyl]-4-(tetrahydro-2-furanylmethyl)-4H-1,2,4-triazol-3-yl]-N-(4-methoxybenzyl)propanamide,
3-{4-(4-chlorophenyl)-5-[(2-methylbenzyl)sulfanyl]-4H-1,2,4-triazol-3-yl}-N-(2-phenylethyl)propanamide,
N-isobutyl-3-{4-(3-methoxyphenyl)-5-[(3-methylbenzyl)sulfanyl]-4H-1,2,4-triazol-3-yl}propanamide,
4-{5-[(3-chlorobenzyl)sulfanyl]-4-phenyl-4H-1,2,4-triazol-3-yl}-N-(2-methoxybenzyl)butanamide,
4-[5-[(3-chlorobenzyl)sulfanyl]-4-(3-chlorophenyl)-4H-1,2,4-triazol-3-yl]-N-(2-methoxybenzyl)butanamide,
4-[5-[(3-chlorobenzyl)sulfanyl]-4-(3-methoxyphenyl)-4H-1,2,4-triazol-3-yl]-N-(2-methoxybenzyl)butanamide,
N-benzyl-4-[5-[(3-chlorobenzyl)sulfanyl]-4-(3-chlorophenyl)-4H-1,2,4-triazol-3-yl]butanamide,
N-(2-methoxybenzyl)-4-{4-(3-methoxyphenyl)-5-[(3-methylbenzyl)sulfanyl]-4H-1,2,4-triazol-3-yl}butanamide,
4-[5-[(3-chlorobenzyl)sulfanyl]-4-(3-methoxypropyl)-4H-1,2,4-triazol-3-yl]-N-(2-methoxybenzyl)butanamide,
4-[5-[(3-chlorobenzyl)sulfanyl]-4-(3-methoxypropyl)-4H-1,2,4-triazol-3-yl]-N-(2-phenylethyl)butanamide,
4-[5-[(3-chlorobenzyl)sulfanyl]-4-(3-methoxyphenyl)-4H-1,2,4-triazol-3-yl]-N-(4-fluorobenzyl)butanamide,
4-[5-[(3,5-dimethylbenzyl)sulfanyl]-4-(3-methoxyphenyl)-4H-1,2,4-triazol-3-yl]-N-(2-methoxybenzyl)butanamide,
N-(4-fluorobenzyl)-4-{4-(3-methoxyphenyl)-5-[(4-methylbenzyl)sulfanyl]-4H-1,2,4-triazol-3-yl}butanamide,
4-[5-[(3-fluorobenzyl)sulfanyl]-4-(3-methoxyphenyl)-4H-1,2,4-triazol-3-yl]-N-2-methoxybenzyl)butanamide,
4-{4-(3-methoxyphenyl)-5-[(3-methylbenzyl)sulfanyl]-4H-1,2,4-triazol-3-yl}-N-(2-phenylethyl)butanamide, N-(1,3-benzodioxol-5-ylmethyl)-4-(4-(3-methoxypropyl)-5-{[(2E)-3-phenyl-2-propenyl]sulfanyl}-4H-1,2,4-triazol-3-yl)butanamide,
4-{4-(3-chlorophenyl)-5-[(2-fluorobenzyl)sulfanyl]-4H-1,2,4-triazol-3-yl}-N-(2-methoxybenzyl)butanamide,
N-benzyl-4-{4-(3-methoxyphenyl)-5-[(2-methylbenzyl)sulfanyl]-4H-1,2,4-triazol-3-yl}butanamide,
N-benzyl-4-[5-[(3-chlorobenzyl)sulfanyl]-4-(3-methoxyphenyl)-4H-1,2,4-triazol-3-yl]butanamide,
N-(4-fluorobenzyl)-4-{4-(3-methoxyphenyl)-5-[(2-methylbenzyl)sulfanyl]-4H-1,2,4-triazol-3-yl}butanamide,
4-[5-[(3-chlorobenzyl)sulfanyl]-4-(3-methoxyphenyl)-4H-1,2,4-triazol-3-yl]-N-isobutylbutanamide,
N-(4-fluorobenzyl)-4-{4-(3-methoxyphenyl)-5-[(2,3,4,5,6-pentafluorobenzyl)sulfanyl]-4H-1,2,4-triazol-3-yl}butanamide,
4-{4-(3-chlorophenyl)-5-[(2-methylbenzyl)sulfanyl]-4H-1,2,4-triazol-3-yl}-N-(2-methoxybenzyl)butanamide,
4-[5-[(3-chlorobenzyl)sulfanyl]-4-(3-methoxyphenyl)-4H-1,2,4-triazol-3-yl]-N-propylbutanamide,
4-[5-[(4-fluorobenzyl)sulfanyl]-4-(3-methoxyphenyl)-4H-1,2,4-triazol-3-yl]-N-(2-methoxybenzyl)butanamide,
4-[5-[(3-chlorobenzyl)sulfanyl]-4-(3-chlorophenyl)-4H-1,2,4-triazol-3-yl]-N-(4-fluorobenzyl)butanamide,
4-[5-[(3-chlorobenzyl)sulfanyl]-4-(3-methoxyphenyl)-4H-1,2,4-triazol-3-yl]-N-(4-methoxybenzyl)butanamide,
4-[5-[(3-chlorobenzyl)sulfanyl]-4-(3-chlorophenyl)-4H-1,2,4-triazol-3-yl]-N-(tetrahydro-2-furanylmethyl)butanamide,
N-benzyl-4-{4-(3-chlorophenyl)-5-[(3,5-dimethylbenzyl)sulfanyl]-4H-1,2,4-triazol-3-yl}butanamide,
4-[5-[(3-fluorobenzyl)sulfanyl]-4-(3-methoxyphenyl)-4H-1,2,4-triazol-3-yl]-N-(2-phenylethyl)butanamide,
4-{4-(3-chlorophenyl)-5-[(3-cyanobenzyl)sulfanyl]-4H-1,2,4-triazol-3-yl}-N-(2-methoxybenzyl)butanamide,
4-[5-[(3-chlorobenzyl)sulfanyl]-4-(3-chlorophenyl)-4H-1,2,4-triazol-3-yl]-N-(4-methoxybenzyl)butanamide,
4-[5-[(3-cyanobenzyl)sulfanyl]-4-(3-methoxyphenyl)-4H-1,2,4-triazol-3-yl]-N-(2-methoxybenzyl)butanamide,
N-isobutyl-4-{4-(3-methoxyphenyl)-5-[(3-methylbenzyl)sulfanyl]-4H-1,2,4-triazol-3-yl}butanamide,
N-(4-methoxybenzyl)-4-{4-(3-methoxyphenyl)-5-[(4-methylbenzyl)sulfanyl]-4H-1,2,4-triazol-3-yl}butanamide,
4-[5-[(3,5-dimethylbenzyl)sulfanyl]-4-(3-methoxyphenyl)-4H-1,2,4-triazol-3-yl]-N-(2-phenylethyl)butanamide,
N-benzyl-4-{4-(3-chlorophenyl)-5-[(3-methylbenzyl)sulfanyl]-4H-1,2,4-triazol-3-yl}butanamide,
4-[5-[(2-chloro-4-fluorobenzyl)sulfanyl]-4-(3-chlorophenyl)-4H-1,2,4-triazol-3-yl]-N-(2-methoxybenzyl)butanamide,
N-allyl-4-[5-[(3-chlorobenzyl)sulfanyl]-4-(3-chlorophenyl)-4H-1,2,4-triazol-3-yl]butanamide,
4-[5-[(3-chlorobenzyl)sulfanyl]-4-(3-chlorophenyl)-4H-1,2,4-triazol-3-yl]-N-isobutylbutanamide,
4-[5-[(3,5-dimethylbenzyl)sulfanyl]-4-(3-methoxyphenyl)-4H-1,2,4-triazol-3-yl]-N-(4-fluorobenzyl)butanamide,
N-benzyl-4-{4-(3-chlorophenyl)-5-[(3-fluorobenzyl)sulfanyl]-4H-1,2,4-triazol-3-yl}butanamide,
N-benzyl-4-[5-(benzylsulfanyl)-4-(3-chlorophenyl)-4H-1,2,4-triazol-3-yl]butanamide,
4-{4-(3-chlorophenyl)-5-[(2-phenylethyl)sulfanyl]-4H-1,2,4-triazol-3-yl}-N-(2-methoxybenzyl)butanamide,
4-[5-[(3,5-dimethylbenzyl)sulfanyl]-4-(3-methoxypropyl)-4H-1,2,4-triazol-3-yl]-N-(2-phenylethyl)butanamide,
N-benzyl-4-{4-(3-methoxyphenyl)-5-[(3-methylbenzyl)sulfanyl]-4H-1,2,4-triazol-3-yl}butanamide,
4-[5-[(3-chlorobenzyl)sulfanyl]-4-(3-chlorophenyl)-4H-1,2,4-triazol-3-yl]-N-propylbutanamide,
4-{4-(3-chlorophenyl)-5-[(2-methylbenzyl)sulfanyl]-4H-1,2,4-triazol-3-yl}-N-(4-fluorobenzyl)butanamide,
4-[5-[(3,5-dimethylbenzyl)sulfanyl]-4-(3-methoxyphenyl)-4H-1,2,4-triazol-3-yl]-N-propylbutanamide,
4-[5-[(cyclohexylmethyl)sulfanyl]-4-(3-methoxyphenyl)-4H-1,2,4-triazol-3-yl]-N-(2-methoxybenzyl)butanamide,
5-[5-[(3-chlorobenzyl)sulfanyl]-4-(3-chlorophenyl)-4H-1,2,4-triazol-3-yl]-N-(2-methoxybenzyl)pentanamide,
5-{5-[(3-chlorobenzyl)sulfanyl]-4-phenyl-4H-1,2,4-triazol-3-yl}-N-(2-methoxybenzyl)pentanamide,
N-(2-methoxybenzyl)-5-{4-(3-methoxypropyl)-5-[(3-methylbenzyl)sulfanyl]-4H-1,2,4-triazol-3-yl}pentanamide,
5-[5-[(3-chlorobenzyl)sulfanyl]-4-(3-chlorophenyl)-4H-1,2,4-triazol-3-yl]-N-isobutylpentanamide,
5-{4-allyl-5-[(3-methylbenzyl)sulfanyl]-4H-1,2,4-triazol-3-yl}-N-(2-methoxybenzyl)pentanamide,
N-(2-methoxybenzyl)-5-[5-[(3-methylbenzyl)sulfanyl]-4-(2-phenylethyl)-4H-1,2,4-triazol-3-yl]pentanamide,
N-(2-methoxybenzyl)-5-{5-[(3-methylbenzyl)sulfanyl]-4-phenyl-4H-1,2,4-triazol-3-yl}pentanamide,
5-{4-(3-chlorophenyl)-5-[(2-fluorobenzyl)sulfanyl]-4H-1,2,4-triazol-3-yl}-N-(2-methoxybenzyl)pentanamide,
5-[5-[(3-fluorobenzyl)sulfanyl]-4-(3-methoxypropyl)-4H-1,2,4-triazol-3-yl]-N-(2-methoxybenzyl)pentanamide,
5-[5-[(3-chlorobenzyl)sulfanyl]-4-(3-chlorophenyl)-4H-1,2,4-triazol-3-yl]-N-(4-fluorobenzyl)pentanamide,
5-[5-[(3,5-dimethylbenzyl)sulfanyl]-4-(2-phenylethyl)-4H-1,2,4-triazol-3-yl]-N-isobutylpentanamide,
N-benzyl-5-{5-[(3-chlorobenzyl)sulfanyl]-4-phenyl-4H-1,2,4-triazol-3-yl}pentanamide,
5-{5-[(3-fluorobenzyl)sulfanyl]-4-phenyl-4H-1,2,4-triazol-3-yl}-N-(2-methoxybenzyl)pentanamide,
5-[5-(benzylsulfanyl)-4-(3-methoxypropyl)-4H-1,2,4-triazol-3-yl]-N-(2-methoxybenzyl)pentanamide,
N-benzyl-5-{4-(3-chlorophenyl)-5-[(4-methylbenzyl)sulfanyl]-4H-1,2,4-triazol-3-yl}pentanamide,
5-{4-allyl-5-[(3,5-dimethylbenzyl)sulfanyl]-4H-1,2,4-triazol-3-yl}-N-(2-methoxybenzyl)pentanamide,
5-{4-allyl-5-[(3-chlorobenzyl)sulfanyl]-4H-1,2,4-triazol-3-yl}-N-(2-methoxybenzyl)pentanamide,
5-[5-(benzylsulfanyl)-4-phenyl-4H-1,2,4-triazol-3-yl]-N-(2-methoxybenzyl)pentanamide,
5-{4-allyl-5-(benzylsulfanyl)-4H-1,2,4-triazol-3-yl]-N-(2-methoxybenzyl)pentanamide,
5-[5-[(3,5-dimethylbenzyl)sulfanyl]-4-(2-phenylethyl)-4H-1,2,4-triazol-3-yl]-N-(2-phenylethyl)pentanamide,
5-[5-[(3-chlorobenzyl)sulfanyl]-4-(2-phenylethyl)-4H-1,2,4-triazol-3-yl]-N-(2-methoxybenzyl)pentanamide,
N-benzyl-5-{4-(3-chlorophenyl)-5-[(2-methylbenzyl)sulfanyl]-4H-1,2,4-triazol-3-yl}pentanamide,
5-{4-allyl-5-[(3-fluorobenzyl)sulfanyl]-4H-1,2,4-triazol-3-yl}-N-(2-methoxybenzyl)pentanamide,
N-(1,3-benzodioxol-5-ylmethyl)-5-[5-[(2-methylbenzyl)sulfanyl]-4-(2-phenylethyl)-4H-1,2,4-triazol-3-yl]pentanamide, 5-[5-[(3,5-dimethylbenzyl)sulfanyl]-4-(2-phenylethyl)-4H-1,2,4-triazol-3-yl]-N-(2-methoxybenzyl)pentanamide,
5-{5-[(2-fluorobenzyl)sulfanyl]-4-phenyl-4H-1,2,4-triazol-3-yl}-N-(2-methoxybenzyl)pentanamide,
5-[5-[(3-chlorobenzyl)sulfanyl]-4-(2-phenylethyl)-4H-1,2,4-triazol-3-yl]-N-(4-fluorobenzyl)pentanamide,
N-benzyl-5-{4-(3-chlorophenyl)-5-[(2,3,4,5,6-pentafluorobenzyl)sulfanyl]-4H-1,2,4-triazol-3-yl}pentanamide,
5-[5-[(3,5-dimethylbenzyl)sulfanyl]-4-(3-methoxypropyl)-4H-1,2,4-triazol-3-yl]-N-(2-methoxybenzyl)pentanamide,
5-{4-(3-chlorophenyl)-5-[(4-methylbenzyl)sulfanyl]-4H-1,2,4-triazol-3-yl}-N-(tetrahydro-2-furanylmethyl)pentanamide,
N-benzyl-5-[5-[(3-chlorobenzyl)sulfanyl]-4-(3-chlorophenyl)-4H-1,2,4-triazol-3-yl]pentanamide,
5-{5-[(3-chlorobenzyl)sulfanyl]-4-phenyl-4H-1,2,4-triazol-3-yl}-N-(4-fluorobenzyl)pentanamide,
5-{4-(3-chlorophenyl)-5-[(3-cyanobenzyl)sulfanyl]-4H-1,2,4-triazol-3-yl}-N-(2-methoxybenzyl)pentanamide,
5-{4-(3-chlorophenyl)-5-[(2-methylbenzyl)sulfanyl]-4H-1,2,4-triazol-3-yl}-N-(tetrahydro-2-furanylmethyl)pentanamide,
5-[5-(benzylsulfanyl)-4-(3-chlorophenyl)-4H-1,2,4-triazol-3-yl]-N-(2-methoxybenzyl)pentanamide,
5-{5-[(3,5-dimethylbenzyl)sulfanyl]-4-phenyl-4H-1,2,4-triazol-3-yl}-N-(2-methoxyethyl)pentanamide,
5-[5-[(3-methylbenzyl)sulfanyl]-4-(2-phenylethyl)-4H-1,2,4-triazol-3-yl]-N-(2-phenylethyl)pentanamide,
N-allyl-5-[5-[(3-chlorobenzyl)sulfanyl]-4-(3-chlorophenyl)-4H-1,2,4-triazol-3-yl]pentanamide,
5-[5-[(2-chloro-4-fluorobenzyl)sulfanyl]-4-(3-chlorophenyl)-4H-1,2,4-triazol-3-yl]-N-isobutylpentanamide,
N-butyl-5-{5-[(3,5-dimethylbenzyl)sulfanyl]-4-phenyl-4H-1,2,4-triazol-3-yl}pentanamide,
5-{4-(3-chlorophenyl)-5-[(2,3,4,5,6-pentafluorobenzyl)sulfanyl]-4H-1,2,4-triazol-3-yl}-N-(2-methoxybenzyl)pentanamide,
5-{5-[(3,5-dimethylbenzyl)sulfanyl]-4-phenyl-4H-1,2,4-triazol-3-yl}-N-[3-(2-oxo-1-pyrrolidinyl)propyl]pentanamide,
5-{5-[(3,5-dimethylbenzyl)sulfanyl]-4-phenyl-4H-1,2,4-triazol-3-yl}-N-(2-methoxybenzyl)pentanamide,
5-[5-[(3,5-dimethylbenzyl)sulfanyl]-4-(3-methoxypropyl)-4H-1,2,4-triazol-3-yl]-N-(4-fluorobenzyl)pentanamide,
5-[5-[(3-chlorobenzyl)sulfanyl]-4-(2-phenylethyl)-4H-1,2,4-triazol-3-yl]-N-propylpentanamide,
5-{4-(3-chlorophenyl)-5-[(3-fluorobenzyl)sulfanyl]-4H-1,2,4-triazol-3-yl}-N-(2-methoxybenzyl)pentanamide,
5-{4-allyl-5-[(4-methylbenzyl)sulfanyl]-4H-1,2,4-triazol-3-yl}-N-(2-methoxybenzyl)pentanamide,
5-[5-[(2-fluorobenzyl)sulfanyl]-4-(2-phenylethyl)-4H-1,2,4-triazol-3-yl]-N-(2-methoxybenzyl)pentanamide,
N-(4-fluorobenzyl)-5-{4-(3-methoxypropyl)-5-[(3-methylbenzyl)sulfanyl]-4H-1,2,4-triazol-3-yl}pentanamide,
5-{4-(3-chlorophenyl)-5-[(2-fluorobenzyl)sulfanyl]-4H-1,2,4-triazol-3-yl}-N-(4-fluorobenzyl)pentanamide,
5-{4-(3-chlorophenyl)-5-[(4-methylbenzyl)sulfanyl]-4H-1,2,4-triazol-3-yl}-N-(4-methoxybenzyl)pentanamide,
N-(4-methoxybenzyl)-5-{5-[(4-methylbenzyl)sulfanyl]-4-phenyl-4H-1,2,4-triazol-3-yl}pentanamide,
5-[5-[(3-chlorobenzyl)sulfanyl]-4-(tetrahydro-2-furanylmethyl)-4H-1,2,4-triazol-3-yl]-N-(2-phenylethyl)pentanamide,
5-{4-(3-chlorophenyl)-5-[(4-methylbenzyl)sulfanyl]-4H-1,2,4-triazol-3-yl}-N-isobutylpentanamide,
5-{4-(3-methoxyphenyl)-5-[(3-methylbenzyl)sulfanyl]-4H-1,2,4-triazol-3-yl}-N-(2-phenylethyl)pentanamide,
5-[5-[(2-chloro-4-fluorobenzyl)sulfanyl]-4-(3-chlorophenyl)-4H-1,2,4-triazol-3-yl]-N-(tetrahydro-2-furanylmethyl)pentanamide,
N-benzyl-5-{5-[(3-methylbenzyl)sulfanyl]-4-phenyl-4H-1,2,4-triazol-3-yl}pentanamide,
N-benzyl-5-[5-[(2-chloro-4-fluorobenzyl)sulfanyl]-4-(3-chlorophenyl)-4H-1,2,4-triazol-3-yl]pentanamide,
N-(4-fluorobenzyl)-5-[5-[(2-methylbenzyl)sulfanyl]-4-(2-phenylethyl)-4H-1,2,4-triazol-3-yl]pentanamide,
5-[5-[(3-chlorobenzyl)sulfanyl]-4-(2-phenylethyl)-4H-1,2,4-triazol-3-yl]-N-isobutylpentanamide,
N-(cyclopropylmethyl)-5-{5-[(3-methylbenzyl)sulfanyl]-4-phenyl-4H-1,2,4-triazol-3-yl}pentanamide,
5-{4-(3-methoxyphenyl)-5-[(4-methylbenzyl)sulfanyl]-4H-1,2,4-triazol-3-yl}-N-propylpentanamide,
5-{5-[(3,5-dimethylbenzyl)sulfanyl]-4-phenyl-4H-1,2,4-triazol-3-yl}-N-(3-methoxypropyl)pentanamide,
N-benzyl-5-[5-[(3,5-dimethylbenzyl)sulfanyl]-4-(2-phenylethyl)-4H-1,2,4-triazol-3-yl]pentanamide,
5-{5-[(3-methylbenzyl)sulfanyl]-4-phenyl-4H-1,2,4-triazol-3-yl}-N-(2-phenylethyl)pentanamide,
N-(4-fluorobenzyl)-5-{5-[(3-methylbenzyl)sulfanyl]-4-phenyl-4H-1,2,4-triazol-3-yl}pentanamide,
N-(cyclopropylmethyl)-5-{5-[(3,5-dimethylbenzyl)sulfanyl]-4-phenyl-4H-1,2,4-triazol-3-yl}pentanamide,
5-{5-[(3,5-dimethylbenzyl)sulfanyl]-4-phenyl-4H-1,2,4-triazol-3-yl}-N-propylpentanamide,
5-[5-[(3,5-dimethylbenzyl)sulfanyl]-4-(3-methoxyphenyl)-4H-1,2,4-triazol-3-yl]-N-(2-phenylethyl)pentanamide,
N-benzyl-5-{4-(3-chlorophenyl)-5-[(3-methylbenzyl)sulfanyl]-4H-1,2,4-triazol-3-yl}pentanamide,
N-benzyl-5-{5-[(4-methylbenzyl)sulfanyl]-4-phenyl-4H-1,2,4-triazol-3-yl}pentanamide,
5-{4-(3-chlorophenyl)-5-[(2-methylbenzyl)sulfanyl]-4H-1,2,4-triazol-3-yl}-N-(4-methoxybenzyl)pentanamide,
5-{4-(3-chlorophenyl)-5-[(3,5-dimethylbenzyl)sulfanyl]-4H-1,2,4-triazol-3-yl}-N-(2-phenylethyl)pentanamide,
5-{4-(3-chlorophenyl)-5-[(3,5-dimethylbenzyl)sulfanyl]-4H-1,2,4-triazol-3-yl}-N-[3-(2-oxo-1-pyrrolidinyl)propyl]pentanamide,
5-{4-(3-chlorophenyl)-5-[(3-methylbenzyl)sulfanyl]-4H-1,2,4-triazol-3-yl}-N-(2-phenylethyl)pentanamide,
55-[5-[(3-fluorobenzyl)sulfanyl]-4-(2-phenylethyl)-4H-1,2,4-triazol-3-yl]-N-(2-methoxybenzyl)pentanamide,
5-{4-(3-chlorophenyl)-5-[(2-methylbenzyl)sulfanyl]-4H-1,2,4-triazol-3-yl}-N-(2-methoxybenzyl)pentanamide,
5-{4-allyl-5-[(3-methylbenzyl)sulfanyl]-4H-1,2,4-triazol-3-yl}-N-(4-fluorobenzyl)pentanamide,
N-benzyl-5-{4-(3-chlorophenyl)-5-[(2-oxo-2-phenylethyl)sulfanyl]-4H-1,2,4-triazol-3-yl}pentanamide,
5-{4-(3-chlorophenyl)-5-[(3-methylbenzyl)sulfanyl]-4H-1,2,4-triazol-3-yl}-N-[3-(2-oxo-1-pyrrolidinyl)propyl]pentanamide,
N-(cyclopropylmethyl)-5-{4-(3-methoxyphenyl)-5-[(2-methylbenzyl)sulfanyl]-4H-1,2,4-triazol-3-yl}pentanamide,
5-{5-[(3-methylbenzyl)sulfanyl]-4-phenyl-4H-1,2,4-triazol-3-yl}-N-[3-(2-oxo-1-pyrrolidinyl)propyl]pentanamide,
N-allyl-5-{4-(3-chlorophenyl)-5-[(4-methylbenzyl)sulfanyl]-4H-1,2,4-triazol-3-yl}pentanamide, N-allyl-5-[5-[(2-chloro-4-fluorobenzyl)sulfanyl]-4-(3-chlorophenyl)-4H-1,2,4-triazol-3-yl]pentanamide,
5-{4-(3-chlorophenyl)-5-[(2-methylbenzyl)sulfanyl]-4H-1,2,4-triazol-3-yl}-N-isobutylpentanamide,
N-(4-fluorobenzyl)-5-{5-[(4-methylbenzyl)sulfanyl]-4-phenyl-4H-1,2,4-triazol-3-yl}pentanamide,
5-[5-[(3-chlorobenzyl)sulfanyl]-4-(3-methoxypropyl)-4H-1,2,4-triazol-3-yl]-N-(2-phenylethyl)pentanamide,
5-[5-[(2-chloro-4-fluorobenzyl)sulfanyl]-4-(2-phenylethyl)-4H-1,2,4-triazol-3-yl]-N-propylpentanamide,
N-benzyl-5-{4-(3-chlorophenyl)-5-[(3-cyanobenzyl)sulfanyl]-4H-1,2,4-triazol-3-yl}pentanamide,
5-[5-[(3-chlorobenzyl)sulfanyl]-4-(3-chlorophenyl)-4H-1,2,4-triazol-3-yl]-N-propylpentanamide,
N-(2-methoxyethyl)-5-{5-[(3-methylbenzyl)sulfanyl]-4-phenyl-4H-1,2,4-triazol-3-yl}pentanamide,
N-[3-(2-oxo-1-pyrrolidinyl)propyl]-5-(4-phenyl-5-{[4-(trifluoromethyl)benzyl]sulfanyl}-4H-1,2,4-triazol-3-yl)pentanamide,
5-{5-[(3,5-dimethylbenzyl)sulfanyl]-4-phenyl-4H-1,2,4-triazol-3-yl}-N-(2-phenylethyl)pentanamide,
N-benzyl-5-{5-[(3,5-dimethylbenzyl)sulfanyl]-4-phenyl-4H-1,2,4-triazol-3-yl}pentanamide,
N-(4-fluorobenzyl)-5-[5-[(4-methylbenzyl)sulfanyl]-4-(2-phenylethyl)-4H-1,2,4-triazol-3-yl]pentanamide,
5-{4-(3-chlorophenyl)-5-[(2-oxo-2-phenylethyl)sulfanyl]-4H-1,2,4-triazol-3-yl}-N-(4-methoxybenzyl)pentanamide,
N-(cyclopropylmethyl)-5-[5-[(3,5-dimethylbenzyl)sulfanyl]-4-(3-methoxyphenyl)-4H-1,2,4-triazol-3-yl]pentanamide,
N-butyl-5-{5-[(3-methylbenzyl)sulfanyl]-4-phenyl-4H-1,2,4-triazol-3-yl}pentanamide,
5-{4-(3-methoxyphenyl)-5-[(4-methylbenzyl)sulfanyl]-4H-1,2,4-triazol-3-yl}-N-[3-(2-oxo-1-pyrrolidinyl)propyl]pentanamide,
5-[5-(benzylsulfanyl)-4-phenyl-4H-1,2,4-triazol-3-yl]-N-(4-fluorobenzyl)pentanamide,
5-[5-[(3-chlorobenzyl)sulfanyl]-4-(3-methoxyphenyl)-4H-1,2,4-triazol-3-yl]-N-(2-phenylethyl)pentanamide,
5-[5-[(4-fluorobenzyl)sulfanyl]-4-(2-phenylethyl)-4H-1,2,4-triazol-3-yl]-N-(2-methoxybenzyl)pentanamide,
N-allyl-5-{5-[(3,5-dimethylbenzyl)sulfanyl]-4-phenyl-4H-1,2,4-triazol-3-yl}pentanamide,
N-(2-methoxybenzyl)-5-{5-[(4-methylbenzyl)sulfanyl]-4-phenyl-4H-1,2,4-triazol-3-yl}pentanamide, N-butyl-5-[5-[(3-chlorobenzyl)sulfanyl]-4-(3-chlorophenyl)-4H-1,2,4-triazol-3-yl]pentanamide,
5-[5-[(3-chlorobenzyl)sulfanyl]-4-(3-chlorophenyl)-4H-1,2,4-triazol-3-yl]-N-(cyclopropylmethyl)pentanamide,
N-(4-fluorobenzyl)-5-[5-[(3-methylbenzyl)sulfanyl]-4-(2-phenylethyl)-4H-1,2,4-triazol-3-yl]pentanamide,
N-(cyclopropylmethyl)-5-(4-phenyl-5-{[4-(trifluoromethyl)benzyl]sulfanyl}-4H-1,2,4-triazol-3-yl)pentanamide,
5-{4-allyl-5-[(3,5-dimethylbenzyl)sulfanyl]-4H-1,2,4-triazol-3-yl}-N-(4-fluorobenzyl)pentanamide,
N-isobutyl-5-[5-[(2-methylbenzyl)sulfanyl]-4-(2-phenylethyl)-4H-1,2,4-triazol-3-yl]pentanamide,
5-[5-[(3,5-dimethylbenzyl)sulfanyl]-4-(3-methoxyphenyl)-4H-1,2,4-triazol-3-yl]-N-[3-(2-oxo-1-pyrrolidinyl)propyl]pentanamide,
5-[5-[(2-chloro-4-fluorobenzyl)sulfanyl]-4-(3-chlorophenyl)-4H-1,2,4-triazol-3-yl]-N-(2-methoxybenzyl)pentanamide,
5-{5-[(3-methylbenzyl)sulfanyl]-4-phenyl-4H-1,2,4-triazol-3-yl}-N-propylpentanamide,
5-[5-[(3-chlorobenzyl)sulfanyl]-4-(3-methoxyphenyl)-4H-1,2,4-triazol-3-yl]-N-(cyclopropylmethyl)pentanamide,
5-{4-(3-chlorophenyl)-5-[(4-fluorobenzyl)sulfanyl]-4H-1,2,4-triazol-3-yl}-N-(2-phenylethyl)pentanamide,
N-(2-methoxyethyl)-5-{4-(3-methoxyphenyl)-5-[(3-methylbenzyl)sulfanyl]-4H-1,2,4-triazol-3-yl}pentanamide,
5-{4-(3-chlorophenyl)-5-[(3-cyanobenzyl)sulfanyl]-4H-1,2,4-triazol-3-yl}-N-(4-fluorobenzyl)pentanamide
5-{5-[(3-chlorobenzyl)sulfanyl]-4-phenyl-4H-1,2,4-triazol-3-yl}-N-isobutylpentanamide,
5-[5-(benzylsulfanyl)-4-(3-chlorophenyl)-4H-1,2,4-triazol-3-yl]-N-(2-phenylethyl)pentanamide,
N-allyl-5-{4-(3-chlorophenyl)-5-[(2,3,4,5,6-pentafluorobenzyl)sulfanyl]-4H-1,2,4-triazol-3-yl}pentanamide,
N-(2-methoxybenzyl)-5-[5-[(2-methylbenzyl)sulfanyl]-4-(2-phenylethyl)-4H-1,2,4-triazol-3-yl]pentanamide,
5-[5-[(3,5-dimethylbenzyl)sulfanyl]-4-(2-phenylethyl)-4H-1,2,4-triazol-3-yl]-N-(4-fluorobenzyl)pentanamide,
N-isobutyl-5-{5-[(4-methylbenzyl)sulfanyl]-4-phenyl-4H-1,2,4-triazol-3-yl}pentanamide,
N-isobutyl-5-{5-[(3-methylbenzyl)sulfanyl]-4-phenyl-4H-1,2,4-triazol-3-yl}pentanamide,
5-{4-benzyl-5-[(3-methylbenzyl)sulfanyl]-4H-1,2,4-triazol-3-yl}-N-[3-(2-oxo-1-pyrrolidinyl)propyl]pentanamide,
N-benzyl-5-{4-(3-methoxypropyl)-5-[(3-methylbenzyl)sulfanyl]-4H-1,2,4-triazol-3-yl}pentanamide,
5-{4-(3-chlorophenyl)-5-[(2,3,4,5,6-pentafluorobenzyl)sulfanyl]-4H-1,2,4-triazol-3-yl}-N-isobutylpentanamide,
N-(4-methoxybenzyl)-5-[5-[(2,3,4,5,6-pentafluorobenzyl)sulfanyl]-4-(2-phenylethyl)-4H-1,2,4-triazol-3-yl]pentanamide,
N-benzyl-5-[5-(benzylsulfanyl)-4-(3-chlorophenyl)-4H-1,2,4-triazol-3-yl]pentanamide,
5-[5-(butylsulfanyl)-4-(3-chlorophenyl)-4H-1,2,4-triazol-3-yl]-N-isobutylpentanamide,
N-(cyclopropylmethyl)-5-{4-(3-methoxyphenyl)-5-[(3-methylbenzyl)sulfanyl]-4H-1,2,4-triazol-3-yl}pentanamide,
5-{4-allyl-5-[(3,5-dimethylbenzyl)sulfanyl]-4H-1,2,4-triazol-3-yl}-N-(2-phenylethyl)pentanamide,
5-[5-[(3,5-dimethylbenzyl)sulfanyl]-4-(2-phenylethyl)-4H-1,2,4-triazol-3-yl]-N-(4-methoxybenzyl)pentanamide,
N-benzyl-5-{4-(3-chlorophenyl)-5-[(2-fluorobenzyl)sulfanyl]-4H-1,2,4-triazol-3-yl}pentanamide,
5-[5-[(3-chlorobenzyl)sulfanyl]-4-(3-chlorophenyl)-4H-1,2,4-triazol-3-yl]-N-(2-methoxyethyl)pentanamide,
N-(cyclopropylmethyl)-5-{4-(3-methoxyphenyl)-5-[(4-methylbenzyl)sulfanyl]-4H-1,2,4-triazol-3-yl}pentanamide,
5-{4-(3-chlorophenyl)-5-[(2-methylbenzyl)sulfanyl]-4H-1,2,4-triazol-3-yl}-N-(4-fluorobenzyl)pentanamide,
5-[5-[(3-chlorobenzyl)sulfanyl]-4-(2-phenylethyl)-4H-1,2,4-triazol-3-yl]-N-(tetrahydro-2-furanylmethyl)pentanamide,
5-{4-(3-chlorophenyl)-5-[(2,3,4,5,6-pentafluorobenzyl)sulfanyl]-4H-1,2,4-triazol-3-yl}-N-(4-methoxybenzyl)pentanamide,
5-[5-(butylsulfanyl)-4-(3-chlorophenyl)-4H-1,2,4-triazol-3-yl]-N-(2-methoxyethyl)pentanamide, N-benzyl-5-[5-(benzylsulfanyl)-4-phenyl-4H-1,2,4-triazol-3-yl]pentanamide,
5-{5-[(3,5-dimethylbenzyl)sulfanyl]-4-phenyl-4H-1,2,4-triazol-3-yl}-N-isobutylpentanamide,
5-{5-[(4-fluorobenzyl)sulfanyl]-4-phenyl-4H-1,2,4-triazol-3-yl}-N-(2-methoxybenzyl)pentanamide,
5-{4-benzyl-5-[(3,5-dimethylbenzyl)sulfanyl]-4H-1,2,4-triazol-3-yl}-N-[3-(2-oxo-1-pyrrolidinyl)propyl]pentanamide,
5-(4-(3-chlorophenyl)-5-{[(2E)-3-phenyl-2-propenyl]sulfanyl}-4H-1,2,4-triazol-3-yl)-N-isobutylpentanamide,
5-{4-(3-chlorophenyl)-5-[(3-fluorobenzyl)sulfanyl]-4H-1,2,4-triazol-3-yl}-N-(2-phenylethyl)pentanamide,
5-[5-[(2-methylbenzyl)sulfanyl]-4-(2-phenylethyl)-4H-1,2,4-triazol-3-yl]-N-propylpentanamide,
N-allyl-5-{4-(3-chlorophenyl)-5-[(2-methylbenzyl)sulfanyl]-4H-1,2,4-triazol-3-yl}pentanamide,
N-butyl-5-(4-phenyl-5-{[4-(trifluoromethyl)benzyl]sulfanyl}-4H-1,2,4-triazol-3-yl)pentanamide,
5-{5-[(3-chlorobenzyl)sulfanyl]-4-phenyl-4H-1,2,4-triazol-3-yl}-N-(tetrahydro-2-furanylmethyl)pentanamide,
5-[5-[(4-fluorobenzyl)sulfanyl]-4-(3-methoxypropyl)-4H-1,2,4-triazol-3-yl]-N-(2-methoxybenzyl)pentanamide,
N-(3-methoxypropyl)-5-{5-[(3-methylbenzyl)sulfanyl]-4-phenyl-4H-1,2,4-triazol-3-yl}pentanamide,
N-isobutyl-5-[5-[(2-oxo-2-phenylethyl)sulfanyl]-4-(2-phenylethyl)-4H-1,2,4-triazol-3-yl]pentanamide,
5-{5-[(3-fluorobenzyl)sulfanyl]-4-phenyl-4H-1,2,4-triazol-3-yl}-N-(2-phenylethyl)pentanamide,
N-(2-methoxyethyl)-5-(4-phenyl-5-{[4-(trifluoromethyl)benzyl]sulfanyl}-4H-1,2,4-triazol-3-yl)pentanamide,
5-{5-[(4-methylbenzyl)sulfanyl]-4-phenyl-4H-1,2,4-triazol-3-yl}-N-(tetrahydro-2-furanylmethyl)pentanamide,
5-{4-(3-chlorophenyl)-5-[(3,5-dimethylbenzyl)sulfanyl]-4H-1,2,4-triazol-3-yl}-N-propylpentanamide,
N-butyl-5-{4-(3-chlorophenyl)-5-[(4-methylbenzyl)sulfanyl]-4H-1,2,4-triazol-3-yl}pentanamide,
5-[5-[(3-chlorobenzyl)sulfanyl]-4-(3-chlorophenyl)-4H-1,2,4-triazol-3-yl]-N-(3-methoxypropyl)pentanamide,
5-{4-(3-chlorophenyl)-5-[(2-oxo-2-phenylethyl)sulfanyl]-4H-1,2,4-triazol-3-yl}-N-(tetrahydro-2-furanylmethyl)pentanamide,
5-{5-[(3,5-dimethylbenzyl)sulfanyl]-4-phenyl-4H-1,2,4-triazol-3-yl}-N-(tetrahydro-2-furanylmethyl)pentanamide,
N-(3-methoxypropyl)-5-(4-phenyl-5-{[4-(trifluoromethyl)benzyl]sulfanyl}-4H-1,2,4-triazol-3-yl)pentanamide,
5-{4-(3-chlorophenyl)-5-[(4-fluorobenzyl)sulfanyl]-4H-1,2,4-triazol-3-yl}-N-(2-methoxybenzyl)pentanamide,
5-(4-(3-chlorophenyl)-5-{[4-(trifluoromethyl)benzyl]sulfanyl}-4H-1,2,4-triazol-3-yl)-N-[3-(2-oxo-1-pyrrolidinyl)propyl]pentanamide,
N-(4-fluorobenzyl)-5-[5-[(2-fluorobenzyl)sulfanyl]-4-(2-phenylethyl)-4H-1,2,4-triazol-3-yl]pentanamide,
5-[5-[(2-chloro-4-fluorobenzyl)sulfanyl]-4-(2-phenylethyl)-4H-1,2,4-triazol-3-yl]-N-(2-methoxybenzyl)pentanamide,
N-benzyl-5-[5-[(3-methylbenzyl)sulfanyl]-4-(2-phenylethyl)-4H-1,2,4-triazol-3-yl]pentanamide,
5-{4-(3-chlorophenyl)-5-[(3-cyanobenzyl)sulfanyl]-4H-1,2,4-triazol-3-yl}-N-(4-methoxybenzyl)pentanamide,
5-{4-(3-chlorophenyl)-5-[(2-oxo-2-phenylethyl)sulfanyl]-4H-1,2,4-triazol-3-yl}-N-isobutylpentanamide,
5-{4-benzyl-5-[(3-methylbenzyl)sulfanyl]-4H-1,2,4-triazol-3-yl}-N-(2-methoxyethyl)pentanamide,
N-(1,3-benzodioxol-5-ylmethyl)-5-[5-[(3-chlorobenzyl)sulfanyl]-4-(2-phenylethyl)-4H-1,2,4-triazol-3-yl]pentanamide,
5-[5-[(3-chlorobenzyl)sulfanyl]-4-(3-chlorophenyl)-4H-1,2,4-triazol-3-yl]-N-(tetrahydro-2-furanylmethyl)pentanamide,
N-(4-methoxybenzyl)-5-[5-[(2-methylbenzyl)sulfanyl]-4-(2-phenylethyl)-4H-1,2,4-triazol-3-yl]pentanamide,
5-{4-(3-chlorophenyl)-5-[(2-fluorobenzyl)sulfanyl]-4H-1,2,4-triazol-3-yl}-N-isobutylpentanamide,
5-(4-phenyl-5-{[4-(trifluoromethyl)benzyl]sulfanyl}-4H-1,2,4-triazol-3-yl)-N-propylpentanamide,
5-{4-allyl-5-[(4-fluorobenzyl)sulfanyl]-4H-1,2,4-triazol-3-yl}-N-(2-methoxybenzyl)pentanamide,
5-[5-(benzylsulfanyl)-4-(2-phenylethyl)-4H-1,2,4-triazol-3-yl]-N-(2-methoxybenzyl)pentanamide, N-benzyl-5-{4-(3-chlorophenyl)-5-[(3-fluorobenzyl)sulfanyl]-4H-1,2,4-triazol-3-yl}pentanamide,
N-(2-methoxybenzyl)-5-(4-(2-phenylethyl)-5-{[(2E)-3-phenyl-2-propenyl]sulfanyl}-4H-1,2,4-triazol-3-yl)pentanamide,
5-{4-(3-chlorophenyl)-5-[(3-methylbenzyl)sulfanyl]-4H-1,2,4-triazol-3-yl}-N-propylpentanamide,
5-{4-(3-chlorophenyl)-5-[(4-methylbenzyl)sulfanyl]-4H-1,2,4-triazol-3-yl}-N-(3-methoxypropyl)pentanamide,
N-butyl-5-{4-(3-chlorophenyl)-5-[(3,5-dimethylbenzyl)sulfanyl]-4H-1,2,4-triazol-3-yl}pentanamide,
N-benzyl-5-{5-[(2-methylbenzyl)sulfanyl]-4-phenyl-4H-1,2,4-triazol-3-yl}pentanamide,
5-[5-[(3,5-dimethylbenzyl)sulfanyl]-4-(3-methoxyphenyl)-4H-1,2,4-triazol-3-yl]-N-(2-methoxyethyl)pentanamide,
5-{4-(3-chlorophenyl)-5-[(3,5-dimethylbenzyl)sulfanyl]-4H-1,2,4-triazol-3-yl}-N-isobutylpentanamide,
5-[5-(butylsulfanyl)-4-(3-chlorophenyl)-4H-1,2,4-triazol-3-yl]-N-(2-methoxybenzyl)pentanamide,
5-{4-allyl-5-[(3-chlorobenzyl)sulfanyl]-4H-1,2,4-triazol-3-yl}-N-benzylpentanamide,
5-{5-[(3-cyanobenzyl)sulfanyl]-4-phenyl-4H-1,2,4-triazol-3-yl}-N-(2-methoxybenzyl)pentanamide,
5-{4-allyl-5-[(3-methylbenzyl)sulfanyl]-4H-1,2,4-triazol-3-yl}-N-benzylpentanamide,
N-(1,3-benzodioxol-5-ylmethyl)-5-[5-[(2-fluorobenzyl)sulfanyl]-4-(2-phenylethyl)-4H-1,2,4-triazol-3-yl]pentanamide,
5-{4-allyl-5-[(3-chlorobenzyl)sulfanyl]-4H-1,2,4-triazol-3-yl}-N-(1,3-benzodioxol-5-ylmethyl)pentanamide,
5-[5-[(3-methylbenzyl)sulfanyl]-4-(2-phenylethyl)-4H-1,2,4-triazol-3-yl]-N-propylpentanamide,
5-[5-[(2-fluorobenzyl)sulfanyl]-4-(tetrahydro-2-furanylmethyl)-4H-1,2,4-triazol-3-yl]-N-(3-methoxypropyl)pentanamide,
N-(2-methoxybenzyl)-5-[5-[(4-methylbenzyl)sulfanyl]-4-(2-phenylethyl)-4H-1,2,4-triazol-3-yl]pentanamide,
5-[5-[(2-chloro-4-fluorobenzyl)sulfanyl]-4-(2-phenylethyl)-4H-1,2,4-triazol-3-yl]-N-(4-methoxybenzyl)pentanamide,
5-{5-[(3-chlorobenzyl)sulfanyl]-4-phenyl-4H-1,2,4-triazol-3-yl}-N-propylpentanamide,
5-[5-[(4-methylbenzyl)sulfanyl]-4-(2-phenylethyl)-4H-1,2,4-triazol-3-yl]-N-(tetrahydro-2-furanylmethyl)pentanamide,
5-{4-(3-chlorophenyl)-5-[(2-phenylethyl)sulfanyl]-4H-1,2,4-triazol-3-yl}-N-(2-methoxybenzyl)pentanamide and 5-[5-[(2-chloro-4-fluorobenzyl)sulfanyl]-4-(3-chlorophenyl)-4H-1,2,4-triazol-3-yl]-N-(cyclopropylmethyl)pentanamide.

7. A pharmaceutical composition comprising the triazole derivative according to claim 1 and a pharmaceutically acceptable carrier, diluent or excipient thereof.

8. A process for the preparation of the triazole derivative according to claim 1, comprising reacting a nucleophilic group of formula $R^4SH$, wherein $R^4$ is defined as in claim 1, with a triazole of formula XXXIII

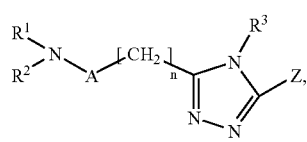

XXXIII wherein Z is a leaving group, and $R^1$, $R^2$, $R^3$, A and n are defined as in claim 1.

9. The process according to claim 8, wherein the leaving group Z of formula XXXIII is Cl.

10. The process according to claim 8, wherein the leaving group Z of formula XXXIII is $SO_2Me$.

11. A triazole derivative of formula XXXIII:

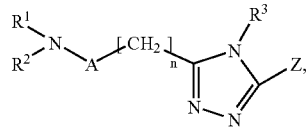

XXXIII wherein $R^1$ and $R^2$ are independently selected from the group consisting of H, $C_1$-$C_6$-alkyl, aryl $C_1$-$C_6$-alkyl, heteroaryl $C_1$-$C_6$-alkyl, $C_3$-$C_6$-cycloalkyl $C_1$-$C_6$-alkyl, and $C_3$-$C_6$-heterocycloarlkyl $C_1$-$C_6$-alkyl;

$R^1$ and $R^2$, together with the nitrogen atom they are linked to, form a substituted or unsubstituted 5-8 membered saturated, partially unsaturated or aromatic ring containing optionally one or more additional heteroatoms selected from O, N, S;

A is C(O);

$R^3$ is selected from the group consisting of H, $C_1$-$C_6$-alkyl, aryl $C_1$-$C_6$-alkyl, heteroaryl $C_1$-$C_6$-alkyl, aryl, heteroaryl, $C_e$-$C_6$-cycloalkyl $C_1$-$C_6$-alkyl, $C_3$-$C_6$-heterocycloalkyl $C_1$-$C_6$-alkyl, $C_2$-$C_6$-alkenyl, B is S;

$R^4$ and $R^5$ are selected from the group consisting of H, $C_1$-$C_6$-alkyl, aryl $C_1$-$C_6$-alkyl, heteroaryl $C_1$-$C_6$-alkyl, acyl, aryl acyl, heteroaryl acyl, $C_3$-$C_6$-cycloalkyl $C_1$-$C_6$-alkyl, $C_3$-$C_6$-heterocycloalkyl $C_1$-$C_6$-alkyl, $C_2$-$C_6$-alkenyl;

n is an integer from 2 to 10, and

Z is Cl or $SO_2Me$.

* * * * *

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Column 3, line 49, "formula L for the preparation of a pharmaceutical"
  should read -- formula I, for the preparation of a pharmaceutical --.

Column 4, line 54, ""Acyl" refers to the group (O)R where R includes"
  should read -- "Acyl" refers to the group –C(O)R where R includes --;
    line 60, ""Alkoxy" refers to the group –R where R includes"
  should read -- "Alkoxy" refers to the group –O-R where R includes --;
    line 65, ""Alkoxycarbonyl" refers to the group –O–R where R"
  should read -- "Alkoxycarbonyl" refers to the group –C(O)OR where R --.

Column 5, line 13, "group, e"aryl", "heteroaryl","
  should read -- group, "aryl", "heteroaryl", --;
    line 63, "malate, sate, citrate, tartrate,"
  should read -- malate, fumarate, citrate, tartrate, --.

Column 6, line 21, "compounds according to formula L mixtures of these, as well"
  should read -- compounds according to formula I, mixtures of these, as well --.

Column 10, line 1, "of an appropriate alkylating agent $R^4X$ (formula m) in"
  should read -- of an appropriate alkylating agent $R^4X$ (formula III) in --.

Column 12, line 38, "formula XIII or a methanesulfonyltriazole of formula XIII"
  should read -- formula XII or a methanesulfonyltriazole of formula XIII --.

Column 17, line 44, "of formula XXV with a suitable resin carrying an"
  should read -- of formula XXIV with a suitable resin carrying an --.

Column 18, line 39, "Amines of formula XV used according to scheme VII are"
  should read -- Amines of formula XXIV used according to scheme VII are --;
    line 56, "Isothiocyanates of formula XXI are either commercial,"
  should read -- Isothiocyanates of formula XXIX are either commercial, --.

Column 19, line 18, "3-bromomethyl-benzonitile,"
  should read -- 3-bromomethyl-benzonitrile, --;
    line 24, "VI) provide enantiomerically pure compounds of general"
  should read -- VII) provide enantiomerically pure compounds of general --.

Column 20, lines 41-42, "and methanol (250 nm)."
  should read -- and methanol (250 mL). --.

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Column 21, line 6, "(0.42 M in anhydrous ml)."
should read -- (0.42 M in anhydrous THF). --;
lines 17-18, "of formula X, were transferred to a clean boiling tube"
should read -- of formula XXX, were transferred to a clean boiling tube --.

Columns 33-34, Example 26, IUPAC-Name,

" 3-[5-[(3-chlorophenyl)-4H-1,2,4-
(3-chlorophenyl)-4H-1,2,4-
triazol-3-yl]-N-
(cyclopropylmethyl)
propanamide "

should read -- 3-[5-[(3-chlorobenzyl)sulfanyl]-4-
(3-chlorophenyl)-4H-1,2,4-
triazol-3-yl]-N-
(cyclopropylmethyl)propanamide --.

Columns 33-34, Example 27, Chemical Structure,

" 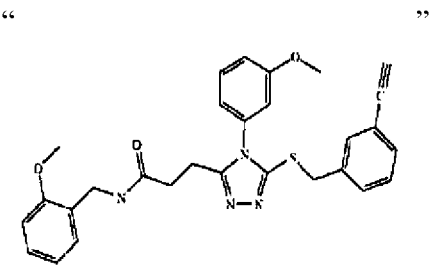 "

should read -- 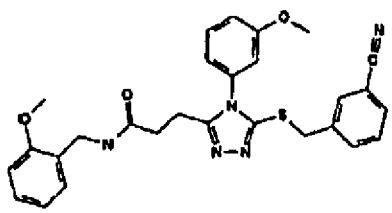 --.

UNITED STATES PATENT AND TRADEMARK OFFICE
CERTIFICATE OF CORRECTION

| | | |
|---|---|---|
| PATENT NO. | : 7,468,385 B2 | |
| APPLICATION NO. | : 10/498356 | |
| DATED | : December 23, 2008 | |
| INVENTOR(S) | : Anna Quattropani et al. | |

It is certified that error appears in the above-identified patent and that said Letters Patent is hereby corrected as shown below:

Columns 51-52, Example 70, M.W., "388.55" should read -- 388.53 --.

Columns 89-90, Example 164, IUPAC-Name,

"4-[3-chlorophenyl]-5-[(3-cyanobenzyl)sulfanyl]-4H-1,2,4-triazol-3-yl}-N-(2-methoxybenzyl)butanamide"

should read -- 4-{4-(3-chlorophenyl)-5-[(3-cyanobenzyl)sulfanyl]-4H-1,2,4-triazol-3-yl}-N-(2-methoxybenzyl)butanamide --.

Columns 97-98, Example 185, IUPAC-Name,

"4-{5-[(3-chlorobenzyl)sulfanyl]-4-phenyl-4H-1,2,4-triazol-3-yl}-N-(2-methoxybenzyl)pentanamide"

should read -- 5-{5-[(3-chlorobenzyl)sulfanyl]-4-phenyl-4H-1,2,4-triazol-3-yl}-N-(2-methoxybenzyl)pentanamide --.

Columns 99-100, Example 188, IUPAC-Name,

"4-{4-allyl-5-[(3-methylbenzyl)sulfanyl]-4H-1,2,4-triazol-3-yl}-N-(2-methoxybenzyl)pentanamide"

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

should read --

5-{4-allyl-5-[(3-methylbenzyl)sulfanyl]-4H-1,2,4-triazol-3-yl}-N-(2-methoxybenzyl)pentanamide

Columns 103-104, Example 197, IUPAC-Name,

" 5-[5-(benzylsulfanyl)-4-(3-methoxypropyl)-4H-1,2,4-triazol-3-yl]-N-(2-methoxypropyl)pentanamide "

should read --

5-[5-(benzylsulfanyl)-4-(3-methoxypropyl)-4H-1,2,4-triazol-3-yl]-N-(2-methoxybenzyl)pentanamide

Columns 105-106, Example 206, IUPAC-Name,

" 4-allyl-5-[(3-fluorobenzyl)sulfanyl]-4H-1,2,4-triazol-3-yl}-N-(2-methoxybenzyl)pentanamide "

should read --

5-{4-allyl-5-[(3-fluorobenzyl)sulfanyl]-4H-1,2,4-triazol-3-yl}-N-(2-methoxybenzyl)pentanamide

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Columns 123-124, Example 249, IUPAC-Name,

" N-(4-fluorobenzyl)-5-{5-[(3-methylbenzyl)sulfanyl]-4-phenyl-4H-1,2,4-triazol-3-pentanamide "

should read -- N-(4-fluorobenzyl)-5-{5-[(3-methylbenzyl)sulfanyl]-4-phenyl-4H-1,2,4-triazol-3-yl}pentanamide --.

Columns 127-128, Example 260, Chemical Structure,

"
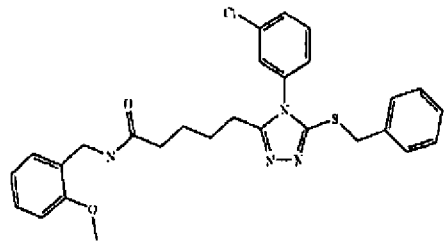
"

should read --
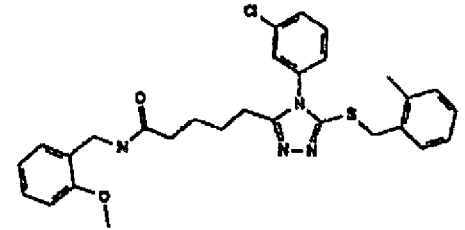
--.

Example 263, (M$^+$(ESI$^+$), the number is missing.
should read -- 540 --.

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Columns 129-130, Example 265, Chemical Structure,

"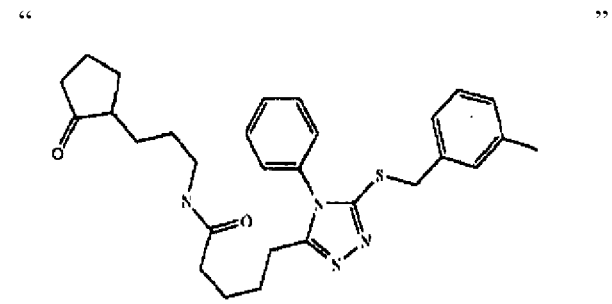"

should read --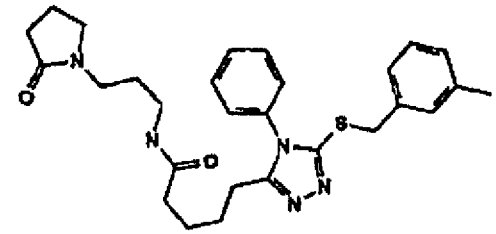--.

Columns 141-142, Example 301, Chemical Structure,

"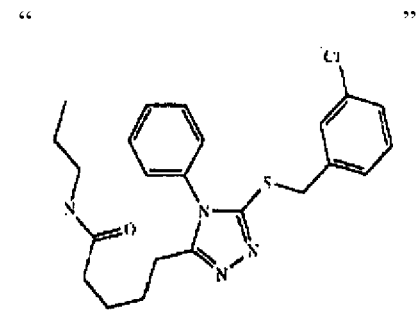"

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

should read -- 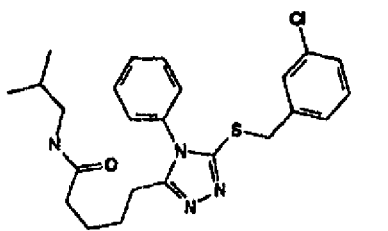 --.

Columns 171-172, Example 376, Chemical Structure,

" 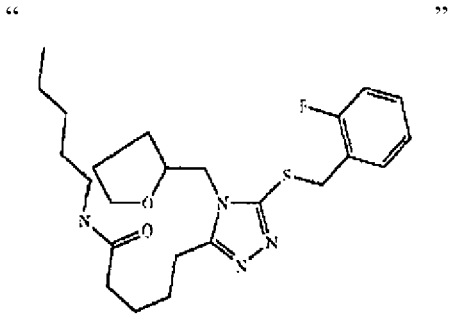 "

should read -- 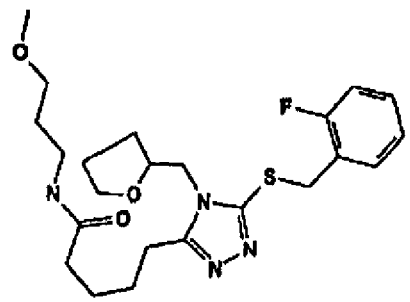 --.

UNITED STATES PATENT AND TRADEMARK OFFICE
CERTIFICATE OF CORRECTION

PATENT NO. : 7,468,385 B2 Page 8 of 10
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Example 378, Chemical Structure,

"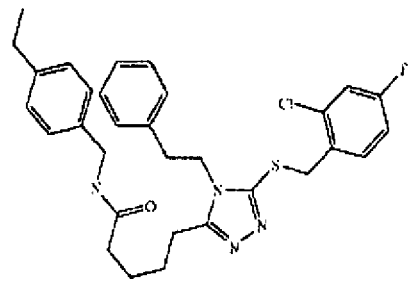"

should read -- 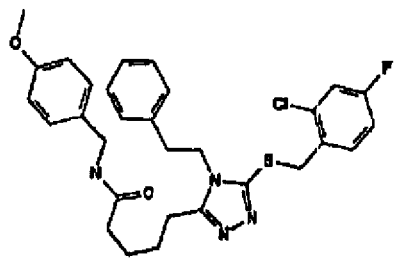 --.

Column 175, lines 32-33, "The membranes (2-4 fg)"
    should read -- The membranes (2-4 $\mu$g) --;
        line 35, "and 0.2 DM of the radiolabelled"
    should read -- and 0.2 nM of the radiolabelled --;
        line 36, "(OVTA being Omithin Vasoactive, and analogue"
    should read -- (OVTA being Ornithin Vasoactive, and analogue --.

Column 178, lines 53-54, "1 $\mu$M, 300nK 100 nM, 10nK,"
    should read -- 1 $\mu$M, 300nM, 100 nM, 10nM, --;
        lines 55-56, "Fluo-4 ($\lambda_{ex}$=488 nm, $\mu_{em}$=590 nm)"
    should read -- Fluo-4 ($\lambda_{ex}$=488 nm, $\lambda_{em}$=590 nm) --.

UNITED STATES PATENT AND TRADEMARK OFFICE
CERTIFICATE OF CORRECTION

PATENT NO. : 7,468,385 B2
APPLICATION NO. : 10/498356
DATED : December 23, 2008
INVENTOR(S) : Anna Quattropani et al.

It is certified that error appears in the above-identified patent and that said Letters Patent is hereby corrected as shown below:

Column 184, lines 43-47,

"
N-allyl-3-[5-[(3,5-dimethylbenzyl)sulfanyl]-4-(3-meth-
oxyphenyl)-4H-1,2,4-triazol-3-yl]propanamide, 3-{4-
(3-chlorophenyl)-5-[(3,5-dimethylbenzyl)sulfanyl]-
4H-1,2,4-triazol-3-yl}-N-(tetrahydro-2-furanylmethyl)
propanamide,
"

should read --

N-allyl-3-[5-[(3,5-dimethylbenzyl)sulfanyl]-4-(3-methoxyphenyl)-4H-1,2,4-triazol-3-
yl]propanamide 3-{4-(3-chlorophenyl)-5-[(3,5-dimethylbenzyl)sulfanyl]-4H-1,2,4-triazol-3-yl)-N-
(tetrahydro-2-furanylmethyl)propanamide

--.

Column 190, lines 49-50,

"
55-[5-[(3-fluorobenzyl)sulfanyl]-4-(2-phenylethyl)-4H-1,
2,4-triazol-3-yl]-N-(2-methoxybenzyl)pentanamide,
"

should read --

5-{5-[(3-fluorobenzyl)sulfanyl]-4-(2-phenylethyl)-4H-1,2,4-triazol-3-yl]-N-(2-
methoxybenzyl)pentanamide

--.

Column 191, lines 45-48,

"
N-(2-methoxybenzyl)-5-{5-[(4-methylbenzyl)sulfanyl]-
4-phenyl-4H-1,2,4-triazol-3-yl}pentanamide, N-butyl-
5-[5-[(3-chlorobenzyl)sulfanyl]-4-(3-chlorophenyl)-
4H-1,2,4-triazol-3-yl]pentanamide,
"

UNITED STATES PATENT AND TRADEMARK OFFICE
CERTIFICATE OF CORRECTION

| | |
|---|---|
| PATENT NO. | : 7,468,385 B2 |
| APPLICATION NO. | : 10/498356 |
| DATED | : December 23, 2008 |
| INVENTOR(S) | : Anna Quattropani et al. |

It is certified that error appears in the above-identified patent and that said Letters Patent is hereby corrected as shown below:

should read --

N-(2-methoxybenzyl)-5-{5-[(4-methylbenzyl)sulfanyl]-4-phenyl-4H-1,2,4-triazol-3-yl}pentanamide N-butyl-5-[5-[(3-chlorobenzyl)sulfanyl]-4-(3-chlorophenyl)-4H-1,2,4-triazol-3-yl]pentanamide

--.

Column 194, lines 15-18,

"
5-[5-(benzylsulfanyl)-4-(2-phenylethyl)-4H-1,2,4-triazol-3-yl]-N-(2-methoxybenzyl)pentanamide, N-benzyl-5-{4-(3-chlorophenyl)-5-[(3-fluorobenzyl)sulfanyl]-4H-1,2,4-triazol-3-yl}pentanamide,
"

should read --

5-[5-(benzylsulfanyl)-4-(2-phenylethyl)-4H-1,2,4-triazol-3-yl]-N-(2-methoxybenzyl)pentanamide N-benzyl-5-{4-(3-chlorophenyl)-5-[(3-fluorobenzyl)sulfanyl]-4H-1,2,4-triazol-3-yl}pentanamide

--.

Column 196, line 18, "$C_e$-$C_6$-cycloalkyl $C_1$-$C_6$-alkyl,"
should read -- $C_3$-$C_6$-cycloalkyl $C_1$-$C_6$-alkyl, --.

Signed and Sealed this

Twenty-first Day of April, 2009

JOHN DOLL
*Acting Director of the United States Patent and Trademark Office*